US011149033B2

(12) United States Patent
Min et al.

(10) Patent No.: US 11,149,033 B2
(45) Date of Patent: Oct. 19, 2021

(54) HETEROARYL COMPOUND, ENANTIOMER, DIASTEREOMER OR PHARMACEUTICALLY ACCEPTABLE SALT THEREOF, AND ANTIVIRAL COMPOSITION CONTAINING SAME AS ACTIVE INGREDIENT

(71) Applicants: INSTITUT PASTEUR KOREA, Gyeonggi-do (KR); ST PHARM CO., LTD., Gyeonggi-do (KR)

(72) Inventors: Ji Young Min, Seoul (KR); So Young Chang, Seoul (KR); Ji Hye Lee, Gyeonggi-do (KR); Sun Hee Kang, Gyeonggi-do (KR); Sun Ju Kong, Gyeonggi-do (KR); Su Yeon Jo, Gyeonggi-do (KR); Young Mi Kim, Gyeonggi-do (KR); Junghwan Choi, Gyeonggi-do (KR)

(73) Assignees: INSTITUT PASTEUR KOREA, Gyeonggi-do (KR); ST PHARM CO., LTD., Gyeonggi-do (KR)

(*) Notice: Subject to any disclaimer, the term of this patent is extended or adjusted under 35 U.S.C. 154(b) by 28 days.

(21) Appl. No.: 16/338,237

(22) PCT Filed: Sep. 29, 2017

(86) PCT No.: PCT/KR2017/011091
§ 371 (c)(1),
(2) Date: Mar. 29, 2019

(87) PCT Pub. No.: WO2018/062978
PCT Pub. Date: Apr. 5, 2018

(65) Prior Publication Data
US 2020/0031816 A1 Jan. 30, 2020

(30) Foreign Application Priority Data
Sep. 30, 2016 (KR) .................. 10-2016-0126997

(51) Int. Cl.
C07D 413/06 (2006.01)
C07D 263/46 (2006.01)
C07D 271/10 (2006.01)
C07D 271/113 (2006.01)
C07D 307/64 (2006.01)
C07D 405/06 (2006.01)

(52) U.S. Cl.
CPC ......... C07D 413/06 (2013.01); C07D 263/46 (2013.01); C07D 271/10 (2013.01); C07D 271/113 (2013.01); C07D 307/64 (2013.01); C07D 405/06 (2013.01)

(58) Field of Classification Search
CPC .................................................... C07D 413/06
USPC ....................................................... 548/132
See application file for complete search history.

(56) References Cited

U.S. PATENT DOCUMENTS 8,722,670 B2 * 5/2014 King .................. A61P 25/00
514/230.5

FOREIGN PATENT DOCUMENTS

| CN | 103880836 A | | 6/2014 | |
|----|---|---|---|---|
| EP | 2390252 A1 | | 11/2011 | |
| GB | 2114566 | * | 2/1953 | .......... C07D 333/36 |
| WO | WO-2013-025858 A1 | | 2/2013 | |

OTHER PUBLICATIONS

Wei, Virology Journal (2014), 11, 195/1-195/28, 28.*
Wang, Journal of Combinatorial Chemistry (2007), 9(3), 513-51.*
Wang, Tetrahedron Letters (2006), 47(1), 105-108.*
Quashie, PLoS One | DOI:10.1371/journal.pone.0128310 Jun. 5, 2015.*
Kerr, Journal of Organic Chemistry (1959), 24, 1861-4.*
Panov Optika i Spektroskopiya (1959), 7(No. 1), 29-34.*
Macarron, Nature Chemical Biology | vol. 11 | Dec. 2015, 904-906.*
Noueiry, Journal of Virology, Nov. 2007, p. 11992-12004.*
Frey, Currents in Pharmacy Teaching and Learning, 12 (2020) 339-346.*
International Search Report from corresponding PCT Application No. PCT/KR2017/011091, dated Feb. 12, 2018.
Chemical Abstract Compound, STN express., RN 1023577-60-7 (May 29, 2008), RN 957947-17-0 (Dec. 13, 2007), RN 1793874-47-1 (Jul. 5, 2015), RN 1793874-41-5 (Jul. 5, 2015).
Chemical Abstract Compound, STN express., RN 1793881-10-3 (Jul. 5, 2015).
Flefel, E. M., et al.; "Heterocyclic Compounds Based on 3-(4-bromophenyl)azo-5-phenyl-2(3H)-furanone: Anti-avian Influenza Virus (H5N1) Activity", Acta Pharm., 2012, vol. 62, pp. 593-606.

* cited by examiner

Primary Examiner — Nizal S Chandrakumar
(74) Attorney, Agent, or Firm — Harness, Dickey & Pierce, P.L.C.

(57) ABSTRACT

The present invention relates to a novel heteroaryl compound, an enantiomer, a diastereomer or a pharmaceutically acceptable salt thereof, and an antiviral composition comprising the same as an active ingredient. The novel compounds represented by formula (I) or formula (II) according to the present invention are remarkably superior in antiviral activity against an influenza virus, and furthermore, have low cytotoxicity and thus low adverse effects on a human body. Therefore, a pharmaceutical composition containing the same as an active ingredient can be effectively used for the prevention or treatment of diseases caused by an influenza virus infection.

5 Claims, 2 Drawing Sheets

HETEROARYL COMPOUND, ENANTIOMER, DIASTEREOMER OR PHARMACEUTICALLY ACCEPTABLE SALT THEREOF, AND ANTIVIRAL COMPOSITION CONTAINING SAME AS ACTIVE INGREDIENT

CROSS-REFERENCE TO RELATED APPLICATIONS

This application is a national phase application of PCT Application No. PCT/KR2017/011091, filed on Sep. 29, 2017, which claims the benefit and priority to Korean Patent Application Nos. 10-2016-0126997, filed on Sep. 30, 2016. The entire disclosures of the applications identified in this paragraph are incorporated herein by references.

FIELD

The present invention relates to novel heteroaryl compounds, its enantiomers, its diastereomers or its pharmaceutically acceptable salts, and an antiviral composition containing the same as an active ingredient.

BACKGROUND

An influenza virus is one of the most common viruses in the world that affect both humans and livestock. The influenza virus is a highly contagious virus that causes acute respiratory diseases and causes serious respiratory symptoms in pediatric, elderly and cardiopulmonary patients by causing mass infections or pandemics in the whole world. Such an influenza virus taxonomically belongs to an orthomyxovirus, and there are 3 types of A, B and C, and in particular, the popularly spreading type is A and B types.

The influenza virus is an RNA enveloped virus having a particle size in which the diameter is about 125 nm. The influenza virus basically consists of an internal nucleocapsid or core of ribonucleic acid (RNA) combined with a nuclear protein surrounded by a lipid bilayer structure and a viral envelope having an external glycoprotein. The internal layer of the viral envelope mainly consists of matrix protein, and the outer layer mostly consists of host-derived lipid substances.

On the surface of these viruses, two kinds of surface antigens that are hemagglutinin (HA) and neuraminidase (HA) which are glycoprotein are present, and in the inside, 8 segmented RNAs are present. The hemagglutinin is a trimer form consisting of head and stem, and among them, the head part is related to most antigen mutations and binds to terminal sialic acid residues on the surface of a host cell to attach a virus, and sequentially, enables the virus to penetrate the host cell (Non-patent document 2). Neuraminidase is a mushroom-shaped tetramer having a head and stem form, and has an active site on the upper surface of the head, and plays an important role in discharging the virus out of the host cell as a virus replicated and proliferated in an infected cell cleaves an alpha-ketosidic bond which links the oligosaccharide part and the terminal neuraminic acid residue of the cell surface, to penetrate a respiratory mucosal cell.

Surface antigens of the virus cause mutations in the same subtype, and new antigenic mutants appear each year. In particular, an avian influenza virus, which has recently become a problem among influenza viruses, infects various kinds of birds such as chickens, turkeys, ducks and wild birds, etc. as a large mutation occurs, and due to rapid propagation, when chickens are infected, more than 80% is dead, and therefore it is a virus disease that gives the biggest damage and threat to the poultry industry in the world, and its ripple effect is not limited to the poultry industry, but it is reported that it causes diseases to people due to infection to human body. To date, specifically looking cases that such an influenza virus causes diseases to people, three times of influenza pandemics in the $20^{th}$ century have been reported, in that about 30 million people by Spanish influenza (H1N1), about million people by Asian influenza (H2N2), and million people by Hong Kong flu (H3N2) were dead. In the $21^{st}$ century, 385 people were infected from 2003 to 2008, resulting in 243 deaths. In recent years, the novel influenza occurred in April, 2009 was already officially declared by WHO as a pandemic, and the infected patients have exceeded 260,000 people in the world, and the number of deaths due to the infection has exceeded 1,000 people in about 20 countries, and in our country, a nun who volunteered in Mexico was found to be the first confirmed patient on May 2, 2009, and based on the announcement on Sep. 16, 2009, about more than 10,000 people were infected, and 8 were hospitalized for severe diseases, and 12 died by chronic complications or acute complications.

As methods for preventing and treating infection of such a virus, inhibition of adsorption to an epithelial cell, inhibition of invasion to a cell, inhibition of transcription and replication of genes, inhibition of protein synthesis, inhibition of releases from a cell, etc. can be considered, and each of them becomes an antiviral target.

From the past, to treat diseases caused by the influenza virus, 4 kinds of substances such as Amatadine, Rimatadine, Zanamivir, Oseltamivir, etc. have been used after approved from U.S. Food and Drug Administration (FDA). However, it has been reported that Amatadine and Rimatadine, which are M2 inhibitors having antiviral action by disturbing uncoating of the virus by blocking an ion channel of M2 protein that is a cell membrane protein necessary for virus proliferation, have an effect only for the influenza virus A type, and for 40 years used, resistant viruses are generated and there are severe side effects in the nervous system and stomach. Since 1999, treatment of virus infection by new drugs such as Zanamivir and Oseltamivir which are inhibitors of neuraminidase, stably present in both A type and B type influenza viruses has been reported.

However, Zanamivir has a high antiviral effect, but has a disadvantage of low bioavailability and rapid release in kidney, and Oseltamivir has a side effect of severe vomiting.

Antiviral agents developed so far show severe side effects, and require a great deal of attention to their application. In addition, the development of a vaccine has a problem of low efficacy when the type of the prevalent virus and the virus of the vaccine are not matched, and therefore, there is an increasing need to develop a new influenza virus agent having an excellent infection inhibition effect and excellent stability.

Accordingly, the present inventors have studied a compound having an antiviral activity against an influenza virus, and confirmed a novel heteroaryl compound exhibiting an excellent antiviral activity against an influenza virus, thereby completing the present invention.

DISCLOSURE

Technical Problem

A purpose of the present invention is to provide a novel compound showing an antiviral activity against an influenza virus, an enantiomer, a diastereomer or a pharmaceutically acceptable salt thereof.

Another purpose of the present invention is to provide an antiviral pharmaceutical composition containing the novel compound, an enantiomer, a diastereomer or a pharmaceutically acceptable salt thereof as an active ingredient.

Other purpose of the present invention is to provide an antiviral health functional food composition containing the novel compound, an enantiomer, a diastereomer or a food acceptable salt thereof as an active ingredient.

Other purpose of the present invention is to provide a composition for disinfecting or cleaning a virus containing the novel compound, an enantiomer or a diastereomer thereof as an active ingredient.

Other purpose of the present invention is to provide a method for inhibiting an influenza virus by using the novel compound, an enantiomer or a diastereomer thereof as an active ingredient.

Technical Solution

To solve the aforementioned problems, the present invention provides a compound represented by the following Chemical formula 1 or Chemical formula, an enantiomer, and a diastereomer or a pharmaceutically acceptable salt thereof:

[Chemical formula 1]

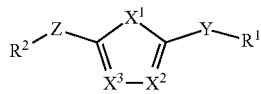

or

[Chemical formula 2]

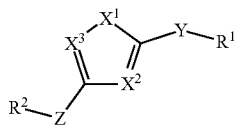

In the Chemical formula 1 or Chemical formula 2, $X^1$, $X^2$, $X^3$, Y, Z, $R^1$ and $R^2$ are as defined herein.

According to preferable one example of the present invention, the present invention provides a compound represented by the following Chemical formula 1a, an enantiomer, and a diastereomer or a pharmaceutically acceptable salt thereof:

[Chemical formula 1a]

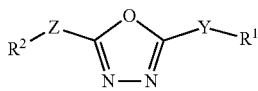

In the Chemical formula 1a, Y, Z, $R^1$ and $R^2$ are as defined herein.

The present invention also provides a method for preparation of a novel compound represented by the Chemical formula 1 or Chemical formula 2.

Moreover, the present invention provides an antiviral pharmaceutical composition containing the compound represented by the Chemical formula 1 or Chemical formula 2, an enantiomer, a diastereomer or a pharmaceutically acceptable salt thereof as an active ingredient.

In addition, the present invention provides an antiviral health functional food composition containing the novel compound represented by the Chemical formula 1 or Chemical formula 2, an enantiomer, a diastereomer or a food acceptable salt thereof as an active ingredient.

Furthermore, the present invention provides a composition for disinfecting or cleaning a virus containing the Chemical formula 1 or Chemical formula 2, an enantiomer or a diastereomer thereof as an active ingredient.

According to preferable one example of the present invention, the virus may be an influenza virus.

According to preferable another example of the present invention, the influenza virus may be an A type influenza virus or a B type influenza virus.

According to preferable other one example of the present invention, the influenza virus may be A/California/07/2009 (H1N1), A/Perth/16/2009 (H3N2) or B/Florida/04/2006.

According to preferable other one example of the present invention, the composition may be used for prevention or treatment of diseases caused by virus infection.

According to preferable other one example of the present invention, the disease caused by virus infection may be one kind of diseases caused by influenza virus infection selected from the group consisting of influenza, cold, sore throat, bronchitis, pneumonia, avian influenza, swine influenza and goat influenza.

Advantageous Effects

The novel compound represented by Chemical formula 1 or Chemical formula 2 according to the present invention has a significantly excellent antiviral activity against an influenza virus and also there is few side effects in the human body as the cytotoxicity is low, and therefore the pharmaceutical composition containing it as an active ingredient can be usefully used for prevention or treatment of diseases caused by influenza virus infection.

DETAILED DESCRIPTION

Figure 1A:
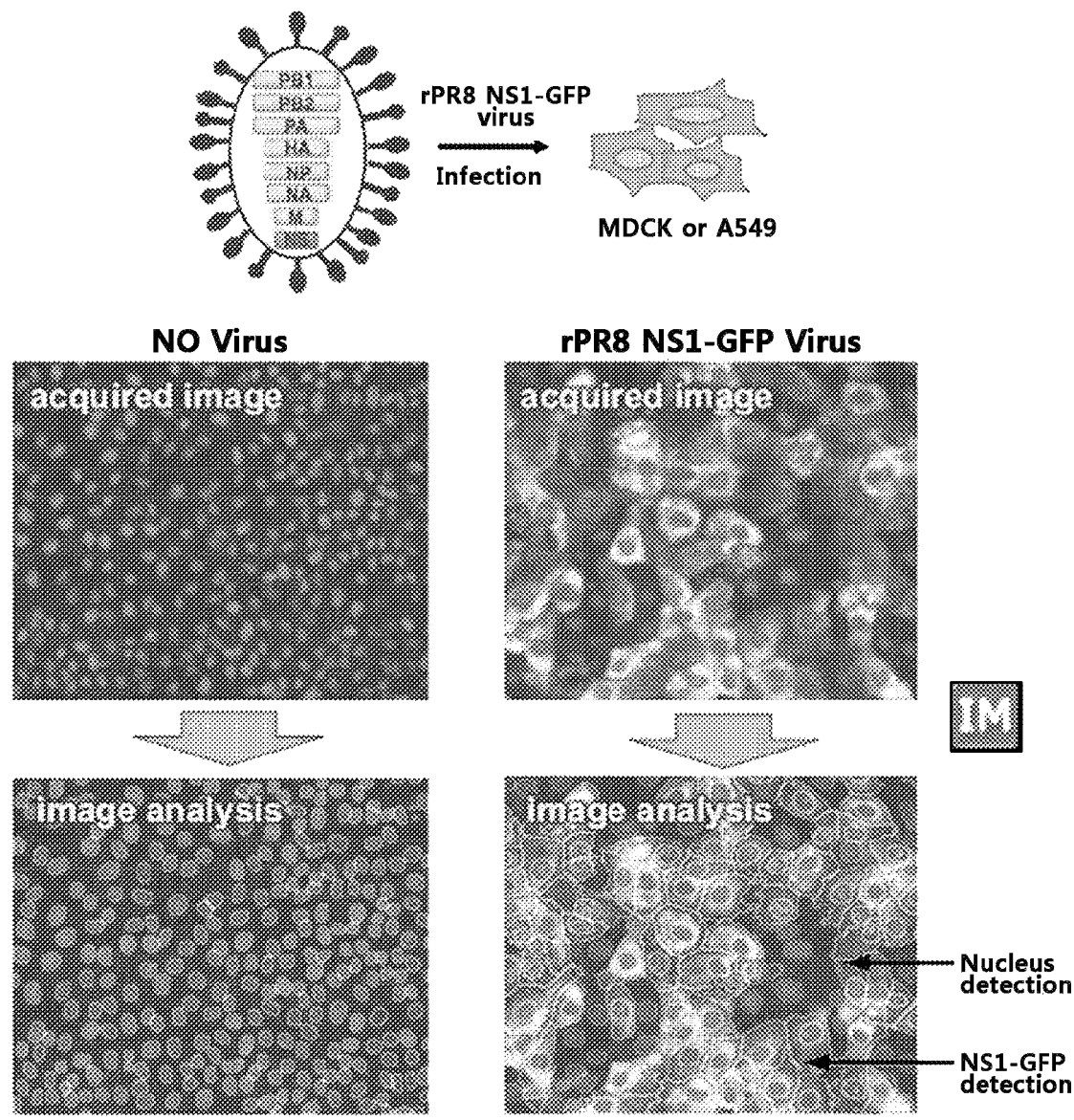
FIG. 1a shows a phenotypic-based assay for measuring influenza infection.

Hereinafter, the present invention will be described in more detail.

As described above, antiviral agents developed so fat show severe side effects, and require a great deal of attention for their application. In addition, the development of a vaccine has a problem of low efficacy when the type of the prevalent virus and the virus of the vaccine are not matched, and therefore, there is an increasing need to develop a new influenza virus agent having an excellent infection inhibition effect and excellent stability.

Accordingly, in the present invention, a novel heteroaryl compound exhibiting an excellent antiviral activity against an influenza virus is confirmed, and the novel compound, an enantiomer, a diastereomer, a pharmaceutically acceptable salt or a food acceptable salt thereof; and an antiviral composition containing the same as an active ingredient is provided, thereby finding a solution of the aforementioned problem.

The present invention provides a compound represented by the following Chemical formula 1 or Chemical formula 2, an enantiomer or a diastereomer thereof:

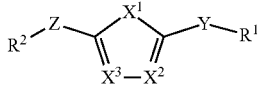

[Chemical formula 1]

or

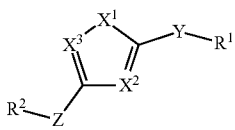

[Chemical formula 2]

wherein, $X^1$ is O, S or —N(CH$_2$CH$_3$)—, $X^2$ and $X^3$ are each independently N or CH, Y is absent, or; is —CH$_2$—; —CH$_2$NH—; —C(=O)—; —CH$_2$CH$_2$—; —NH—; —NHC(=O)—; —C(=O)NH—; —CH(CH$_3$)—; —CF$_2$—; —CH(OCH$_3$)—; —CH$_2$O—; —N(CH$_3$)—; or —CH$_2$NHC(=O)—, Z is absent, or, is —CH$_2$S—; —CH$_2$S(=O)—; —CH$_2$NH—; —CH(R$^c$)S—; —CH$_2$CH$_2$S—; —CH$_2$N(CH$_3$)—;

—CH=CH—; —S—; —CH$_2$—; —O—; —CH$_2$S(=O)$_2$—; —C(=O)—; —SCH$_2$—; —CH$_2$CH$_2$—; —CH(OH)—; —CH(CH$_3$)CH$_2$—; —OCH$_2$—; —C(=O)CH$_2$S—; —C(=O)—NH—; —CH=C(CH$_3$)—; —CH$_2$-cyclopropyl-; —NH—S(=O)$_2$—; —S(=O)$_2$—NH—; or —NH—C(=O)—, $R^c$ is benzene, $R^1$ is

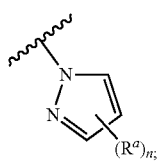

benzene unsubstituted, or substituted with one or more kinds selected from the group consisting of halogen, linear or branched C$_{1-4}$ alkyl, C$_{3-6}$ cycloalkyl, —OCF$_3$, —CF$_3$, —CHF$_2$, —OH, phenoxy, phenyl, C$_{1-4}$ alkoxy, —CN, —NH$_2$, and —N(CH$_3$)$_2$;

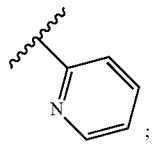 [SMILES: *c1ccccn1 ; ";"]

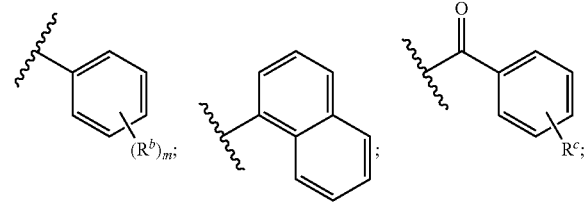

unsubstituted or substituted pyridine; naphthalene unsubstituted, or substituted with C$_{1-4}$ alkoxy; benzotriazole; quinoline or isoquinoline unsubstituted, or substituted with C$_{1-4}$ alkyl, C$_{1-4}$ alkoxy; indazole unsubstituted, or substituted with C$_{1-4}$ alkyl; C$_{3-6}$ cycloalkyl; benzothiophene; benzofuran; indole unsubstituted or substituted with C$_{1-4}$ alkyl; or thiophene, $R^a$ is halogen; linear or branched C$_{1-4}$ alkyl; OCF$_3$; CF$_3$; or unsubstituted benzene, $R^c$ is benzene, n is an integer in the range of 0 to 3, $R^2$ is H;

C$_{1-4}$ alkyl; naphthalene unsubstituted or substituted with halogen;

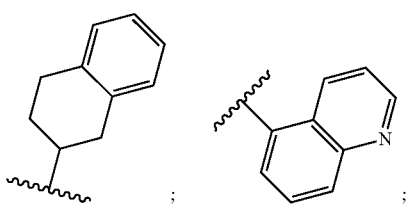 [SMILES: *C1CCc2ccccc2C1 ; ";" ; *c1cccc2ncccc12 ; ";"]

benzofuran unsubstituted or substituted with halogen; benzodioxole unsubstituted or substituted with halogen; quinoline or isoquinoline unsubstituted or substituted with halogen; pyrazole unsubstituted, or substituted with linear or branched $C_{1-4}$ alkyl or halogen; indole substituted with $C_{1-4}$ alkyl; or imidazopyridine, $R^b$ is benzene unsubstituted, or substituted with one or more kinds selected from the group consisting of linear $C_{1-4}$ alkyl and halogen; linear $C_{1-4}$ alkyl; branched $C_{3-5}$ alkyl; —$OCH_3$; 5-membered or 6-membered heteroaryl comprising N, O or S; cycloalkyl of 5 to 7 carbon atoms; —C(=O)$CH_3$; —$OR^c$; —C(=O)$OCH_3$; —$CH_2R^C$; —$CF_3$; —$OCF_3$; —OH; —N($CH_3$)$_2$; —C(=O)—OH; pyrrolidine; piperidine; pyrrole; furan; thiophene; morpholine; $C_{1-4}$ alkoxy substituted with morpholine; —NRdRe (wherein Rd is H or methyl, and Re is —$CH_2CH_2OCH_3$ or —$CH_2CH_2Ph$); or halogen, $R^c$ is benzene unsubstituted or substituted with halogen, $C_{1-4}$ alkyl or halogen, and m is an integer in the range of 0 to 2.

Preferably, a compound represented by the following Chemical formula 1a, an enantiomer or a diastereomer thereof is provided:

[Chemical formula 1a]

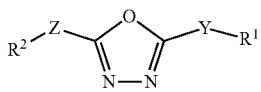

wherein

Y is absent, or; is —$CH_2$—; —$CH_2NH$—; —C(=O)—; —$CH_2CH_2$—; —NH—; —$CH_2O$—; —N($CH_3$)—; —CH($CH_3$)—; —$CF_2$—; or —CH($OCH_3$)—, Z is —$CH_2S$—; —$CH_2S$(=O)—; —CH($R^c$)S—; —$CH_2CH_2S$—; —S—; $CH_2S$(=O)$_2$—; or —$SCH_2$—, $R^1$ is

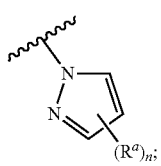

benzene unsubstituted, or substituted with one or more kinds selected from the group consisting of halogen, $C_{1-4}$ alkyl and $OCF_3$, and $CF_3$;

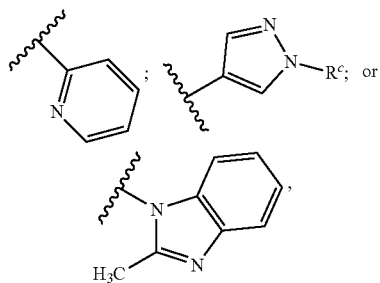

$R^a$ is $C_{1-4}$ alkyl; halogen; or unsubstituted benzene,
$R^c$ is benzene,
n is an integer in the range of 0 to 3,
$R^2$ is

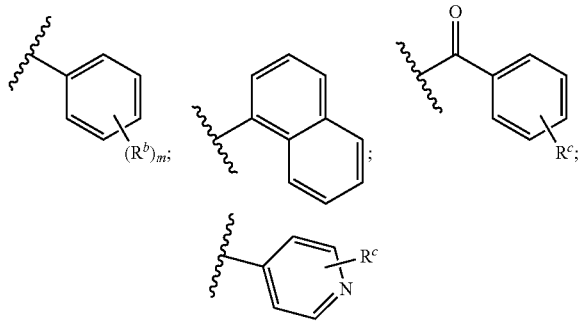

or $C_{1-4}$ alkyl, $R^b$ is benzene unsubstituted, or substituted with one or more kinds selected from the group consisting of linear $C_{1-4}$ alkyl and halogen; linear $C_{1-4}$ alkyl; branched $C_{3-5}$ alkyl; $OCH_3$; 5-membered or 6-membered heteroaryl comprising N, O or S; cycloalkyl of 5 to 7 carbon atoms; C(=O)$CH_3$; $OR^c$; C(=O)$OCH_3$; $CH_2R^C$; or halogen, $R^c$ is benzene, and
m is an integer in the range of 0 to 2.

Preferably, the compound represented by Chemical formula 1 or Chemical formula 2 is as follows:
the compound of Chemical formula 1 or Chemical formula 2 may be selected in the followings.

1
2-(([1,1'-biphenyl]-2-ylmethyl)thio)-5-((4-bromo-3,5-dimethyl-1H-pyrazol-1-yl)methyl)-1,3,4-oxadiazole
2
2-(([1,1'-biphenyl]-4-ylmethyl)thio)-5-((4-bromo-3,5-dimethyl-1H-pyrazol-1-yl)methyl)-1,3,4-oxadiazole
3
2-(([1,1'-biphenyl]-2-ylmethyl)thio)-5-((4-bromo-1H-pyrazol-1-yl)methyl)-1,3,4-oxadiazole
4
2-((1H-pyrazol-1-yl)methyl)-5-(([1,1'-biphenyl]-2-ylmethyl)thio)-1,3,4-oxadiazole
5
2-(([1,1'-biphenyl]-2-ylmethyl)thio)-5-((3,5-dimethyl-1H-pyrazol-1-yl)methyl)-1,3,4-oxadiazole
6
2-(([1,1'-biphenyl]-3-ylmethyl)thio)-5-((4-bromo-3,5-dimethyl-1H-pyrazol-1-yl)methyl)-1,3,4-oxadiazole
7
2-(([1,1'-biphenyl]-2-ylmethyl)thio)-5-((4-chloro-3,5-dimethyl-1H-pyrazol-1-yl)methyl)-1,3,4-oxadiazole
8
2-((4-bromo-3,5-dimethyl-1H-pyrazol-1-yl)methyl)-5-((naphthalen-1-ylmethyl)thio)-1,3,4-oxadiazole
9
2-((4-bromo-3,5-dimethyl-1H-pyrazol-1-yl)methyl)-5-((2-methylbenzyl)thio)-1,3,4-oxadiazole
10
2-((4-bromo-3,5-dimethyl-1H-pyrazol-1-yl)methyl)-5-((2-methoxybenzyl)thio)-1,3,4-oxadiazole
11
2-(([1,1'-biphenyl]-2-ylmethyl)thio)-5-((3-bromo-1H-pyrazol-1-yl)methyl)-1,3,4-oxadiazole
12
2-(([1,1'-biphenyl]-2-ylmethyl)sulfinyl)-5-((4-bromo-3,5-dimethyl-1H-pyrazol-1-yl)methyl)-1,3,4-oxadiazole 13 1-([1,1'-biphenyl]-2-yl)-2-((5-((4-bromo-3,5-dimethyl-1H-pyrazol-1-yl)methyl)-1,3,4-oxadiazol-2-yl)thio)ethan-1-on 14 2-(benzylthio)-5-((4-bromo-3,5-dimethyl-1H-pyrazol-1-yl)methyl)-1,3,4-oxadiazole 15 2-((4-bromo-3,5-dimethyl-1H-pyrazol-1-yl)methyl)-5-((2-(pyridin-4-yl)benzyl)thio)-1,3,4-oxadiazole 16 2-((4-bromo-3,5-dimethyl-1H-pyrazol-1-yl)methyl)-5-(((3-phenylpyridin-4-yl)methyl)thio)-1,3,4-oxadiazole 17 N-([1,1'-biphenyl]-2-ylmethyl)-5-((4-bromo-3,5-dimethyl-1H-pyrazol-1-yl)methyl)-1,3,4-oxadiazol-2-amine 18 2-(([1,1'-biphenyl]-2-ylmethyl)thio)-5-benzyl-1,3,4-oxadiazole 19 2-((4-bromo-3,5-dimethyl-1H-pyrazol-1-yl)methyl)-5-((2-(pyridin-3-yl)benzyl)thio)-1,3,4-oxadiazole 20 2-((4-bromo-3,5-dimethyl-1H-pyrazol-1-yl)methyl)-5-((2-(pyridin-4-yl)benzyl)thio)-1,3,4-oxadiazole 21 2-((4-bromo-3,5-dimethyl-1H-pyrazol-1-yl)methyl)-5-(((3-phenylpyridin-4-yl)methyl)thio)-1,3,4-oxadiazole 22 2-(([1,1'-biphenyl]-2-ylmethyl)thio)-5-(4-bromobenzyl)-1,3,4-oxadiazole 23 2-((4-bromo-3,5-dimethyl-1H-pyrazol-1-yl)methyl)-5-((2-isopropylbenzyl)thio)-1,3,4-oxadiazole 24 3-(([1,1'-biphenyl]-2-ylmethyl)thio)-5-((4-bromo-3,5-dimethyl-1H-pyrazol-1-yl)methyl)-4-ethyl-4H-1,2,4-triazole 25 2-(benzhydrylthio)-5-((4-bromo-3,5-dimethyl-1H-pyrazol-1-yl)methyl)-1,3,4-oxadiazole 26 2-((4-bromo-3,5-dimethyl-1H-pyrazol-1-yl)methyl)-5-((2-methylphenethyl)thio)-1,3,4-oxadiazole 27 2-(([1,1'-biphenyl]-2-ylmethyl)thio)-5-(pyridin-2-ylmethyl)-1,3,4-oxadiazole 28 1-(2-(((5-((4-bromo-3,5-dimethyl-1H-pyrazol-1-yl)methyl)-1,3,4-oxadiazol-2-yl)thio)methyl)phenyl)ethan-1-one 29 2-((4-bromo-3,5-dimethyl-1H-pyrazol-1-yl)methyl)-5-((2-phenoxybenzyl)thio)-1,3,4-oxadiazole 30 2-(([1,1'-biphenyl]-2-ylmethyl)thio)-5-((4-phenyl-1H-pyrazol-1-yl)methyl)-1,3,4-oxadiazole 31 2-((2-(1H-pyrrol-1-yl)benzyl)thio)-5-((4-bromo-3,5-dimethyl-1H-pyrazol-1-yl)methyl)-1,3,4-oxadiazole 32 2-((4-bromo-3,5-dimethyl-1H-pyrazol-1-yl)methyl)-5-(((4'-methyl-[1,1'-biphenyl]-2-yl)methyl)thio)-1,3,4-oxadiazole 33 2-((4-bromo-3,5-dimethyl-1H-pyrazol-1-yl)methyl)-5-(((4'-chloro-[1,1'-biphenyl]-2-yl)methyl)thio)-1,3,4-oxadiazole 34 2-((4-bromo-3,5-dimethyl-1H-pyrazol-1-yl)methyl)-5-((2-(furan-3-yl)benzyl)thio)-1,3,4-oxadiazole 35 2-((4-bromo-3,5-dimethyl-1H-pyrazol-1-yl)methyl)-5-((2-(thiophen-3-yl)benzyl)thio)-1,3,4-oxadiazole 36 2-(([1,1'-biphenyl]-2-ylmethyl)thio)-5-(1-phenyl-1H-pyrazol-4-yl)-1,3,4-oxadiazole 37 methyl 2-(((5-((4-bromo-3,5-dimethyl-1H-pyrazol-1-yl)methyl)-1,3,4-oxadiazol-2-yl)thio)methyl)benzoate 38 2-((2-benzylbenzyl)thio)-5-((4-bromo-3,5-dimethyl-1H-pyrazol-1-yl)methyl)-1,3,4-oxadiazole 39 2-(([1,1'-biphenyl]-3-ylmethyl)thio)-5-((4-phenyl-1H-pyrazol-1-yl)methyl)-1,3,4-oxadiazole 40 2-((4-bromo-3,5-dimethyl-1H-pyrazol-1-yl)methyl)-5-((2,6-dimethylbenzyl)thio)-1,3,4-oxadiazole 41 2-(([1,1'-biphenyl]-2-ylmethyl)thio)-5-((2-methyl-1H-benzo[d]imidazol-1-yl)methyl)-1,3,4-oxadiazole 42 2-(([1,1'-biphenyl]-2-ylmethyl)thio)-5-(4-bromophenyl)-1,3,4-oxadiazole 43 2-(([1,1'-biphenyl]-2-ylmethyl)thio)-5-phenyl-1,3,4-oxadiazole 44 N-([1,1'-biphenyl]-2-ylmethyl)-5-((4-bromo-3,5-dimethyl-1H-pyrazol-1-yl)methyl)-N-methyl-1,3,4-oxadiazol-2-amine 45 N-([1,1'-biphenyl]-2-ylmethyl)-N-(5-((4-bromo-3,5-dimethyl-1H-pyrazol-1-yl)methyl)-1,3,4-oxadiazol-2-yl)acetamide 46 2-((4-bromo-3,5-dimethyl-1H-pyrazol-1-yl)methyl)-5-(3-chlorobenzyl)-1,3,4-oxadiazole 47 N-((5-(([1,1'-biphenyl]-2-ylmethyl)thio)-1,3,4-oxadiazol-2-yl)methyl)-4-bromoaniline 48 (4-bromo-3,5-dimethyl-1H-pyrazol-1-yl)(5-((2-methylbenzyl)thio)furan-2-yl)methanone 49 2-(([1,1'-biphenyl]-2-ylmethyl)thio)-5-(2-(4-bromo-3,5-dimethyl-1H-pyrazol-1-yl)ethyl)-1,3,4-oxadiazole 50 (E)-2-((4-bromo-3,5-dimethyl-1H-pyrazol-1-yl)methyl)-5-(2-isopropylstyryl)-1,3,4-oxadiazole 51 N-((5-(([1,1'-biphenyl]-2-ylmethyl)thio)-1,3,4-oxadiazol-2-yl)methyl)-4-bromobenzamide 52 5-(([1,1'-biphenyl]-2-ylmethyl)thio)-N-(4-bromophenyl)-1,3,4-oxadiazol-2-amine 53 2-((4-bromo-3,5-dimethyl-1H-pyrazol-1-yl)methyl)-5-(o-tolylthio)-1,3,4-oxadiazole 54 2-(2-(4-bromo-3,5-dimethyl-1H-pyrazol-1-yl)ethyl)-5-(o-tolylthio)-1,3,4-oxadiazole 55 (4-bromo-3,5-dimethyl-1H-pyrazol-1-yl)(2-((2-methylbenzyl)thio)oxazol-5-yl)methanone
56 (4-bromo-3,5-dimethyl-1H-pyrazol-1-yl)(5-((2-isopropylphenyl)thio)furan-2-yl)methanone
57 (4-bromo-3,5-dimethyl-1H-pyrazol-1-yl)(5-(2-isopropylphenoxy)furan-2-yl)methanone
58 2-(([1,1'-biphenyl]-2-ylmethyl)thio)-5-((4-bromophenoxy)methyl)-1,3,4-oxadiazole
59 2-(([1,1'-biphenyl]-2-ylmethyl)sulfinyl)-5-(4-bromobenzyl)-1,3,4-oxadiazole
60 2-(([1,1'-biphenyl]-2-ylmethyl)sulfonyl)-5-(4-bromobenzyl)-1,3,4-oxadiazole
61 5-(([1,1'-biphenyl]-2-ylmethyl)thio)-N-(4-bromo-2,6-dimethylphenyl)-1,3,4-oxadiazol-2-amine
62 5-(([1,1'-biphenyl]-2-ylmethyl)thio)-N-(4-bromo-3-methylphenyl)-1,3,4-oxadiazol-2-amine
63 5-(([1,1'-biphenyl]-2-ylmethyl)sulfinyl)-N-(4-bromophenyl)-1,3,4-oxadiazol-2-amine
64 (5-(4-bromobenzyl)-1,3,4-oxadiazol-2-yl)(phenyl)methanone
65 5-(([1,1'-biphenyl]-2-ylmethyl)thio)-N-(4-bromophenyl)-N-methyl-1,3,4-oxadiazol-2-amine
66 2-((4-bromo-3,5-dimethyl-1H-pyrazol-1-yl)methyl)-5-(((2-isopropylphenyl)thio)methyl)-1,3,4-oxadiazole
67 2-((4-bromo-3,5-dimethyl-1H-pyrazol-1-yl)methyl)-5-(2-isopropylphenethyl)-1,3,4-oxadiazole
68 5-(([1,1'-biphenyl]-2-ylmethyl)thio)-N-(3,5-dimethylphenyl)-1,3,4-oxadiazol-2-amine
69 [1,1'-biphenyl]-3-yl(5-(4-bromobenzyl)-1,3,4-oxadiazol-2-yl)methanone
70 [1,1'-biphenyl]-3-yl(5-(4-bromobenzyl)-1,3,4-oxadiazol-2-yl)methanol
71 5-(([1,1'-biphenyl]-2-ylmethyl)thio)-N-phenyl-1,3,4-oxadiazol-2-amine
72 5-(([1,1'-biphenyl]-2-ylmethyl)thio)-N-(4-bromophenyl)-1,3,4-oxadiazole-2-carboxamide
73 2-(([1,1'-biphenyl]-2-ylmethyl)thio)-5-(1-phenylethyl)-1,3,4-oxadiazole
74 2-(([1,1'-biphenyl]-2-ylmethyl)thio)-5-((4-bromophenyl)difluoromethyl)-1,3,4-oxadiazole
75 4-bromo-N-((5-((2-methylbenzyl)thio)furan-2-yl)methyl)aniline
76 (5-((2,6-dimethylphenyl)amino)-1,3,4-oxadiazol-2-yl)(phenyl)methanone
77 (5-((2,6-dimethylphenyl)amino)-1,3,4-oxadiazol-2-yl)(phenyl)methanol
78 (3-chloro-4-fluorophenyl)(5-((2,6-dimethylphenyl)amino)-1,3,4-oxadiazol-2-yl)methanone
79 (3-chloro-4-fluorophenyl)(5-((2,6-dimethylphenyl)amino)-1,3,4-oxadiazol-2-yl)methanol
80 2-benzyl-5-(methylthio)-1,3,4-oxadiazole
81 (E)-2-(2-isopropylstyryl)-5-(4-(trifluoromethoxy)benzyl)-1,3,4-oxadiazole
82 (E)-2-(4-bromobenzyl)-5-(2-isopropylstyryl)-1,3,4-oxadiazole
83 (E)-N-(4-bromophenyl)-5-(2-bromostyryl)-1,3,4-oxadiazol-2-amine
84 N-(4-bromophenyl)-5-(2-isopropylphenethyl)-1,3,4-oxadiazol-2-amine
85 N-(2,6-dimethylphenyl)-5-(2-isopropylphenethyl)-1,3,4-oxadiazol-2-amine
86 (E)-2-(4-bromobenzyl)-5-(2-chloro-4-fluorostyryl)-1,3,4-oxadiazole
87 (E)-N-(4-bromophenyl)-5-(2-chloro-4-fluorostyryl)-1,3,4-oxadiazol-2-amine
88 (E)-N-(4-bromo-3-fluorophenyl)-5-(2-bromostyryl)-1,3,4-oxadiazol-2-amine
89 N-(4-bromophenyl)-5-(2-methylphenethyl)-1,3,4-oxadiazol-2-amine
90 N-(4-bromo-3-methylphenyl)-5-(2-methylphenethyl)-1,3,4-oxadiazol-2-amine
91 N-(4-bromo-3-fluorophenyl)-5-(2-methylphenethyl)-1,3,4-oxadiazol-2-amine
92 2-(4-bromobenzyl)-5-(2-isopropylphenethyl)-1,3,4-oxadiazole
93 2-(2-isopropylphenethyl)-5-(4-(trifluoromethoxy)benzyl)-1,3,4-oxadiazole
94 2-(3,5-dimethylbenzyl)-5-(2-isopropylphenethyl)-1,3,4-oxadiazole
95 2-(([1,1'-biphenyl]-2-ylmethyl)thio)-5-(3-chlorobenzyl)-1,3,4-oxadiazole
96 2-(([1,1'-biphenyl]-2-ylmethyl)sulfonyl)-5-((4-bromo-3,5-dimethyl-1H-pyrazol-1-yl)methyl)-1,3,4-oxadiazole
97 2-(([1,1'-biphenyl]-2-ylmethyl)thio)-5-(methoxy(phenyl)methyl)-1,3,4-oxadiazole
98 2-(4-bromobenzyl)-5-(naphthalen-2-yl)-1,3,4-oxadiazole
99 4-bromo-N-((2-((2-methylbenzyl)thio)oxazol-5-yl)methyl)aniline 100 2-(4-bromobenzyl)-5-(naphthalen-1-ylmethyl)-1,3,4-oxadiazole
101 2-(3-bromobenzyl)-5-(2-isopropylphenethyl)-1,3,4-oxadiazole
102 2-(3-chlorobenzyl)-5-(2-isopropylphenethyl)-1,3,4-oxadiazole
103 2-(4-bromobenzyl)-5-(2-methylphenethyl)-1,3,4-oxadiazole
104 2-(([1,1'-biphenyl]-2-ylmethyl)thio)-5-(3-bromobenzyl)-1,3,4-oxadiazole
105 2-(([1,1'-biphenyl]-2-ylmethyl)thio)-5-(3,5-dimethylbenzyl)-1,3,4-oxadiazole
106 2-(([1,1'-biphenyl]-2-ylmethyl)thio)-5-(4-(trifluoromethoxy)benzyl)-1,3,4-oxadiazole
107 2-(([1,1'-biphenyl]-2-ylmethyl)thio)-5-(4-isopropylbenzyl)-1,3,4-oxadiazole
108 2-(3-chloro-4-fluorobenzyl)-5-(2-methylphenethyl)-1,3,4-oxadiazole
109 2-(4-bromobenzyl)-5-((1,2,3,4-tetrahydronaphthalen-1-yl)methyl)-1,3,4-oxadiazole
110 2-(4-bromobenzyl)-5-(2-(o-tolyl)propyl)-1,3,4-oxadiazole
111 2-(4-bromobenzyl)-5-(2-cyclohexylstyryl)-1,3,4-oxadiazole
112 2-(4-bromobenzyl)-5-(2-cyclohexylstyryl)-1,3,4-oxadiazole
113 2-(3,5-dimethylbenzyl)-5-(2-isopropylstyryl)-1,3,4-oxadiazole
114 2-benzyl-5-((2-isopropylphenoxy)methyl)-1,3,4-oxadiazole
115 2-(4-bromobenzyl)-5-((2-isopropylphenoxy)methyl)-1,3,4-oxadiazole
116 (E)-N-(4-bromophenyl)-5-(2-cyclohexylstyryl)-1,3,4-oxadiazol-2-amine
117 (E)-N-(4-bromophenyl)-5-(2-isopropylstyryl)-1,3,4-oxadiazol-2-amine
118 5-(2-([1,1'-biphenyl]-2-yl)ethyl)-N-(4-bromophenyl)-1,3,4-oxadiazol-2-amine
119 2-(2-([1,1'-biphenyl]-2-yl)ethyl)-5-(4-bromobenzyl)-1,3,4-oxadiazole
120 (E)-N-(4-bromophenyl)-5-(2-methoxystyryl)-1,3,4-oxadiazol-2-amine
121 (E)-N-(4-bromophenyl)-5-(2-(quinolin-5-yl)vinyl)-1,3,4-oxadiazol-2-amine
122 N-(3-chloro-4-fluorophenyl)-5-(2-methylphenethyl)-1,3,4-oxadiazol-2-amine
123 5-(2-methylphenethyl)-N-(4-(trifluoromethyl)phenyl)-1,3,4-oxadiazol-2-amine
124 (E)-5-(2-([1,1'-biphenyl]-2-yl)vinyl)-N-(4-bromophenyl)-1,3,4-oxadiazol-2-amine
125 (E)-N-(4-bromophenyl)-5-(2-phenoxystyryl)-1,3,4-oxadiazol-2-amine
126 (E)-2-(2-([1,1'-biphenyl]-2-yl)vinyl)-5-(4-bromobenzyl)-1,3,4-oxadiazole
127 (E)-2-(4-bromobenzyl)-5-(2-phenoxystyryl)-1,3,4-oxadiazole
128 (E)-2-(4-bromobenzyl)-5-(2-bromostyryl)-1,3,4-oxadiazole
129 2-(4-bromobenzyl)-5-(1-(2-methylbenzyl)cyclopropyl)-1,3,4-oxadiazole
130 2-(3-bromobenzyl)-5-(2-isopropylstyryl)-1,3,4-oxadiazole
131 2-(3-chloro-4-fluorobenzyl)-5-(2-isopropylstyryl)-1,3,4-oxadiazole
132 2-(2-isopropylstyryl)-5-(naphthalen-1-ylmethyl)-1,3,4-oxadiazole
133 2-(4-isopropylbenzyl)-5-(2-isopropylstyryl)-1,3,4-oxadiazole
134 2-(4-bromobenzyl)-5-(2,6-dimethylstyryl)-1,3,4-oxadiazole
135 2-(4-bromobenzyl)-5-(2,6-dimethylphenethyl)-1,3,4-oxadiazole
136 2-([1,1'-biphenyl]-4-ylmethyl)-5-(2-isopropylstyryl)-1,3,4-oxadiazole
137 2-(4-bromobenzyl)-5-(1-(o-tolyl)propan-2-yl)-1,3,4-oxadiazole
138 2-(4-bromobenzyl)-5-(1-(o-tolyl)prop-1-en-2-yl)-1,3,4-oxadiazole
139 2-([1,1'-biphenyl]-4-ylmethyl)-5-(2-isopropylstyryl)-1,3,4-oxadiazole
140 2-(4-bromobenzyl)-5-(1-(o-tolyl)propan-2-yl)-1,3,4-oxadiazole
141 2-(4-bromobenzyl)-5-(1-(o-tolyl)prop-1-en-2-yl)-1,3,4-oxadiazole
142 2-([1,1'-biphenyl]-4-ylmethyl)-5-(2-isopropylstyryl)-1,3,4-oxadiazole
143 2-(4-bromobenzyl)-5-(1-(o-tolyl)propan-2-yl)-1,3,4-oxadiazole
144 2-(4-bromobenzyl)-5-(1-(o-tolyl)prop-1-en-2-yl)-1,3,4-oxadiazole
145 2-(3-bromo-4-methylbenzyl)-5-(2-isopropylstyryl)-1,3,4-oxadiazole
146 2-(3,4-dimethylbenzyl)-5-(2-isopropylstyryl)-1,3,4-oxadiazole 147 2-(2-isopropylstyryl)-5-(1-phenylethyl)-1,3,4-oxadiazole
148 2-(1-(4-isobutylphenyl)ethyl)-5-(2-isopropylstyryl)-1,3,4-oxadiazole
149 2-(4-bromobenzyl)-5-(3,4-dichlorostyryl)-1,3,4-oxadiazole
150 2-(4-bromobenzyl)-5-(2,3-dimethylstyryl)-1,3,4-oxadiazole
151 2-(4-bromobenzyl)-5-(3-isopropylstyryl)-1,3,4-oxadiazole
152 2-(4-bromobenzyl)-5-(2-chloro-3-(trifluoromethyl)styryl)-1,3,4-oxadiazole
153 2-(4-bromobenzyl)-5-(2-(4'-chloro-[1,1'-biphenyl]-2-yl)vinyl)-1,3,4-oxadiazole
154 2-(4-bromobenzyl)-5-(4-isopropylstyryl)-1,3,4-oxadiazole
155 2-(4-bromobenzyl)-5-(2-(4-fluorophenoxy)styryl)-1,3,4-oxadiazole
156 2-(benzofuran-2-yl)-5-(4-bromobenzyl)-1,3,4-oxadiazole
157 2-(4-bromobenzyl)-5-(5-chlorobenzofuran-2-yl)-1,3,4-oxadiazole
158 (E)-2-benzyl-5-(2-chloro-4-fluorostyryl)-1,3,4-oxadiazole
159 (E)-2-(3-chloro-4-fluorobenzyl)-5-(2-chloro-4-fluorostyryl)-1,3,4-oxadiazole
160 (E)-N-(4-bromo-3-fluorophenyl)-5-(2-chloro-4-fluorostyryl)-1,3,4-oxadiazol-2-amine
161 (E)-N-(4-bromo-3-fluorophenyl)-5-(2-chloro-4-fluorostyryl)-N-methyl-1,3,4-oxadiazol-2-amine
162 2-(4-bromobenzyl)-5-(2-(6-chlorobenzo[d][1,3]dioxol-5-yl)vinyl)-1,3,4-oxadiazole
163 2-(4-bromobenzyl)-5-(2-methoxystyryl)-1,3,4-oxadiazole
164 2-(4-bromo-3-fluorobenzyl)-5-(2-isopropylstyryl)-1,3,4-oxadiazole
165 2-(4-bromobenzyl)-5-styryl-1,3,4-oxadiazole
166 2-(4-bromobenzyl)-5-(2-chlorostyryl)-1,3,4-oxadiazole
167 2-(4-bromobenzyl)-5-(3-chlorostyryl)-1,3,4-oxadiazole
168 2-(4-bromobenzyl)-5-(2,6-dichlorostyryl)-1,3,4-oxadiazole
169 2-(4-bromo-2-fluorobenzyl)-5-(2-isopropylstyryl)-1,3,4-oxadiazole
170 2-(4-bromobenzyl)-5-(2-methylstyryl)-1,3,4-oxadiazole
171 2-(4-bromobenzyl)-5-(4-chlorostyryl)-1,3,4-oxadiazole
172 2-(4-bromo-3-methylbenzyl)-5-(2-isopropylstyryl)-1,3,4-oxadiazole
173 2-(2-fluoro-5-methylbenzyl)-5-(2-isopropylstyryl)-1,3,4-oxadiazole
174 (E)-3-(4-bromobenzyl)-5-styryl-1,2,4-oxadiazole
175 (E)-3-(4-bromobenzyl)-5-(2-isopropylstyryl)-1,2,4-oxadiazole
176 (E)-2-(4-bromo-3-methylbenzyl)-5-(2-chloro-4-fluorostyryl)-1,3,4-oxadiazole
177 (E)-2-(2-chloro-4-fluorostyryl)-5-(2-fluoro-5-methylbenzyl)-1,3,4-oxadiazole
178 (E)-2-(3-bromobenzyl)-5-(2-chloro-4-fluorostyryl)-1,3,4-oxadiazole
179 (E)-2-(2-chloro-4-fluorostyryl)-5-(3-chlorobenzyl)-1,3,4-oxadiazole
180 (E)-2-(2-chloro-4-fluorostyryl)-5-((6-chloropyridin-3-yl)methyl)-1,3,4-oxadiazole
181 (E)-2-(3-bromo-4-methylbenzyl)-5-(2-chloro-4-fluorostyryl)-1,3,4-oxadiazole
182 (E)-2-(2-chloro-4-fluorostyryl)-5-(3-isopropylbenzyl)-1,3,4-oxadiazole
183 (E)-5-(4-bromobenzyl)-3-styryl-1,2,4-oxadiazole
184 (E)-2-(4-bromo-3-fluorobenzyl)-5-(2-chloro-4-fluorostyryl)-1,3,4-oxadiazole
185 (E)-2-(2-chloro-4-fluorostyryl)-5-(naphthalen-1-ylmethyl)-1,3,4-oxadiazole
186 2-(3-bromobenzyl)-5-(4-fluoro-2-methylstyryl)-1,3,4-oxadiazole
187 2-(3-chlorobenzyl)-5-(2-fluorostyryl)-1,3,4-oxadiazole
188 2-(3-bromobenzyl)-5-(4-fluorostyryl)-1,3,4-oxadiazole
189 2-(3-bromobenzyl)-5-(2,4-difluorostyryl)-1,3,4-oxadiazole
190 2-(3-bromobenzyl)-5-(4-chloro-2-fluorostyryl)-1,3,4-oxadiazole
191 2-(3-bromobenzyl)-5-(3,4-difluorostyryl)-1,3,4-oxadiazole
192 2-(3-bromobenzyl)-5-(2,4-dichlorostyryl)-1,3,4-oxadiazole
193 2-(3-bromobenzyl)-5-(2-chloro-5-fluorostyryl)-1,3,4-oxadiazole
194 2-(3-bromobenzyl)-5-(2-chloro-3-fluorostyryl)-1,3,4-oxadiazole
195 2-(3-bromobenzyl)-5-(2-chloro-4-methylstyryl)-1,3,4-oxadiazole
196 2-benzyl-5-(2-isopropylstyryl)-1,3,4-oxadiazole
197 2-(4-bromobenzyl)-5-(2-(naphthalen-1-yl)vinyl)-1,3,4-oxadiazole
198 2-(3-bromobenzyl)-5-(2-methyl-4-(trifluoromethyl)styryl)-1,3,4-oxadiazole 199 2-(3-bromobenzyl)-5-(2-chloro-5-(trifluoromethyl)styryl)-1,3,4-oxadiazole
200 2-(3-bromobenzyl)-5-(2,4-dimethylstyryl)-1,3,4-oxadiazole
201 (E)-3-((5-(2-chloro-4-fluorostyryl)-1,3,4-oxadiazol-2-yl)methyl)phenol
202 (E)-2-(2-chloro-4-fluorostyryl)-5-(3-methoxybenzyl)-1,3,4-oxadiazole
203 (E)-2-(2-chloro-4-fluorostyryl)-5-((2-methyl-1H-benzo[d]imidazol-1-yl)methyl)-1,3,4-oxadiazole
204 (E)-2-(3-bromobenzyl)-5-(2-(2-methylpyridin-3-yl)vinyl)-1,3,4-oxadiazole
205 (E)-2-((5-bromopyridin-3-yl)methyl)-5-(2-chloro-4-fluorostyryl)-1,3,4-oxadiazole
206 (E)-2-(2-chloro-4-fluorostyryl)-5-((4-chloropyridin-2-yl)methyl)-1,3,4-oxadiazole
207 2-(3-bromo-4-fluorobenzyl)-5-(2-chloro-4-fluorostyryl)-1,3,4-oxadiazole
208 2-(2-chloro-4-fluorostyryl)-5-(3,4-dichlorobenzyl)-1,3,4-oxadiazole
209 2-(2-(5-(4-bromobenzyl)-1,3,4-oxadiazol-2-yl)vinyl)phenol
210 2-(3-bromobenzyl)-5-(2-methoxystyryl)-1,3,4-oxadiazole
211 2-(2-chloro-4-fluorostyryl)-5-(3-methylbenzyl)-1,3,4-oxadiazole
212 2-((1H-benzo[d][1,2,3]triazol-1-yl)methyl)-5-(2-chloro-4-fluorostyryl)-1,3,4-oxadiazol
213 2-(2-chloro-4-fluorostyryl)-5-((1-methyl-1H-indol-3-yl)methyl)-1,3,4-oxadiazole
214 (E)-2-(2-chloro-4-fluorostyryl)-5-((1-methyl-1H-indazol-3-yl)methyl)-1,3,4-oxadiazole
215 2-(2-bromo-4-fluorostyryl)-5-(3-bromobenzyl)-1,3,4-oxadiazole
216 2-(3-bromobenzyl)-5-(2-(3-methylpyridin-4-yl)vinyl)-1,3,4-oxadiazole
217 3-((5-(2-chloro-4-fluorostyryl)-1,3,4-oxadiazol-2-yl)methyl)-N,N-dimethylaniline
218 2-(2-(5-(3-bromobenzyl)-1,3,4-oxadiazol-2-yl)vinyl)phenol
219 2-(2-chloro-4-fluorostyryl)-5-((6-chloropyridin-2-yl)methyl)-1,3,4-oxadiazole
220 2-(3-bromobenzyl)-5-(2-ethylstyryl)-1,3,4-oxadiazole
221 2-(2-chloro-4-fluorostyryl)-5-(2,3-dimethylbenzyl)-1,3,4-oxadiazole
222 2-(2-bromobenzyl)-5-(2-chloro-4-fluorostyryl)-1,3,4-oxadiazole
223 2-(3-bromophenethyl)-5-(2-chloro-4-fluorostyryl)-1,3,4-oxadiazole
224 2-(2-(5-(3-bromobenzyl)-1,3,4-oxadiazol-2-yl)vinyl)-N,N-dimethylaniline
225 2-(3-bromobenzyl)-5-(2-(2-chloropyridin-3-yl)vinyl)-1,3,4-oxadiazole
226 2-(2-chloro-4-fluorostyryl)-5-(3-fluorobenzyl)-1,3,4-oxadiazole
227 (E)-2-(2-chloro-4-fluorostyryl)-5-(3,5-dibromobenzyl)-1,3,4-oxadiazole
228 (E)-2-(2-chloro-4-fluorostyryl)-5-(naphthalen-2-ylmethyl)-1,3,4-oxadiazole
229 (E)-2-(3-bromo-4-methoxybenzyl)-5-(2-chloro-4-fluorostyryl)-1,3,4-oxadiazole
230 (E)-2-bromo-4-((5-(2-chloro-4-fluorostyryl)-1,3,4-oxadiazol-2-yl)methyl)phenol
231 (E)-2-(2-(5-(3-bromobenzyl)-1,3,4-oxadiazol-2-yl)vinyl)-5-fluoro-N,N-dimethylaniline
232 (E)-2-(3-bromobenzyl)-5-(4-fluoro-2-(pyrrolidin-1-yl)styryl)-1,3,4-oxadiazole
233 (E)-2-(3-bromobenzyl)-5-(2,4,6-trifluorostyryl)-1,3,4-oxadiazole
234 (E)-3-((5-(2-chloro-4-fluorostyryl)-1,3,4-oxadiazol-2-yl)methyl)benzonitrile
235 (E)-2-(2-chloro-4-fluorostyryl)-5-(3-(trifluoromethoxy)benzyl)-1,3,4-oxadiazole
236 2-(2-chloro-4-fluorostyryl)-5-(quinolin-8-ylmethyl)-1,3,4-oxadiazole
237 2-(2-chloro-4-fluorostyryl)-5-(isoquinolin-1-ylmethyl)-1,3,4-oxadiazole
238 2-(2-chloro-4-fluorostyryl)-5-(isoquinolin-4-ylmethyl)-1,3,4-oxadiazole
239 2-(3-bromobenzyl)-5-(2-(5-fluoropyridin-2-yl)vinyl)-1,3,4-oxadiazole
240 2-((6-bromopyridin-3-yl)methyl)-5-(2-chloro-4-fluorostyryl)-1,3,4-oxadiazole
241 2-((6-bromopyridin-3-yl)methyl)-5-(2-chloro-4-fluorostyryl)-1,3,4-oxadiazole
242 methyl-2-(2-(5-(3-bromobenzyl)-1,3,4-oxadiazol-2-yl)vinyl)benzoate
243 2-(2-(5-(3-bromobenzyl)-1,3,4-oxadiazol-2-yl)vinyl)benzoic acid
244 5-(3-bromobenzyl)-N-(2-chloro-4-fluorophenyl)-1,3,4-oxadiazole-2-carboxamide 245
2-(3-bromobenzyl)-5-(2-chloro-4,6-difluorostyryl)-1,3,4-oxadiazole
246
N-(5-(3-bromobenzyl)-1,3,4-oxadiazol-2-yl)-2-chloro-4-fluorobenzenesulfonamide
247
(E)-2-(2-chloro-4-fluorostyryl)-5-(3-(trifluoromethyl)benzyl)-1,3,4-oxadiazole
248
(E)-2-(3-bromobenzyl)-5-(2-(1-isopropyl-1H-pyrazol-5-yl)vinyl)-1,3,4-oxadiazole
249
(E)-2-((1H-indazol-3-yl)methyl)-5-(2-chloro-4-fluorostyryl)-1,3,4-oxadiazole
250
(E)-2-(2-chloro-4-fluorostyryl)-5-(cyclohexylmethyl)-1,3,4-oxadiazole
251
(E)-2-(benzo[b]thiophen-3-ylmethyl)-5-(2-chloro-4-fluorostyryl)-1,3,4-oxadiazole
252
(E)-2-(3-bromobenzyl)-5-(4-fluoro-2-(piperidin-1-yl)styryl)-1,3,4-oxadiazole
253
N-(3-bromophenyl)-5-(2-chloro-4-fluorostyryl)-1,3,4-oxadiazole-2-carboxamide
254
(E)-2-(3-bromobenzyl)-5-(2-(4-chloro-1-isopropyl-1H-pyrazol-3-yl)vinyl)-1,3,4-oxadiazole
255
2-(2-chloro-4-fluorostyryl)-5-(3-fluoro-5-methylbenzyl)-1,3,4-oxadiazole
256
2-(3-bromobenzyl)-5-(2-(trifluoromethoxy)styryl)-1,3,4-oxadiazole
257
2-(3-bromobenzyl)-5-(2-(3-chloro-5-fluoropyridin-2-yl)vinyl)-1,3,4-oxadiazole
258
2-(5-bromo-2-fluorobenzyl)-5-(2-chloro-4-fluorostyryl)-1,3,4-oxadiazole
259
(E)-2-(3-bromobenzyl)-5-(2-(1-isopropyl-1H-imidazol-2-yl)vinyl)-1,3,4-oxadiazole
260
(E)-2-(3-bromobenzyl)-5-(2,6-dichloro-4-fluorostyryl)-1,3,4-oxadiazole
261
(E)-2-(2-chloro-4-fluorostyryl)-5-((1-isopropyl-1H-indazol-3-yl)methyl)-1,3,4-oxadiazole
262
2-(3-bromo-4-methylbenzyl)-5-(2,4-difluorostyryl)-1,3,4-oxadiazole
263
2-(3-bromo-4-fluorobenzyl)-5-(2,4-difluorostyryl)-1,3,4-oxadiazole
264
2-(3-bromobenzyl)-5-(4-fluoro-2-(trifluoromethyl)styryl)-1,3,4-oxadiazole
265
2-(2-bromo-4-fluorostyryl)-5-(3-bromo-4-methylbenzyl)-1,3,4-oxadiazole
266
2-(3-bromo-4-fluorobenzyl)-5-(2-bromo-4-fluorostyryl)-1,3,4-oxadiazole
267
2-(2-chloro-4-fluorostyryl)-5-(3-cyclopropylbenzyl)-1,3,4-oxadiazole
268
(E)-2-(2-(5-(3-Bromobenzyl)-1,3,4-oxadiazol-2-yl)vinyl)-5-fluoro-N-(2-methoxyethyl)-N-methylaniline
269
(E)-2-(3-bromobenzyl)-5-(4-fluoro-2-(furan-3-yl)styryl)-1,3,4-oxadiazole
270
(E)-2-(3-bromobenzyl)-5-(4-fluoro-2-(thiophen-3-yl)styryl)-1,3,4-oxadiazole
271
(E)-4-(2-(2-(5-(3-bromobenzyl)-1,3,4-oxadiazol-2-yl)vinyl)-5-fluorophenyl)morpholine
272
(E)-2-(benzofuran-3-ylmethyl)-5-(2-chloro-4-fluorostyryl)-1,3,4-oxadiazole
273
(E)-2-(3-bromobenzyl)-5-(4-fluoro-2-isopropylstyryl)-1,3,4-oxadiazole
274
(E)-2-(2-(1H-pyrrol-1-yl)styryl)-5-(3-bromobenzyl)-1,3,4-oxadiazole
275
2-(3-bromobenzyl)-5-(2-chloro-4-fluorophenethyl)-1,3,4-oxadiazole
276
(E)-2-(3-bromobenzyl)-5-(2-(naphthalen-1-yl)vinyl)-1,3,4-oxadiazole
277
(E)-2-(3-bromobenzyl)-5-(2-(4-fluoronaphthalen-1-yl)vinyl)-1,3,4-oxadiazole
278
(E)-2-((1H-indazol-3-yl)methyl)-5-(2-chloro-4-fluorostyryl)-1,3,4-oxadiazole
279
(E)-2-(2-chloro-4-fluorostyryl)-5-((2-methyl-1H-indol-1-yl)methyl)-1,3,4-oxadiazole
280
2-(3-bromobenzyl)-5-(2,3-difluorostyryl)-1,3,4-oxadiazole
281
2-(3-bromobenzyl)-5-(2-(trifluoromethyl)styryl)-1,3,4-oxadiazole
282
2-(5-bromo-2-methylbenzyl)-5-(2-chloro-4-fluorostyryl)-1,3,4-oxadiazole
283
2-((4-bromopyridin-2-yl)methyl)-5-(2-chloro-4-fluorostyryl)-1,3,4-oxadiazole
284
2-(3-bromobenzyl)-5-(2-(3,5-difluoropyridin-2-yl)vinyl)-1,3,4-oxadiazole
285
2-(3-bromo-4-methylbenzyl)-5-(2-chloro-4-fluorophenethyl)-1,3,4-oxadiazole
286
(E)-2-(2-chloro-4-fluorostyryl)-5-(thiophen-3-ylmethyl)-1,3,4-oxadiazole
287
(E)-2-(3-bromobenzyl)-5-(2-(naphthalen-2-yl)vinyl)-1,3,4-oxadiazole
288
(E)-2-(3-bromobenzyl)-5-(2,3-dimethylstyryl)-1,3,4-oxadiazole
289
(E)-2-(3-bromobenzyl)-5-(2-(quinolin-5-yl)vinyl)-1,3,4-oxadiazole 290 2-(2-bromo-4,6-difluorostyryl)-5-(3-bromobenzyl)-1,3,4-oxadiazole
291 2-(3-chloro-2-fluorobenzyl)-5-(2-chloro-4-fluorostyryl)-1,3,4-oxadiazole
292 2-(3-bromo-5-fluorobenzyl)-5-(2-chloro-4-fluorostyryl)-1,3,4-oxadiazole
293 2-(3-bromo-2-fluorobenzyl)-5-(2-chloro-4-fluorostyryl)-1,3,4-oxadiazole
294 2-(3-bromo-2-methylbenzyl)-5-(2-chloro-4-fluorostyryl)-1,3,4-oxadiazole
295 2-(2-chloro-4-fluorostyryl)-5-((2-methylquinolin-8-yl)methyl)-1,3,4-oxadiazole
296 2-(2-chloro-4-fluorostyryl)-5-((3-chloroisoquinolin-1-yl)methyl)-1,3,4-oxadiazole
297 2-(2-chloro-4-fluorostyryl)-5-((3-methoxyisoquinolin-1-yl)methyl)-1,3,4-oxadiazole
298 2-(2-chloro-4-fluorostyryl)-5-((7-methoxynaphthalen-1-yl)methyl)-1,3,4-oxadiazole
299 2-(2-chloro-4-fluorostyryl)-5-(3-(difluoromethyl)benzyl)-1,3,4-oxadiazole
300 2-(2-chloro-4-fluorostyryl)-5-(3-chloro-4-methylbenzyl)-1,3,4-oxadiazole
301 (E)-2-(3-bromobenzyl)-5-(2-(quinolin-8-yl)vinyl)-1,3,4-oxadiazole
302 (E)-4-(2-(2-(2-(5-(3-bromobenzyl)-1,3,4-oxadiazol-2-yl)vinyl)-5-fluorophenoxy)ethyl)morpholine
303 (E)-2-(3-bromobenzyl)-5-(2-(isoquinolin-5-yl)vinyl)-1,3,4-oxadiazole
304 (E)-2-(3-bromobenzyl)-5-(2-(1-methyl-1H-indol-3-yl)vinyl)-1,3,4-oxadiazole
305 2-(2-(5-(3-bromo-4-methylbenzyl)-1,3,4-oxadiazol-2-yl)vinyl)-5-fluoro-N-methyl-N-phenethylaniline
306 (E)-2-(3-bromobenzyl)-5-(2-(imidazo[1,2-a]pyridin-3-yl)vinyl)-1,3,4-oxadiazole
307 (E)-2-(3-bromobenzyl)-5-(2-(1-methyl-1H-indol-4-yl)vinyl)-1,3,4-oxadiazole The novel compound represented by Chemical formula 1 or Chemical formula 2 according to the present invention may be used in a form of pharmaceutically acceptable salt. As the salt, an acid addition salt formed by various pharmaceutically or physiologically acceptable organic acids or inorganic acids is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono and dicarboxylate, phenyl-substituted alkanoate, hydroxy alkanoate and alkanedioate, aromatic acids, aliphatic and aromatic sulfonic acids. It may be prepared by using sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caprate, heptanoate, propionic acid, oxalic acid, malonic acid, succinic acid, suberate, sebacate, fumarate, maleate, butyne-1,4-dioate, hexane-1,6-dioic acid, benzoic acid, chlorobenzoic acid, methylbenzoic acid, dinitrobenzoic acid, hydroxybenzoate, methoxybenzoic acid, phthalic acid, terephthalate, benzene sulfonic acid, toluene sulfonic acid, chlorobenzene sulfonic acid, xylene sulfonic acid, phenyl acetic acid, phenyl propionic acid, phenyl butyrate, citrate, lactate, β-hydroxybutyrate, glycolate, malate, tartrate, methane sulfonate, propane sulfonate, naphthalene-1-sulfonate, naphthalene-2-sulfonate, mandelate, trifluoroacetic acid, etc. as such pharmaceutically nontoxic salts.

Then, the acid addition salt according to the present invention may be prepared by a common method, for example, by dissolving the compound of Chemical formula 1 or Chemical formula 2 in an excessive amount of acid aqueous solution and precipitating this salt by using a water-miscible organic solvent, for example, methanol, ethanol, acetone or acetonitrile. In addition, it may be prepared by drying after evaporating a solvent or excessive amount of acid in this mixture, or suction filtering the precipitated salt.

In addition, a pharmaceutically acceptable metal salt may be prepared by using a base. An alkali metal or alkali earth metal salt is obtained for example, by dissolving a compound in an excessive amount of alkali metal hydroxide or alkali earth metal hydroxide solution, and filtering a non-dissolved compound salt, and evaporating and drying a filtrate. Then, as the metal salt, it is pharmaceutically suitable to prepare a lithium, sodium, potassium or calcium salt. Moreover, a silver salt corresponding thereto may be obtained by reacting an alkali metal or alkali earth metal salt with an appropriate silver salt (for example, silver nitrate).

Furthermore, a pharmaceutically acceptable salt may be prepared by using an amino acid. As an amino acid salt, it is pharmaceutically suitable to prepare a natural amino acid, for example, glycine, alanine, phenylalanine, valine, lysine, glutamic acid, etc.

Hereinafter, a method for preparation of the novel compound represented by Chemical formula 1 or Chemical formula 2 according to the present invention will be described in detail.

The novel compound of the present invention may be prepared by any one of reaction formulas among the following Reaction formulas 1 to 21, but not limited thereto, and it may be prepared by a commonly used method for preparation in the art in addition to the following method for preparation.

Preparation Method 1

The novel compound represented by Chemical formula 1 according to the present invention may be prepared as shown in the following Reaction formula 1.

[Reaction formula 1]
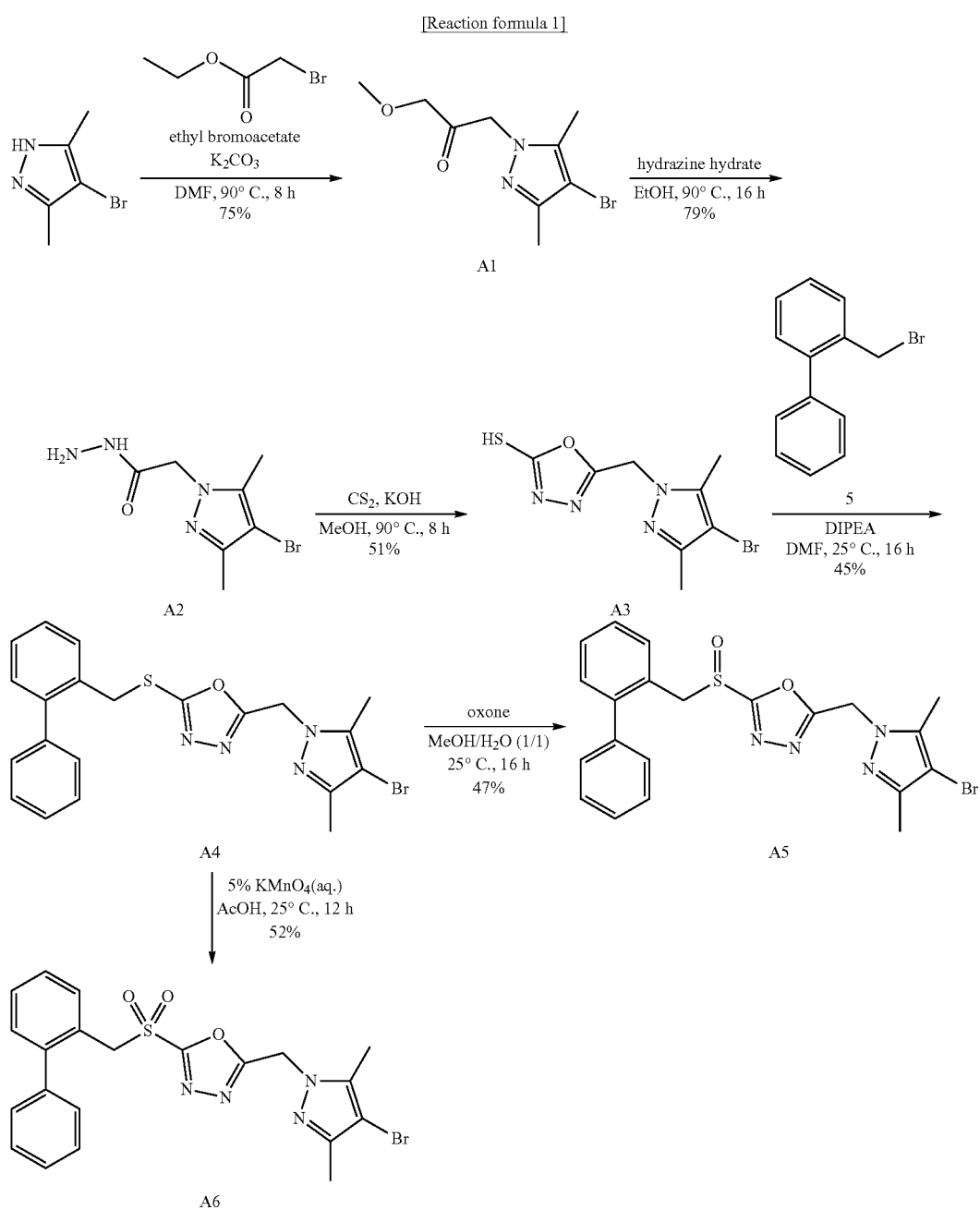
Preparation Method 2
The novel compound represented by Chemical formula 1 according to the present invention may be prepared as shown in the following Reaction formula 2.
[Reaction formula 2]
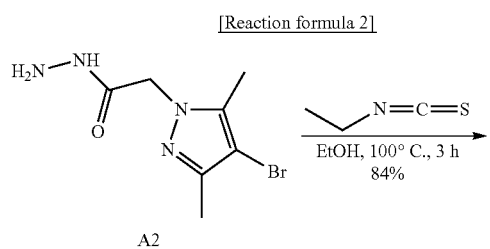
-continued
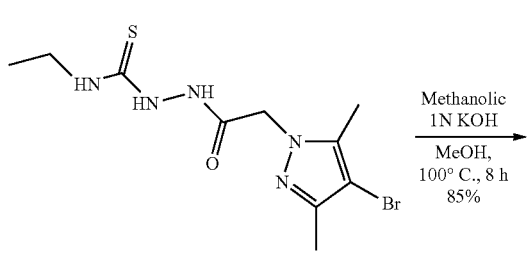

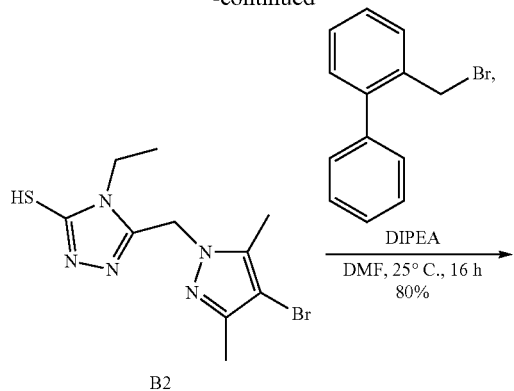
Preparation Method 3
The novel compound represented by Chemical formula 1 according to the present invention may be prepared as shown in the following Reaction formula 3.
[Reaction formula 3]

Preparation Method 4

The novel compound represented by Chemical formula 1 according to the present invention may be prepared as shown in the following Reaction formula 4.

[Reaction formula 4]

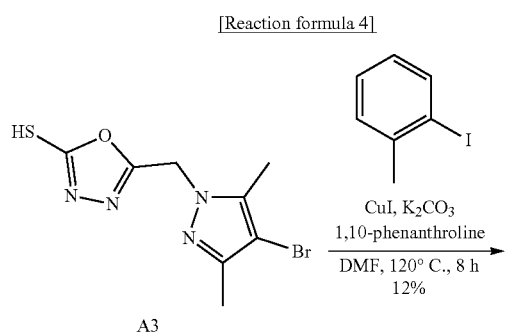

Preparation Method 5

The novel compound represented by Chemical formula 1 according to the present invention may be prepared as shown in the following Reaction formula 5.

[Reaction formula 5]

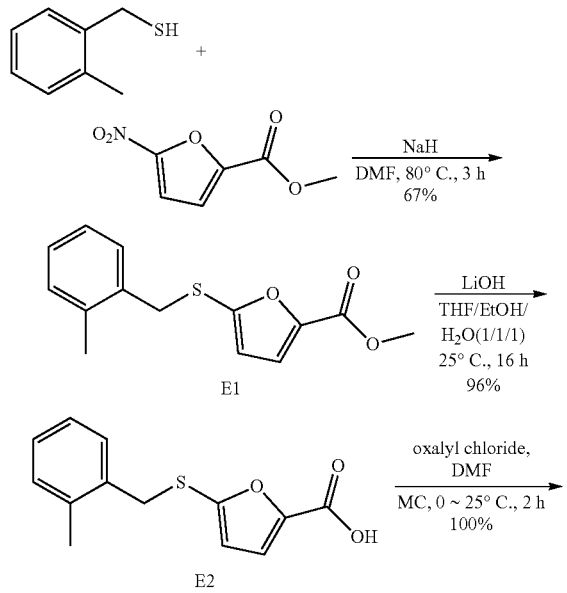

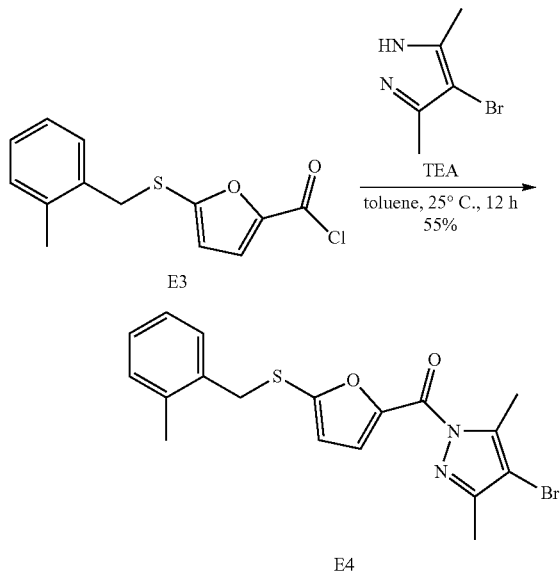

Preparation Method 6

The novel compound represented by Chemical formula 1 according to the present invention may be prepared as shown in the following Reaction formula 6.

[Reaction formula 6]

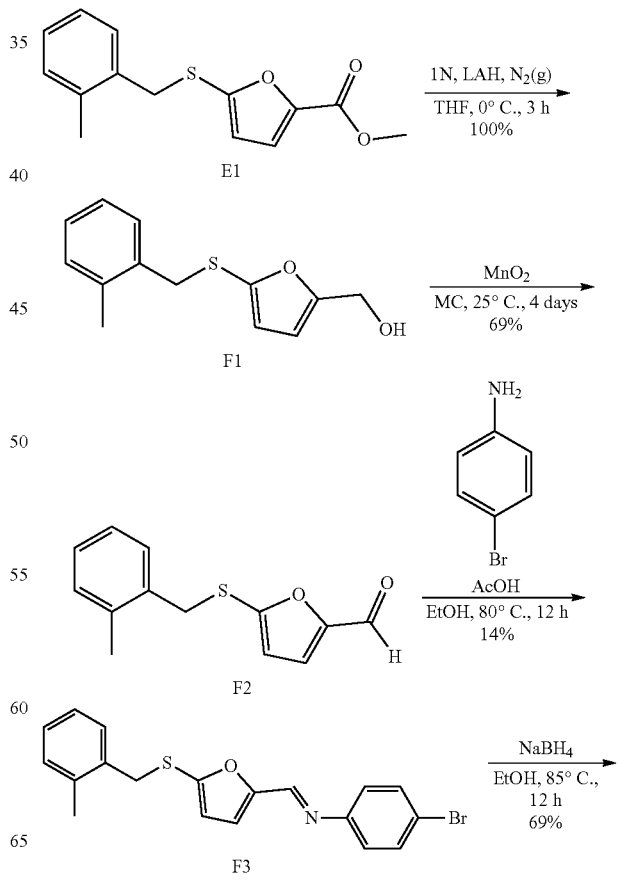

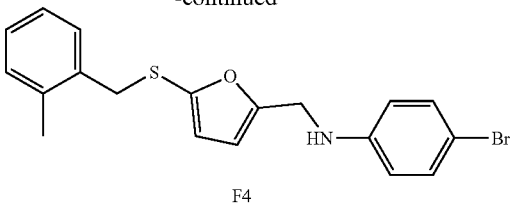

Preparation Method 7

The novel compound represented by Chemical formula 1 according to the present invention may be prepared as shown in the following Reaction formula 7.

[Reaction formula 8]

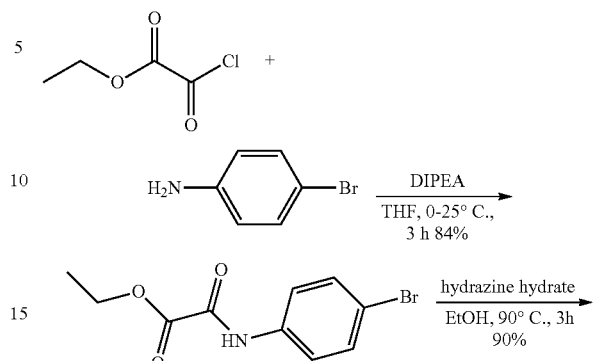

[Reaction formula 7]

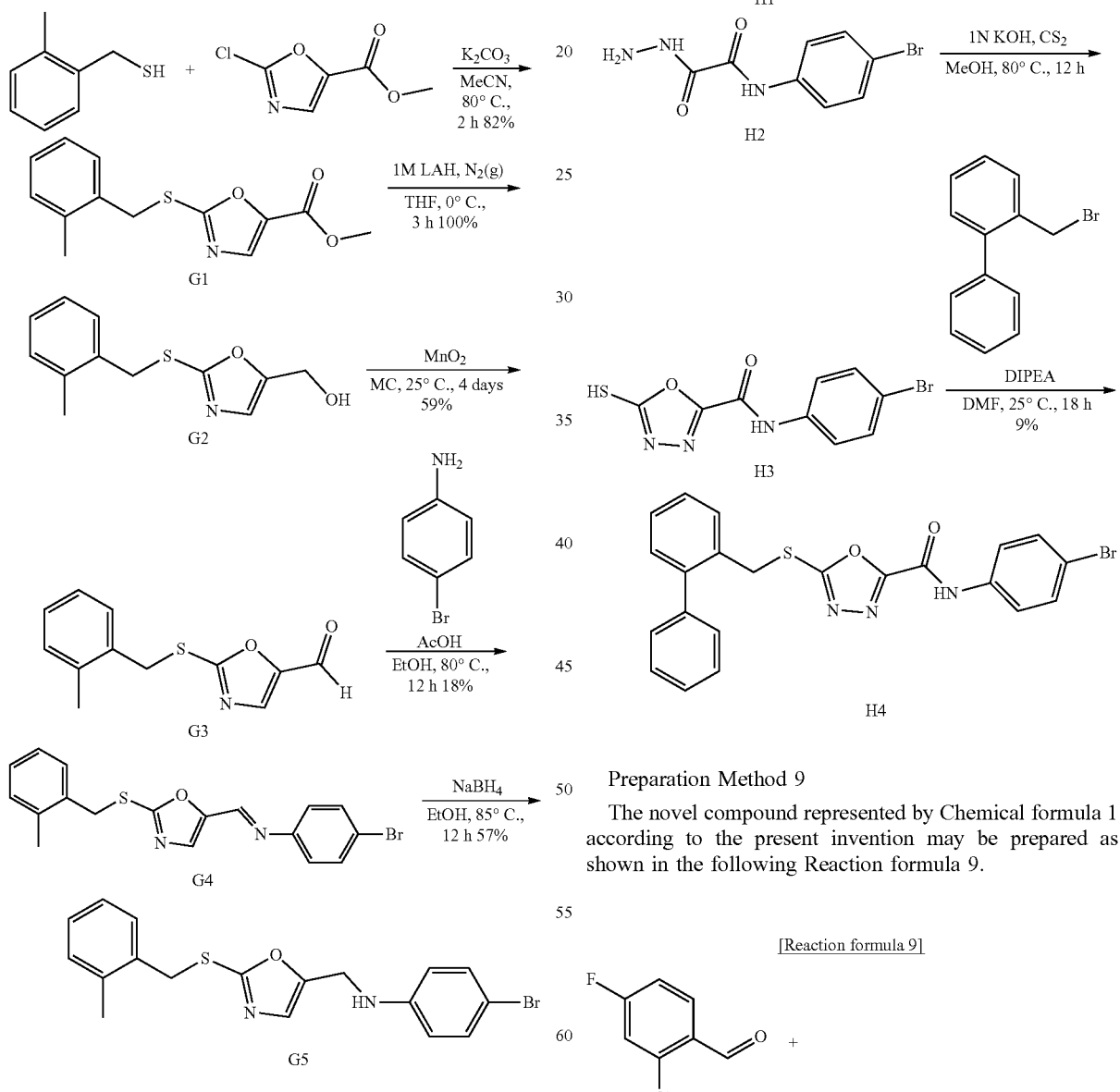

Preparation Method 9

The novel compound represented by Chemical formula 1 according to the present invention may be prepared as shown in the following Reaction formula 9.

[Reaction formula 9]

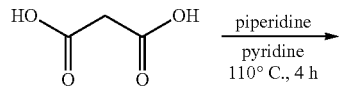

Preparation Method 8

The novel compound represented by Chemical formula 1 according to the present invention may be prepared as shown in the following Reaction formula 8.

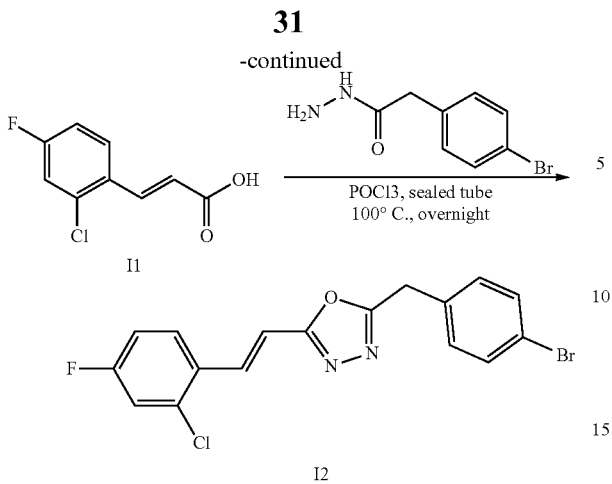

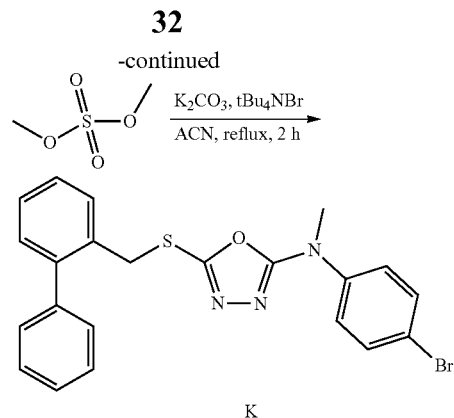

Preparation Method 10

The novel compound represented by Chemical formula 1 according to the present invention may be prepared as shown in the following Reaction formula 10.

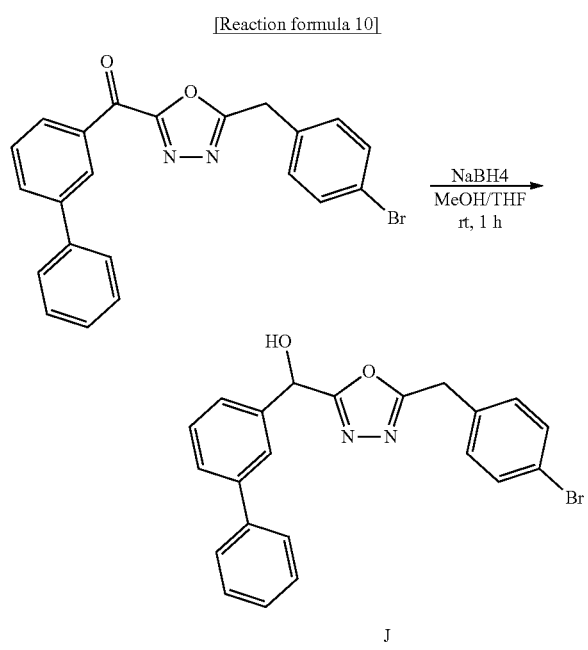

Preparation Method 11

The novel compound represented by Chemical formula 1 according to the present invention may be prepared as shown in the following Reaction formula 11.

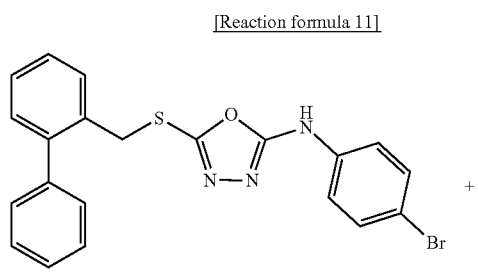

Preparation Method 12

The novel compound represented by Chemical formula 2 according to the present invention may be prepared as shown in the following Reaction formula 12.

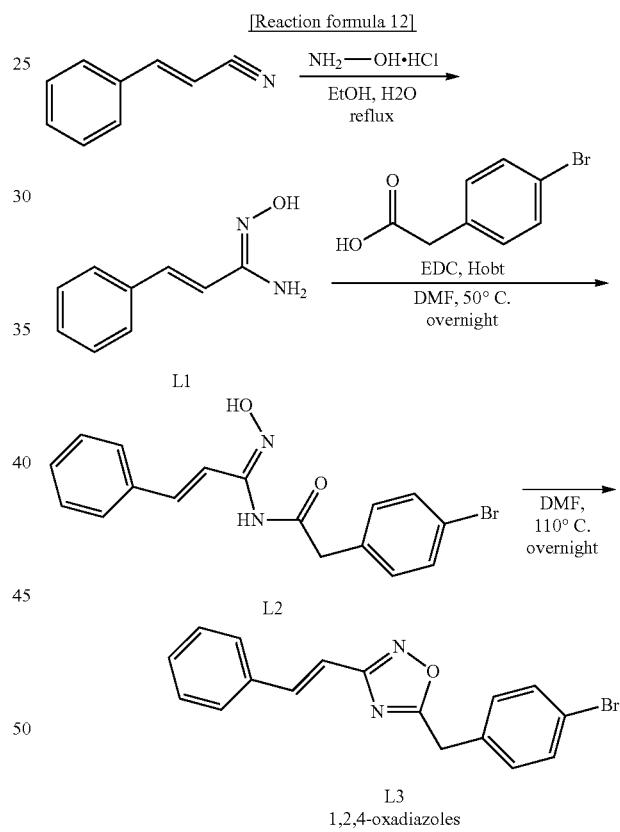

Preparation Method 13

In the present invention, a compound may be prepared as shown in the following Reaction formula 13.

[Reaction formula 13]

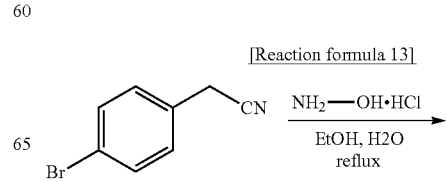

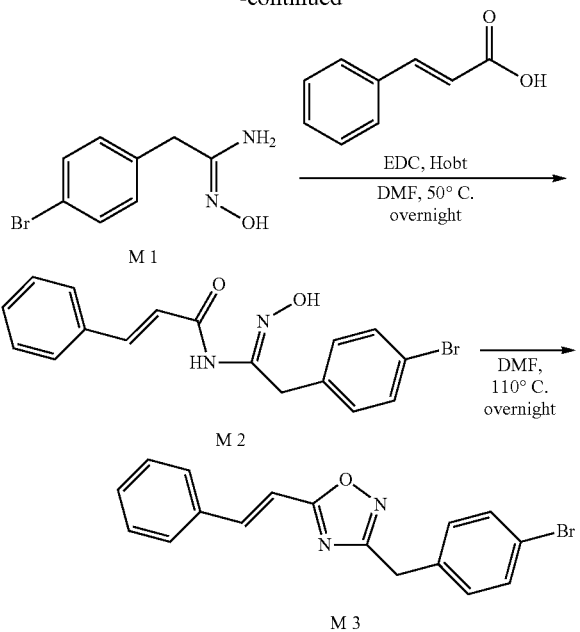

Preparation Method 14

In the present invention, a compound may be prepared as shown in the following Reaction formula 14.

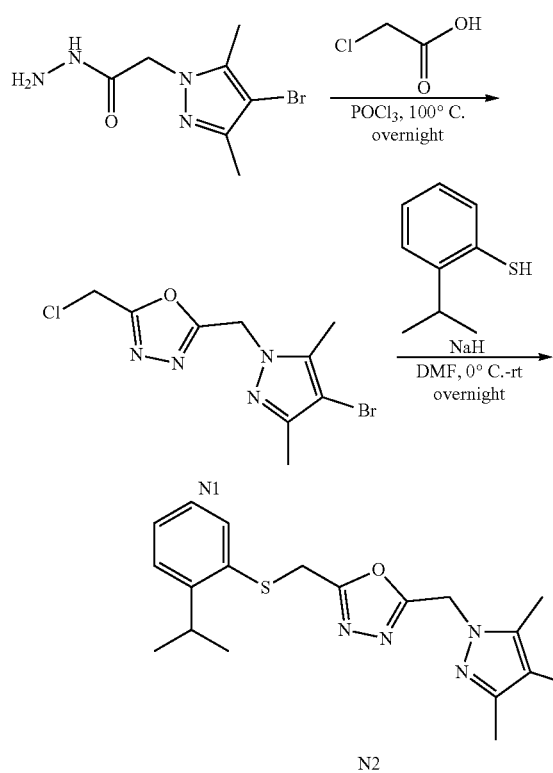

Preparation Method 15

In the present invention, a compound may be prepared as shown in the following Reaction formula 15.

[Reaction formula 15]

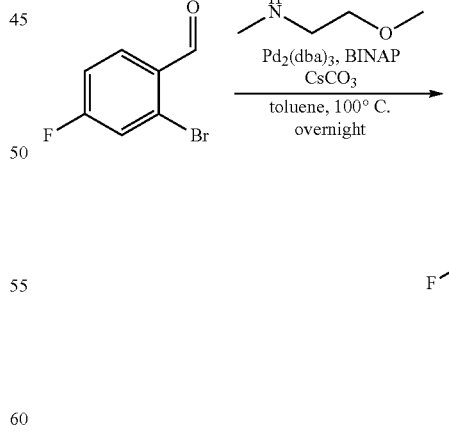

Preparation Method 16

In the present invention, a compound may be prepared as shown in the following Reaction formula 16.

[Reaction formula 16]

Preparation Method 17

In the present invention, a compound may be prepared as shown in the following Reaction formula 17.

[Reaction formula 17]

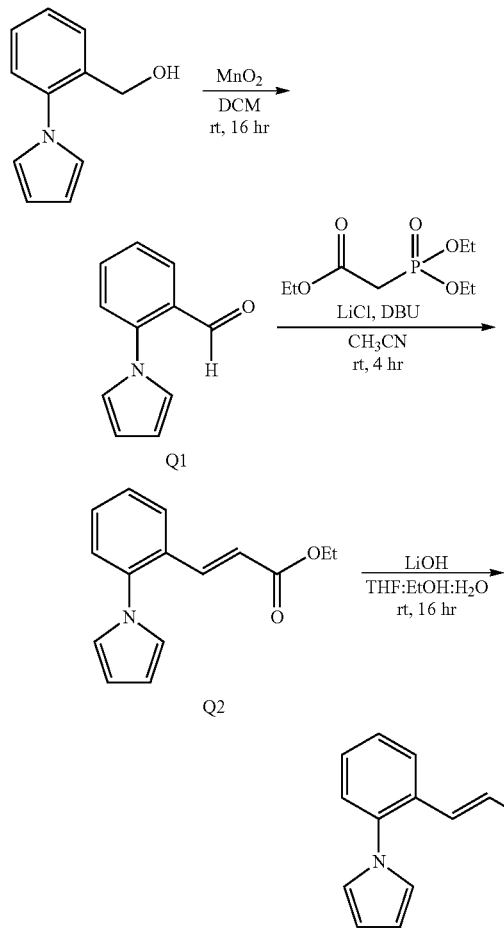

Preparation Method 18

In the present invention, a compound may be prepared as shown in the following Reaction formula 18.

[Reaction formula 18]

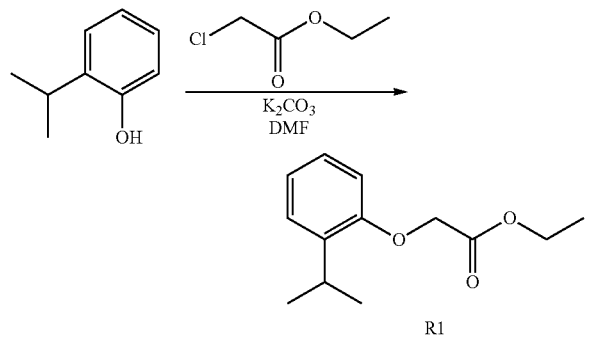

Preparation Method 19

In the present invention, a compound may be prepared as shown in the following Reaction formula 19.

[Reaction formula 19]

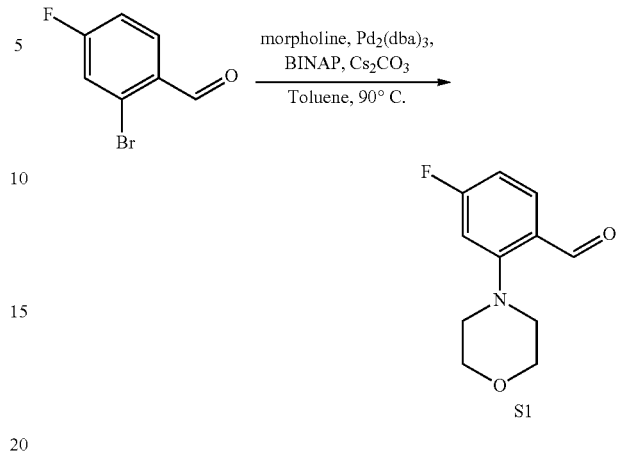

Preparation Method 20

In the present invention, a compound may be prepared as shown in the following Reaction formula 20.

[Reaction formula 20]

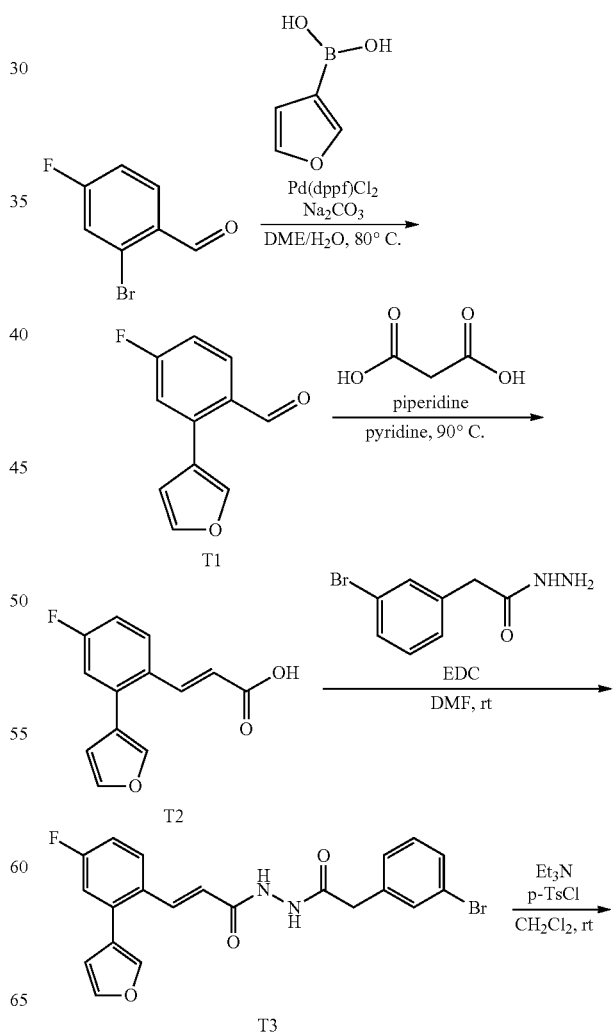

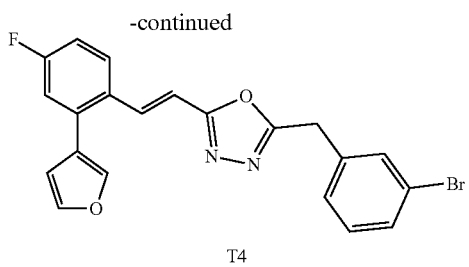

T4

Preparation Method 21

In the present invention, a compound may be prepared as shown in the following Reaction formula 21.

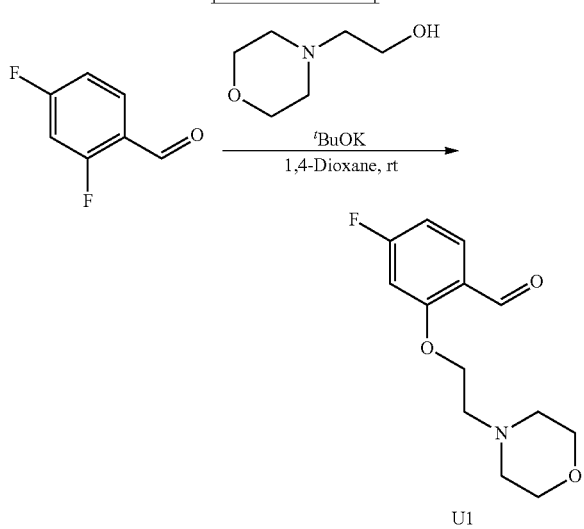

In addition, the present invention provides an antiviral pharmaceutical composition containing a compound represented by the following Chemical formula 1 or Chemical formula 2, an enantiomer, a diastereomer or a pharmaceutically acceptable salt thereof as an active ingredient:

[Chemical formula 1]

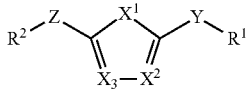

or

[Chemical formula 2]

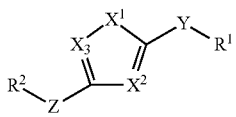

in the Chemical formula 1 or Chemical formula 2, $X^1$, $X^2$, $X^3$, Y, Z, $R^1$ and $R^2$ are as defined herein.

In the composition of the present invention, the virus may be an influenza virus, and preferably may be an A type influenza virus or a B type influenza virus. More preferably, the influenza virus may be A/California/07/2009 (H1N1), A/Perth/16/2009 (H3N2) or B/Florida/04/2006.

In the composition of the present invention, as diseases caused by infection of the virus, for example, there are diseases caused by influenza virus infection such as influenza, cold, sore throat, bronchitis, pneumonia, avian influenza, swine influenza, goat influenza, etc., but not limited thereto.

The antiviral activity against an A type influenza virus and a B type influenza virus for the novel compound represented by Chemical formula 1 or Chemical formula 2 according to the present invention was evaluated. As a result, it was confirmed that the compound represented by Chemical formula 1 or Chemical formula 2 according to the present invention had the excellent antiviral activity against influenza viruses, and at the same time, it was shown that the toxicity to cells was low.

The compound of the present invention may be administered as various oral or parenteral formulations, and when formulated, it may be prepared by using a commonly used diluent or excipient such as fillers, extenders, binding agents, wetting agents, disintegrating agents, surfactants, etc.

Solid formulations for oral administration include tablets, pills, powders, granules, capsules, troches, etc., and such solid formulations are prepared by mixing at least one or more of excipients, for example, starch, calcium carbonate, sucrose or lactose or gelatin, etc. to one or more of compounds of the present invention. In addition, lubricants such as magnesium stearate talc are used in addition to simple excipients. Suspension, liquid dosage forms, emulsions or syrups, etc., are applicable to liquid formulations for oral administration, and in addition to commonly used simple diluents, water, liquid paraffin, various excipients, for example, wetting agents, sweetening agents, air fresheners, preservatives, etc. may be included.

For formulations for parenteral administration, sterile aqueous solutions, non-aqueous solutions, suspension, emulsions, lyophilized formulations, suppositories, etc. are included. As the non-aqueous solutions and suspension, propylene glycol, polyethylene glycol, plant oil such as olive oil, injectable ester such as ethyl oleate, etc. may be used. As a base of suppositories, witepsol, macrogol, tween 61, cacao butter, laurin, glycerol, gelatin, etc. may be used.

In addition, the effective does of the compound represented by Chemical formula 1 or Chemical formula 2 according to the present invention to the human body may vary depending on patients' age, weight, gender, dosage form, health condition and disease severity, and generally, it is approximately 0.001-100 mg/kg/day, and preferably, it is 0.01-35 mg/kg/day. On the basis of an adult patient whose weight is 70 kg, it is generally 0.07-7000 mg/day, and preferably 0.7-2500 mg/day, and it may be administered once or several times a day at certain time intervals, depending on the judgement of a doctor or pharmacist.

Moreover, the present invention provides a health functional food composition for prevention or improvement of disease caused by virus infection containing the compound represented by Chemical formula 1 or Chemical formula 2 or a food acceptable salt thereof as an active ingredient.

Since the compound of Chemical formula 1 or Chemical formula 2 comprised in the health functional food composition of the present invention as an active ingredient and its antiviral activity are as previously described in the pharmaceutical composition, the description thereof is omitted.

The health functional food composition according to the present invention may be added to a health functional food such as food, beverage, etc. for a purpose of prevention or improvement of diseases caused by pathogenic bacteria.

There is no particular limitation on the kind of food. As an example of food to which the material can be added, there are drinks, meat, sausage, bread, biscuits, rice cake, chocolate, candies, snacks, crackers, pizza, ramen, other noodles, gums, dairy products including ice creams, various kinds of soups, beverages, alcohol beverages and vitamin complexes, milk products and milk processing products, etc., and it includes all health functional foods in the usual sense.

The health functional food composition containing the compound of Chemical formula 1 or Chemical formula 2 or a food acceptable salt according to the present invention as an active ingredient may be added to food as it is or may be used together with other food or food ingredients, and may be used appropriately according to conventional methods. The mixing amount of the active ingredient may be properly determined depending on its use purpose (for prevention or improvement). Generally, the amount of the composition in the health functional food may be 0.1 to 90 parts by weight of the total food weight. However, in case of long-term ingestion intended for health and hygiene purposes or health control purposes, the amount may be the above range or less, and since there is no problem in terms of safety, the active ingredient may be used in an amount of the above range or more.

The health functional food composition of the present invention is an essential component in the indicated ratio, and there is no particular limitation on other components except for containing the compound, and it may contain various flavors or natural carbohydrates such as ordinary beverages as an additional component. The examples of the aforementioned natural carbohydrates are common sugars such as monosaccharides, for example, glucose, fructose, etc.; disaccharides, for example, maltose, sucrose, etc.; and polysaccharides, for example, dextrin, cyclodextrin, etc., and sugar-alcohols such as xylitol, sorbitol, erythritol, etc. As other flavors in addition to the above, natural flavors (thaumatin, stevia extracts (for example, rebaudioside A, glycyrrhizin, etc.) and synthetic flavors (saccharin, aspartame, etc.) may be beneficially used. The ratio of the natural carbohydrates is generally about 1 to 20 g, preferably about 5 to 12 g, per 100 of the health functional food composition of the present invention.

In addition to the above, the health functional food composition containing the compound of Chemical formula 1 or Chemical formula 2 or the food acceptable salt thereof of the present invention as an active ingredient may contain various nutrients, vitamins, minerals (electrolytes), flavors such as synthetic flavors and natural flavors, etc., coloring agents and fillers (cheese, chocolate, etc.), pectic acid and its salts, alginic acid and its salts, organic acids, protective colloid thickeners, pH regulators, stabilizers, preservatives, glycerin, alcohols, carbonating agents used for carbonated drinks, etc. In addition to that, the health functional food composition of the present invention may contain flesh for preparation of natural fruit juices and fruit juice beverages and vegetable beverages.

Such components may be used independently or in combination. The ratio of such additives is not so important, but it is common to be selected in the range of 0.1 to about 20 parts by weight per 100 parts by weight of the health functional food composition containing the compound of Chemical formula 1 or Chemical formula 2 of the present invention or a pharmaceutically acceptable salt thereof as an active ingredient.

In addition, the present invention provides a composition for disinfecting or cleaning a virus containing the compound represented by Chemical formula 1 or Chemical formula 2 as an active ingredient.

Since the compound of Chemical formula 1 or Chemical formula 2 comprised in the composition for disinfecting or cleaning of the present invention as an active ingredient and its antiviral activity is also as previously described in the pharmaceutical composition, the description thereof is omitted.

The composition for disinfecting or cleaning according to the present invention may be used for uses of dishwashing detergents, laundry detergents, vegetable washing agents, handwash, etc., but not limited thereto.

The composition for disinfecting or cleaning according to the present invention may comprise one or more of surfactants. The surfactant may be an anionic, non-ionic, cationic, amphoteric or zwitter ionic type, or a mixture thereof.

The representative examples of the anionic surfactants include linear alkyl benzene sulfonate (LAS), alkyl sulfate (AS), alpha olefin sulfonate (AOS), alcohol ethoxy sulfate (AES) or alkali metal salts of natural fatty acids. The examples of the non-ionic surfactants include alkyl polyethylene glycol ether, nonylphenol polyethylene glycol ether, fatty acid ester of sucrose and glucose, or ester of polyethoxylated alkyl glucoside.

In addition, the composition of the present invention may further comprise other detergent components known in the art such as abrasives, bleaching agents, surface-active agents, anticorrosive agents, sequestering agents, stain-redeposition preventing agents, perfumes, stabilizers of enzymes and bleaching agents, formulation aids, optical brightening agents, bubble boosters, chelating agents, fillers, fabric softeners, and the like. The composition for disinfecting or cleaning of the present invention may be formulated in any convenient form of powder, liquid, etc.

Mode for Invention

Hereinafter, the present invention will be described in detail by examples, However, the following examples are intended to illustrate the present invention only, but the content of the present invention is not limited thereto.

Example 1

Construction of Phenotypic-Based Assay for Measuring the Influenza Infection Degree The present inventors constructed a phenotypic-based assay for measuring the influenza infection degree using an influenza virus expressing NS1A-GFP fusion protein (rA/Puerto Rico/8/34/NS1-GFP (H1N1)) (Manicassamy B, Manicassamy S, Belicha-Villanueva A, Pisanelli G, Pulendran B, Garcia-Sastre A. (2010) Analysis of in vivo dynamics of influenza virus infection in mice using a GFP reporter virus. Proc Natl Acad Sci USA 107(25):11531-11536).

MDCK cells were plated on a 384-well plate and were infected by an influenza virus expressing NS1-GFP fusion protein and were cultured at 37° C. for 24 hours. After 24 hours from the infection, images for NS1A-GFP (green) and cell nucleus (blue) were obtained by using a confocal microscope (ImageXpress®, Molecular Devices, Sunnyvale, Calif., USA), and the images were analyzed by an in-house development software. By measuring the number of GFP positive cells and negative cells, the infection rate of influenza virus and the cytotoxicity were calculated. For measurement and evaluation of the infection degree using the phenotypic-based assay, after culturing previously known inhibitors, Oseltamivir, T-705 and Nucleozin ((De Clercq E1. (2006) Antiviral agents active against an influenza A viruses. Nat Rev Drug Discov. 5(12):1015-25) with the NS1A-GFP virus at 37° C. for 24 hours respectively, the antiviral activity was evaluated. Through a drug efficacy evaluation by concentration (DRC; dose-response curve), $EC_{50}$ and $CC_{50}$ values of each inhibitor were calculated using Prism, version 5.0c software (GraphPad Software, Inc., La Jolla, Calif., USA).

Figure 1B:
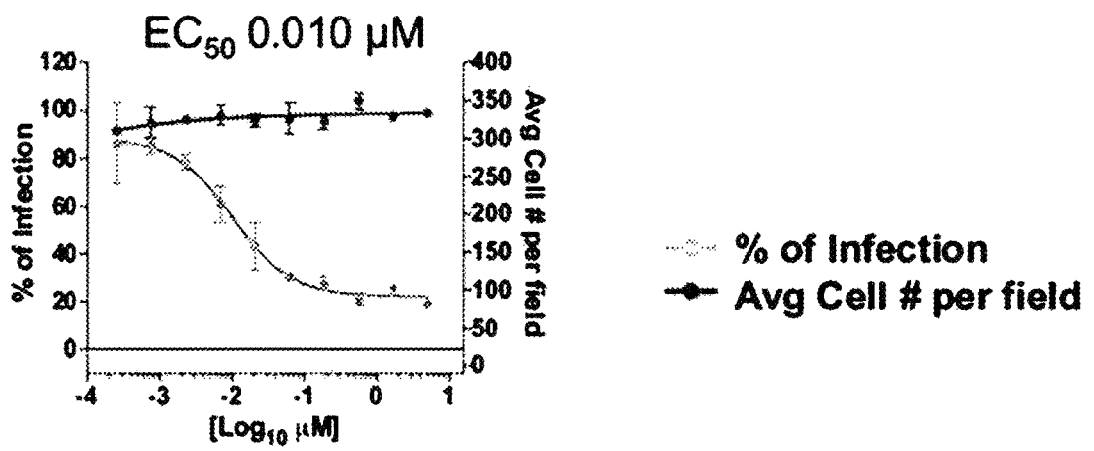
FIG. 1b shows the result of evaluating the antiviral activity of Oseltamivir, T-705 and Nucleozin using a phenotypic-based assay for measuring influenza infection.
Figure 1B:
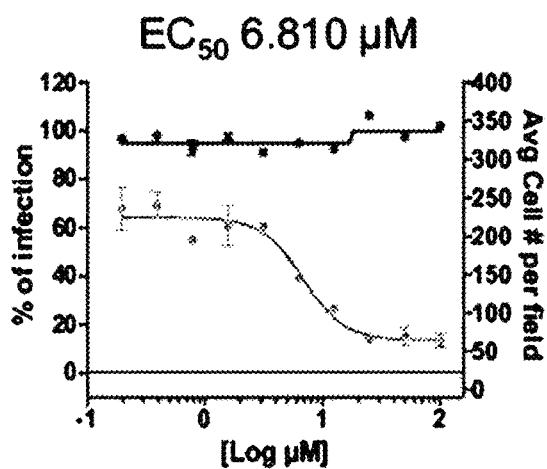
Figure 1B:
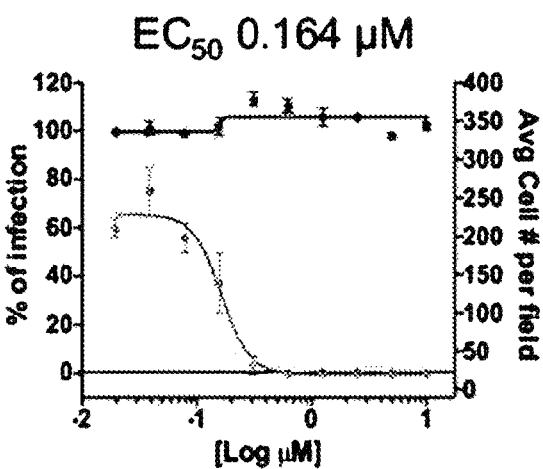

It was confirmed that the phenotypic-based assay for measurement of the influenza infection degree constructed in the present example was useful to evaluate the antiviral activity as shown in FIG. 1.

Example 2

Identification of a Novel Compound Scaffold Having Anti-Influenza Efficacy

The present inventors identified a new compound scaffold having anti-influenza efficacy by using the influenza virus expressing the NS1A-GFP fusion protein (rA/Puerto Rico/8/34/NS1-GFP (H1N1)) and the compound library in Institute Pasteur Korea consisting of approximately 110,000 compounds.

To test the antiviral activity of compounds, MDCK cells were plated to a 384-well plate, and after treating the compound diluted to the concentration of 10 uM and infecting the influenza virus expressing NS1-GFP fusion protein, they were cultured at 37° C. for 24 hours. In 24 hours after infection, by measuring the number of GFP positive cells and negative cells by using a confocal microscope ImageXpress®, Molecular Devices, Sunnyvale, Calif., USA), the influenza virus infection rate and the cytotoxicity were calculated. The obtained images were analyzed by an in-house development software. The influenza virus infection inhibition rate was calculated by using $EC_{100}$ of 1% DMSO-treated cell and previously known influenza infection inhibitor, Nucleozin-treated cell, and they were set as 0% and 100% inhibition rates, respectively. The antiviral activity of the compound was evaluated by DRC (dose-response curve) analysis, and $EC_{50}$ and $CC_{50}$ values were calculated by using Prism, version 5.0c software (GraphPad Software, Inc., La Jolla, Calif., USA).

As hits, compounds showing >90% HCV infection inhibition and >70% cell viability were selected and the antiviral effect of these compounds were reconfirmed through 10-point drug efficacy analysis by concentration. To evaluate the possibility as a universal influenza virus inhibitor, the drug efficacy evaluation by concentration for three kinds of seasonal influenza viruses (A/Perth/16/09(H3N2), A/California/7/09(H1N1), B/Florida/4/06) was conducted. In addition, to select compounds having a drug mechanism different from the currently most widely used anti-influenza drug, neuraminidase inhibitor, a neuraminidase assay was performed. Through the above process, a thio oxadiazole (THO) scaffold was selected.

Example 3

Preparation Method of the Compound Represented by Chemical Formula 1 of the Present Invention Using Reaction Formula 1

The present inventors synthesized a compound comprising the THO scaffold selected in Example 2 and its various derivatives, and the following Reaction formula 1 was used.

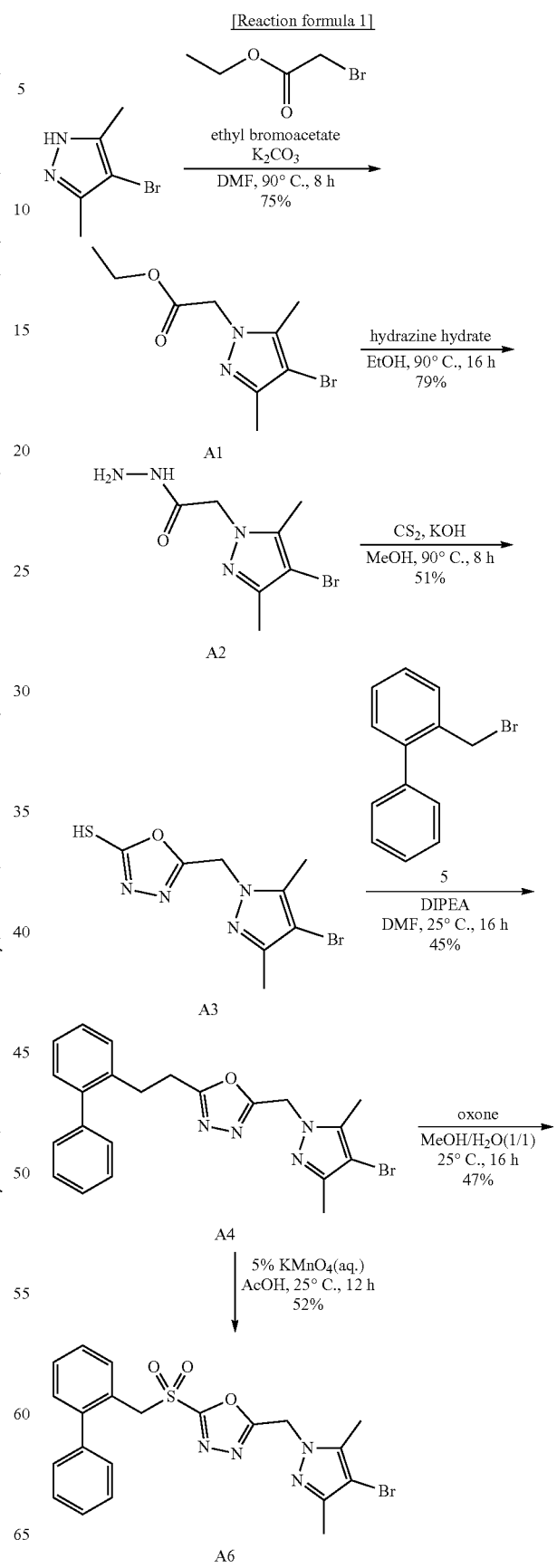

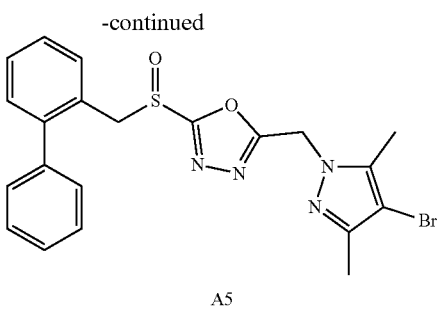

A5

General Method of A1 Synthesis

4-Bromo-3,5-dimethyl-1H-pyrazole (1 g, 5.71 mmol) and $K_2CO_3$ (1.58 g, 11.43 mmol) were dissolved in anhydrous DMF (8 mL). Ethyl bromoacetate (1.25 mL, 11.43 mmol) was added to the reaction mixture and was stirred at 90° C. for 8 hours. The reaction mixture was cooled to a room temperature and then was poured to water and was extracted with EtOAc, and was washed with water and was dried with $MgSO_4$. The reaction mixture was concentrated to form a crude solid. By washing it with hexane, a preferable product A1 of a brown solid was prepared.

General Method of A2 Synthesis

The substance A1 (747 mg, 2.86 mmol) was dissolved in anhydrous EtOH (10 mL). Hydrazine monohydrate (0.90 mL, 28.61 mmol) was added to the reaction mixture and was stirred at 90° C. for 16 hours. The reaction mixture was dried in vacuo, and by filtering solid formed thereby, a preferable product A2 of a white solid was prepared.

General Method of A3 Synthesis

The substance A2 (500 mg, 2.02 mmol) and 1N KOH (2.02 mL, 2.02 mmol) were dissolved in MeOH (6 mL). $CS_2$ (0.30 mL, 5.06 mmol) was added to the reaction mixture and was stirred at 90° C. for 8 hours. The reaction mixture was concentrated, and then water was poured to it, and it was adjusted by pH 6 using 1N HCl(aq.). The formed solid was filtered and washed, and then was dried at 60° C. in an oven, and thereby a preferable product A3 of a beige solid was prepared.

General Method of A4 Synthesis

The substance A3 (35 mg, 0.12 mmol), DIPEA (0.021 mL, 0.12 mmol) and 2-(bromomethyl)-1,1'-biphenyl (33 mg, 0.13 mmol) were dissolved in anhydrous DMF (1 mL). The reaction mixture was stirred at 25° C. for 16 hours and then was diluted in EtOAc and was washed with $NH_4Cl$(aq.) solution and water. The organic layer was dried with anhydrous $MgSO_4$, and then was evaporated in vacuo. A preferable product A4 of colorless oil was obtained by column chromatography (EtOAc/Hexane, 1:1).

General Method of A5 Synthesis

The substance A4 (119 mg, 0.26 mmol) dissolved in MeOH (15 mL) was suspended in the mixture of oxon (803 mg, 1.31 mmol) and water (15 mL). The reaction mixture was stirred at 25° C. for about 16 hours. After completion of the reaction, the solvent was dried in vacuo. The reaction mixture was extracted with EtOAc and was washed with water. The organic layer was dried with anhydrous $MgSO_4$, and then was evaporated in vacuo. A preferable product A5 of a white solid was obtained by column chromatography (EtOAc/Hexane, 1:3).

General Method of A6 Synthesis

The solution of the substance A4 (41 mg, 0.09 mmol) dissolved in AcOH (2 mL) was suspended in 5% $KMnO_4$ (19 mg, 0.12 mmol) dissolved in $H_2O$ (0.4 mL). The reaction mixture was stirred at 25° C. for about 12 hours. After completion of the reaction, the sodium hydrogen sulfite aqueous solution of 40% concentration (strength) was added until the mixture was colored, and then $H_2O$ was added. The reaction mixture was extracted with EtOAc and was washed with water. The organic layer was dried with anhydrous $MgSO_4$, and then was evaporated in vacuo. A preferable product A6 of a white solid was obtained by column (EtOAc/Hexane, 1:3).

Example 4

Preparation Method of the Compound Represented by Chemical Formula 1 of the Present Invention Using Reaction Formula 2

[Reaction formula 2]

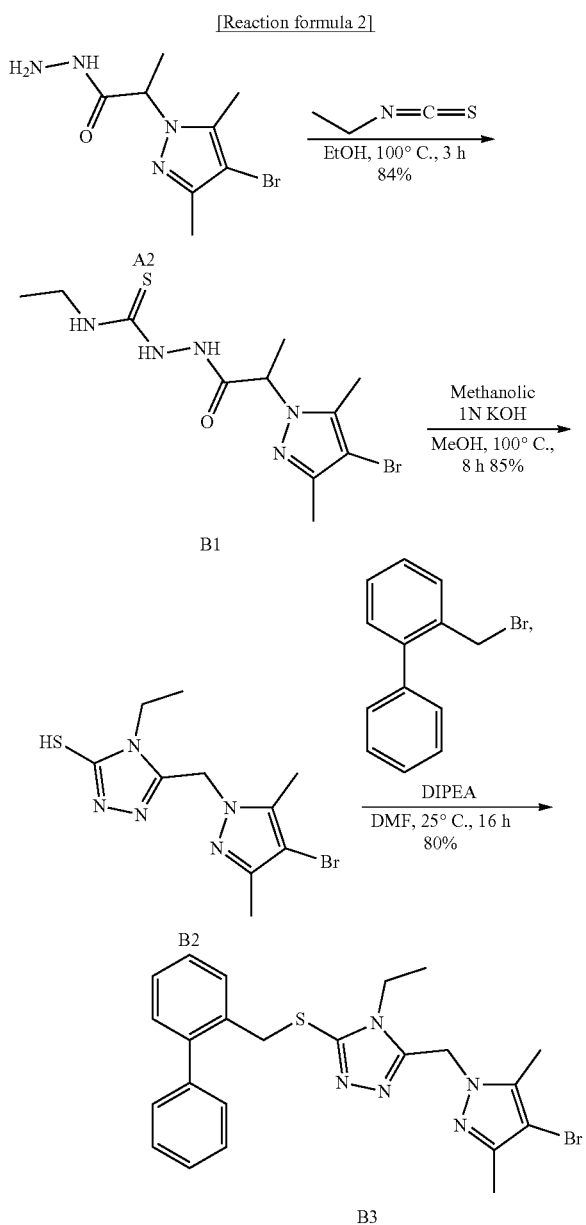

General Method of B1 Synthesis

The substance A2 (200 mg, 0.81 mmol) was dissolved in aqueous EtOH (4 mL). Isothiocyanatoethane (0.071 mL, 0.81 mmol) was added to the reaction mixture and was stirred at 100° C. for about 3 hours. The reaction mixture was cooled by 0° C. and then by filtering the formed solid and washing it with EtOH, a preferable product B1 of a white solid was prepared.

General Method of B2 Synthesis

To the solution of the substance B1 (228 mg, 0.68 mmol) dissolved in MeOH (3 mL), methanolic 1N KOH (2.73 mL, 1.00 mmol) was added, and it was stirred at 100° C. for 8 hours. The reaction mixture was cooled by 0° C. and it was adjusted by pH 2 using 1N HCl(aq.). By filtering the formed solid and washing it with water, and then drying it at 60° C. in an oven, a preferable product of a white solid was prepared.

General Method of B3 Synthesis

The substance B2 (50 mg, 0.16 mmol), DIPEA (0.028 mL, 0.16 mmol) and 2-(bromomethyl)-1,1'-biphenyl (32 mg, 0.17 mmol) were dissolved in anhydrous DMF (2 mL). The reaction mixture was stirred at 25° C. for 16 hours and was diluted in EtOAc, and then it was washed with NH$_4$Cl (aq.) solution and water. The organic layer was dried with anhydrous MgSO$_4$ and then was evaporated in vacuo. A preferable product B3 of a white solid was obtained by column chromatography.

Example 5

Preparation Method of the Compound Represented by Chemical Formula 1 of the Present Invention Using Reaction Formula 3

[Reaction formula 3]

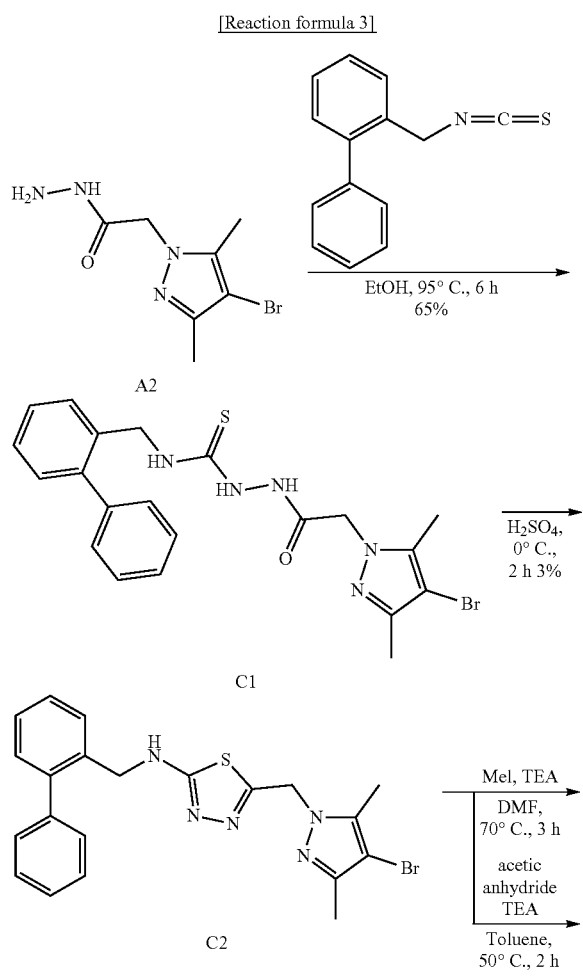

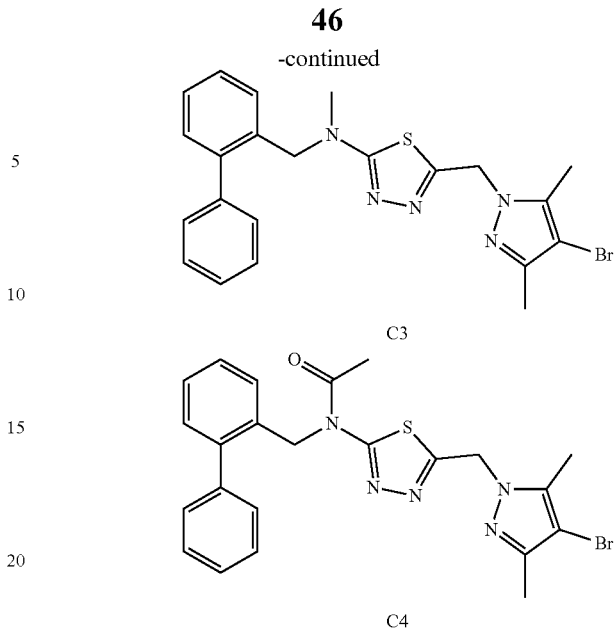

General Method of C1 Synthesis

The substance A2 (405 mg, 1.55 mmol) was dissolved in anhydrous EtOH (6 mL). 2-(Isothiocyanatomethyl)-1,1'-biphenyl (349 mg, 1.55 mmol) was added to the reaction mixture and was stirred at 95° C. for 6 hours. The reaction mixture was cooled by 0° C. and then the formed solid was filtered and washed with EtOH and thereby a preferable product C1 of a white solid was prepared.

General Method of C2 Synthesis

The substance C1 (200 mg, 0.40 mmol) was dissolved in H$_2$SO$_4$ (2 mL) of 0° C., and it was stirred at the same temperature for 2 hours. After pouring ice water to the reaction mixture, the formed solid was filtered and washed with water. The solid formed finally was dissolved in MC and the organic layer was dried with anhydrous MgSO$_4$ and then was evaporated in vacuum. A preferable product C2 of a white solid was obtained by column chromatography (EtOAc/Hexane, 1:1).

General Method of C3 Synthesis

The substance C2 (21 mg, 0.05 mmol), TEA (0.010 mL, 0.07 mmol) and iodomethane (0.006 mL, 0.10 mmol) were dissolved in anhydrous DMF (1 mL). The reaction mixture was stirred at 70° C. for 3 hours and then was diluted in EtOAc, and was washed with NaHCO$_3$(aq.) solution and water. The organic layer was dried with anhydrous MgSO$_4$ and then was evaporated in vacuo. A preferable product C3 of yellow oil was obtained by column chromatography (EtOAc/Hexane, 1:1).

General Method of C4 Synthesis

To the solution of TEA (0.010 mL, 0.07 mmol) and the substance C2 (21 mg, 0.05 mmol) dissolved in toluene (2 mL), anhydrous acetic acid (0.014 mL, 0.14 mmol) was added and it was stirred at 50° C. for 2 hours. The reaction mixture was diluted in EtOAc and was washed with NaHCO$_3$(aq.) and water. The organic layer was dried with anhydrous MgSO$_4$ and then was evaporated in vacuo. A preferable product C4 of yellow oil was obtained by column chromatography (EtOAc/Hexane, 1:1).

Example 6

Preparation Method of the Compound Represented by Chemical Formula 1 of the Present Invention Using Reaction Formula 4

[Reaction formula 4]

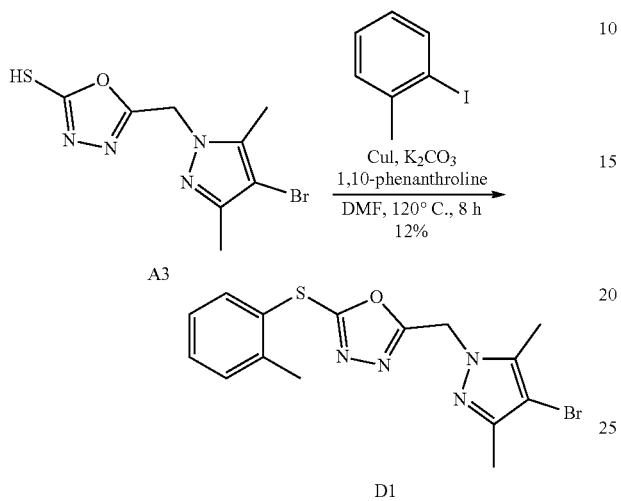

General Method of D1 Synthesis

The substance A3 (50 mg, 0.19 mmol) was added to 1-iodo-2-methylbenzene (0.029 mL, 0.22 mmol), 1,10-phenanthroline (44 mg, 0.24 mmol), CuI (2 mg, 0.01 mmol) and $K_2CO_3$ (33 mg, 0.24 mmol) dissolved in anhydrous DMF (1 mL), and then it was stirred at 120° C. for 8 hours. After completion of the reaction, the reaction mixture was extracted with EtOAc, and was washed with water. The organic layer was dried with anhydrous $MgSO_4$ and then was evaporated in vacuo. A preferable product D1 of a yellow solid was obtained by column chromatography (EtOAc/Hexane, 1:5).

Example 7

Preparation Method of the Compound Represented by Chemical Formula 1 of the Present Invention Using Reaction Formula 5

[Reaction formula 5]

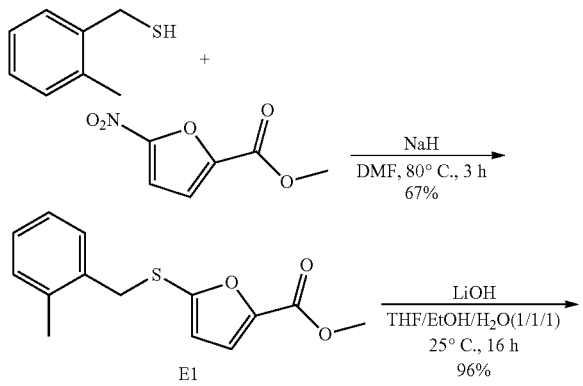

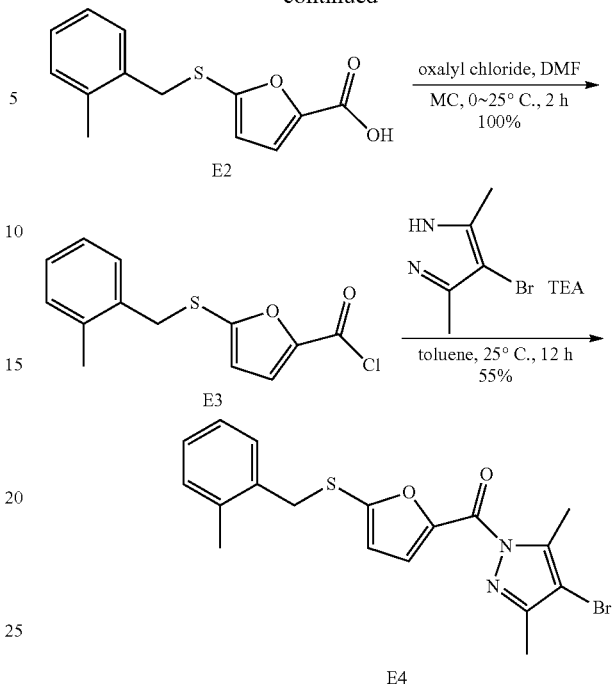

General Method of E1 Synthesis

60% NaH (31 mg, 0.78 mmol) dissolved in oil was added to o-tolylmethanethiol (54 mg, 0.39 mmol) solution dissolved in anhydrous DMF (2 mL) at 0° C. and then the solution was left at a room temperature. Methyl 5-nitro-furan-2-carboxylate (67 mg, 0.39 mmol) was added to the reaction mixture and it was stirred at 70° C. for 3 hours. The mixture formed finally was cooled to a room temperature and was cooled down with water, and then was extracted with EtOAc and was washed with $NaHCO_3$(aq.) solution. The organic layer was dried with anhydrous $MgSO_4$ and then was evaporated in vacuo. A preferable product E1 of colorless oil was obtained by column chromatography (EtOAc/Hexane, 1:10).

General Method of E2 Synthesis

To the solution of the substance E1 (69 mg, 0.26 mmol) dissolved in $THF/EtOH/H_2O(1:1:1, v/v)$ (2 mL), LiOH (12 mg, 0.29 mmol) was added, and it was stirred at 25° C. for 16 hours. After completion of the reaction, the solvent was evaporated. The reaction mixture was diluted in EtOAc and water and then the solution was acidified with 1N HCl(aq.). The solution was extracted with EtOAc and was washed with water. The organic layer was dried with anhydrous $MgSO_4$ and then was evaporated in vacuo, and thereby a preferable product E2 of a white solid was prepared.

General Method of E3 Synthesis

The substance E2 (62 mg, 0.20 mmol) was dissolved in anhydrous MC (4 mL). Oxalyl chloride (0.026 mL, 0.24 mmol) and DMF 1 drop were added to the reaction mixture at 0° C. The mixture formed finally was stirred at 25° C. for 2 hours and then the solvent was evaporated in vacuo, and thereby a preferable product E3 of yellow oil was prepared.

General Method of E4 Synthesis

To the solution of the substance E3 (96 mg, 0.36 mmol) dissolved in toluene (2 mL), TEA (0.10 mL, 0.72 mmol) and 4-bromo-3,5-dimethyl-1H-pyrazole (63 mg, 0.36 mmol) were added. The reaction mixture was stirred at 25° C. for 12 hours. After completion of the reaction, the solvent was evaporated in vacuo. The reaction mixture was diluted in EtOAc and water, and then the solution was extracted with EtOAc. The organic layer was washed with water and was dried with anhydrous MgSO$_4$ and then was evaporated in vacuo. By washing the solid formed thereby with MC, a preferable product E4 of a yellow solid was prepared.

Example 8

Preparation Method of the Compound Represented by Chemical Formula 1 of the Present Invention Using Reaction Formula 6

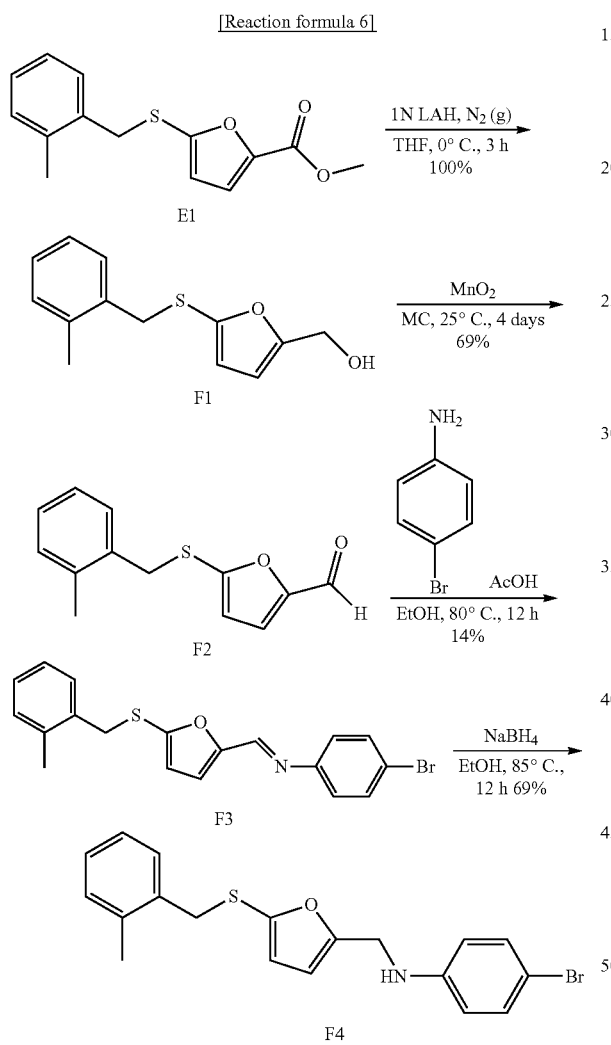

General Method of F1 Synthesis

Under the N$_2$ (g) condition, at 0° C., 1N LiAlH$_4$ (0.66 mL, 0.66 mmol) was added to the solution of the substance E1 (157 mg, 0.60 mmol) dissolved in anhydrous THF (10 mL) and it was stirred at the same temperature for 3 hours. After completion of the reaction, the reacted product was cooled down by adding ice water of 0° C. The reaction mixture was extracted with EtOAc and was evaporated in vacuo. A preferable product F2 of colorless oil was obtained by column chromatography (EtOAc/Hexane, 1:5).

General Method of F2 Synthesis

To the solution of the substance F1 (122 mg, 0.52 mmol) dissolved in anhydrous MC (10 mL), MnO$_2$ (455 mg, 5.23 mmol) was added, and under the N$_2$ (g) condition, it was stirred at 25° C. for 4 days. After completion of the reaction, the residues were filtered through a celite pad and was evaporated in vacuo, and thereby F2 of yellow oil was prepared.

General Method of F3 Synthesis

The substance F2 (84 mg, 0.36 mmol) dissolved in anhydrous EtOH (1 mL) was added to AcOH (0.3 mL) and 4-bromoaniline (62 mg, 0.36 mmol) dissolved in EtOH (2 mL). The reaction mixture was stirred at 80° C. for 12 hours. After completion of the reaction, by evaporating EtOH in vacuo, F3 of orange oil was prepared.

General Method of F4 Synthesis

Under the N$_2$ (g) condition, at 25° C., NaBH$_4$ (4 mg, 0.11 mmol) was added to the solution of the substance F3 (30 mg, 0.08 mmol) dissolved in anhydrous EtOH (1 mL) and it was stirred at 85° C. for 12 hours. After completion of the reaction, the reacted product was cooled down with water of 0° C. The reaction mixture was extracted with EtOAc, and was evaporated in vacuo. A preferable product F4 of yellow oil was obtained by column chromatography (EtOAc/Hexane, 1:6).

Example 9

Preparation Method of the Compound Represented by Chemical Formula 1 of the Present Invention Using Reaction Formula 7

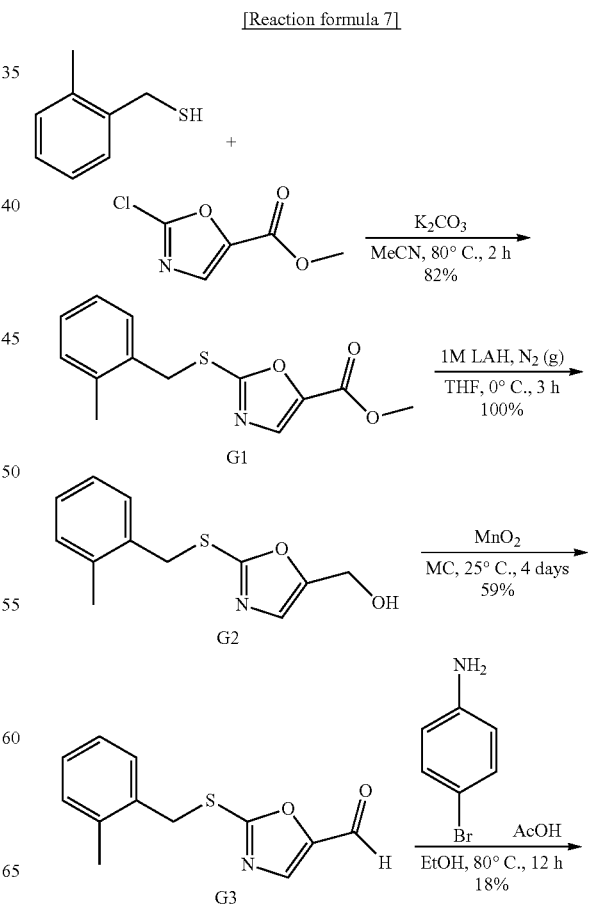

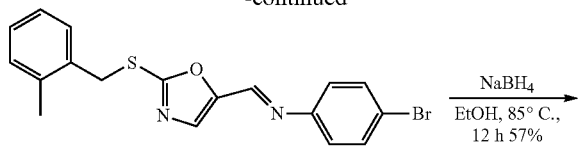

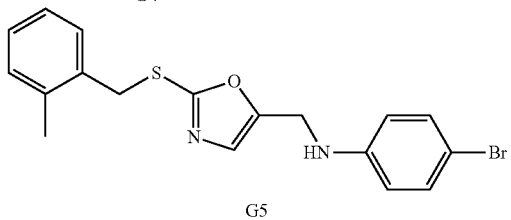

General Method of G1 Synthesis

To the solution of o-tolylmethanethiol (128 mg, 0.93 mmol) dissolved in anhydrous MeCN (4 mL), $K_2CO_3$ (214 mg, 1.55 mmol) and methyl 2-chlorooxazole-5-carboxylate (100 mg, 0.62 mmol) were added, and the mixture formed finally was stirred at 80° C. for 2 hours. The mixture was cooled to the room temperature and was extracted with EtOAc and then it was washed with $NaHCO_3$(aq.). The organic layer was dried with anhydrous $MgSO_4$ and then was evaporated in vacuo. A preferable product G1 of colorless oil was obtained by column chromatography (EtOAc/Hexane, 1:10).

General Method of G2 Synthesis

Under the $N_2$ (g) condition, at 0° C., $LiAlH_4$ (0.56 mL, 0.56 mmol) was added to the solution of the substance G1 (135 mg, 0.51 mmol) dissolved in anhydrous THF (10 mL), and the mixture was stirred for 3 hours. After completion of the reaction, the reacted product was cooled down with cool water. The reaction mixture was extracted with EtOAc and the organic layer was evaporated. A preferable product G2 of colorless oil was obtained by column chromatography (EtOAc/Hexane, 1:5).

General Method of G3 Synthesis

To the solution of the substance G2 (124 mg, 0.53 mmol) dissolved in anhydrous MC (10 mL), $MnO_2$ (458 mg, 5.27 mmol) was added, and under the $N_2$ (g) condition, it was stirred at 25° C. for 4 days. After completion of the reaction, the reaction residues were filtered through a celite pad and was evaporated in vacuo, and thereby G2 of yellow oil was prepared.

General Method of G4 Synthesis

The substance G3 (73 mg, 0.31 mmol) dissolved in anhydrous EtOH (1 mL) was added to AcOH (0.2 mL) and 4-bromoaniline (54 mg, 0.31 mmol) dissolved in EtOH (2 mL). The reaction mixture was stirred at 80° C. for 12 hours. After completion of the reaction, by evaporating EtOH in vacuo, G4 of yellow oil was prepared.

General Method of G5 Synthesis

To the solution of the substance G4 (22 mg, 0.06 mmol) dissolved in anhydrous EtOH (1 mL), $NaBH_4$ (3 mg, 0.09 mmol) was added, and the mixture was stirred at 85° C. for 12 hours. After completion of the reaction, the reacted product was cooled down with cool water. The reaction mixture was extracted with EtOAc and was evaporated in vacuo. A preferable product G5 of yellow oil was obtained by column chromatography (EtOAc/Hexane, 1:4).

Example 10

Preparation Method of the Compound Represented by Chemical Formula 1 of the Present Invention Using Reaction Formula 8

[Reaction formula 8]

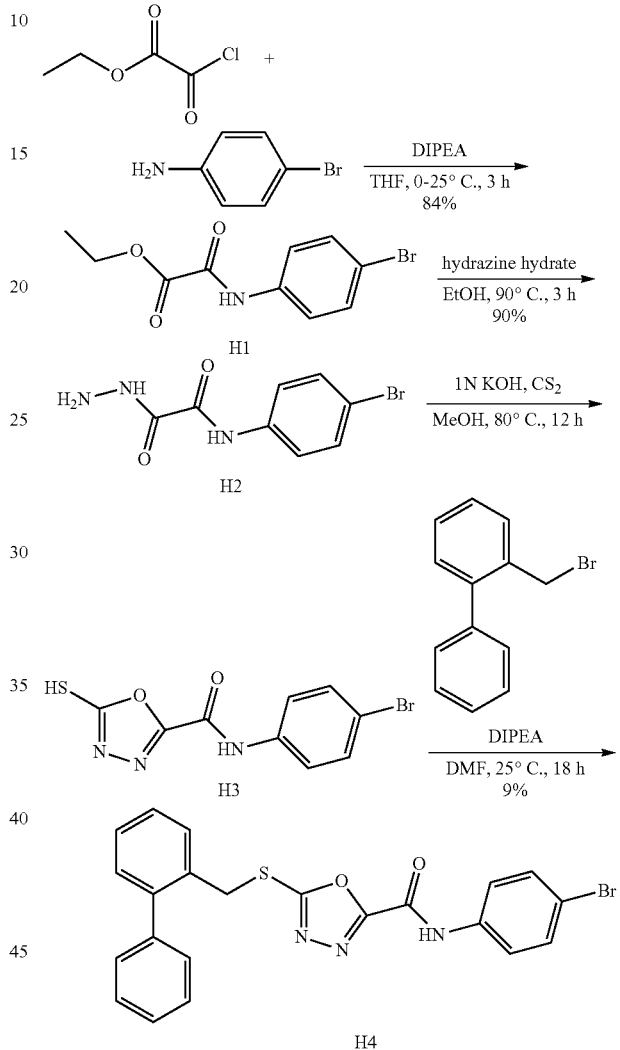

General Method of H1 Synthesis

To the solution of 4-bromo-aniline (1 g, 5.71 mmol) dissolved in THF (15 mL), DIPEA (1.58 g, 11.43 mmol) was added, and the mixture was stirred for 40 min. Then, the mixture was cooled and ethyl chloroformate (1 g, 5.71 mmol) was added to the reaction mixture in an ice-bath. In 3 hours, the reaction mixture was extracted with EtOAc and was washed with $NaHCO_3$(aq.) and water. The organic layer was dried with $MgSO_4$ and was evaporated in vacuo. A preferable product H1 of colorless oil was obtained by column chromatography (EtOAc/Hexane, 1:10).

General Method of H2 Synthesis

Hydrazine monohydrate (0.404 mL, 12.86 mmol) was added to the stirred solution of H1 (350 mg, 1.29 mmol) dissolved in anhydrous EtOH (10 mL), and it was stirred at 90° C. for 3 hours. The reaction mixture was evaporated in vacuo and the formed solid was filtered and dried, and thereby a preferable product H2 of a white solid was prepared.

General Method of H3 Synthesis

To the mixture of 1N KOH (1.17 mL, 1.00 mmol) and H2 (302 mg, 1.17 mmol) dissolved in MeOH (6 mL), $CS_2$ (0.16 mL, 2.69 mmol) was added, and the mixture formed finally was stirred at 80° C. for 12 hours. After completion of the reaction, the mixture was concentrated and was poured to water, and then it was adjusted by pH 6 using 1N HCl(aq.). By filtering the formed solid and washing it with water and then drying, a preferable product H3 of an ivory solid was prepared.

General Method of H4 Synthesis

The substance H3 (60 mg, 0.20 mmol), DIPEA (0.035 mL, 0.22 mmol) and 2-(bromomethyl)-1,1'-biphenyl (0.040 mL, 0.22 mmol) were dissolved in anhydrous DMF (2 mL). The reaction mixture was stirred at 25° C. for about 16 hours and then was diluted in EtOAc and was washed with $NH_4Cl$(aq.) and water. The organic layer was dried with anhydrous $MgSO_4$ and then was evaporated in vacuo. A preferable product H4 of a white solid was obtained by column chromatography (10% EtOAc in hexane/MC, 2:1).

Example 11

Preparation Method of the Compound Represented by Chemical Formula 1 of the Present Invention Using Reaction Formula 9

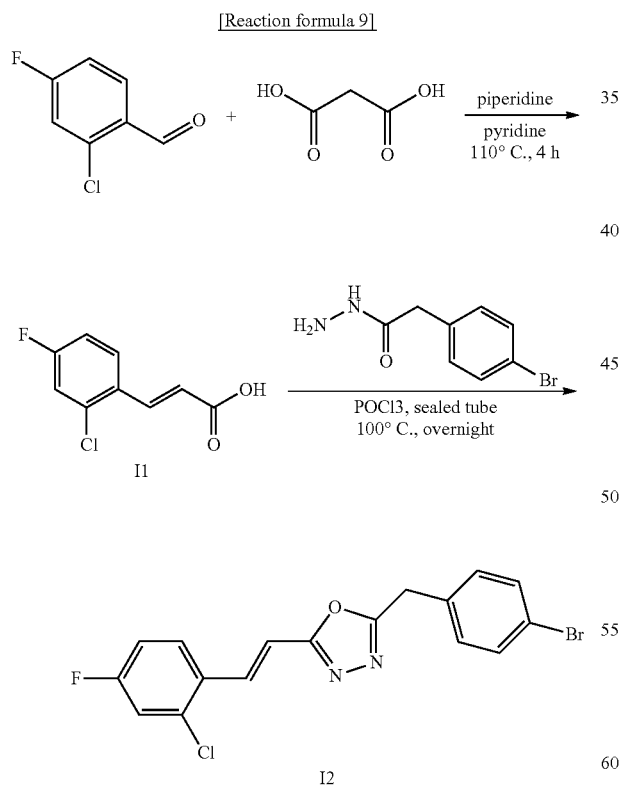

General Method of I1 Synthesis

The catalyst, piperidine (0.3 mmol), aldehyde (1 mmol) and malonic acid (1 mmol) were suspended in pyridine (2 mL), and the solution was stirred at 100° C. for 4 hours. Then, the reaction mixture was cooled to 0° C., and then it was acidified with HCl solution (conc., 5 mL). By filtering the solid formed finally and drying, I1 was prepared (95%).

General Method of I2 Synthesis (E)-3-(2-chloro-4-fluorophenyl)acrylic acid I1 (1 mmol) and 2-(4-bromophenyl)acetohydrazide (1 mmol) were suspended in $POCl_3$ (2 mL), and the mixture was heated by 100° C. overnight. After completion of the reaction, the solvent was evaporated and the residues were cooled down with 2N NaOH. The mixture was extracted with EtOAc and was washed with water. The organic layer was dried with $MgSO_4$ and was concentrated. By purifying the crude residues were purified by column chromatography (n-hexane:ethyl acetate=5:1), I2 of a pale yellow solid was prepared (85%).

Example 12

Preparation Method of the Compound Represented by Chemical Formula 1 of the Present Invention Using Reaction Formula 10

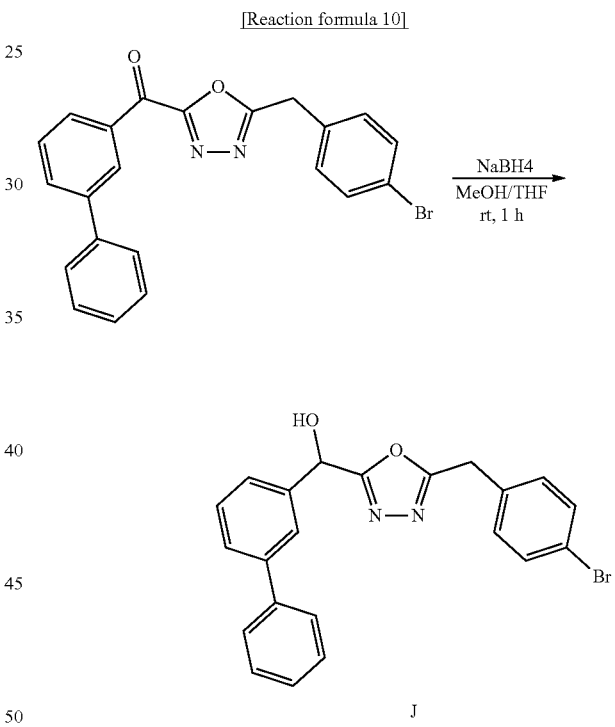

General Method of J Synthesis

To the stirred solution of [1,1'-biphenyl]-3-yl(5-(4-bromobenzyl)-1,3,4-oxadiazole-2-yl)methanone (1 mmol) dissolved in MeOH/THF (5:1=5 mL:1 mL), $NaBH_4$ (2 mmol) was added, and the mixture was stirred at a room temperature for 1 hour. After completion of the reaction, the reaction mixture was cooled down with $H_2O$, and was extracted with dichloromethane. The organic layer was dried with $MgSO_4$ and was concentrated under the reduced pressure. By purifying the crude residues by column chromatography (n-hexane:ethyl acetate=3:1), J of a white solid was prepared (70%).

Example 13

Preparation method of the compound represented by Chemical formula 1 of the present invention using Reaction formula 11

[Reaction formula 11]

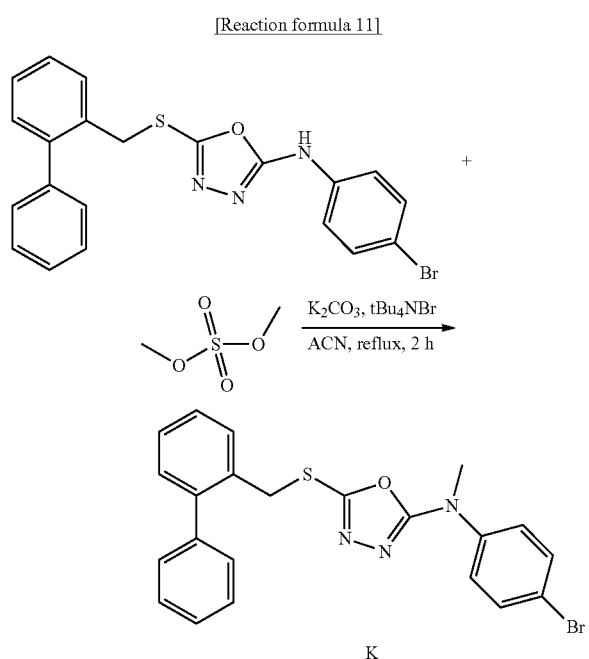

General Method of K Synthesis

The mixture of 5-(([1,1'-biphenyl]-2-ylmethyl)thio)-N-(4-bromophenyl)-1,3,4-oxadiazole-2-amine (1 mmol), $K_2CO_3$ (5 mmol), $^tBu_4NBr$ (1 mmol) and dimethyl sulfate (1 mmol) dissolved in acetonitrile (10 mL) was refluxed for 2 hours. After completion of the reaction, the reaction mixture was extracted with dichloromethane and the organic layer was dried with $MgSO_4$ and then was concentrated under the reduced pressure. By purifying the crude residues by column chromatography (n-hexane:ethyl acetate=3:1), K of colorless oil was prepared (60%).

Example 14

Preparation method of the compound using Reaction formula 12

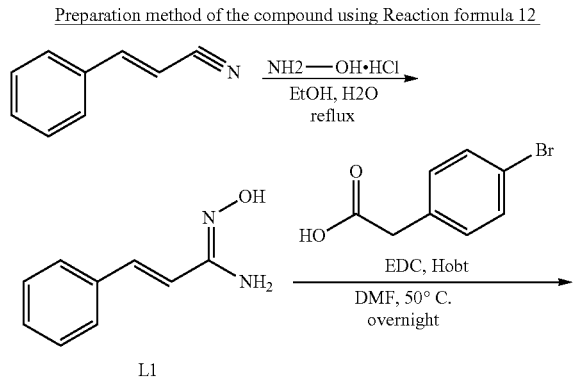

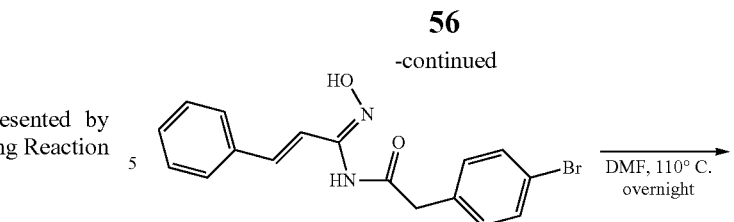

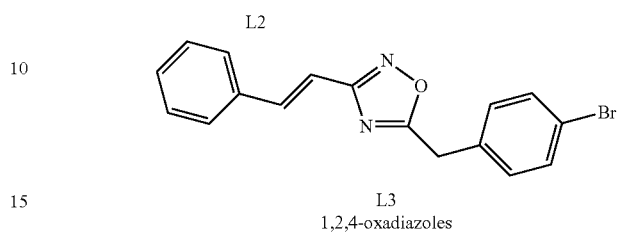

L3
1,2,4-oxadiazoles

L1 Synthetic Procedure

The mixture of cinnamon nitrile (1.0 mmol), hydroxyl amine (3.0 mmol) and $K_2CO_3$ (3.0 mmol) in EtOH (5 mL) was refluxed for 4 hours. After completion of the reaction, the mixture was evaporated and was extracted with EtOAc. The organic layer was dried on $MgSO_4$ and was concentrated under the reduced pressure. By purifying the crude residues by column chromatography (n-hexane:ethyl acetate=1:1 ratio), L1 of a white solid was obtained (60%).

L2 Synthetic Procedure

The mixture of (Z)—N'-hydroxycinnamimidamide) (1.0 mmol), 2-(4-bromophenyl)acetic acid (1.2 mmol), 1-ethyl-3-(3-dimethylaminopropyl)carbodiimide (1.5 mmol) and 1-hydroxybenzotriazole hydrate (0.5 mmol) in DMF (3 mL) was heated at 50° C. overnight. After completion of the reaction, the reaction mixture was extracted with EtOAc. The organic layer was dried on $MgSO_4$ and was concentrated under the reduced pressure. By purifying the crude residues by column chromatography (n-hexane:ethyl acetate=2:1 ratio), L2 of a lemon yellow was obtained (80%).

L3 Synthetic Procedure 2-(4-Bromophenyl)-N-((1E,2E)-1-(hydroxyimino)-3-phenylallyl)acetamide (1.0 mmol) in DMF (3 mL) was heated at 130° C. overnight. After completion of the reaction, the mixture was extracted with ethyl acetate. The organic layer was dried on $MgSO_4$ and was concentrated under the reduced pressure. By purifying the crude residues by column chromatography (n-hexane:ethyl acetate=10:1 ratio), L3 of a white solid was obtained (50%).

Example 15

Preparation method of the compound using Reaction formula 13

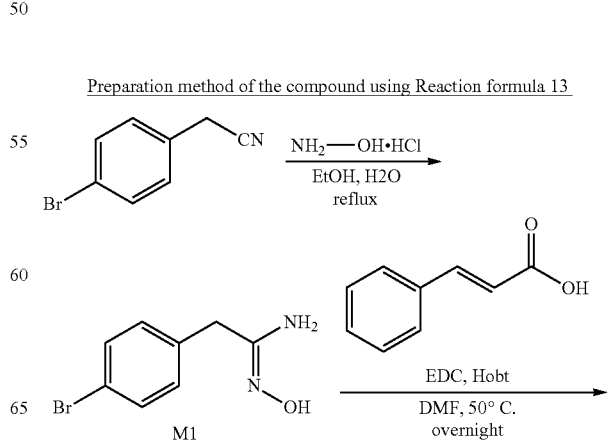

-continued

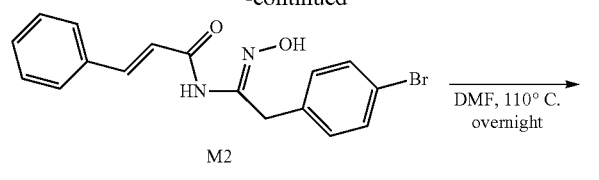

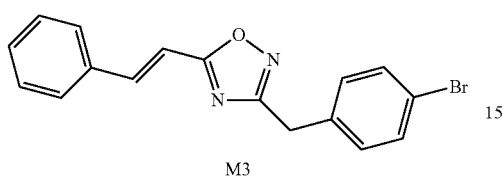

M 1 Synthetic Procedure

The mixture of 2-(4-Bromophenyl)acetonitrile (1.0 mmol), hydroxylamine (3.0 mmol) and $K_2CO_3$ (3.0 mmol) in EtOH (5 mL) was refluxed for 4 hours. After completion of the reaction, the mixture was evaporated and was extracted with ethyl acetate. The organic layer was dried on $MgSO_4$ and was concentrated under the reduced pressure. By purifying the crude residues by column chromatography (n-hexane:ethyl acetate=1:1 ratio), M1 of a white solid was obtained (60%).

M 2 Synthetic Procedure

The mixture of (Z)-2-(4-bromophenyl)-N'-hydroxyacetimideamide (1.0 mmol), cinnamic acid (1.2 mmol), 1-ethyl-3-(3-dimethylaminopropyl)carbodiimide (1.5 mmol) and 1-hydroxybenzotriazole hydrate (0.5 mmol) in DMF (3 mL) was heated at 50° C. overnight. After completion of the reaction, the mixture was extracted with ethyl acetate. The organic layer was dried on $MgSO_4$ and was concentrated under the reduced pressure. By purifying the crude residues by column chromatography (n-hexane:ethyl acetate=1:1 ratio), M2 of a lemon yellow solid was obtained (80%).

M 3 Synthetic Procedure

N—((E)-2-(4-bromophenyl)-1-(hydroxyimino)ethyl)cinnamamide (1.0 mmol) in DMF (3 mL) was heated at 130° C. overnight. After completion of the reaction, the mixture was extracted with ethyl acetate. The organic layer was dried on $MgSO_4$ and was concentrated under the reduced pressure. By purifying the crude residues by column chromatography (n-hexane:ethyl acetate=10:1 ratio), M3 of a white solid was obtained (50%).

Example 16

Preparation method of the compound using Reaction formula 14

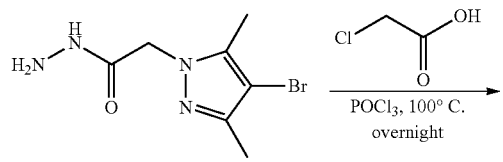

-continued

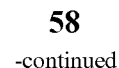

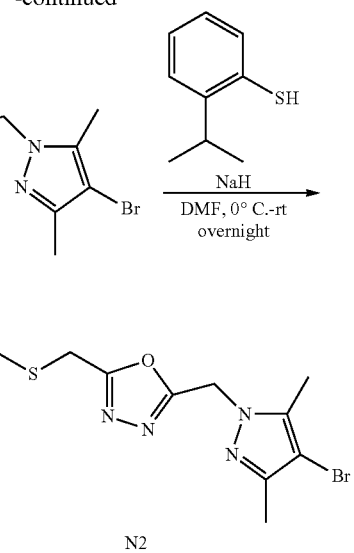

N 1 Synthetic Procedure

The mixture of 2-(4-Bromo-3,5-dimethyl-1H-pyrazole-1-yl)acetohydrizide (0.61 mmol) and 2-chloroacetic acid (1.21 mmol) in $POCl_3$ (2 mL) was heated at 100° C. overnight. After cooling, the reaction mixture was poured to ice and was extracted with methylene (3 times). The organic layer was dried on $MgSO_4$ and was concentrated in vacuo, and thereby a crude product of a white solid was obtained.

N 2 Synthetic Procedure

In an ice bath, NaH (60% dispersions in paraffin, 0.24 mmol) was added to the stirred solution of 2-isopropyl benzenethiol (0.19 mmol) in DMF (3 mL). In 10 minutes, N1 (0.16 mmol) solution in DMF (2 mL) was added to the reaction mixture, and it was left to be reacted at a room temperature. After the night passed, the reaction was terminated with water, the mixture was extracted with EtOAc (2 times). The organic layer was washed with salt water, and it was dried on $MgSO_4$ and was concentrated in vacuo. By purifying the crude residues by flash column chromatography (n-hexane:EtOAc=3:1 ratio), a target compound of a white solid was obtained.

Example 17

Preparation method of the compound using Reaction formula 15

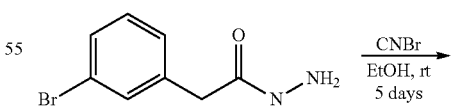

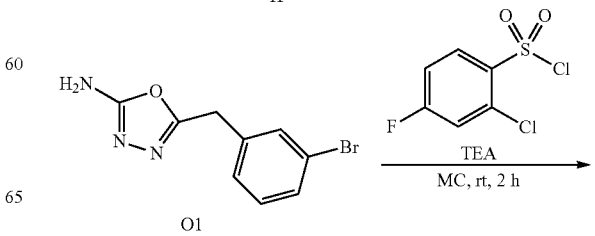

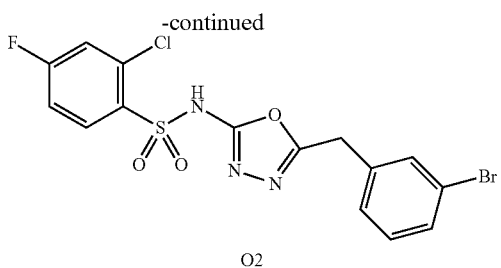

O2

O1 Synthetic Procedure

The mixture of 2-(3-bromophenyl)acetohydrazide (1.25 mmol) and cyanogen bromide (1.88 mmol) in EtOH (5 mL) was stirred at a room temperature for 5 days. The filtrate obtained by filtering insoluble solids was concentrated in vacuo to obtain a crude target compound.

O2 Synthetic Procedure

To the stirred solution of O1 (0.26 mmol) and trimethylamine (0.34 mmol) in methylene chloride (2 mL), 2-chloro-4-fluorobenzenesulfonyl chloride (0.23 mmol) was added, and the mixture was stirred at a room temperature for 2 hours. By purifying the crude residues by flash column chromatography (n-hexne:EtOAc=3:1 ratio), a target compound of a white solid was obtained.

Example 18

Preparation method of the compound using Reaction formula 16

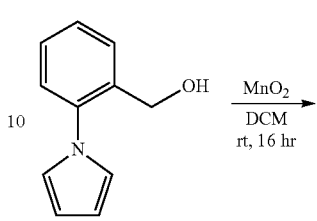

P1

P1 Synthetic Procedure

To the stirred solution of 2-bromo-4-fluorobenzaldehyde (1.48 mmol), $Pd_2(dba)_3$ (0.14 mmol), BINAP (0.29 mmol) and $CsCO_3$ (2.22 mmol) in toluene (5 mL), 2-methoxy-N-methylethane-1-amine (1.78 mmol) was added. The mixture was heated at 100° C. and was stirred overnight. Insoluble solids were filtered and the filtrate was diluted with EtOAC. The organic solution was washed with water and salt water and was concentrated in vacuo. By purifying the crude residues by flash column chromatography (n-hexane:EtOAc=9:1 ratio), a target compound of yellow oil was obtained (68%).

Example 19

Preparation method of the compound using Reaction formula 17

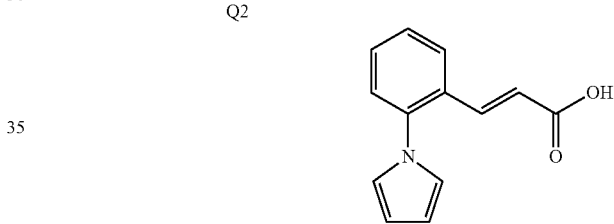

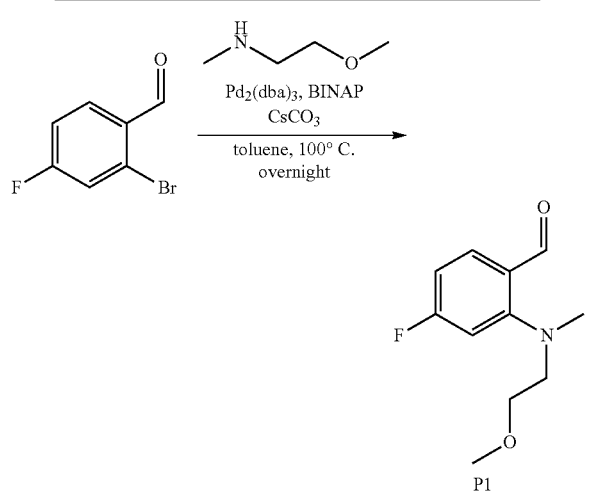

Q3

Q1 Synthetic Procedure

To the solution of [2-(1H-pyrrole-1-yl)phenyl]methanol (1.44 mmol) in dichloromethane (18 mL), $MnO_2$ (7.22 mmol) was added, and the mixture was stirred at a room temperature for 16 hours. Insoluble residues were filtered, and the filtrate was concentrated, and thereby a crude target compound of yellow oil was obtained (89%).

Q2 Synthetic Procedure

To the solution of A1 (1.29 mmol), LiCl (1.75 mmol) in $CH_3CN$ (8 mL), triethyl phosphoacetate (1.75 mmol) and DBU (1.45 mmol) were added, and the mixture was stirred at a room temperature. In 4 hours, the residues obtained by removing the organic solvent were dissolved in EtOAc. The organic solution was washed with salt water and was dried on $MgSO_4$ and was concentrated, and thereby a crude target compound of yellow oil was obtained (94%).

Q3 Synthetic Procedure

To the solution of A2 (1.20 mmol) in THF:EtOH:$H_2O$ (1:1:1, 6 mL), LiOH (6.01 mmol) was added. The mixture was stirred at a room temperature for 16 hours. The aqueous solution obtained by removing the organic solvent was acidified by using 2N HCl (aq.). The obtained precipitates were filtered and were washed with water and n-hexane, and were dried under the reduced pressure. By purifying the crude residues by column chromatography (n-hexane:EtOAc=1:1 ratio), a target compound of a lemon yellow solid was obtained.

Example 20

Preparation method of the compound using Reaction formula 18

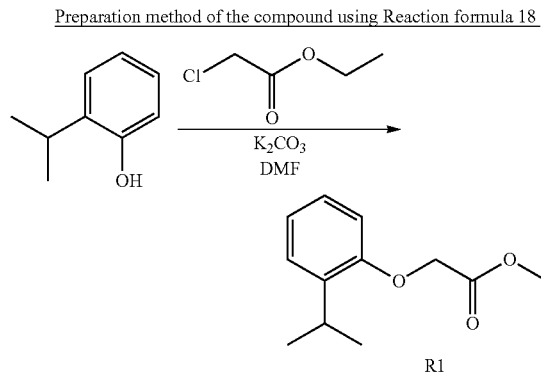

R1 Synthetic Procedure

The solution of 2-isopropylphenol (1.0 g, 7.34 mmol) and $K_2CO_3$ (3.04 g, 22.03 mmol) in DMF (5 mL), ethyl 2-chloroacetate (1.08 g, 8.81 mmol) was added, and then the mixture was stirred at 25° C. for 24 hours. After completion of the reaction, the reaction mixture was diluted in EtOAc, and was washed by using water and sat. $NaHCO_3$(aq.). The organic layer was dried on anhydrous $MgSO_4$ and was concentrated in vacuo. By purifying the crude residues by column chromatography, a target compound of yellow oil was obtained.

Example 21

Preparation method of the compound using Reaction formula 19

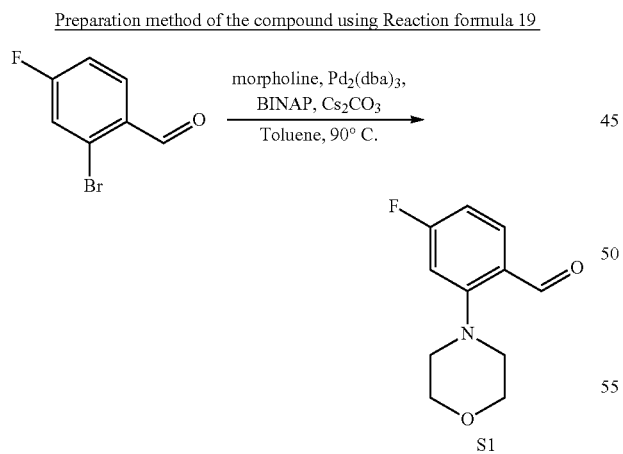

S1 Synthetic Procedure

To the solution of 2-bromo-4-fluorobenzaldehyde (1.97 mmol) in toluene (3 mL), $Pd_2(dba)_3$ (0.20 mmol), 2,2'-bis(diphenylphosphino)-1,1'-binaphthyl) (0.39 mmol), $Cs_2CO_3$ (2.96 mmol) and morpholine (2.36 mmol) were added. The reaction mixture was heated by 90° C. for 24 hours. Insoluble solids were filtered and the filtrate was concentrated in vacuo. By purifying the crude residues by column chromatography (n-hexane:EtOAc=5:1 ratio), a target compound of yellow oil was obtained.

Example 22

Preparation method of the compound using Reaction formula 20

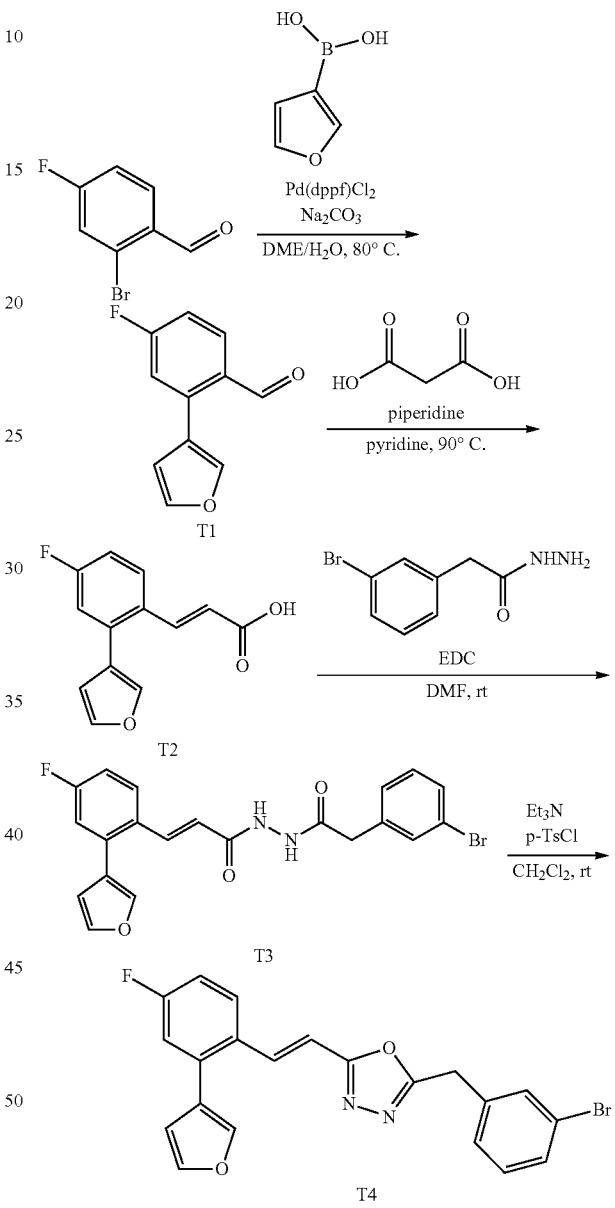

T1 Synthetic Procedure

To the solution of 2-bromo-4-fluorobenzaldehyde (2.46 mmol), Pd(dppf)Cl$_2$ (0.25 mmol), furan-3-yl-boronic acid (2.71 mmol) in DME (3 mL), $Na_2CO_3$ (4.93 mmol, 1 mL) aqueous solution was added. The reaction mixture was heated by 80° C. for 24 hours. The residues obtained by removing the reaction solvent were dissolved in $CH_2Cl_2$. The organic layer was washed with water and was dried on anhydrous $MgSO_4$ and was evaporated in vacuo. By purifying the crude residues by column chromatography (n-hexane:EtOAc=1:5 ratio), a target compound was obtained.

T2 Synthetic Procedure

By a similar method, according to the synthetic procedure of I1, a target compound T2 was synthesized.

T3 Synthetic Procedure

The mixture of T3 (1.1 mmol), 2-(3-bromophenyl)acetohydrizide (1.0 mmol) and EDC (1.5 mmol) in DMF (10 mL) was stirred at a room temperature overnight. After completion of the reaction, the solvent was removed. By washing the obtained residues with water and diethyl ether, a crude target compound was obtained.

T4 Synthetic Procedure

To the solution of (E)-N'-(2-(3-bromophenyl)acetyl)-3-(4-fluoro-2-(furan-3-yl)phenyl) acrylohydrazide (0.41 mmol) and p-TsCl (0.41 mmol) in $CH_2Cl_2$, $Et_3N$ (1.22 mmol) was added, and the reaction mixture was stirred at a room temperature. After the night passed, insoluble solids were filtered, and the filtrate was concentrated in vacuo. By purifying the crude residues by column chromatography (n-hexane:EtOAc=3:1 ratio), a target compound of a yellow solid was obtained.

Example 23

Preparation method of the compound using Reaction formula 21

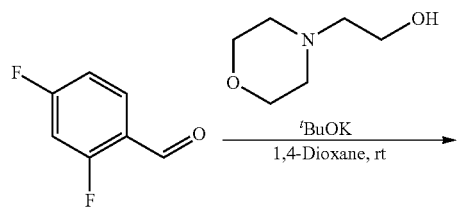

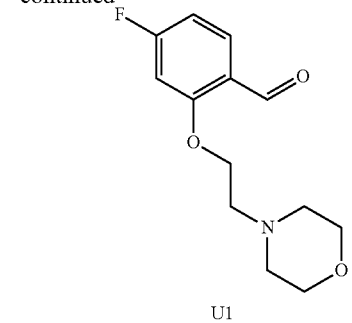

U1

U1 Synthetic Procedure

To the solution of 2,4-difluorobenzaldehyde (3.52 mmol) and t-BuOK (4.22 mmol) in 1,4-dioxane (3 mL), 2-morpholinoethan-1-ol (4.22 mmol) was added, and the reaction mixture was stirred at 25° C. for 24 hours. After completion of the reaction, the mixture was diluted with EtOAc, and was washed with water. The organic layer was dried on anhydrous $MgSO_4$ and was concentrated in vacuo. By purifying the crude residues by column chromatography (n-hexane: EtOAc=3:1 ratio), a target compound of yellow oil was obtained.

Example 24

Preparation of Novel Compounds of Chemical Formula 1 or Chemical Formula 2 According to the Present Invention and Evaluation of Antiviral Activity Using exemplary preparation methods of Examples 1 to 23, 307 kinds of compounds represented by Chemical formula 1 or 2 of the present invention were prepared (Tables 1 to 31), and the anti-influenza virus activity and cytotoxicity of the prepared compounds were evaluated (Tables 32 to 62).

TABLE 1

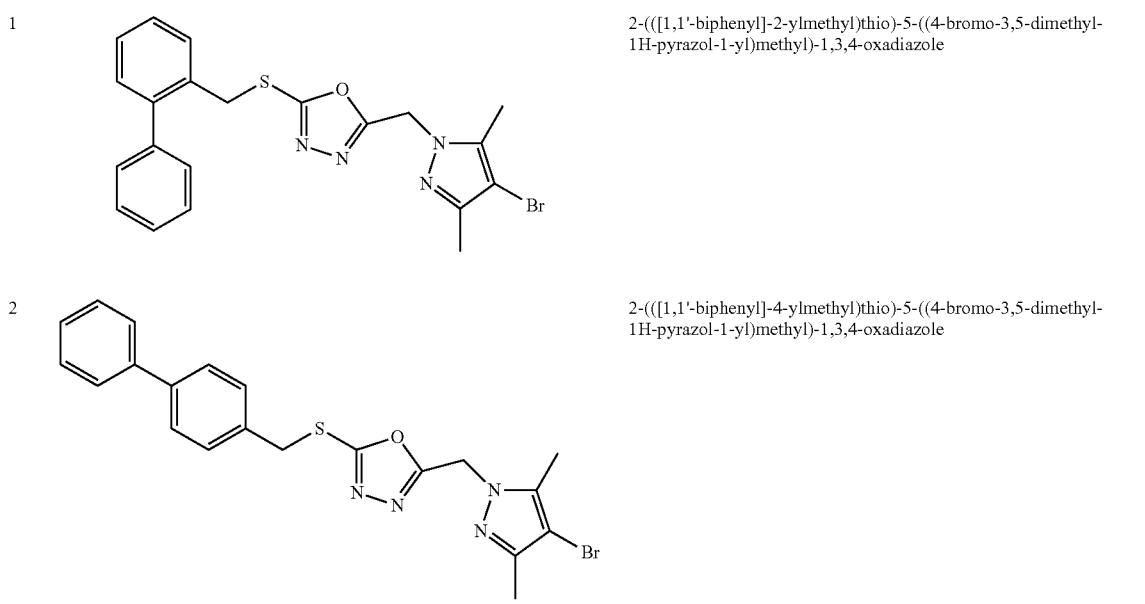

1: 2-(([1,1'-biphenyl]-2-ylmethyl)thio)-5-((4-bromo-3,5-dimethyl-1H-pyrazol-1-yl)methyl)-1,3,4-oxadiazole 2: 2-(([1,1'-biphenyl]-4-ylmethyl)thio)-5-((4-bromo-3,5-dimethyl-1H-pyrazol-1-yl)methyl)-1,3,4-oxadiazole TABLE 1-continued

| | | |
|---|---|---|
| 3 | 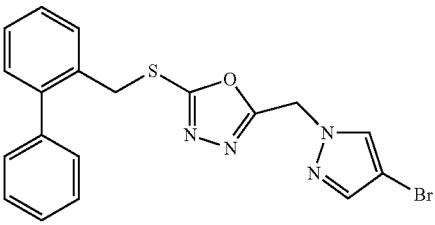 [SMILES: Brc1cnn(Cc2nnc(SCc3ccccc3-c3ccccc3)o2)c1] | 2-(([1,1'-biphenyl]-2-ylmethyl)thio)-5-((4-bromo-1H-pyrazol-1-yl)methyl)-1,3,4-oxadiazole |
| 4 | 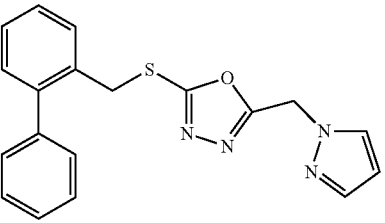 [SMILES: c1ccc(-c2ccccc2CSc2nnc(Cn3cccn3)o2)cc1] | 2-((1H-pyrazol-1-yl)methyl)-5-(([1,1'-biphenyl]-2-ylmethyl)thio)-1,3,4-oxadiazole |
| 5 | 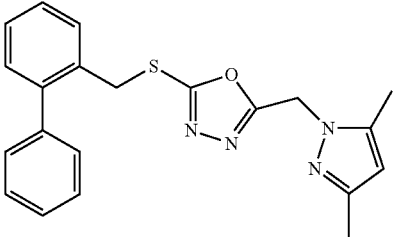 [SMILES: Cc1cc(C)n(Cc2nnc(SCc3ccccc3-c3ccccc3)o2)n1] | 2-(([1,1'-biphenyl]-2-ylmethyl)thio)-5-((3,5-(dimethyl-1H-pyrazol-1-yl)methyl)-1,3,4-oxadiazole |
| 6 | 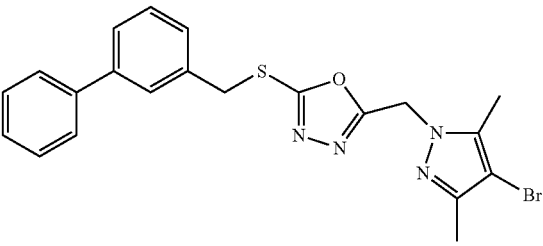 [SMILES: Cc1nn(Cc2nnc(SCc3cccc(-c4ccccc4)c3)o2)c(C)c1Br] | 2-(([1,1'-biphenyl]-3-ylmethyl)thio)-5-((4-bromo-3,5-dimethyl-1H-pyrazol-1-yl)methyl)-1,3,4-oxadiazole |
| 7 | 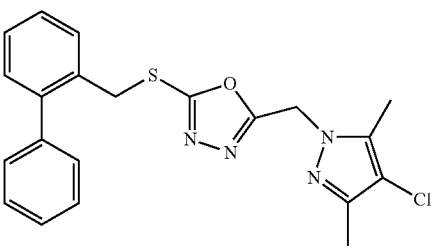 [SMILES: Cc1nn(Cc2nnc(SCc3ccccc3-c3ccccc3)o2)c(C)c1Cl] | 2-(([1,1'-biphenyl]-2-ylmethyl)thio)-5-((4-chloro-3,5-dimethyl-1H-pyrazol-1-yl)methyl)-1,3,4-oxadiazole |
| 8 | 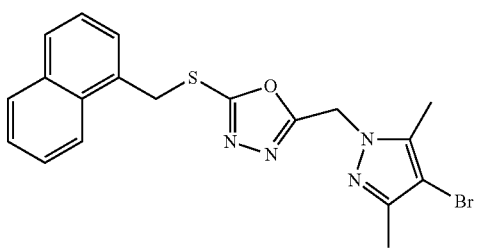 [SMILES: Cc1nn(Cc2nnc(SCc3cccc4ccccc34)o2)c(C)c1Br] | 2-((4-bromo-3,5-dimethyl-1H-pyrazol-1-yl)methyl)-5-((naphthalen-1-ylmethyl)thio)-1,3,4-oxadiazole |

TABLE 1-continued

| | | |
|---|---|---|
| 9 | 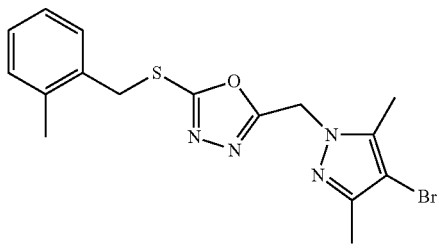 [SMILES: Cc1ccccc1CSc1nnc(Cn2nc(C)c(Br)c2C)o1] | 2-((4-bromo-3,5-dimethyl-1H-pyrazol-1-yl)methyl)-5-((2-methylbenzyl)thio)-1,3,4-oxadiazole |
| 10 | 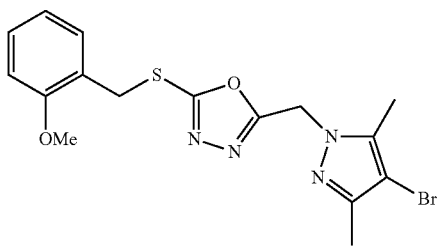 [SMILES: COc1ccccc1CSc1nnc(Cn2nc(C)c(Br)c2C)o1] | 2-((4-bromo-3,5-dimethyl-1H-pyrazol-1-yl)methyl)-5-((2-methoxybenzyl)thio)-1,3,4-oxadiazole |

TABLE 2

| | | |
|---|---|---|
| 11 | 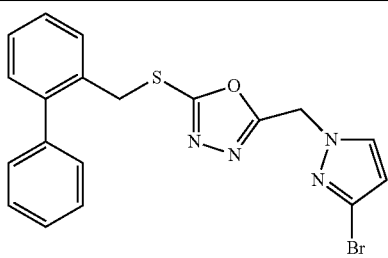 | 2-((([1,1'-biphenyl]-2-ylmethyl)thio)-5-((3-bromo-1H-pyrazol-1-yl)methyl)-1,3,4-oxadiazole |
| 12 | 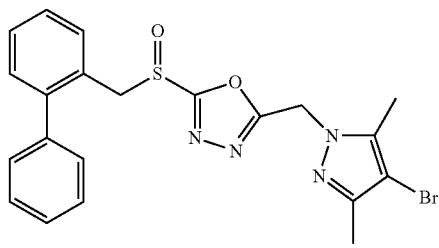 [SMILES: Cc1nn(Cc2nnc(S(=O)Cc3ccccc3-c3ccccc3)o2)c(C)c1Br] | 2-((([1,1'-biphenyl]-2-ylmethyl)sulfinyl)-5-((4-bromo-3,5-dimethyl-1H-pyrazol-1-yl)methyl)-1,3,4-oxadiazole |
| 13 | 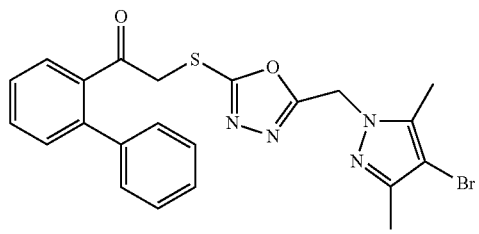 [SMILES: Cc1nn(Cc2nnc(SCC(=O)c3ccccc3-c3ccccc3)o2)c(C)c1Br] | 1-([1,1'-biphenyl]-2-yl)-2-((5-((4-bromo-3,5-dimethyl-1H-pyrazol-1-yl)methyl)-1,3,4-oxadiazol-2-yl)thio)ethan-1-on |
| 14 | 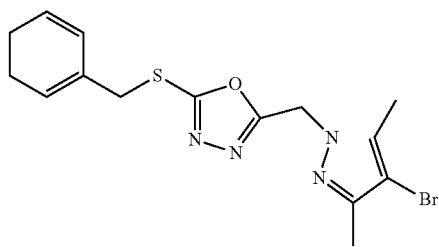 [SMILES: C/C=C(Br)/C(C)=N\NCc1nnc(SCC2=CCCC=C2)o1] | 2-(benzylthio)-5-((4-bromo-3,5-dimethyl-1H-pyrazol-1-yl)methyl)-1,3,4-oxadiazole |

TABLE 2-continued

| | | |
|---|---|---|
| 15 | 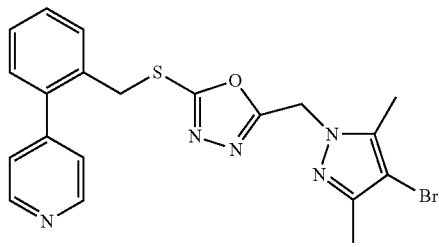 [SMILES: Cc1nn(Cc2nnc(SCc3ccccc3-c3ccncc3)o2)c(C)c1Br] | 2-((4-bromo-3,5-dimethyl-1H-pyrazol-1-yl)methyl)-5-((2-(pyridin-4-yl)benzyl)thio)-1,3,4-oxadiazole |
| 16 | 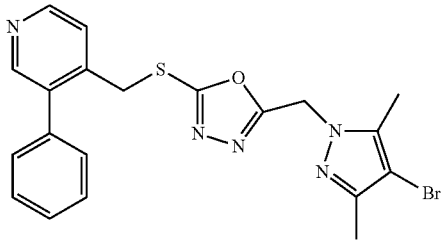 [SMILES: Cc1nn(Cc2nnc(SCc3ccncc3-c3ccccc3)o2)c(C)c1Br] | 2-((4-bromo-3,5-dimethyl-1H-pyrazol-1-yl)methyl)-5-(((3-phenylpyridin-4-yl)methyl)thio)-1,3,4-oxadiazole |
| 17 | 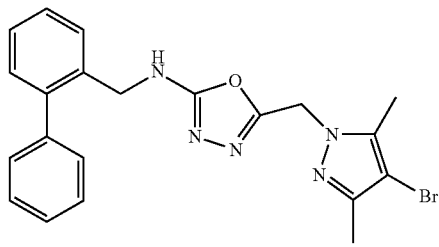 [SMILES: Cc1nn(Cc2nnc(NCc3ccccc3-c3ccccc3)o2)c(C)c1Br] | N-([1,1'-biphenyl]-2-ylmethyl)-5-((4-bromo-3,5-dimethyl-1H-pyrazol-1-yl)methyl)-1,3,4-oxadiazol-2-amine |
| 18 | 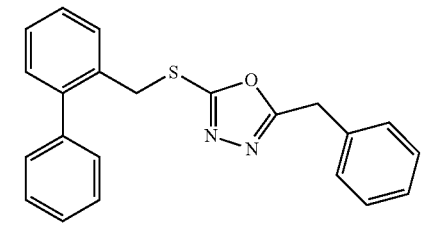 | 2-(([1,1'-biphenyl]-ylmethyl)thio)-5-benzyl-1,3,4-oxadiazole |
| 19 | 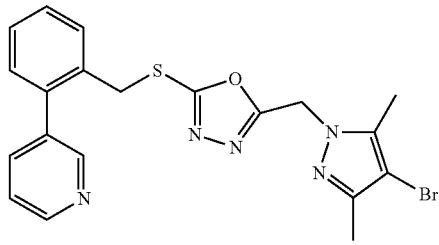 | 2-((4-bromo-3,5-dimethyl-1H-pyrazol-1-yl)methyl)-5-((2-(pyridin-3-yl)benzyl)thio)-1,3,4-oxadiazole |
| 20 | 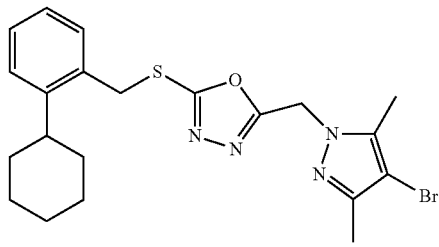 [SMILES: Cc1nn(Cc2nnc(SCc3ccccc3C3CCCCC3)o2)c(C)c1Br] | 2-((1-bromo-3,5-dimethyl-1H-pyrazol-1-yl)methyl)-5-((2-(pyridin-4-yl)benzyl)thio)-1,3,4-oxadiazole |

TABLE 3

| 21 | 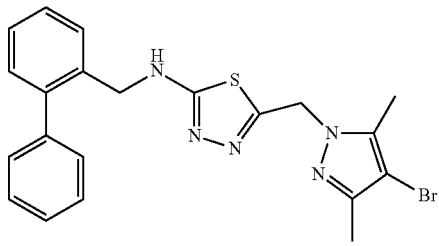 | 2-((4-bromo-3,5-dimethyl-1H-pyrazol-1-yl)methyl)-5-(((3-phenylpyridin-4-yl)methyl)thio)-1,3,4-oxadiazole |
| --- | --- | --- |
| 22 | 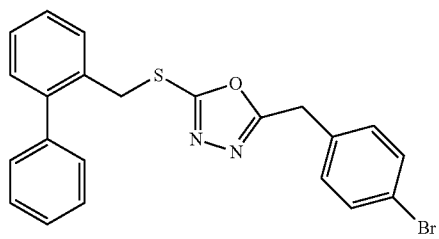 [SMILES: Brc1ccc(Cc2nnc(SCc3ccccc3-c3ccccc3)o2)cc1] | 2-((([1,1'-biphenyl]-2-ylmethyl)thio)-5-(4-bromobenzyl)-1,3,4-oxadiazole |
| 23 | 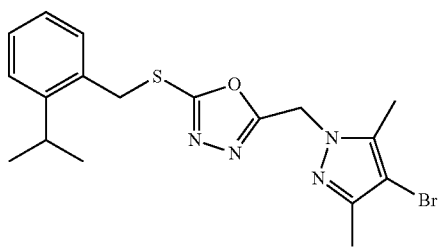 [SMILES: Cc1nn(Cc2nnc(SCc3ccccc3C(C)C)o2)c(C)c1Br] | 2-((4-bromo-3,5-dimethyl-1H-pyrazol-1-yl)methyl)-5-((2-isopropylbenzyl)thio)-1,3,4-oxadiazole |
| 24 | 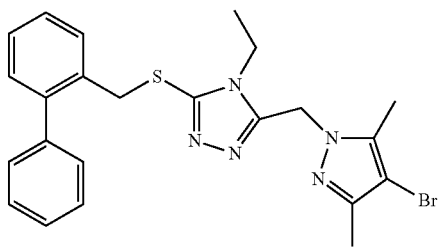 [SMILES: CCn1c(Cn2nc(C)c(Br)c2C)nnc1SCc1ccccc1-c1ccccc1] | 3-((([1,1'-biphenyl]-2-ylmethyl)thio)-5-((4-bromo-3,5-dimethyl-1H-pyrazol-1-yl)methyl)-4-ethyl-4H-1,2,4-triazole |
| 25 | 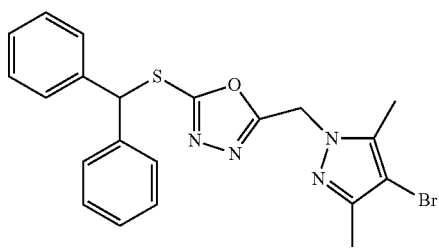 [SMILES: Cc1nn(Cc2nnc(SC(c3ccccc3)c3ccccc3)o2)c(C)c1Br] | 2-(benzhydrylthio)-5-((4-bromo-3,5-dimethyl-1H-pyrazol-1-yl)methyl)-1,3,4-oxadiazole |
| 26 | 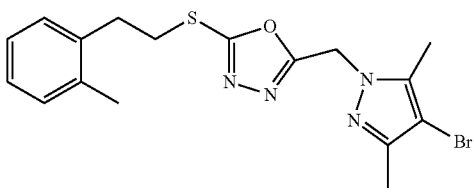 [SMILES: Cc1ccccc1CCSc1nnc(Cn2nc(C)c(Br)c2C)o1] | 2-((4-bromo-3,5-dimethyl-1H-pyrazol-1-yl)methyl)-5-((2-methylphenethyl)thio)-1,3,4-oxadiazole |

TABLE 3-continued

| | | |
|---|---|---|
| 27 | | 2-((([1,1'-biphenyl]-2-ylmethyl)thio)-5-(pyridin-2-ylmethyl)-1,3,4-oxadiazole |
| 28 | | 1-(2-(((5-((4-bromo-3,5-dimethyl-1H-pyrazol-1-yl)methyl)-1,3,4-oxadiazol-2-yl)thio)methyl)phenyl)ethan-1-one |
| 29 | | 2-((4-bromo-3,5-dimethyl-1H-pyrazol-1-yl)methyl)-5-((2-phenoxybenzyl)thio)-1,3,4-oxadiazole |
| 30 | | 2-((([1,1'-biphenyl]-2-ylmethyl)thio)-5-((4-phenyl-1H-pyrazol-1-yl)methyl)-1,3,4-oxadiazole |

TABLE 4

| | | |
|---|---|---|
| 31 | | 2-((2-(1H-pyrrol-1-yl)benzyl)thio)-5-((4-bromo-3,5-dimethyl-1H-pyrazol-1-yl)methyl)-1,3,4-oxadiazole |
| 32 | | 2-((4-bromo-3,5-dimethyl-1H-pyrazol-1-yl)methyl)-5-(((4'-methyl-[1,1'-biphenyl]-2-yl)methyl)thio)-1,3,4-oxadiazole |

TABLE 4-continued

| 33 | 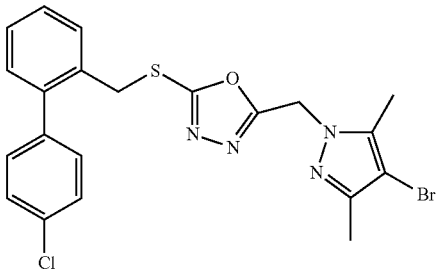 [SMILES: Cc1nn(Cc2nnc(SCc3ccccc3-c3ccc(Cl)cc3)o2)c(C)c1Br] | 2-((4-bromo-3,5-dimethyl-1H-pyrazol-1-yl)methyl)-5-(((4'-chloro-[1,1'-biphenyl]-2-yl)methyl)thio)-1,3,4-oxadiazole |
| --- | --- | --- |
| 34 | 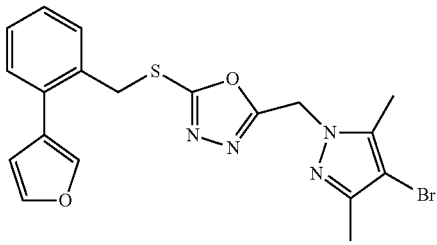 [SMILES: Cc1nn(Cc2nnc(SCc3ccccc3-c3ccoc3)o2)c(C)c1Br] | 2-((4-bromo-3,5-dimethyl-1H-pyrazol-1-yl)methyl)-5-((2-(furan-3-yl)benzyl)thio)-1,3,4-oxadiazole |
| 35 | 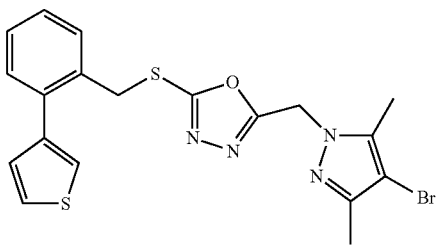 [SMILES: Cc1nn(Cc2nnc(SCc3ccccc3-c3ccsc3)o2)c(C)c1Br] | 2-((4-bromo-3,5-dimethyl-1H-pyrazol-1-yl)methyl)-5-((2-(thiophen-3-yl)benzyl)thio)-1,3,4-oxadiazole |
| 36 | 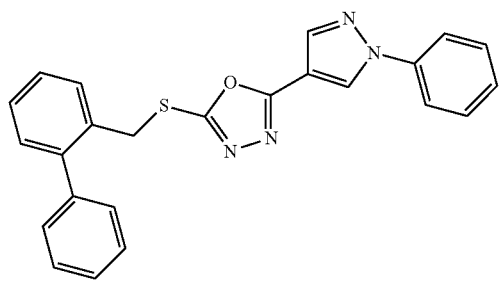 [SMILES: c1ccc(-c2ccccc2CSc2nnc(-c3cnn(-c4ccccc4)c3)o2)cc1] | 2-(([1,1'-biphenyl]-2-ylmethyl)thio)-5-(1-phenyl-1H-pyrazol-4-yl)-1,3,4-oxadiazole |
| 37 | 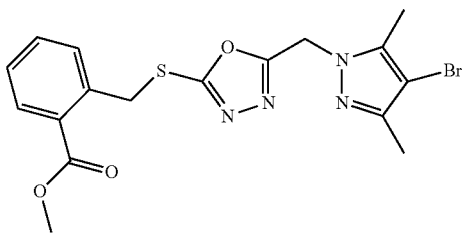 [SMILES: COC(=O)c1ccccc1CSc1nnc(Cn2nc(C)c(Br)c2C)o1] | methyl 2-(((5-((4-bromo-3,5-dimethyl-1H-pyrazol-1-yl)methyl)-1,3,4-oxadiazol-2-yl)thio)methyl)benzoate |
| 38 | 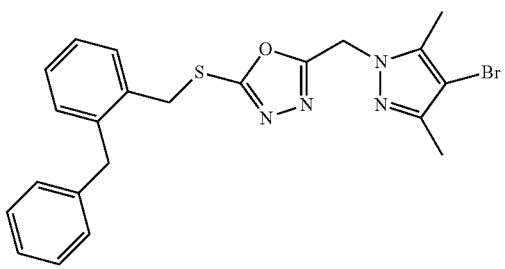 [SMILES: Cc1nn(Cc2nnc(SCc3ccccc3Cc3ccccc3)o2)c(C)c1Br] | 2-((2-benzylbenzyl)thio)-5-((4-bromo-3,5-dimethyl-1H-pyrazol-1-yl)methyl)-1,3,4-oxadiazole |

TABLE 4-continued

| # | Structure | Name |
|---|---|---|
| 39 | 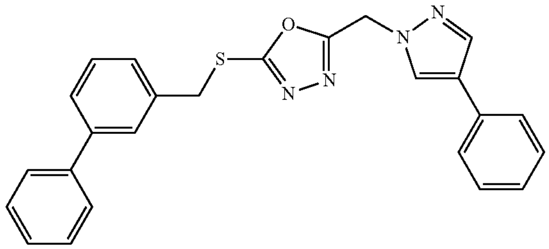 [SMILES: c1ccc(-c2cccc(CSc3nnc(Cn4cc(-c5ccccc5)cn4)o3)c2)cc1] | 2-(([1,1'-biphenyl]-3-ylmethyl)thio)-5-((4-phenyl-1H-pyrazol-1-yl)methyl)-1,3,4-oxadiazole |
| 40 | 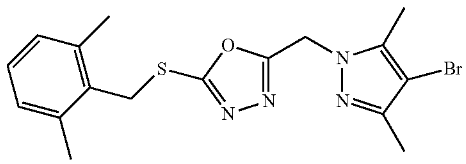 [SMILES: Cc1cccc(C)c1CSc1nnc(Cn2nc(C)c(Br)c2C)o1] | 2-((4-bromo-3,5-dimethyl-1H-pyrazol-1-yl)methyl)-5-((2,6-dimethylbenzylthio)-1,3,4-oxadiazole |

TABLE 5

| # | Structure | Name |
|---|---|---|
| 41 | 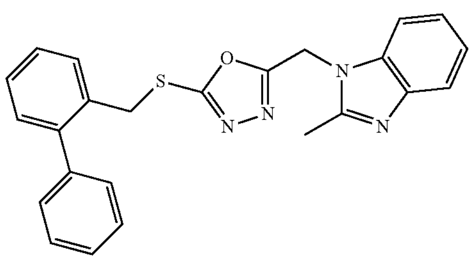 [SMILES: Cc1nc2ccccc2n1Cc1nnc(SCc2ccccc2-c2ccccc2)o1] | 2-(([1,1'-biphenyl]-2-ylmethyl)thio)-5-((2-methyl-1H-benzo[d]imidazol-1-yl)methyl)-1,3,4-oxadiazole |
| 42 | 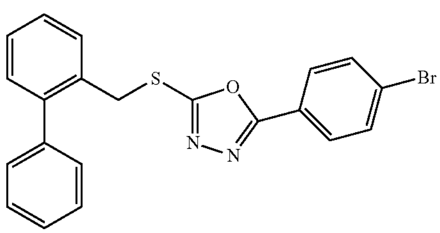 [SMILES: Brc1ccc(-c2nnc(SCc3ccccc3-c3ccccc3)o2)cc1] | 2-(([1,1'-biphenyl]-2-ylmethyl)thio)-5-(4-bromophenyl)-1,3,4-oxadiazole |
| 43 | 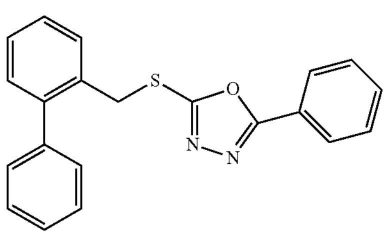 [SMILES: c1ccc(-c2nnc(SCc3ccccc3-c3ccccc3)o2)cc1] | 2-(([1,1'-biphenyl]-2-ylmethyl)thio)-5-phenyl-1,3,4-oxadiazole |
| 44 | 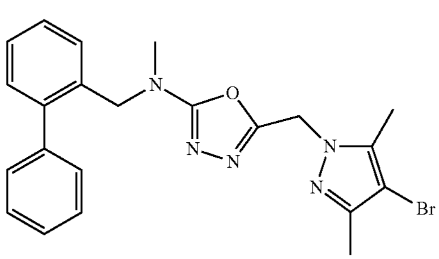 [SMILES: Cc1nn(Cc2nnc(N(C)Cc3ccccc3-c3ccccc3)o2)c(C)c1Br] | N-([1,1'-biphenyl]-2-ylmethyl)-5-((4-bromo-3,5-dimethyl-1H-pyrazol-1-yl)methyl)-N-methyl-1,3,4-oxadiazole-2-amine |

TABLE 5-continued

| | | |
|---|---|---|
| 45 | 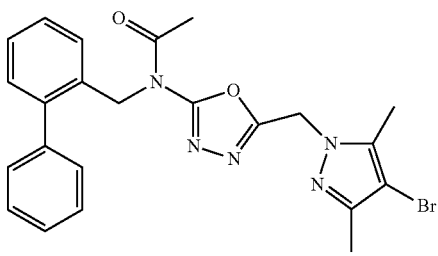 [SMILES: CC(=O)N(Cc1ccccc1-c1ccccc1)c1nnc(Cn2nc(C)c(Br)c2C)o1] | N-([1,1'-biphenyl]-2-ylmethyl)-N-(5-((4-bromo-3,5-dimethyl-1H-pyrazol-1-yl)methyl)-1,3,4-oxadiazol-2-yl)acetamide |
| 46 | 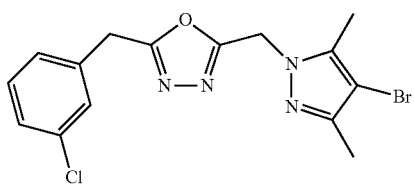 [SMILES: Cc1nn(Cc2nnc(Cc3cccc(Cl)c3)o2)c(C)c1Br] | 2-((4-bromo-3,5-dimethyl-1H-pyrazol-1-yl)methyl)-5-(3-chlorobenzyl)-1,3,4-oxadiazole |
| 47 | 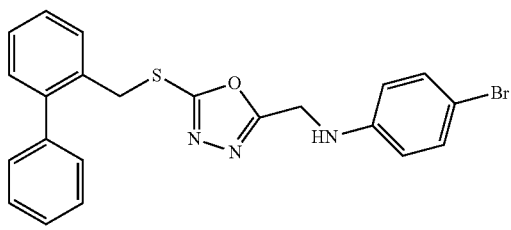 [SMILES: Brc1ccc(NCc2nnc(SCc3ccccc3-c3ccccc3)o2)cc1] | N-((5-(([1,1'-biphenyl]-2-ylmethyl)thio)-1,3,4-oxadiazol-2-yl)methyl)-4-bromoaniline |
| 48 | 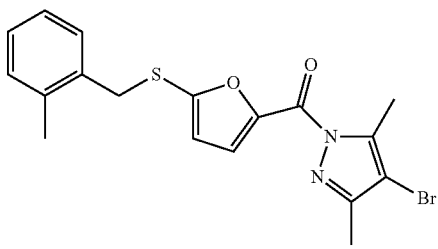 [SMILES: Cc1ccccc1CSc1ccc(C(=O)n2nc(C)c(Br)c2C)o1] | (4-bromo-3,5-dimethyl-1H-pyrazol-1-yl)(5-((2-methylbenzyl)thio)furan-2-yl)methanone |
| 49 | 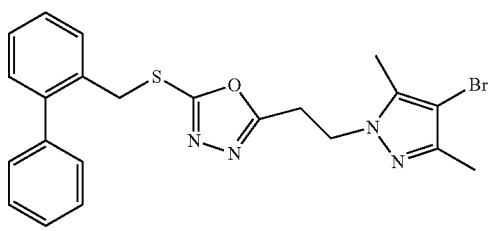 [SMILES: Cc1nn(CCc2nnc(SCc3ccccc3-c3ccccc3)o2)c(C)c1Br] | 2-(([1,1'-biphenyl]-2-ylmethyl)thio)-5-(2-(4-bromo-3,5-dimethyl-1H-pyrazol-1-yl)ethyl)-1,3,4-oxadiazole |
| 50 | 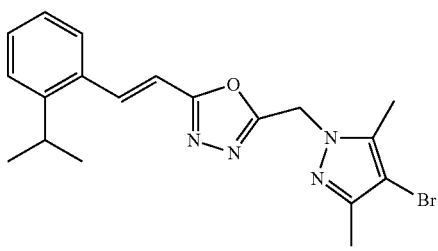 [SMILES: Cc1nn(Cc2nnc(/C=C/c3ccccc3C(C)C)o2)c(C)c1Br] | (E)-2-((4-bromo-3,5-dimethyl-1H-pyrazol-1-yl)methyl)-5-(2-isopropylstyryl)-1,3,4-oxadiazole |

TABLE 6

| | | |
|---|---|---|
| 51 | | N-((5-((([1,1'-biphenyl]-2-ylmethyl)thio)-1,3,4-oxadiazol-2-yl)methyl)-4-bromobenzamide |
| 52 | | 5-((([1,1'-biphenyl]-2-ylmethyl)thio)-N-(4-bromophenyl)-1,3,4-oxadiazol-2-amine |
| 53 | | 2-((4-bromo-3,5-dimethyl-1H-pyrazol-1-yl)methyl)-5-(o-tolylthio)-1,3,4-oxadiazole |
| 54 | | 2-(2-(4-bromo-3,5-dimethyl-1H-pyrazol-1-yl)ethyl)-5-(o-tolylthio)-1,3,4-oxadiazole |
| 55 | | (4-bromo-3,5-dimethyl-1H-pyrazol-1-yl)(2-((2-methylbenzyl)thio)oxazol-5-yl)methanone |
| 56 | | (4-bromo-3,5-dimethyl-1H-pyrazol-1-yl)(5-((2-isopropylphenyl)thio)furan-2-yl)methanone |
| 57 | | (4-bromo-3,5-dimethyl-1H-pyrazol-1-yl)(5-(2-isopropylphenoxy)furan-2-yl)methanone |

TABLE 6-continued

| | | |
|---|---|---|
| 58 | | 2-(([1,1'-biphenyl]-2-ylmethyl)thio)-5-((4-bromophenoxy)methyl)-1,3,4-oxadiazole |
| 59 | | 2-(([1,1'-biphenyl]-2-ylmethyl)sulfinyl)-5-(4-bromobenzyl)-1,3,4-oxadiazole |
| 60 | | 2-(([1,1'-biphenyl]-2-ylmethyl)sulfonyl)-5-(4-bromobenzyl)-1,3,4-oxadiazole |

TABLE 7

| | | |
|---|---|---|
| 61 | | 5-(([1,1'-biphenyl]-2-ylmethyl)thio)-N-(4-bromo-2,6-dimethylphenyl)-1,3,4-oxadiazol-2-amine |
| 62 | | 5-(([1,1'-biphenyl]-2-ylmethyl)thio)-N-(4-bromo-3-methylphenyl)-1,3,4-oxadiazol-2-amine |
| 63 | | 5-(([1,1'-biphenyl]-2-ylmethyl)sulfinyl)-N-(4-bromophenyl)-1,3,4-oxadiazol-2-amine |

TABLE 7-continued

| | | |
|---|---|---|
| 64 | 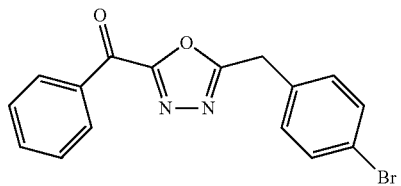 [SMILES: O=C(c1ccccc1)c1nnc(Cc2ccc(Br)cc2)o1] | (5-(4-bromobenzyl)-1,3,4-oxadiazol-2-yl)(phenyl)methanone |
| 65 | 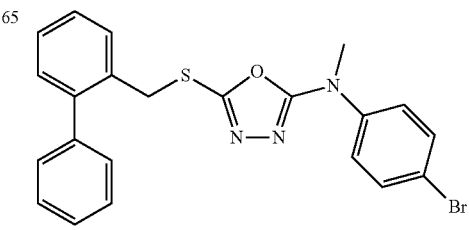 | 5-(([1,1'-biphenyl]-2-ylmethyl)thio)-N-(4-bromophenyl)-N-methyl-1,3,4-oxadiazol-2-amine |
| 66 | 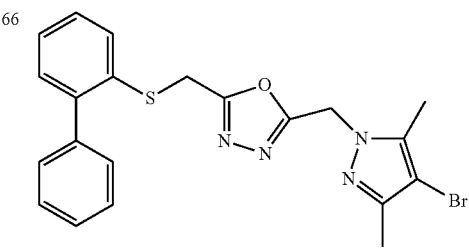 | 2-((4-bromo-3,5-dimethyl-1H-pyrazol-1-yl)methyl)-5-(((2-isopropylphenyl)thio)methyl)-1,3,4-oxadiazole |
| 67 | 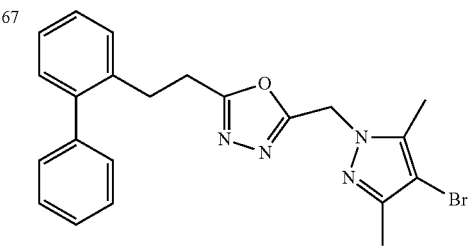 | 2-((4-bromo-3,5-dimethyl-1H-pyrazol-1-yl)methyl)-5-(2-isopropylphenethyl)-1,3,4-oxadiazole |
| 68 | 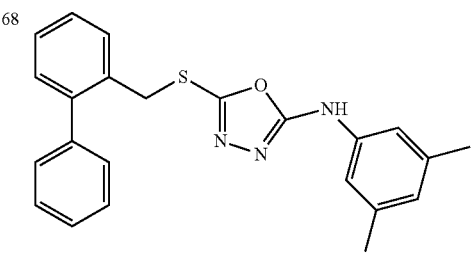 | 5-(([1,1'-biphenyl]-2-ylmethyl)thio)-N-(3,5-dimethylphenyl)-1,3,4-oxadiazol-2-amine |
| 69 | 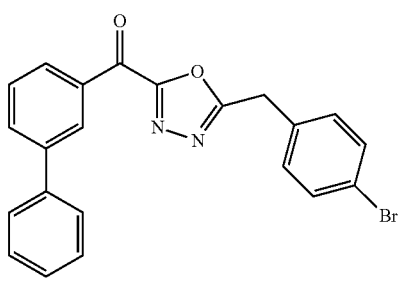 [SMILES: O=C(c1cccc(-c2ccccc2)c1)c1nnc(Cc2ccc(Br)cc2)o1] | [1,1'-biphenyl]-3-yl(5-(4-bromobenzyl)-1,3,4-oxadiazol-2-yl)methanone |

TABLE 7-continued

| 70 | [1,1'-biphenyl]-3-yl(5-(4-bromobenzyl)-1,3,4-oxadiazol-2-yl)methanol |

TABLE 8

| 71 | 5-(([1,1'-biphenyl]-2-ylmethyl)thio)-N-phenyl-1,3,4-oxadiazol-2-amine |
| 72 | 5-(([1,1'-biphenyl]-2-ylmethyl)thio)-N-(4-bromophenyl)-1,3,4-oxadiazole-2-carboxamide |
| 73 | 2-(([1,1'-biphenyl]-2-ylmethyl)thio)-5-(1-phenylethyl)-1,3,4-oxadiazole |
| 74 | 2-(([1,1'-biphenyl]-2-ylmethyl)thio)-5-((4-bromophenyl)difluoromethyl)-1,3,4-oxadiazole |
| 75 | 4-bromo-N-((5-(2-methylbenzyl)thio)furan-2-yl)methyl)aniline |

TABLE 8-continued

| 76 | [structure] | (5-((2,6-dimethylphenyl)amino)-1,3,4-oxadiazol-2-yl)phenyl)methanone |
| --- | --- | --- |
| 77 | [structure] | (5-((2,6-dimethylphenyl)amino)-1,3,4-oxadiazol-2-yl)phenyl)methanol |
| 78 | [structure] | (3-chloro-4-fluorophenyl)(5-((2,6-dimethylphenyl)amino)-1,3,4-oxadiazol-2-yl)methanone |
| 79 | [structure] | (3-chloro-4-fluorophenyl)(5-((2,6-dimethylphenyl)amino)-1,3,4-oxadiazol-2-yl)methanol |
| 80 | [structure] | 2-benzyl-5-(methylthio)-1,3,4-oxadiazole |

TABLE 9

| 81 | [structure] | (E)-2-(2-isopropylstyryl)-5-(4-(trifluoromethoxy)benzyl)-1,3,4-oxadiazole |
| --- | --- | --- |
| 82 | [structure] | (E)-2-(4-bromobenzyl)-5-(2-isopropylstyryl)-1,3,4-oxadiazole |

TABLE 9-continued

| | Structure | Name |
|---|---|---|
| 83 | 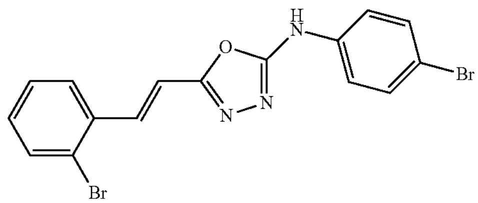 [SMILES: Brc1ccc(Nc2nnc(/C=C/c3ccccc3Br)o2)cc1] | (E)-N-(4-bromophenyl)-5-(2-bromostyryl)-1,3,4-oxadiazol-2-amine |
| 84 | 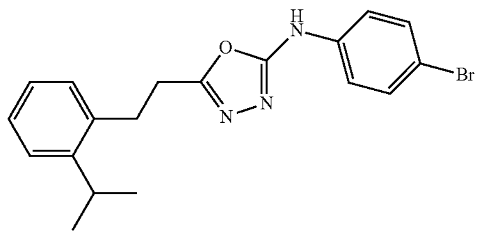 [SMILES: CC(C)c1ccccc1CCc1nnc(Nc2ccc(Br)cc2)o1] | N-(4-bromophenyl)-5-(2-isopropylphenethyl)-1,3,4-oxadiazol-2-amine |
| 85 | 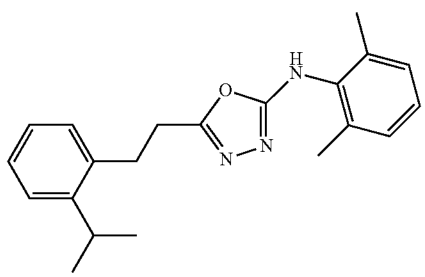 [SMILES: Cc1cccc(C)c1Nc1nnc(CCc2ccccc2C(C)C)o1] | N-(2,6-dimethylphenyl)-5-(2-isopropylphenethyl)-1,3,4-oxadiazol-2-amine |
| 86 | 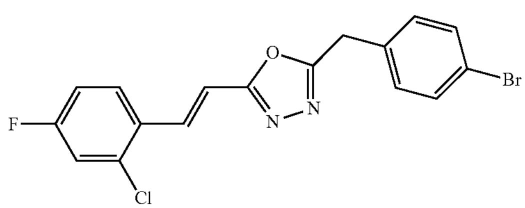 [SMILES: Fc1ccc(/C=C/c2nnc(Cc3ccc(Br)cc3)o2)c(Cl)c1] | (E)-2-(4-bromobenzyl)-5-(2-chloro-4-fluorostyryl)-1,3,4-oxadiazole |
| 87 | 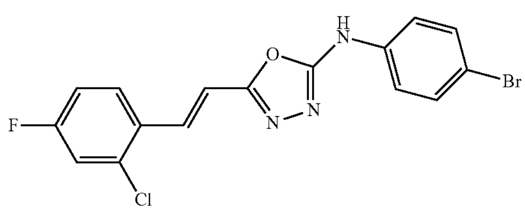 [SMILES: Fc1ccc(/C=C/c2nnc(Nc3ccc(Br)cc3)o2)c(Cl)c1] | (E)-N-(4-bromophenyl)-5-(2-chloro-4-fluorostyryl)-1,3,4-oxadiazol-2-amine |
| 88 | 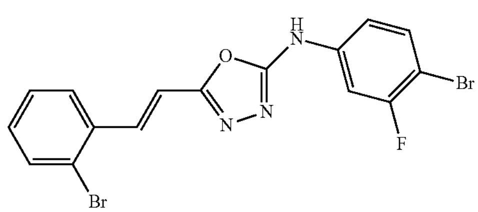 [SMILES: Fc1cc(Nc2nnc(/C=C/c3ccccc3Br)o2)ccc1Br] | (E)-N-(4-bromo-3-fluorophenyl)-5-(2-bromostyryl)-1,3,4-oxadiazol-2-amine |
| 89 | 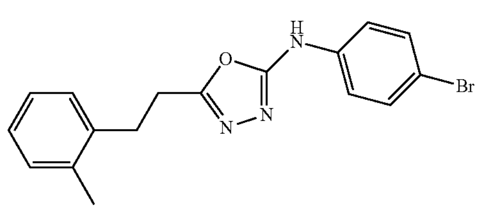 [SMILES: Cc1ccccc1CCc1nnc(Nc2ccc(Br)cc2)o1] | N-(4-bromophenyl)-5-(2-methylphenethyl)-1,3,4-oxadiazol-2-amine |

US 11,149,033 B2
93                                                                                    94
TABLE 9-continued
| 90 | 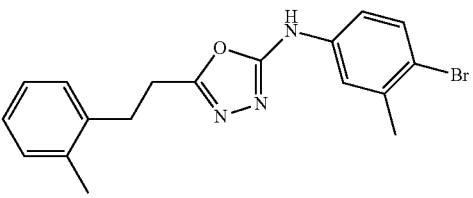 [SMILES: Cc1cc(Nc2nnc(CCc3ccccc3C)o2)ccc1Br] | N-(4-bromo-3-methylphenyl)-5-(2-methylphenethyl)-1,3,4-oxadiazol-2-amine |
TABLE 10
| 91 | 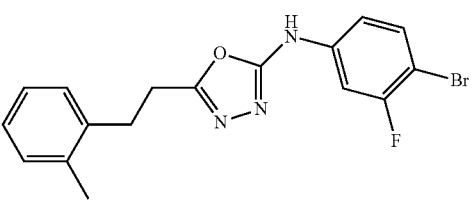 [SMILES: Cc1ccccc1CCc1nnc(Nc2ccc(Br)c(F)c2)o1] | N-(4-bromo-3-fluorophenyl)-5-(2-methylphenethyl)-1,3,4-oxadiazol-2-amine |
| 92 | 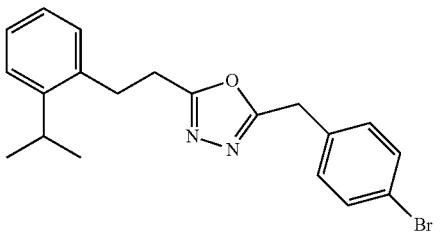 [SMILES: CC(C)c1ccccc1CCc1nnc(Cc2ccc(Br)cc2)o1] | 2-(4-bromobenzyl)-5-(2-isopropylphenethyl)-1,3,4-oxadiazole |
| 93 | 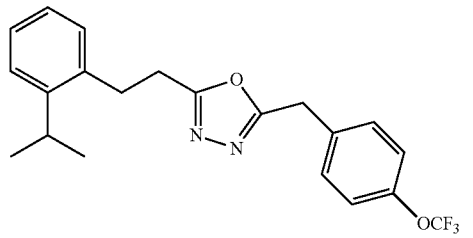 [SMILES: CC(C)c1ccccc1CCc1nnc(Cc2ccc(OC(F)(F)F)cc2)o1] | 2-(2-isopropylphenethyl)-5-(4-(trifluoromethoxy)benzyl)-1,3,4-oxadiazole |
| 94 | 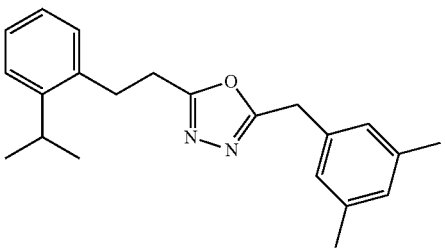 [SMILES: Cc1cc(C)cc(Cc2nnc(CCc3ccccc3C(C)C)o2)c1] | 2-(3,5-dimethylbenzyl)-5-(2-isopropylphenethyl)-1,3,4-oxadiazole |
| 95 | 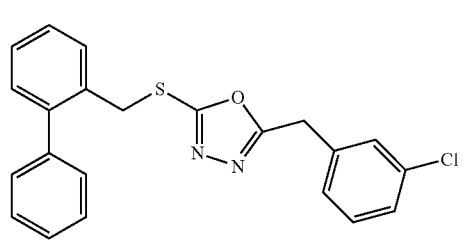 [SMILES: Clc1cccc(Cc2nnc(SCc3ccccc3-c3ccccc3)o2)c1] | 2-((([1,1'-biphenyl]-2-ylmethyl)thio)-5-(3-chlorobenzyl)-1,3,4-oxadiazole |

TABLE 10-continued

| | | |
|---|---|---|
| 96 | | 2-(([1,1'-biphenyl]-2-ylmethyl)sulfonyl)-5-((4-bromo-3,5-dimethyl-1H-pyraozl-1-yl)methyl)-1,3,4-oxadiazole |
| 97 | | 2-(([1,1'-biphenyl]-2-ylmethyl)thio)-5-(methoxy(phenyl)methyl)-1,3,4-oxadiazole |
| 98 | | 2-(4-bromobenzyl)-5-(naphthalen-2-yl)-1,3,4-oxadiazole |
| 99 | | 4-bromo-N-((2-((2-methylbenzyl)thio)oxazol-5-yl)methyl)aniline |
| 100 | | 2-(4-bromobenzyl)-5-(naphthalen-1-ylmethyl)-1,3,4-oxadiazole |

TABLE 11

| | | |
|---|---|---|
| 101 | | 2-(3-bromobenzyl)-5-(2-isopropylphenethyl)-1,3,4-oxadiazole |

TABLE 11-continued
| 102 | 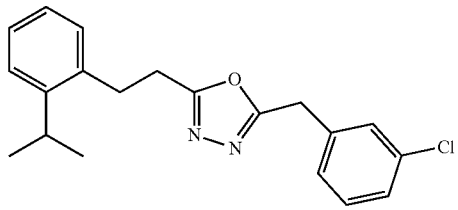 [SMILES: CC(C)c1ccccc1CCc1nnc(Cc2cccc(Cl)c2)o1] | 2-(3-chlorobenzyl)-5-(2-isopropylphenethyl)-1,3,4-oxadiazole |
| 103 | 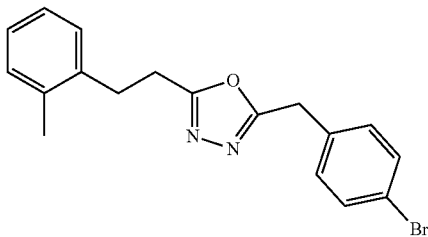 [SMILES: Cc1ccccc1CCc1nnc(Cc2ccc(Br)cc2)o1] | 2-(4-bromobenzyl)-5-(2-methylphenethyl)-1,3,4-oxadiazole |
| 104 | 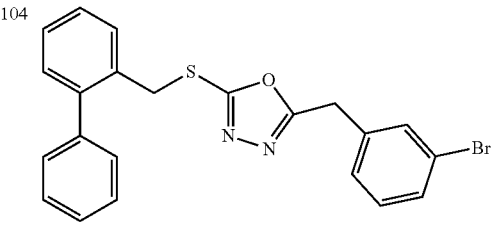 | 2-((([1,1'-biphenyl]-2-ylmethyl)thio)-5-(3-bromobenzyl)-1,3,4-oxadiazole |
| 105 | 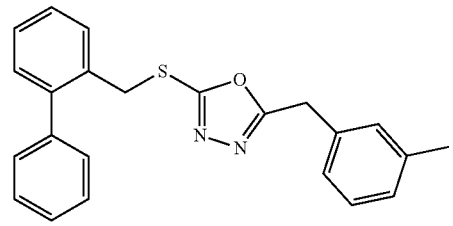 [SMILES: Cc1cccc(Cc2nnc(SCc3ccccc3-c3ccccc3)o2)c1] | 2-((([1,1'-biphenyl]-2-ylmethyl)thio)-5-(3,5-dimethylbenzyl)-1,3,4-oxadiazole |
| 106 | 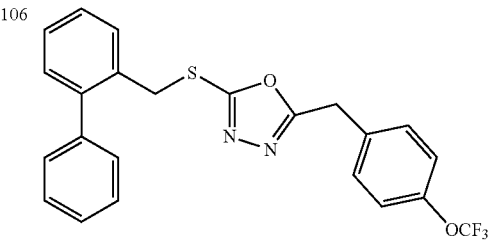 | 2-(([1,1'-biphenyl]-2-ylmethyl)thio)-5-(4-(trifluoromethoxy)benzyl)-1,3,4-oxadiazole |
| 107 | 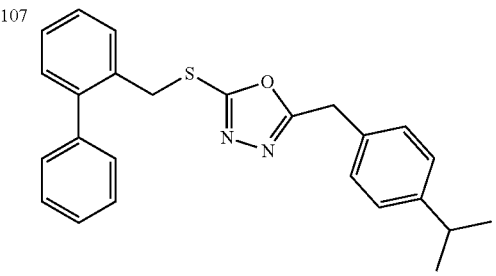 | 2-(([1,1'-biphenyl]-2-ylmethyl)thio)-5-(4-isopropylbenzyl)-1,3,4-oxadiazole |

TABLE 11-continued

| | | |
|---|---|---|
| 108 | | 2-(3-chloro-4-fluorobenzyl)-5-(2-methylphenethyl)-1,3,4-oxadiazole |
| 109 | | 2-(4-bromobenzyl)-5-((1,2,3,4-tetrahydronaphthalen-1-yl)methyl)-1,3,4-oxadiazole |
| 110 | | 2-(4-bromobenzyl)-5-(2-(o-tolyl)propyl)-1,3,4-oxadiazole |

TABLE 12

| | | |
|---|---|---|
| 111 | | 2-(4-bromobenzyl)-5-(2-cyclohexylstyryl)-1,3,4-oxadiazole |
| 112 | | 2-(4-bromobenzyl)-5-(2-cyclohexylstyryl)-1,3,4-oxadiazole |
| 113 | | 2-(3,5-dimethylbenzyl)-5-(2-isopropylstyryl)-1,3,4-oxadiazole |

TABLE 12-continued
| | | |
|---|---|---|
| 114 | 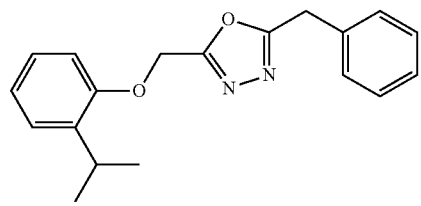 [SMILES: CC(C)c1ccccc1OCc1nnc(Cc2ccccc2)o1] | 2-benzyl-5-((2-isopropylphenoxy)methyl)-1,3,4-oxadiazole |
| 115 | 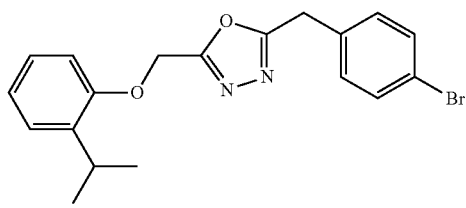 [SMILES: CC(C)c1ccccc1OCc1nnc(Cc2ccc(Br)cc2)o1] | 2-(4-bromobenzyl)-5-((2-isopropylphenoxy)methyl)-1,3,4-oxadiazole |
| 116 | 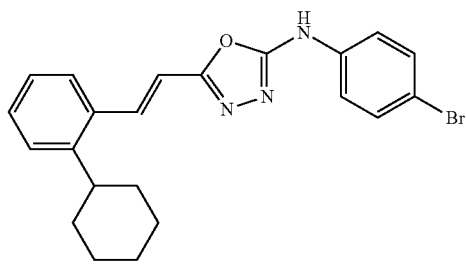 [SMILES: Brc1ccc(Nc2nnc(/C=C/c3ccccc3C3CCCCC3)o2)cc1] | (E)-N-(4-bromophenyl)-5-(2-cyclohexylstyryl)-1,3,4-oxadiazol-2-amine |
| 117 | 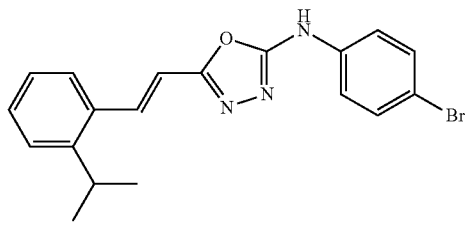 [SMILES: CC(C)c1ccccc1/C=C/c1nnc(Nc2ccc(Br)cc2)o1] | (E)-N-(4-bromophenyl)-5-(2-isopropylstyryl)-1,3,4-oxadiazol-2-amine |
| 118 | 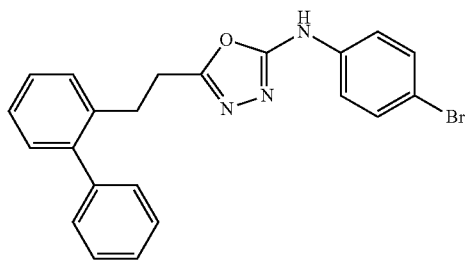 [SMILES: Brc1ccc(Nc2nnc(CCc3ccccc3-c3ccccc3)o2)cc1] | 5-(2-([1,1'-biphenyl]-2-yl)ethyl)-N-(4-bromophenyl)-1,3,4-oxadiazol-2-amine |
| 119 | 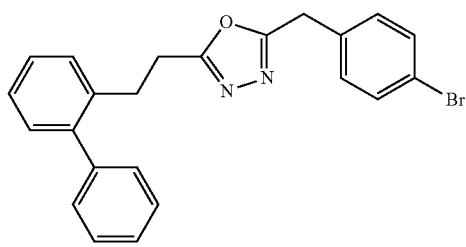 [SMILES: Brc1ccc(Cc2nnc(CCc3ccccc3-c3ccccc3)o2)cc1] | 2-(2-([1,1'-biphenyl]-2-yl)ethyl)-5-(4-bromobenzyl)-1,3,4-oxadiazole |
| 120 | 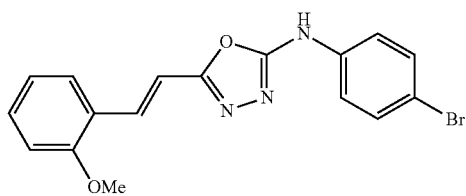 [SMILES: COc1ccccc1/C=C/c1nnc(Nc2ccc(Br)cc2)o1] | (E)-N-(4-bromophenyl)-5-(2-methoxystyryl)-1,3,4-oxadiazol-2-amine |

TABLE 13
| | | |
|---|---|---|
| 121 | 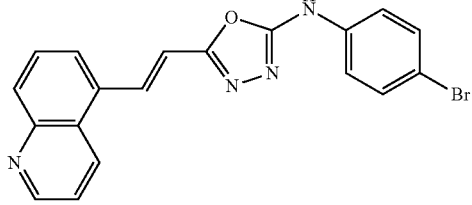 | (E)-N-(4-bromophenyl)-5-(2-(quinolin-5-yl)vinyl)-1,3,4-oxadiazol-2-amine |
| 122 | 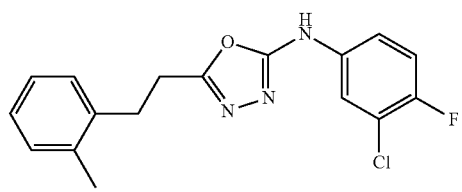 [SMILES: Cc1ccccc1CCc1nnc(Nc2ccc(F)c(Cl)c2)o1] | N-(3-chloro-4-fluorophenyl)-5-(2-methylphenethyl)-1,3,4-oxadiazol-2-amine |
| 123 | 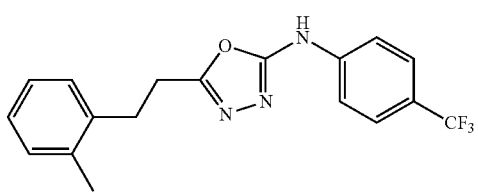 [SMILES: Cc1ccccc1CCc1nnc(Nc2ccc(C(F)(F)F)cc2)o1] | 5-(2-methylphenethyl)-N-(4-(trifluoromethyl)phenyl)-1,3,4-oxadiazol-2-amine |
| 124 | 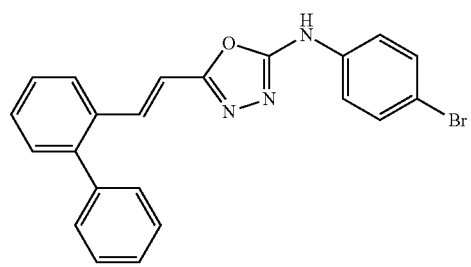 [SMILES: Brc1ccc(Nc2nnc(/C=C/c3ccccc3-c3ccccc3)o2)cc1] | (E)-5-(2-([1,1'-biphenyl]-2-yl)vinyl)-N-(4-bromophenyl)-1,3,4-oxadiazol-2-amine |
| 125 | 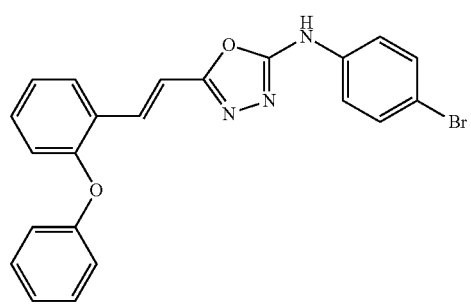 [SMILES: Brc1ccc(Nc2nnc(/C=C/c3ccccc3Oc3ccccc3)o2)cc1] | (E)-N-(4-bromophenyl)-5-(2-phenoxystyryl)-1,3,4-oxadiazol-2-amine |
| 126 | 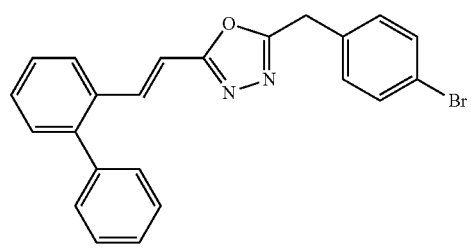 [SMILES: Brc1ccc(Cc2nnc(/C=C/c3ccccc3-c3ccccc3)o2)cc1] | (E)-2-(2-([1,1'-biphenyl]-2-yl)vinyl)-5-(4-bromobenzyl)-1,3,4-oxadiazole |

TABLE 13-continued

| | | |
|---|---|---|
| 127 | | (E)-2-(4-bromobenzyl)-5-(2-phenoxystryryl)-1,3,4-oxadiazole |
| 128 | | (E)-2-(4-bromobenzyl)-5-(2-bromostyryl)-1,3,4-oxadiazole |
| 129 | | 2-(4-bromobenzyl)-5-(1-(2-methylbenzyl)cyclopropyl)-1,3,4-oxadiazole |
| 130 | | 2-(3-bromobenzyl)-5-(2-isopropylstyryl)-1,3,4-oxadiazole |

TABLE 14

| | | |
|---|---|---|
| 131 | | 2-(3-chloro-4-fluorobenzyl)-5-(2-isopropylstyryl)-1,3,4-oxadiazole |
| 132 | | 2-(2-isopropylstyryl)-5-(naphthalen-1-ylmethyl)-1,3,4-oxadiazole |

TABLE 14-continued

| | | |
|---|---|---|
| 133 | | 2-(4-isopropylbenzyl)-5-(2-isopropylstyryl)-1,3,4-oxadiazole |
| 134 | | 2-(4-bromobenzyl)-5-(2,6-dimethylstyryl)-1,3,4-oxadiazole |
| 135 | | 2-(4-bromobenzyl)-5-(2,6-dimethylphenethyl)-1,3,4-oxadiazole |
| 136 | | 2-([1,1'-biphenyl]-4-ylmethyl)-5-(2-isopropylstyryl)-1,3,4-oxadiazole |
| 137 | | 2-(4-bromobenzyl)-5-(1-(o-tolyl)propan-2-yl)-1,3,4-oxadiazole |
| 138 | | 2-(4-bromobenzyl)-5-(1-(o-tolyl)prop-1-en-2-yl)-1,3,4-oxadiazole |

TABLE 14-continued
| | | |
|---|---|---|
| 139 | 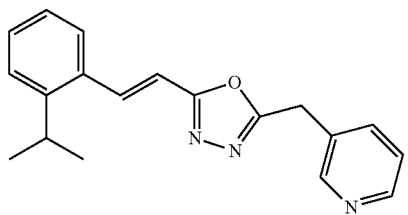 [SMILES: CC(C)c1ccccc1/C=C/c1nnc(Cc2cccnc2)o1] | 2-([1,1'-biphenyl]-4-ylmethyl)-5-(2-isopropylstyryl)-1,3,4-oxadiazole |
| 140 | 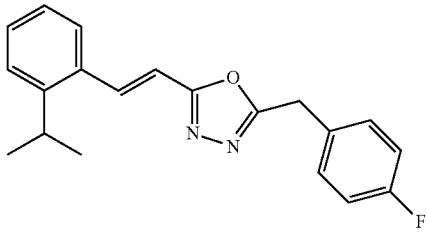 [SMILES: CC(C)c1ccccc1/C=C/c1nnc(Cc2ccc(F)cc2)o1] | 2-(4-bromobenzyl)-5-(1-(o-tolyl)propan-2-yl)-1,3,4-oxadiazole |
TABLE 15
| | | |
|---|---|---|
| 141 | 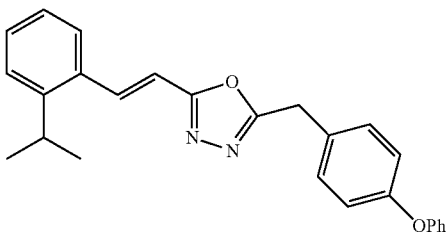 [SMILES: CC(C)c1ccccc1/C=C/c1nnc(Cc2ccc(Oc3ccccc3)cc2)o1] | 2-(4-bromobenzyl)-5-(1-(o-tolyl)prop-1-en-2-yl)-1,3,4-oxadiazole |
| 142 | 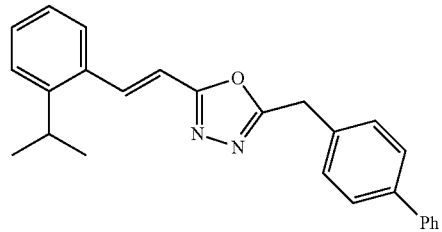 [SMILES: CC(C)c1ccccc1/C=C/c1nnc(Cc2ccc(-c3ccccc3)cc2)o1] | 2-([1,1'-biphenyl]-4-ylmethyl)-5-(2-isopropylstyryl)-1,3,4-oxadiazole |
| 143 | 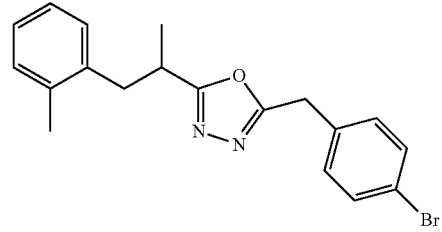 [SMILES: Cc1ccccc1CC(C)c1nnc(Cc2ccc(Br)cc2)o1] | 2-(4-bromobenzyl)-5-(1-(o-tolyl)propan-2-yl)-1,3,4-oxadiazole |
| 144 | 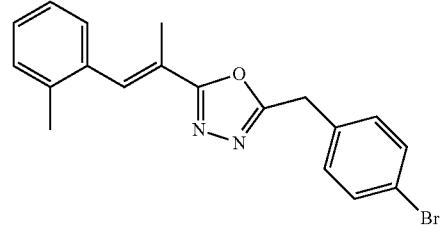 [SMILES: C/C(=C\c1ccccc1C)c1nnc(Cc2ccc(Br)cc2)o1] | 2-(4-bromobenzyl)-5-(1-o-tolyl)prop-1-en-2-yl)-1,3,4-oxadiazole |

TABLE 15-continued
| 145 | 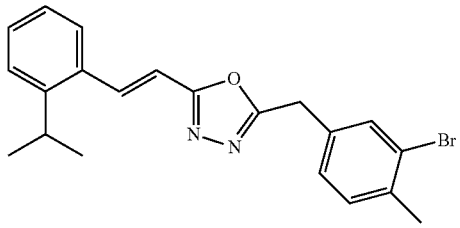 [SMILES: Cc1ccc(Cc2nnc(/C=C/c3ccccc3C(C)C)o2)cc1Br] | 2-(3-bromo-4-methylbenzyl)-5-(2-isopropylstyryl)-1,3,4-oxadiazole |
| 146 | 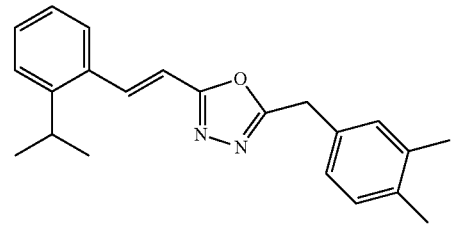 [SMILES: Cc1ccc(Cc2nnc(/C=C/c3ccccc3C(C)C)o2)cc1C] | 2-(3,4-dimethylbenzyl)-5-(2-isopropylstyryl)-1,3,4-oxadiazole |
| 147 | 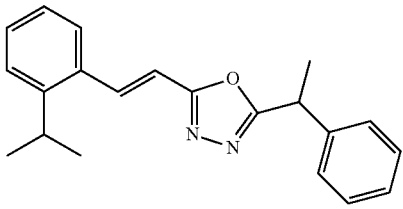 [SMILES: CC(C)c1ccccc1/C=C/c1nnc(C(C)c2ccccc2)o1] | 2-(2-isopropylstyryl)-5-(1-phenylethyl)-1,3,4-oxadiazole |
| 148 | 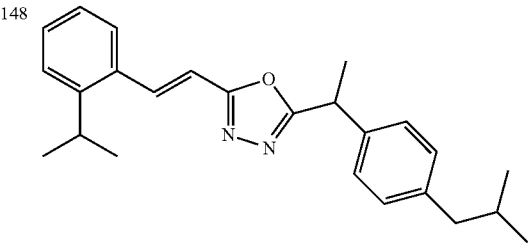 | 2-(1-(4-isobutylphenyl)ethyl)-5-(2-isopropylstyryl)-1,3,4-oxadiazole |
| 149 | 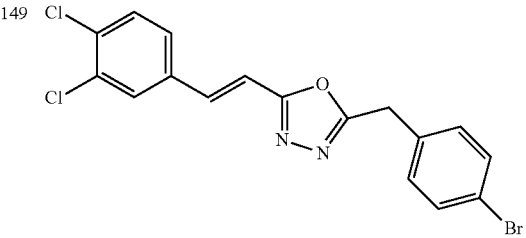 | 2-(4-bromobenzyl)-5-(3,4-dichlorostyryl)-1,3,4-oxadiazole |
| 150 | 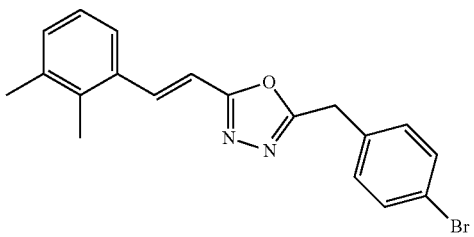 [SMILES: Cc1cccc(/C=C/c2nnc(Cc3ccc(Br)cc3)o2)c1C] | 2-(4-bromobenzyl)-5-(2,3-dimethylstyryl)-1,3,4-oxadiazole |

TABLE 16

| | | |
|---|---|---|
| 151 | *(structure)* | 2-(4-bromobenzyl)-5-(3-isopropylstyryl)-1,3,4-oxadiazole |
| 152 | *(structure)* | 2-(4-bromobenzyl)-5-(2-chloro-3-(trifluoromethyl)styryl)-1,3,4-oxadiazole |
| 153 | *(structure)* | 2-(4-bromobenzyl)-5-(2-(4'-chloro-[1,1'-biphenyl]-2-yl)vinyl)-1,3,4-oxadiazole |
| 154 | *(structure)* | 2-(4-bromobenzyl)-5-(4-isopropylstyryl)-1,3,4-oxadiazole |
| 155 | *(structure)* | 2-(4-bromobenzyl)-5-(2-(4-fluorophenoxy)styryl)-1,3,4-oxadiazole |
| 156 | *(structure)* | 2-(benzofuran-2-yl)-5-(4-bromobenzyl)-1,3,4-oxadiazole |
| 157 | *(structure)* | 2-(4-bromobenzyl)-5-(5-chlorobenzofuran-2-yl)-1,3,4-oxadiazole |

TABLE 16-continued
| 158 | 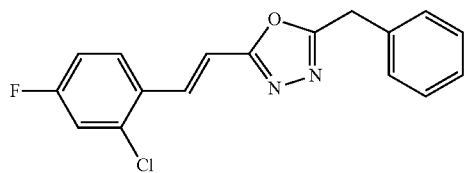 [SMILES: Fc1ccc(/C=C/c2nnc(Cc3ccccc3)o2)c(Cl)c1] | (E)-2-benzyl-5-(2-chloro-4-fluorostyryl)-1,3,4-oxadiazole |
| 159 | 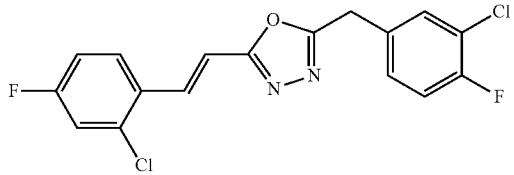 [SMILES: Fc1ccc(/C=C/c2nnc(Cc3ccc(F)c(Cl)c3)o2)c(Cl)c1] | (E)-2-(3-chloro-4-fluorobenzyl)-5-(2-chloro-4-fluorostyryl)-1,3,4-oxadiazole |
| 160 | 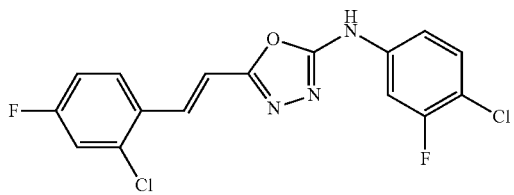 [SMILES: Fc1ccc(/C=C/c2nnc(Nc3ccc(Cl)c(F)c3)o2)c(Cl)c1] | (E)-N-(4-bromo-3-fluorophenyl)-5-(2-chloro-4-fluorostyryl)-1,3,4-oxadiazol-2-amine |
TABLE 17
| 161 | 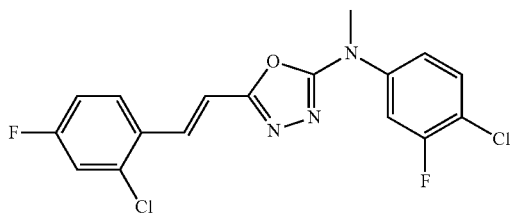 [SMILES: CN(c1ccc(Cl)c(F)c1)c1nnc(/C=C/c2ccc(F)cc2Cl)o1] | (E)-N-(4-bromo-3-fluorophenyl)-5-(2-chloro-4-fluorostyryl)-N-methyl-1,3,4-oxadiazol-2-amine |
| 162 | 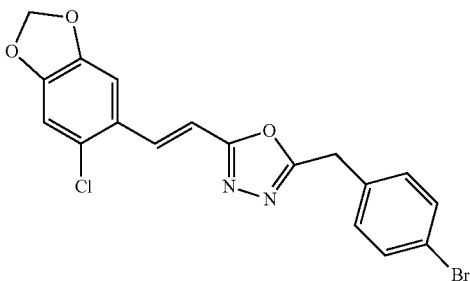 [SMILES: Clc1cc2c(cc1/C=C/c1nnc(Cc3ccc(Br)cc3)o1)OCO2] | 2-(4-bromobenzyl)-5-(2-(6-chlorobenzo[d][1,3]dioxol-5-yl)vinyl)-1,3,4-oxadiazole |
| 163 | 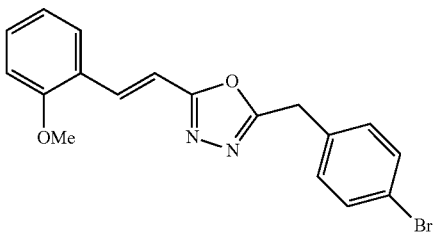 [SMILES: COc1ccccc1/C=C/c1nnc(Cc2ccc(Br)cc2)o1] | 2-(4-bromobenzyl)-5-(2-methoxystyryl)-1,3,4-oxadiazole |

TABLE 17-continued
| 164 | 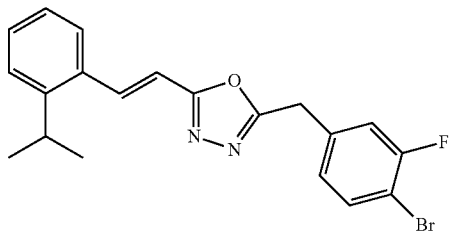 [SMILES: CC(C)c1ccccc1/C=C/c1nnc(Cc2ccc(Br)c(F)c2)o1] | 2-(4-bromo-3-fluorobenzyl)-5-(2-isopropylstyryl)-1,3,4-oxadiazole |
| 165 | 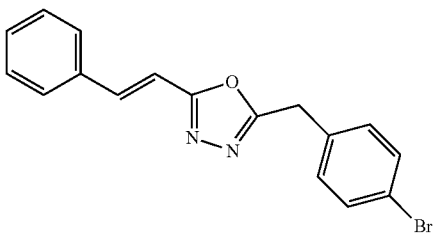 [SMILES: Brc1ccc(Cc2nnc(/C=C/c3ccccc3)o2)cc1] | 2-(4-bromobenzyl)-5-styryl-1,3,4-oxadiazole |
| 166 | 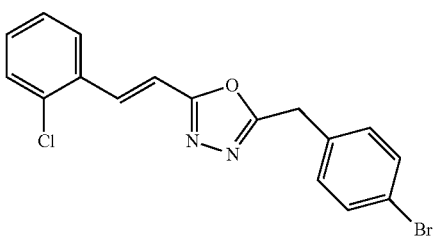 [SMILES: Clc1ccccc1/C=C/c1nnc(Cc2ccc(Br)cc2)o1] | 2-(4-bromobenzyl)-5-(2-chlorostyryl)-1,3,4-oxadiazole |
| 167 | 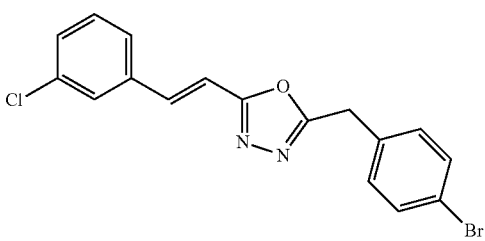 [SMILES: Clc1cccc(/C=C/c2nnc(Cc3ccc(Br)cc3)o2)c1] | 2-(4-(bromobenzyl)-5-(3-chlorostyryl)-1,3,4-oxadiazole |
| 168 | 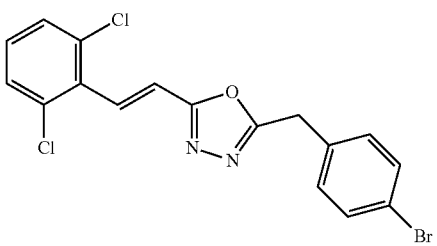 [SMILES: Clc1cccc(Cl)c1/C=C/c1nnc(Cc2ccc(Br)cc2)o1] | 2-(4-bromobenzyl)-5-(2,6-dichlorostyryl)-1,3,4-oxadiazole |
| 169 | 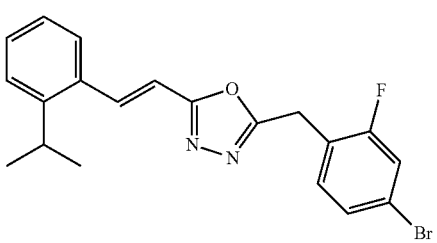 [SMILES: CC(C)c1ccccc1/C=C/c1nnc(Cc2ccc(Br)cc2F)o1] | 2-(4-bromo-2-fluorobenzyl)-5-(2-isopropylstyryl)-1,3,4-oxadiazole |

TABLE 17-continued
| 170 | 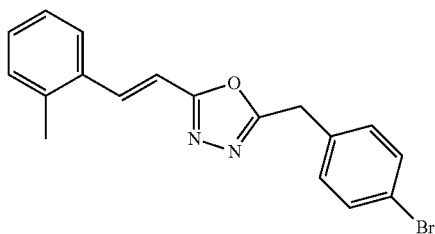 [SMILES: Cc1ccccc1/C=C/c1nnc(Cc2ccc(Br)cc2)o1] | 2-(4-bromobenzyl)-5-(2-methylstyryl)-1,3,4-oxadiazole |
TABLE 18
| 171 | 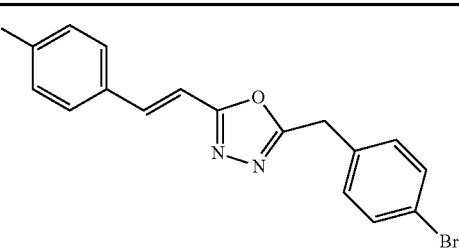 | 2-(4-bromobenzyl)-5-(4-chlorostyryl)-1,3,4-oxadiazole |
| 172 | 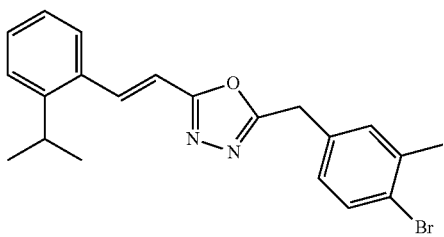 [SMILES: Cc1cc(Cc2nnc(/C=C/c3ccccc3C(C)C)o2)ccc1Br] | 2-(4-bromo-3-methylbenzyl)-5-(2-isopropylstyryl)-1,3,4-oxadiazole |
| 173 | 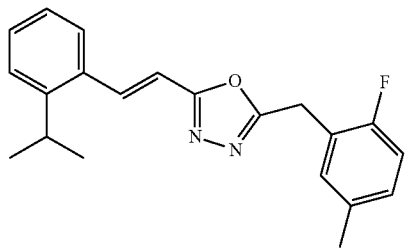 [SMILES: Cc1ccc(F)c(Cc2nnc(/C=C/c3ccccc3C(C)C)o2)c1] | 2-(2-fluoro-5-methylbenzyl)-5-(2-isopropylstyryl)-1,3,4-oxadiazole |
| 174 | 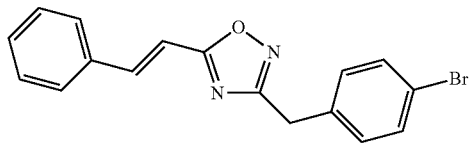 [SMILES: Brc1ccc(Cc2noc(/C=C/c3ccccc3)n2)cc1] | (E)-3-(4-bromobenzyl)-5-styryl-1,2,4-oxadiazole |
| 175 | 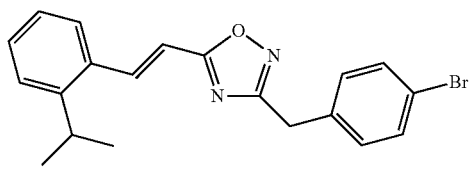 [SMILES: CC(C)c1ccccc1/C=C/c1nc(Cc2ccc(Br)cc2)no1] | (E)-3-(4-bromobenzyl)-5-(2-isopropylstyryl)-1,2,4-oxadiazole |
| 176 | 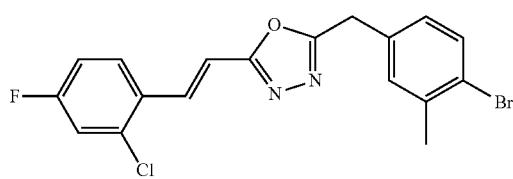 [SMILES: Cc1cc(Cc2nnc(/C=C/c3ccc(F)cc3Cl)o2)ccc1Br] | (E)-2-(4-bromo-3-methylbenzyl)-5-(2-chloro-4-fluorostyryl)-1,3,4-oxadiazole |

TABLE 18-continued

| | | |
|---|---|---|
| 177 | | (E)-2-(2-chloro-4-fluorostyryl)-5-(2-fluoro-5-methylbenzyl)-1,3,4-oxadiazole |
| 178 | | (E)-2-(3-bromobenzyl)-5-(2-chloro-4-fluorostyryl)-1,3,4-oxadiazole |
| 179 | | (E)-2-(2-chloro-4-fluorostyryl)-5-(3-chlorobenzyl)-1,3,4-oxadiazole |
| 180 | | (E)-2-(2-chloro-4-fluorostyryl)-5-((6-chloropyridin-3-yl)methyl)-1,3,4-oxadiazole |

TABLE 19

| | | |
|---|---|---|
| 181 | | (E)-2-(3-bromo-4-methylbenzyl)-5-(2-chloro-4-fluorostyryl)-1,3,4-oxadiazole |
| 182 | | (E)-2-(2-chloro-4-fluorostyryl)-5-(3-isopropylbenzyl)-1,3,4-oxadiazole |
| 183 | | (E)-5-(4-bromobenzyl)-3-styryl-1,2,4-oxadiazole |
| 184 | | (E)-2-(4-bromo-3-fluorobenzyl)-5-(2-chloro-4-fluorostyryl)-1,3,4-oxadiazole |

TABLE 19-continued
| 185 | 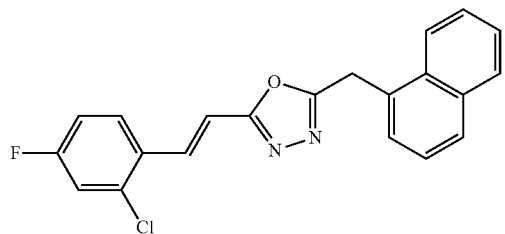 [SMILES: Fc1ccc(/C=C/c2nnc(Cc3cccc4ccccc34)o2)c(Cl)c1] | (E)-2-(2-chloro-4-fluorostyryl)-5-(naphthalen-1-ylmethyl)-1,3,4-oxadiazole |
| 186 | 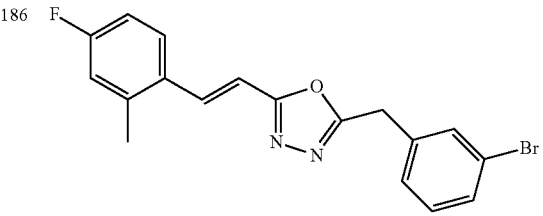 | 2-(3-bromobenzyl)-5-(4-fluoro-2-methylstyryl)-1,3,4-oxadiazole |
| 187 | 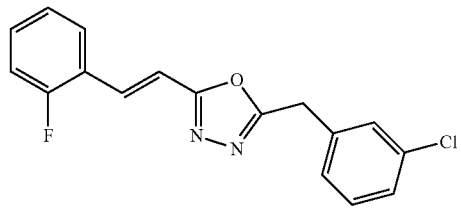 [SMILES: Fc1ccccc1/C=C/c1nnc(Cc2cccc(Cl)c2)o1] | 2-(3-chlorobenzyl)-5-(2-fluorostyryl)-1,3,4-oxadiazole |
| 188 | 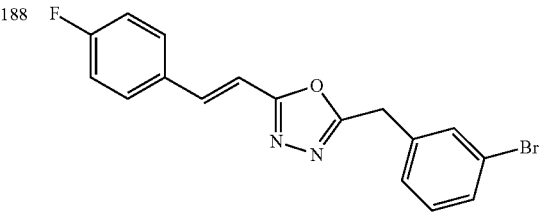 | 2-(3-bromobenzyl)-5-(4-fluorostyryl)-1,3,4-oxadiazole |
| 189 | 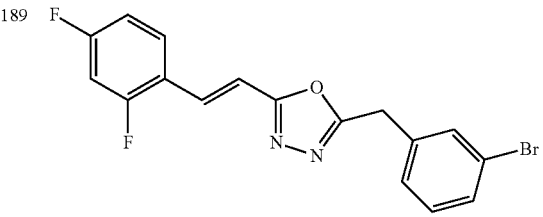 | 2-(3-bromobenzyl)-5-(2,4-difluorostyryl)-1,3,4-oxadiazole |
| 190 | 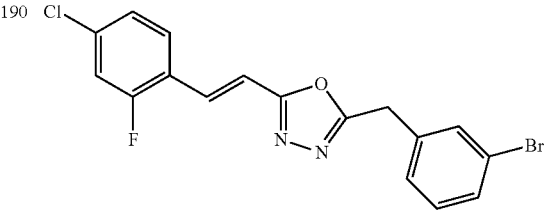 | 2-(3-bromobenzyl)-5-(4-chloro-2-fluorostyryl)-1,3,4-oxadiazole |

TABLE 20

| | | |
|---|---|---|
| 191 | *[structure]* | 2-(3-bromobenzyl)-5-(3,4-difluorostyryl)-1,3,4-oxadiazole |
| 192 | *[structure]* | 2-(3-bromobenzyl)-5-(2,4-dichlorostyryl)-1,3,4-oxadiazole |
| 193 | *[structure]* | 2-(3-bromobenzyl)-5-(2-chloro-5-fluorostyryl)-1,3,4-oxadiazole |
| 194 | *[structure]* | 2-(3-bromobenzyl)-5-(2-chloro-3-fluorostyryl)-1,3,4-oxadiazole |
| 195 | *[structure]* | 2-(3-bromobenzyl)-5-(2-chloro-4-methylstyryl)-1,3,4-oxadiazole |
| 196 | *[structure]* | 2-benzyl-5-(2-isopropylstyryl)-1,3,4-oxadiazole |
| 197 | *[structure]* | 2-(4-bromobenzyl)-5-(2-(naphthalen-1-yl)vinyl)-1,3,4-oxadiazole |

TABLE 20-continued

| | | |
|---|---|---|
| 198 | (structure) | 2-(3-bromobenzyl)-5-(2-methyl-4-(trifluoromethyl)styryl)-1,3,4-oxadiazole |
| 199 | (structure) | 2-(3-bromobenzyl)-5-(2-chloro-5-(trifluoromethyl)styryl)-1,3,4-oxadiazole |
| 200 | (structure) | 2-(3-bromobenzyl)-5-(2,4-dimethylstyryl)-1,3,4-oxadiazole |

TABLE 21

| | | |
|---|---|---|
| 201 | (structure) | (E)-3-((5-(2-chloro-4-fluorostyryl)-1,3,4-oxadiazol-2-yl)methyl)phenol |
| 202 | (structure) | (E)-2-(2-chloro-4-fluorostyryl)-5-(3-methoxybenzyl)-1,3,4-oxadiazole |
| 203 | (structure) | (E)-2-(2-chloro-4-fluorostyryl)-5-((2-methyl-1H-benzo[d]imidazol-1-yl)methyl)-1,3,4-oxadiazole |

TABLE 21-continued

| | | |
|---|---|---|
| 204 | | E)-2-(3-bromobenzyl)-5-(2-(2-methylpyridin-3-yl)vinyl)-1,3,4-oxadiazole |
| 205 | | (E)-2-((5-bromopyridin-3-yl)methyl)-5-(2-chloro-4-fluorostyryl)-1,3,4-oxadiazole |
| 206 | | (E)-2-(2-chloro-4-fluorostyryl)-5-((4-chloropyridin-2-yl)methyl)-1,3,4-oxadiazole |
| 207 | | 2-(3-bromo-4-fluorobenzyl)-5-(2-chloro-4-fluorostyryl)-1,3,4-oxadiazole |
| 208 | | 2-(2-chloro-4-fluorostyryl)-5-(3,4-dichlorobenzyl)-1,3,4-oxadiazole |
| 209 | | 2-(2-(5-(4-bromobenzyl)-1,3,4-oxadiazol-2-yl)vinyl)phenol |
| 210 | | 2-(3-bromobenzyl)-5-(2-methoxystyryl)-1,3,4-oxadiazole |

TABLE 22

| | | |
|---|---|---|
| 211 | 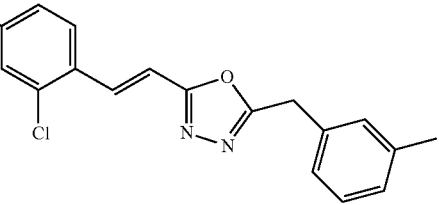 | 2-(2-chloro-4-fluorostyryl)-5-(3-methylbenzyl)-1,3,4-oxadiazole |
| 212 | 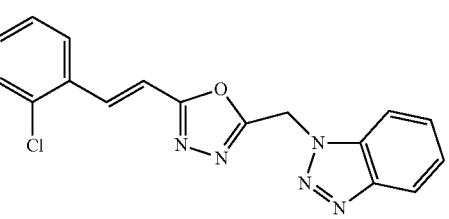 | 2-((1H-benzo[d][1,2,3]triazol-1-yl)methyl)-5-(2-chloro-4-fluorostyryl)-1,3,4-oxadiazol |
| 213 | 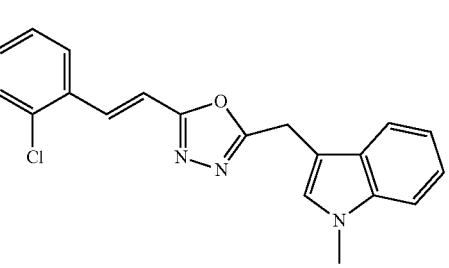 | 2-(2-chloro-4-fluorostyryl)-5-((1-methyl-1H-indol-3-yl)methyl)-1,3,4-oxadiazole |
| 214 | 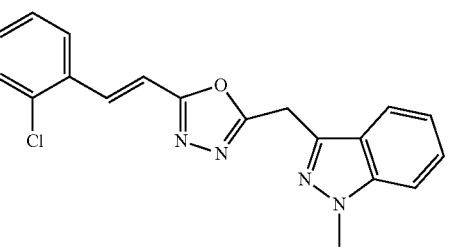 | (E)-2-(2-chloro-4-fluorostyryl)-5-((1-methyl-1H-indazol-3-yl)methyl)-1,3,4-oxadiazole |
| 215 | 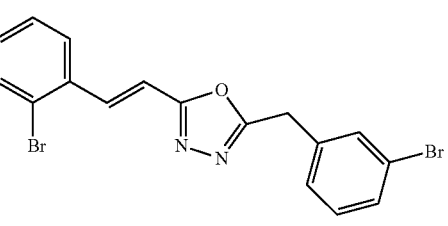 | 2-(2-bromo-4-fluorostyryl)-5-(3-bromobenzyl)-1,3,4-oxadiazole |
| 216 | 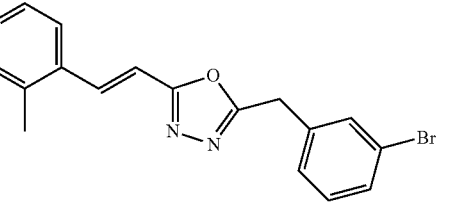 | 2-(3-bromobenzyl)-5-(2-(3-methylpyridin-4-yl)vinyl)-1,3,4-oxadiazole |
| 217 | 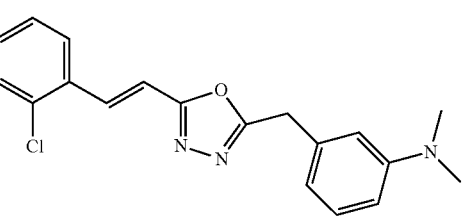 | 3-((5-(2-chloro-4-fluorostyryr)-1,3,4-oxadiazol-2-yl)methyl)-N,N-dimethylaniline |

TABLE 22-continued

| | | |
|---|---|---|
| 218 | 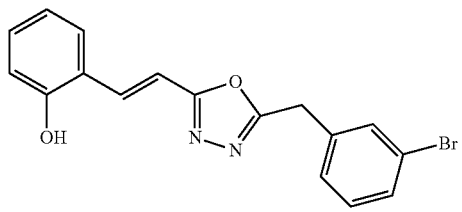 [SMILES: Oc1ccccc1/C=C/c1nnc(Cc2cccc(Br)c2)o1] | 2-(2-(5-(3-bromobenzyl)-1,3,4-oxadiazol-2-yl)vinyl)phenol |
| 219 | 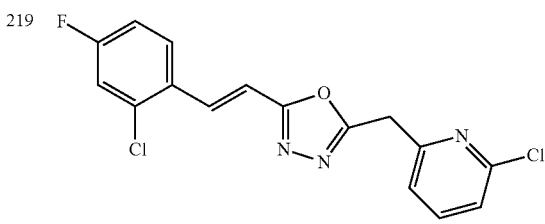 | 2-(2-chloro-4-fluorostyryl)-5-((6-chloropyridin-2-yl)methyl)-1,3,4-oxadiazole |
| 220 | 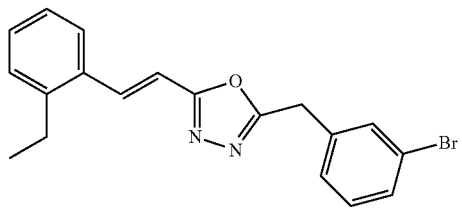 [SMILES: CCc1ccccc1/C=C/c1nnc(Cc2cccc(Br)c2)o1] | 2-(3-bromobenzyl)-5-(2-ethylstyryl)-1,3,4-oxadiazole |

TABLE 23

| | | |
|---|---|---|
| 221 | 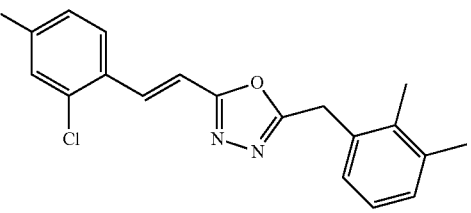 | 2-(2-chloro-4-fluorostyryl)-5-(2,3-dimethylbenzyl)-1,3,4-oxadiazole |
| 222 | 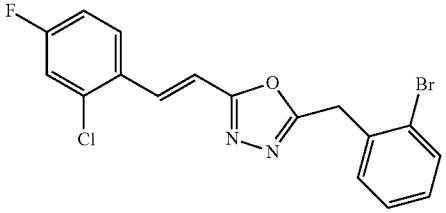 [SMILES: Fc1ccc(/C=C/c2nnc(Cc3ccccc3Br)o2)c(Cl)c1] | 2-(2-bromobenzyl)-5-(2-chloro-4-fluorostyryl)-1,3,4-oxadiazole |
| 223 | 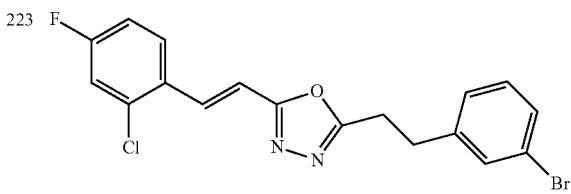 | 2-(3-bromophenethyl)-5-(2-chloro-4-fluorostyryl)-1,3,4-oxadiazole |
| 224 | 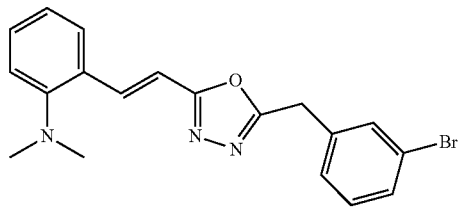 [SMILES: CN(C)c1ccccc1/C=C/c1nnc(Cc2cccc(Br)c2)o1] | 2-(2-(5-(3-bromobenzyl)-1,3,4-oxadiazol-2-yl)vinyl)-N,N-dimethylaniline |

TABLE 23-continued
| | | |
|---|---|---|
| 225 | 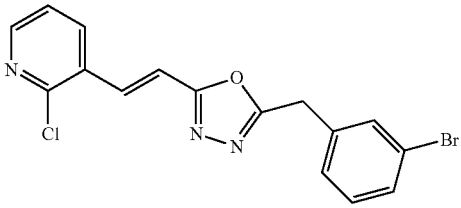 [SMILES: Clc1ncccc1/C=C/c1nnc(Cc2cccc(Br)c2)o1] | 2-(3-bromobenzyl)-5-(2-(2-chloropyridin-3-yl)vinyl)-1,3,4-oxadiazole |
| 226 | 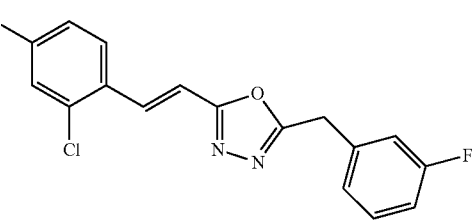 | 2-(2-chloro-4-fluorostyryl)-5-(3-fluorobenzyl)-1,3,4-oxadiazole |
| 227 | 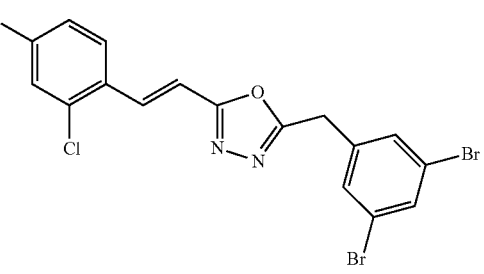 | (E)-2-(2-chloro-4-fluorostyryl)-5-(3,5-dibromobenzyl)-1,3,4-oxadiazole |
| 228 | 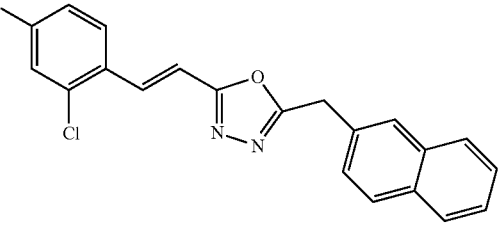 | (E)-2-(2-chloro-4-fluorostyryl)-5-(naphthalen-2-ylmethyl)-1,3,4-oxadiazole |
| 229 | 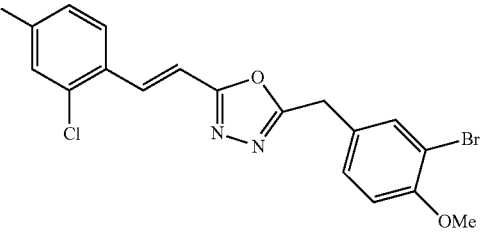 | (E)-2-(3-bromo-4-methoxybenzyl)-5-(2-chloro-4-fluorostyryl)-1,3,4-oxadiazole |
| 230 | 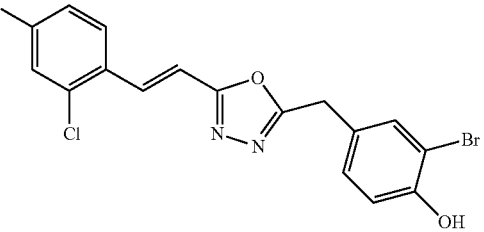 | (E)-2-bromo-4-((5-(2-chloro-4-fluorostyryl)-1,3,4-oxadiazol-2-yl)methyl)phenol |

US 11,149,033 B2

TABLE 24

| | | |
|---|---|---|
| 231 | 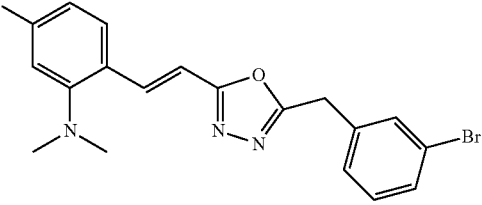 | (E)-2-(2-(5-(3-bromobenzyl)-1,3,4-oxadiazol-2-yl)vinyl)-5-fluoro-N,N-dimethylaniline |
| 232 | 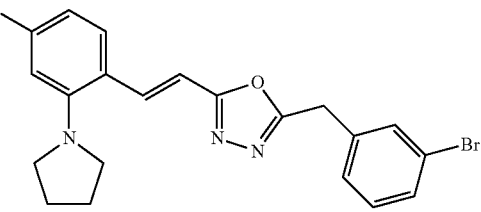 | (E)-2-(3-bromobenzyl)-5-(4-fluoro-2-(pyrrolidin-1-yl)styryl)-1,3,4-oxadiazole |
| 233 | 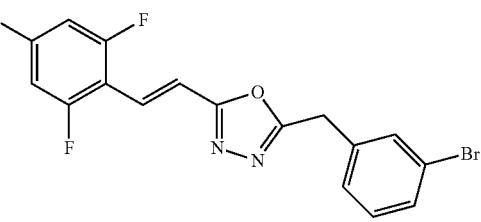 | (E)-2-(3-bromobenzyl)-5-(2,4,6-trifluorostyryl)-1,3,4-oxadiazole |
| 234 | 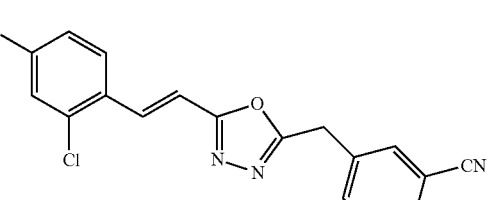 | (E)-3-((5-(2-chloro-4-fluorostyryl)-1,3,4-oxadiazol-2-yl)methyl)benzonitrile |
| 235 | 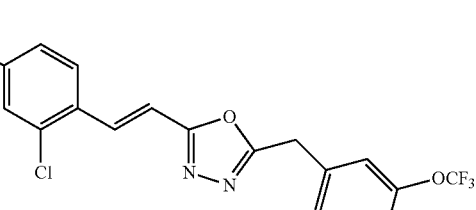 | (E)-2-(2-chloro-4-fluorostyryl)-5-(3-(trifluoromethoxy)benzyl)-1,3,4-oxadiazole |
| 236 | 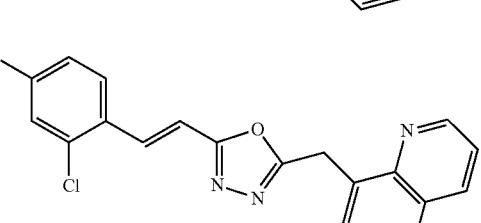 | 2-(2-chloro-4-fluorostyryl)-5-(quinolin-8-ylmethyl)-1,3,4-oxadiazole |
| 237 | 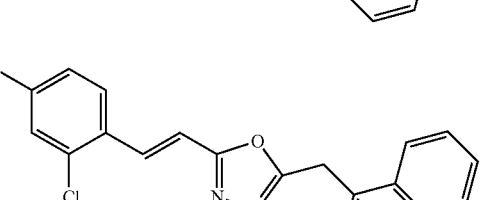 | 2-(2-chloro-4-fluorostyryl)-5-(isoquinolin-1-ylmethyl)-1,3,4-oxadiazole |

TABLE 24-continued

| | | |
|---|---|---|
| 238 | [structure] | 2-(2-chloro-4-fluorostyryl)-5-(isoquinolin-4-ylmethyl)-1,3,4-oxadiazole |
| 239 | [structure] HCl | 2-(3-bromobenzyl)-5-(2-(5-fluoropyridin-2-yl)vinyl)-1,3,4-oxadiazole |
| 240 | [structure] | 2-((6-bromopyridin-3-yl)methyl)-5-(2-chloro-4-fluorostyryl)-1,3,4-oxadiazole |

TABLE 25

| | | |
|---|---|---|
| 241 | [structure] | 2-((6-bromopyridin-3-yl)methyl)-5-(2-chloro-4-fluorostyryl)-1,3,4-oxadiazole |
| 242 | [structure] | methyl-2-(2-(5-(3-bromobenzyl)-1,3,4-oxadiazol-2-yl)vinyl)benzoate |
| 243 | [structure] | 2-(2-(5-(3-bromobenzyl)-1,3,4-oxadiazol-2-yl)vinyl)benzoic acid |

TABLE 25-continued

| | | |
|---|---|---|
| 244 | | 5-(3-bromobenzyl)-N-(2-chloro-4-fluorophenyl)-1,3,4-oxadiazole-2-carboxamide |
| 245 | | 2-(3-bromobenzyl)-5-(2-chloro-4,6-difluorostyryl)-1,3,4-oxadiazole |
| 246 | | N-(5-(3-bromobenzyl)-1,3,4-oxadiazol-2-yl)-2-chloro-4-fluorobenzenesulfonamide |
| 247 | | (E)-2-(2-chloro-4-fluorostyryl)-5-(3-(trifluoromethyl)benzyl)-1,3,4-oxadiazole |
| 248 | | (E)-2-(3-bromobenzyl)-5-(2-(1-isopropyl-1H-pyrazol-5-yl)vinyl)-1,3,4-oxadiazole |
| 249 | | (E)-2-((1H-indazol-3-yl)methyl)-5-(2-chloro-4-fluorostyryl)-1,3,4-oxadiazole |
| 250 | | (E)-2-(2-chloro-4-fluorostyryl)-5-(cyclohexylmethyl)-1,3,4-oxadiazole |

TABLE 26

| | | |
|---|---|---|
| 251 | | (E)-2-(benzo[b]thiophen-3-ylmethyl)-5-(2-chloro-4-fluorostyryl)-1,3,4-oxadiazole |
| 252 | | (E)-2-(3-bromobenzyl)-5-(4-fluoro-2-(piperidin-1-yl)styryl)-1,3,4-oxadiazole |
| 253 | | N-(3-bromophenyl)-5-(2-chloro-4-fluorostyryl)-1,3,4-oxadiazole-2-carboxamide |
| 254 | | (E)-2-(3-bromobenzyl)-5-(2-(4-chloro-1-isopropyl-1H-pyraozol-3-yl)vinyl)-1,3,4-oxadiazole |
| 255 | | 2-(2-chloro-4-fluorostyryl)-5-(3-fluoro-5-methylbenzyl)-1,3,4-oxadiazole |
| 256 | | 2-(3-bromobenzyl)-5-(2-(trifluoromethoxy)styryl)-1,3,4-oxadiazole |
| 257 | | 2-(3-bromobenzyl)-5-(2-(3-chloro-5-fluoropyridin-2-yl)vinyl)-1,3,4-oxadiazole |

TABLE 26-continued

| | | |
|---|---|---|
| 258 | (structure) | 2-(5-bromo-2-fluorobenzyl)-5-(2-chloro-4-fluorostyryl)-1,3,4-oxadiazole |
| 259 | (structure) | (E)-2-(3-bromobenzyl)-5-(2-(1-isopropyl-1H-imidazol-2-yl)vinyl)-1,3,4-oxadiazole |
| 260 | (structure) | (E)-2-(3-bromobenzyl)-5-(2,6-dichloro-4-fluorostyryl)-1,3,4-oxadiazole |

TABLE 27

| | | |
|---|---|---|
| 261 | (structure) | (E)-2-(2-chloro-4-fluorostyryl)-5-((1-isopropyl-1H-indazol-3-yl)methyl)-1,3,4-oxadiazole |
| 262 | (structure) | 2-(3-bromo-4-methylbenzyl)-5-(2,4-difluorostyryl)-1,3,4-oxadiazole |
| 263 | (structure) | 2-(3-bromo-4-fluorobenzyl)-5-(2,4-difluorostyryl)-1,3,4-oxadiazole |

TABLE 27-continued
| | | |
|---|---|---|
| 264 | 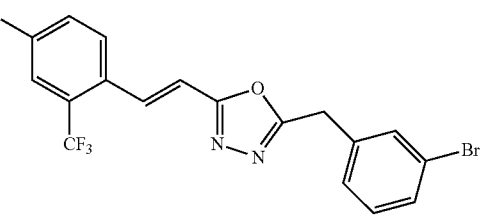 | 2-(3-bromobenzyl)-5-(4-fluoro-2-(trifluoromethyl)styryl)-1,3,4-oxadiazole |
| 265 | 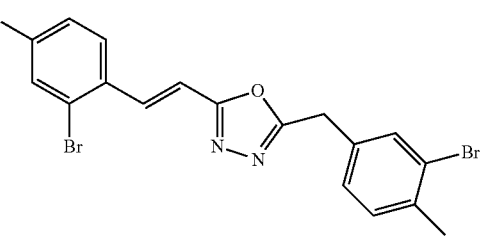 | 2-(2-bromo-4-fluorostyryl)-5-(3-bromo-4-fmethylbenzyl)-1,3,4-oxadiazole |
| 266 | 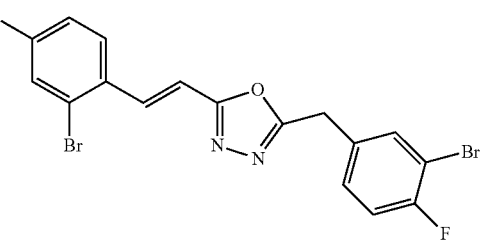 | 2-(3-bromo-4-fluorobenzyl)-5-(2-bromo-4-fluorostyryl)-1,3,4-oxadiazole |
| 267 | 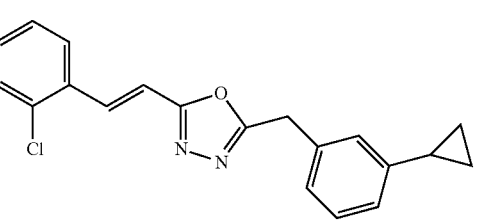 | 2-(2-chloro-4-fluorostyryl)-5-(3-cyclopropylbenzyl)-1,3,4-oxadiazole |
| 268 | 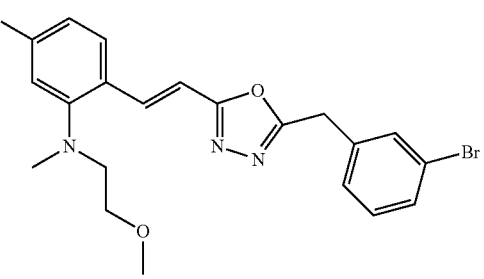 | (E)-2-(2-(5-(3-Bromobenzyl)-1,3,4-oxadiazol-2-yl)vinyl)-5-fluoro-N-(2-methoxyethyl)-N-methylaniline |
| 269 | 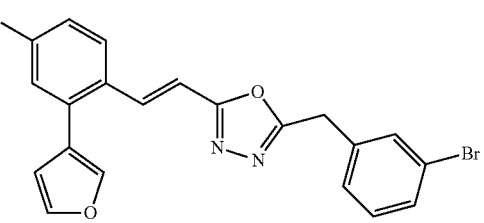 | (E)-2-(3-bromobenzyl)-5-(4-fluoro-2-(furan-3-yl)styryl)-1,3,4-oxadiazole |

TABLE 27-continued
| | | |
|---|---|---|
| 270 | 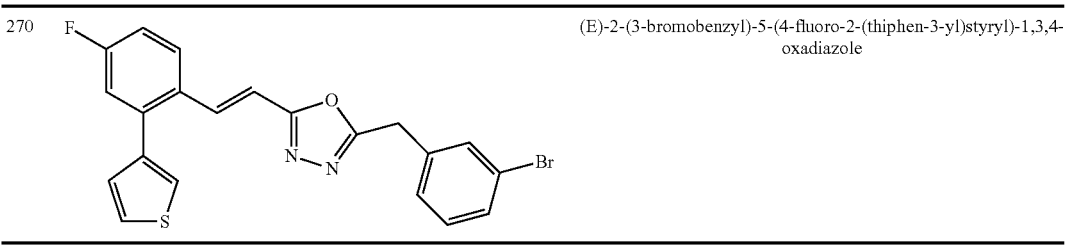 | (E)-2-(3-bromobenzyl)-5-(4-fluoro-2-(thiphen-3-yl)styryl)-1,3,4-oxadiazole |
TABLE 28
| | | |
|---|---|---|
| 271 | 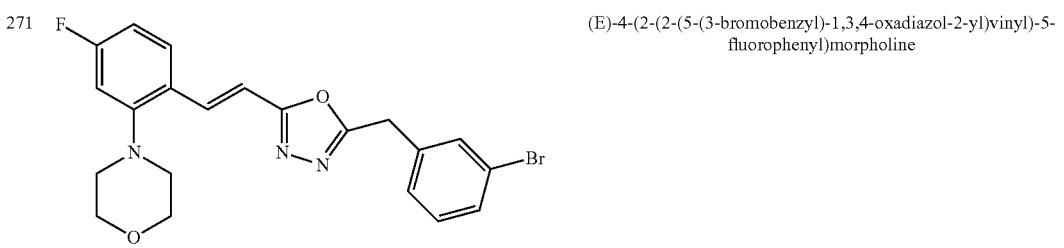 | (E)-4-(2-(2-(5-(3-bromobenzyl)-1,3,4-oxadiazol-2-yl)vinyl)-5-fluorophenyl)morpholine |
| 272 | 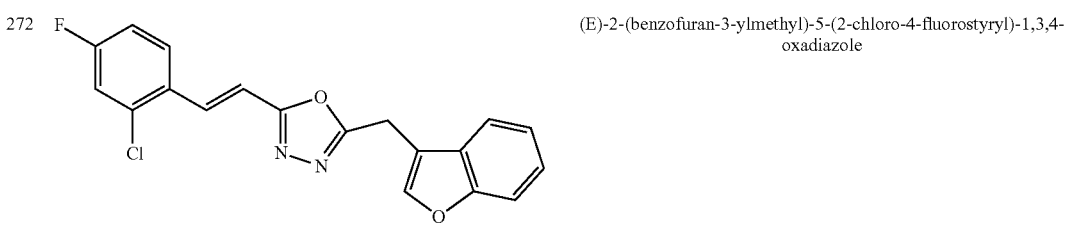 | (E)-2-(benzofuran-3-ylmethyl)-5-(2-chloro-4-fluorostyryl)-1,3,4-oxadiazole |
| 273 | 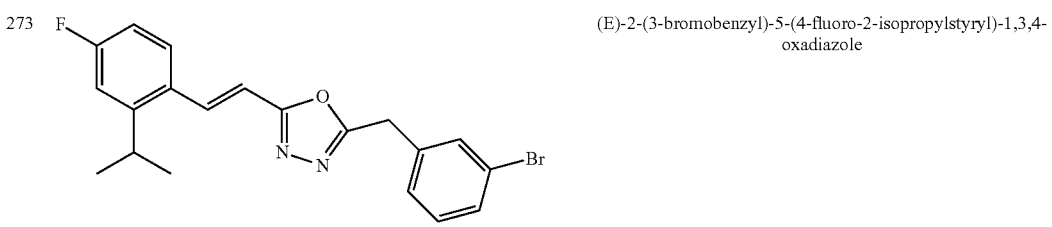 | (E)-2-(3-bromobenzyl)-5-(4-fluoro-2-isopropylstyryl)-1,3,4-oxadiazole |
| 274 | 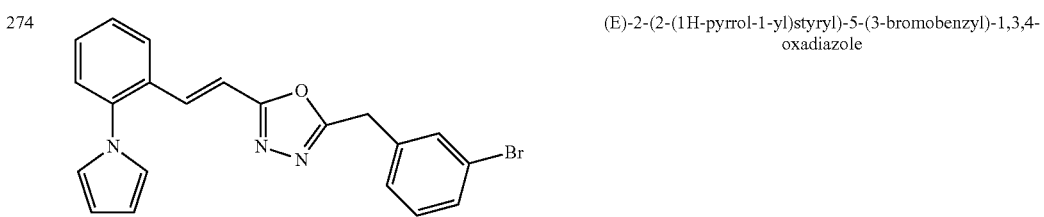 | (E)-2-(2-(1H-pyrrol-1-yl)styryl)-5-(3-bromobenzyl)-1,3,4-oxadiazole |
| 275 | 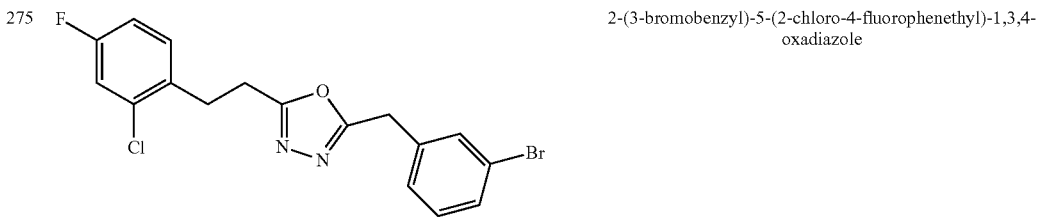 | 2-(3-bromobenzyl)-5-(2-chloro-4-fluorophenethyl)-1,3,4-oxadiazole |

TABLE 28-continued
| | | |
|---|---|---|
| 276 | 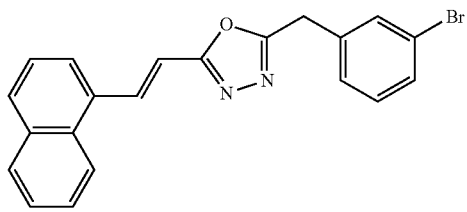 [SMILES: Brc1cccc(Cc2nnc(/C=C/c3cccc4ccccc34)o2)c1] | (E)-2-(3-bromobenzyl)-5-(2-(naphthalen-1-yl)vinyl)-1,3,4-oxadiazole |
| 277 | 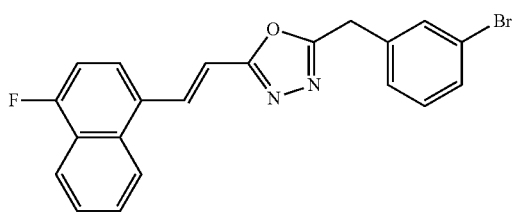 [SMILES: Fc1ccc(/C=C/c2nnc(Cc3cccc(Br)c3)o2)c2ccccc12] | (E)-2-(3-bromobenzyl)-5-(2-(4-fluoronaphthalen-1-yl)vinyl)-1,3,4-oxadiazole |
| 278 | 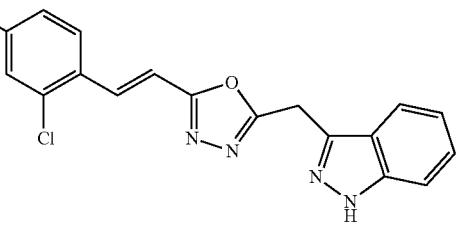 | (E)-2-((1H-indazol-3-yl)methyl)-5-(2-chloro-4-fluorostyryl)-1,3,4-oxadiazole |
| 279 | 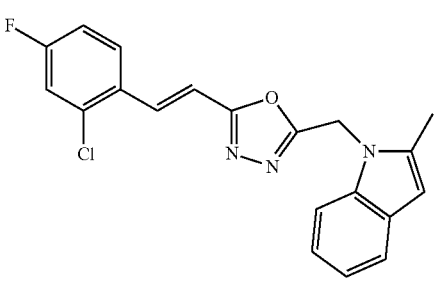 [SMILES: Cc1cc2ccccc2n1Cc1nnc(/C=C/c2ccc(F)cc2Cl)o1] | (E)-2-(2-chloro-4-fluorostyryl)-5-((2-methyl-1H-indol-1-yl)methyl)-1,3,4-oxadiazole |
| 280 | 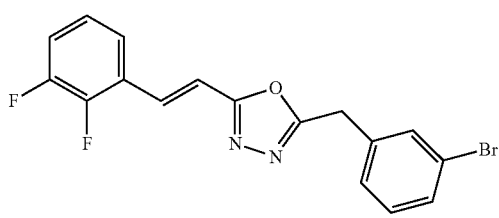 [SMILES: Fc1cccc(/C=C/c2nnc(Cc3cccc(Br)c3)o2)c1F] | 2-(3-bromobenzyl)-5-(2,3-difluorostyryl)-1,3,4-oxadiazole |
TABLE 29
| | | |
|---|---|---|
| 281 | 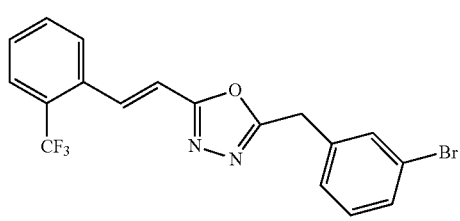 [SMILES: FC(F)(F)c1ccccc1/C=C/c1nnc(Cc2cccc(Br)c2)o1] | 2-(3-bromobenzyl)-5-(2-(trifluoromethyl)styryl)-1,3,4-oxadiazole |

TABLE 29-continued

| | | |
|---|---|---|
| 282 | | 2-(5-bromo-2-methylbenzyl)-5-(2-chloro-4-fluorostyryl)-1,3,4-oxadiazole |
| 283 | | 2-((4-bromopyridin-2-yl)methyl)-5-(2-chloro-4-fluorostyryl)-1,3,4-oxadiazole |
| 284 | | 2-(3-bromobenzyl)-5-(2-(3,5-difluoropyridin-2-yl)vinyl)-1,3,4-oxadiazole |
| 285 | | 2-(3-bromo-4-methylbenzyl)-5-(2-chloro-4-fluorophenethyl)-1,3,4-oxadiazole |
| 286 | | (E)-2-(2-chloro-4-fluorostyryl)-5-(thiophen-3-ylmethyl)-1,3,4-oxadiazole |
| 287 | | (E)-2-(3-bromobenzyl)-5-(2-(naphthalen-2-yl)vinyl)-1,3,4-oxadiazole |
| 288 | | (E)-2-(3-bromobenzyl)-5-(2,3-dimethylstyryl)-1,3,4-oxadiazole |

TABLE 29-continued
| | | |
|---|---|---|
| 289 | 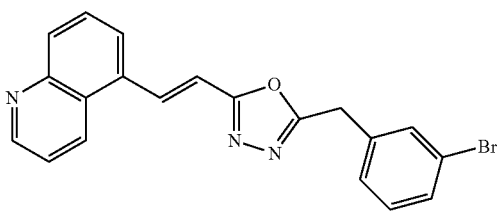 [SMILES: Brc1cccc(Cc2nnc(/C=C/c3cccc4ncccc34)o2)c1] | (E)-2-(3-bromobenzyl)-5-(2-(quinolin-5-yl)vinyl)-1,3,4-oxadiazole |
| 290 | 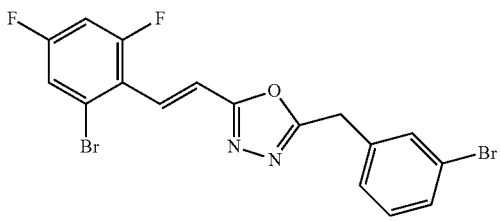 [SMILES: Fc1cc(F)c(/C=C/c2nnc(Cc3cccc(Br)c3)o2)c(Br)c1] | 2-(2-bromo-4,6-difluorostyryl)-5-(3-bromobenzyl)-1,3,4-oxadiazole |
TABLE 30
| | | |
|---|---|---|
| 291 | 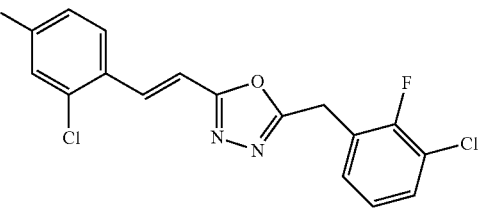 | 2-(3-chloro-2-fluorobenzyl)-5-(2-chloro-4-fluorostyryl)-1,3,4-oxadiazole |
| 292 | 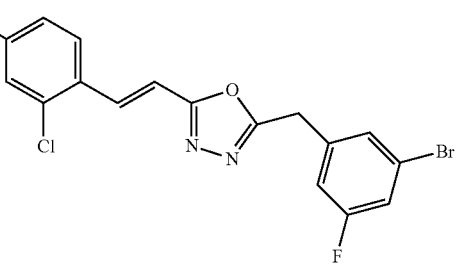 | 2-(3-bromo-5-fluorobenzyl)-5-(2-chloro-4-fluorostyryl)-1,3,4-oxadiazole |
| 293 | 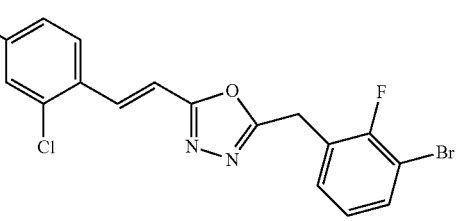 | 2-(3-bromo-2-fluorobenzyl)-5-(2-chloro-4-fluorostyryl)-1,3,4-oxadiazole |
| 294 | 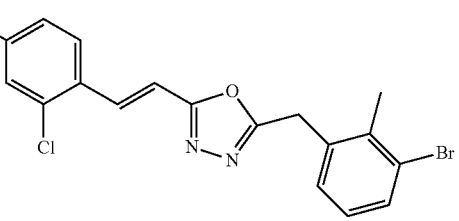 | 2-(3-bromo-2-methylbenzyl)-5-(2-chloro-4-fluorostyryl)-1,3,4-oxadiazole |

TABLE 30-continued

| | | |
|---|---|---|
| 295 | | 2-(2-chloro-4-fluorostyryl)-5-((2-methylquinolin-8-yl)methyl)-1,3,4-oxadiazole |
| 296 | | 2-(2-chloro-4-fluorostyryl)-5-((3-chloroisoquinolin-1-yl)methyl)-1,3,4-oxadiazole |
| 297 | | 2-(2-chloro-4-fluorostyryl)-5-((3-methoxyisoquinolin-1-yl)methyl)-1,3,4-oxadiazole |
| 298 | | 2-(2-chloro-4-fluorostyryl)-5-((7-methoxynaphthalen-1-yl)methyl)-1,3,4-oxadiazole |
| 299 | | 2-(2-chloro-4-fluorostyryl)-5-(3-(difluoromethyl)benzyl)-1,3,4-oxadiazole |
| 300 | | 2-(2-chloro-4-fluorostyryl)-5-(3-chloro-4-methylbenzyl)-1,3,4-oxadiazole |

TABLE 31
| | | |
|---|---|---|
| 301 | 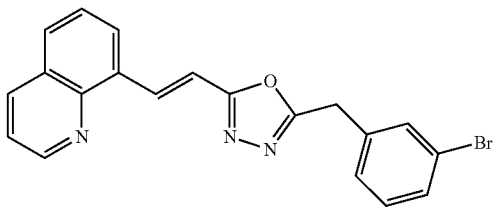 [SMILES: Brc1cccc(Cc2nnc(/C=C/c3cccc4cccnc34)o2)c1] | (E)-2-(3-bromobenzyl)-5-(2-(quinolin-8-yl)vinyl)-1,3,4-oxadiazole |
| 302 | 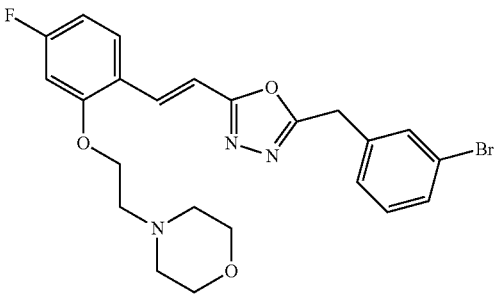 [SMILES: Fc1ccc(/C=C/c2nnc(Cc3cccc(Br)c3)o2)c(OCCN2CCOCC2)c1] | (E)-4-(2-(2-(2-(5-(3-bromobenzyl)-1,3,4-oxadiazol-2-yl)vinyl)-5-fluorophenoxy)ethyl)morpholine |
| 303 | 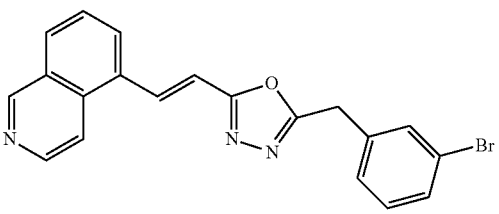 [SMILES: Brc1cccc(Cc2nnc(/C=C/c3cccc4cnccc34)o2)c1] | (E)-2-(3-bromobenzyl)-5-(2-(isoquinolin-5-yl)vinyl)-1,3,4-oxadiazole |
| 304 | 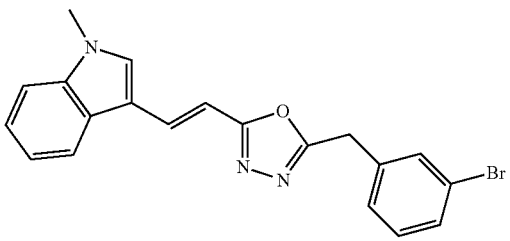 [SMILES: Cn1cc(/C=C/c2nnc(Cc3cccc(Br)c3)o2)c2ccccc21] | (E)-2-(3-bromobenzyl)-5-(2-(1-methyl-1H-indol-3-yl)vinyl)-1,3,4-oxadiazole |
| 305 | 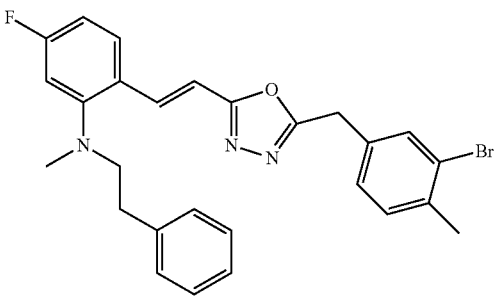 [SMILES: Cc1ccc(Cc2nnc(/C=C/c3ccc(F)cc3N(C)CCc3ccccc3)o2)cc1Br] | 2-(2-(5-(3-bromo-4-methylbenzyl)-1,3,4-oxadiazol-2-yl)vinyl)-5-fluoro-N-methyl-N-phenethylaniline |
| 306 | 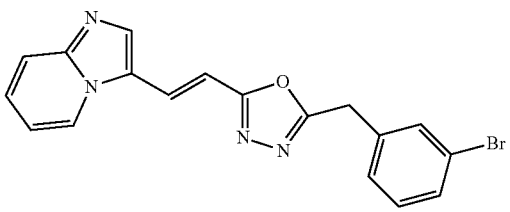 [SMILES: Brc1cccc(Cc2nnc(/C=C/c3cnc4ccccn34)o2)c1] | (E)-2-(3-bromobenzyl)-5-(2-(imidazo[1,2-a]pyridin-3-yl)vinyl)-1,3,4-oxadiazole |

TABLE 31-continued

| 307 | (E)-2-(3-bromobenzyl)-5-(2-(1-methyl-1H-indol-4-yl)vinyl)-1,3,4-oxadiazole |

TABLE 32

| cpd # | Characterization-color, solid, melting point, 1H NMR, LC/MS data are essential for all compounds | Activity (uM) | | | | | |
|---|---|---|---|---|---|---|---|
| | | B/Florida/04/2006 | | A/California/07/2009 (H1N1) | | A/Perth/16/2009 (H3N2) | |
| | | EC50 (uM) | CC50 (uM) | EC50 (uM) | CC50 (uM) | EC50 (uM) | CC50 (uM) |
| 1 | Colorless oil; $^1$H NMR (400 MHz, (CD$_3$)$_2$CO) δ 7.45-7.29 (m, 8H), 7.22 (d, J = 8.0 Hz, 1H), 5.47 (s, 2H), 4.41 (s, 2H), 2.28 (s, 3H), 2.16 (s, 3H); LCMS (ESI) m/z 456 [M + H]$^+$ | 0.98 | 41.33 | 0.77 | 38.47 | 1.15 | >50 |
| 2 | White solid; mp = 135.9° C.; H NMR (400 MHz, (CD$_3$)$_2$CO) δ 7.58 (d, J = 8.0 Hz, 2H), 7.53 (d, J = 8.4 Hz, 2H), 7.44-7.35 (m, 4H), 7.33 (t, J = 6.8 Hz, 1H) 5.52 (s, 2H), 4.47 (s, 2H), 2.30 (s, 3H); 2.15 (s, 3H); LCMS (ESI) m/z 456 [M + H]$^+$ | >50 | >50 | 47.51 | >50 | 46.74 | >50 |
| 3 | Yellow oil; $^1$H NMR (400 MHz, (CD$_3$)$_2$CO) δ 7.99 (s, 1H), 7.57 (d, J = 5.6 Hz, 1H), 7.54 (s, 1H), 7.48-7.35 (m, 7H), 7.27 (d, J = 7.2 Hz, 1H), 5.65 (s, 2H), 4.48 (s, 2H); LCMS (ESI) m/z 428 [M + H]$^+$ | 1.21 | >50 | 1.36 | >50 | 1.75 | >50 |
| 4 | Yellow oil; $^1$H NMR (400 MHz, (CD$_3$)$_2$CO) δ 7.59 (s, 1H), 7.53 (d, J = 5.2 Hz, 2H), 7.44-7.25 (m, 8H), 6.36 (d, J = 3.6 Hz, 1H), 5.30 (s, 2H), 4.43 (s, 2H); LCMS (ESI) m/z 349 [M + H]$^+$ | >50 | >50 | >50 | >50 | >50 | >50 |
| 5 | Colorless oil; $^1$H NMR (400 MHz, (CD$_3$)$_2$CO) δ 7.53 (d, J = 7.2 Hz, 1H), 7.43-7.25 (m, 8H), 5.91 (s, 1H), 5.43 (s, 2H), 4.42 (s, 2H), 2.26 (s, 3H), 2.20 (s, 3H); LCMS (ESI) m/z 377 [M + H]$^+$ | 9.49 | >50 | 8.68 | >50 | 10.65 | >50 |
| 6 | White solid; mp = 90.3° C.; $^1$H NMR (400 MHz, CDCl$_3$) δ 7.62 (s, 1H), 7.56 (d, J = 7.6 Hz, 2H), 7.52 (d, J = 7.2 Hz, 1H), 7.44 (t, J = 7.6 Hz, 2H), 7.39 (t, J = 7.4 Hz, 2H), 7.35 (m, 1H), 5.40 (s, 2H), 4.51 (s, 2H), 2.29 (s, 3H), 2.21 (s, 3H); LCMS (ESI) m/z 456 [M + H]$^+$ | 3 | >50 | 2.91 | >50 | 2.74 | >50 |
| 7 | Yellow oil; $^1$H NMR (400 MHz, CDCl$_3$) δ 7.52 (d, J = 7.6 Hz, 1H), 7.43-7.25 (m, 8H), 7.35 (s, 2H), 4.42 (s, 2H), 2.27 (s, 3H), 2.21 (s, 3H); LCMS (ESI) m/z 411 [M + H]$^+$ | 1.11 | >50 | 1.26 | >50 | 1.89 | >50 |
| 8 | White solid; mp = 112.1° C.; $^1$H NMR (400 MHz, CDCl$_3$) δ 8.04 (d, J = 8.0 Hz, 1H), 7.89 (d, J = 8.8 Hz, 1H), 7.83 (d, J = 8.4 Hz, 1H), 7.58-7.52 (m, 3H), 7.39 (t, J = 7.8 Hz, 1H), 5.46 (s, 2H), 4.94 (s, 2H), 2.32 (s, 3H), 2.21 (s, 3H); LCMS (ESI) [M + H]$^+$ 430 | 7.48 | >50 | 6.94 | >50 | 10.54 | >50 |
| 9 | Colorless oil; $^1$H NMR (400 MHz, CDCl$_3$) δ 7.32 (d, J = 7.2 Hz, 1H); 7.23-7.11 (m, 3H), 5.44 (s, 2H), 4.47 (s, 2H), 2.40 (s, 3H), 2.29 (s, 3H), 2.24 (s, 3H); LCMS (ESI) m/z 394 [M + H]$^+$ | 4.70 | >50 | 4.20 | >50 | 5.55 | >50 |
| 10 | White solid; mp = 87.3° C.; $^1$H NMR (400 MHz, CDCl$_3$) δ 7.35 (d, J = 7.6 Hz, 1H), 7.30-7.26 (m, 1H), 6.88-6.85 (m, 2H), 5.44 (s, 2H); 4.44 (s, 2H), 3.85 (s, 3H), 2.30 (s, 3H), 2.24 (s, 3H); LCMS (ESI) m/z 410 [M + H]$^+$ | 15.47 | >50 | 16.76 | >50 | 18.45 | >50 |

TABLE 33

| 11 | Yellow oil; $^1$H NMR (400 MHZ, CDCl$_3$) δ 7.54 (d, J-6.8 Hz, 1H), 7.44-7.31 (m, 8H), 7.28-7.26 (m, 1H), 6.35 (s, 1H), 5.43 (s, 2H), 4.44 (s, 2H); LCMS (ESI) m/z 428 [M + H]$^+$ | 12.87 | >50 | 13.25 | >50 | 12.53 | >50 |
| 12 | White solid; mp = 48.2° C.; $^1$H NMR (400 MHZ, CD$_3$OD) δ 7.44-7.39 (m, 4H); 7.28-7.21 (m, 5H), 5.55 (s, 2H), 4.71 (q, J = 18.3 Hz, 2H), 2.28 (s, 3H), 2.17 (s, 3H); LCMS (ESI) m/z 472 [M + H]$^+$ | 2.61 | 7.81 | 2.51 | 6.85 | 3.26 | 5.21 |
| 13 | Yellow oil; $^1$H NMR (400 MHZ, CDCl$_3$) δ 7.57 (t, J = 7.0 Hz, 2H), 7.46-7.40 (m, 5H), 7.35 (d, J = 7.2 Hz, 2H), 5.34 (s, 2H), 3.91 (s, 2H), 2.28 (s, 3H), 2.21 (s, 3H); LCMS (ESI) m/z 484 [M + H]$^+$ | 42.5 | >50 | >50 | >50 | >50 | >50 |

TABLE 33-continued

| | | | | | | | |
|---|---|---|---|---|---|---|---|
| 14 | Colorless oil; $^1$H NMR (400 MHZ, CDCl$_3$) δ 7.38-7.28 (m, 5H), 5.39 (s, 2H), 4.43 (s, 2H), 2.29 (s, 3H), 2.22 (s, 3H); LCMS (ESI) m/z 380 [M + H]$^+$ | 16.41 | >50 | 18.0 | >50 | 20.5 | >50 |
| 15 | Colorless oil; $^1$H NMR (400 MHZ, CDCl$_3$) δ 8.73 (br, 2H), 7.59-7.54 (m, 3H), 7.43-7.41 (m, 2H), 7.26-7.23 (m, 1H), 5.35 (s, 2H), 4.39 (s, 2H), 2.28 (s, 3H), 2.20 (s, 3H); LCMS (ESI) m/z 457 [M + H]$^+$ | 8.18 | >50 | 8.9 | >50 | 11.6 | >50 |
| 16 | Colorless oil; $^1$H NMR (400 MHZ, CDCl$_3$) δ 8.60 (br, 2H), 7.99 (br, 1H), 7.54-7.49 (m, 3H), 7.36-7.35 (m, 2H), 5.36 (s, 2H), 4.47 (s, 2H), 2.29 (s, 3H), 2.19 (s, 3H); LCMS (ESI) m/z 457 [M + H]$^+$ | >50 | >50 | N/D | >50 | >50 | >50 |
| 17 | Colorless oil; $^1$H NMR (400 MHZ, CDCl$_3$) δ 9.38 (br, 1H), 7.40-7.34 (m, 7H), 7.29-7.26 (m, 2H), 5.21 (d, J = 12.0 Hz, 2H), 4.55 (s, 2H), 2.25 (d, J = 6.8 Hz, 3H), 2.22 (s, 3H); LCMS (ESI) m/z 439 [M + H]$^+$ | 19.03 | 38.09 | 35.2 | >50 | 30.0 | >50 |
| 18 | Colorless oil; $^1$H NMR (400 MHZ, CDCl$_3$) δ 7.51 (d, J = 7.6 Hz, 1H), 7.41-7,24 (m, 13H), 4.10 (s, 2H), 4.13 (s, 2H); LCMS (ESI) m/z 359 [M + H]$^+$ | 5.18 | >50 | 6.1 | >50 | 6.8 | >50 |
| 19 | Colorless oil; $^1$H NMR (400 MHZ, CDCl$_3$) δ 8.68 (br, 2H), 7.91 (d, J = 7.2 Hz, 1H), 7.57-7.54 (m, 2H), 7.43-7.38 (m, 2H), 7.26-7.23 (m, 1H), 5.36 (s, 2H), 4.37 (s, 2H), 2.29 (s, 3H), 2.19 (s, 3H); LCMS (ESI) m/z 457 [M + H]$^+$ | >50 | >50 | >50 | >50 | >50 | >50 |
| 20 | Colorless oil; $^1$H NMR (400 MHZ, CDCl$_3$) δ 8.73 (br, 2H), 7.59-7.54 (m, 3H), 7.43-7.41 (m, 2H), 7.26-7.23 (m, 1H), 5.35 (s, 2H), 4.39 (s, 2H), 2.28 (s, 3H), 2.20 (s, 3H); LCMS (ESI) m/z 457 [M + H]$^+$ | 0.66 | 10.22 | 0.7 | 8.3 | 0.7 | 10.2 |

TABLE 34

| | | | | | | | |
|---|---|---|---|---|---|---|---|
| 21 | Colorless oil; $^1$H NMR (400 MHz, CDCl$_3$) δ 8.60 (br, 2H); 7.99 (br, 1H), 7.54-7.49 (m, 3H), 7.36-7.35 (m, 2H), 5.36 (s, 2H), 4.47 (s, 2H), 2.29 (s, 3H), 2.19 (s, 3H); LCMS (ESI) m/z 457 [M + H]$^+$ | >50 | >50 | >50 | >50 | >50 | >50 |
| 22 | Colorless oil; $^1$H NMR (400 MHz, CDCl$_3$) δ 7.52 (d, J-8.0 Hz, 1H), 7.46 (d, J-8.4 Hz, 2H), 7.41-7.24 (m, 8H), 7.14 (d, J = 8.0 Hz, 2H), 4.40 (s, 2H), 4.08 (s, 2H); LCMS (ESI) m/z 438 [M + H]$^+$ | 4.88 | >50 | 4.9 | >50 | 5.0 | >50 |
| 23 | White solid; mp-84.7° C.; $^1$H NMR (400 MHz, CDCl$_3$) δ 7.32-7.26 (m, 3H), 7.14-7.10 (m, 1H), 5.41 (s, 2H), 5.23 (s, 2H), 3.25-3.17 (m, 1H), 2.31 (s, 3H), 2.22 (s, 3H), 1.26 (d, J-6.8 Hz, 1H); LCMS (ESI) m/z 422 [M + H]$^+$ | 0.82 | 14.17 | 0.6 | 16.7 | 1.1 | 16.3 |
| 24 | White solid; mp-137.8° C.; $^1$H NMR (400 MHz, CDCl$_3$) δ 7.42-7.30 (m, 9H), 5.45 (s, 2H), 4.49 (s, 2H), 3.99 (q, J = 7.2 Hz, 2H), 2.33 (s, 3H), 2.18 (s, 3H), 1.00 (t, J = 7.0 Hz, 3H); LCMS (ESI) m/z 483 [M + H]$^+$ | >50 | >50 | N/D | >50 | >50 | >50 |
| 25 | Colorless oil; $^1$H NMR (400 MHz, (CD$_3$)$_2$CO) δ 7.50 (d, J-7.2 Hz, 4H), 7.34 (t, J-7.8 Hz, 4H), 7.30-7.28 (m, 2H), 6.19 (s, 1H), 5.19 (s, 2H), 2.24 (s, 3H), 2.05 (s, 3H); LCMS (ESI) m/z 456 [M + H]$^+$ | 5.177 | 9.4 | 2.5 | 9.8 | 2.0 | 10.0 |
| 26 | Colorless oil; $^1$H NMR (400 MHz, (CD$_3$)$_2$CO) δ 7.21-7.20 (m, 1H), 7.15-7.11 (m, 3H), 5.57 (s, 1H), 3.15 (t, J = 5.0 Hz, 2H), 3.12 (t, J = 4.2 Hz, 2H), 2.36 (s, 3H), 2.34 (s, 3H), 2.06 (s, 3H); LCMS (ESI) m/z 408 [M + H]$^+$ | 36.24 | >50 | 31.2 | >50 | 29.4 | >50 |
| 27 | Brown oil; $^1$H NMR (400 MHz, (CD$_3$)$_2$CO) δ 8.49 (d, J = 4.4 Hz, 1H), 7.78 (t, J = 7.0 Hz, 1H), 7.59 (d, J = 7.2 Hz, 1H), 7.48-7.26 (m, 10H), 4.46 (s, 2H), 4.38 (s, 2H); LCMS (ESI) m/z 360 [M + H]$^+$ | 13.38 | >50 | 8.7 | 48.0 | 6.8 | 46.0 |
| 28 | Yellow solid; mp = 63.7° C.; $^1$H NMR (400 MHz, (CD$_3$)$_2$CO) δ 7.95 (d, J = 7.6 Hz, 1H), 7.49 (t, J = 7.4 Hz, 1H), 7.39-7.34 (m, 2H), 5.56 (s, 2H), 4.94 (s, 2H), 2.45 (s, 3H), 2.10 (s, 3H), 2.05 (s, 3H); LCMS (ESI) m/z 422 [M + H]$^+$ | >50 | >50 | >50 | >50 | >50 | >50 |
| 29 | Yellow solid; mp = 92.3° C.; $^1$H NMR (400 MHz, (CD$_3$)$_2$CO) δ 7.50 (d, J = 7.6 Hz, 1H), 7.40 (t, J = 8.0 Hz, 2H), 7.30 (t, J = 7.8 Hz, 1H), 7.17 (t, J-7.6 Hz, 1H), 7.08 (t, J-7.6 Hz, 1H), 7.02 (d, J = 9.6 Hz, 2H), 7.02 (d, J = 7.6 Hz, 1H), 5.54 (s, 2H), 4.54 (s, 2H), 2.33 (s, 3H), 2.10 (s, 3H); LCMS (ESI) m/z 472 [M + H]$^+$ | 1.99 | 5.23 | 1.2 | 6.2 | 1.4 | 5.3 |
| 30 | Colorless oil; $^1$H NMR (400 MHz, (CD$_3$)$_2$CO) δ 8.20 (s, 4H), 7.90 (s, 1H), 7.59 (t, J = 9.2 Hz, 3H), 7.47-7.32 (m, 7H); 7.27-7.20 (m, 1H), 5.66 (s, 2H), 4.48 (s, 2H); LCMS (ESI) m/z 425 [M + H]$^+$ | >50 | >50 | >50 | >50 | 13.0 | >50 |

TABLE 35

| | | | | | | | |
|---|---|---|---|---|---|---|---|
| 31 | Colorless oil; ¹H NMR (400 MHZ, (CD₃)₂CO) δ 7.59 (d, J = 9.2 Hz, 1H), 7.45 (t, J = 6.8 Hz, 1H), 7.39 (t, J = 7.6 Hz, 1H), 7.32 (d, J = 7.6 Hz, 1H), 6.90 (s, 2H), 6.27 (s, 2H), 5.54 (s, 2H), 4.38 (s, 2H), 2.32 (s, 3H), 2.10 (s, 3H); LCMS (ESI) m/z 445 [M + H]⁺ | 3.57 | 11.82 | 1.8 | 11.4 | 2.3 | 9.4 |
| 32 | White solid; mp = 102.3° C.; ¹H NMR (400 MHZ, (CD₃)₂CO) δ 7.55 (d, J = 7.6 Hz, 1H), 7.40-7.31 (m, 2H), 7.31-7.23 (m, 5H), 5.53 (s, 2H), 4.47 (s, 2H), 2.38 (s, 3H), 2.32 (s, 3H), 2.10 (s, 3H); LCMS (ESI) m/z 470 [M + H]⁺ | 1.38 | 7.32 | 0.6 | 9.9 | 0.5 | 11.5 |
| 33 | White solid; mp = 84.7° C.; ¹H NMR (400 MHZ, (CD₃)₂CO) δ 7.57 (d, J = 7.2 Hz, 1H), 7.50 (d, J = 8.0 Hz, 2H), 7.43-7.37 (m, 4H), 7.27 (d, J = 7.2 Hz, 1H), 5.53 (s, 2H), 4.47 (s, 2H), 2.31 (s, 3H), 2.10 (s, 3H); LCMS (ESI) m/z 490 [M + H]⁺ | 1.46 | 6.28 | 0.6 | 7.1 | 0.5 | 6.7 |
| 34 | Colorless oil; ¹H NMR (400 MHZ, (CD₃)₂CO) δ 7.78 (s, 1H), 7.68 (s, 1H), 7.53 (d, J = 7.6 Hz, 1H), 7.38-7.28 (m, 3H), 6.71 (s, 1H), 5.55 (s, 2H), 4.59 (s, 2H), 2.32 (s, 3H), 2.07 (s, 3H); LCMS (ESI) m/z 446 [M + H]⁺ | 4.48 | 22.83 | 1.4 | 21.9 | 1.8 | 21.9 |
| 35 | White solid; mp = 86.9° C.; ¹H NMR (400 MHZ, (CD₃)₂CO) δ 7.59 (d, J = 7.6 Hz, 1H), 7.54 (d, J = 7.6 Hz, 1H), 7.50 (s, 1H), 7.37-7.31 (m, 3H), 7.24 (d, J = 6.4 Hz, 1H), 5.54 (s, 2H), 4.54 (s, 2H), 2.32 (s, 3H), 2.11 (s, 3H); LCMS (ESI) m/z 462 [M + H]⁺ | 1.88 | >50 | 0.7 | 22.9 | 0.8 | 12.1 |
| 36 | White solid; mp-114.2° C.; ¹H NMR (400 MHZ, (CD₃)₂CO) δ 8.93 (s, 1H), 8.18 (s, 1H), 7.97 (d, J = 8.8 Hz, 2H), 7,67 (t, J = 4.6 Hz, 1H), 7.58 (t, J = 8.0 Hz, 1H), 7.49-7.37 (m, 7H), 7.30 (t, J = 4.8 Hz, 1H), 4.56 (s, 2H); LCMS (ESI) m/z 411 [M + H]⁺ | N/D | >50 | N/D | >50 | >50 | >50 |
| 37 | White solid; mp = 123.6° C.; ¹H NMR (400 MHZ, (CD₃)₂CO) δ 8.00 (d, J = 7.6 Hz, 1H), 7.58-7.51 (m, 2H), 7.45 (t, J = 7.6 Hz, 1H), 5.55 (s, 2H), 4.80 (s, 2H), 3.90 (s, 3H), 2.33 (s, 3H), 2.10 (s, 3H); LCMS (ESI) m/z 438 [M + H]⁺ | >50 | >50 | 37.8 | >50 | 41.8 | >50 |
| 38 | Colorless oil; ¹H NMR (400 MHZ, (CD₃)₂CO) δ 7.41 (d, J = 8.8 Hz, 1H), 7.28 (t, J = 8.0 Hz, 3H), 7.21-7.15 (m, 5H), 5.56 (s, 2H), 4.50 (s, 2H), 4.17 (s, 2H), 2.80 (s, 3H), 2.11 (s, 3H); LCMS (ESI) m/z 470 [M + H]⁺ | 1.18 | >50 | 1.03 | >50 | 1.04 | >50 |
| 39 | White solid; mp = 74.1° C.; ¹H NMR (400 MHZ, (CD₃)₂CO) δ 8.21 (s, 1H), 8.88 (s, 1H), 7.79 (s, 1H), 7.64 (d, J = 8.0 Hz, 2H), 7.58 (t, J = 9.2 Hz, 3H), 7.46 (t, J = 7.8 Hz, 2H), 7.41 (t, J = 7.2 Hz, 1H), 7.36 (t, J = 6.2 Hz, 2H), 7.22 (t, J = 8.0 Hz, 1H), 5.69 (s, 2H), 4.59 (s, 2H); LCMS (ESI) m/z 425 [M + H]⁺ | | | | | | |
| 40 | White solid; mp = 106.3° C.; ¹H NMR (400 MHZ, (CD₃)₂CO) δ 7.13-7.06 (m, 3H) 5.58 (s, 2H), 4.50 (s, 2H), 2.41 (s, 6H), 2.35 (s, 3H), 2.21 (s, 3H); LCMS (ESI) m/z 408 [M + H]⁺ | N/D | >50 | >50 | >50 | N/D | >50 |

TABLE 36

| | | | | | | | |
|---|---|---|---|---|---|---|---|
| 41 | Colorless oil; ¹H NMR (400 MHz, (CD₃)₂CO) δ 7.57 (d, J = 6.0 Hz, 1H), 7.50 (d, J-8.8 Hz, 1H), 7.47-7.33 (m, 7H), 7.29-7.19 (m, 4H), 5.73 (s, 2H), 4.43 (s, 2H), 2.63 (s, 3H); LCMS (ESI) m/z 413 [M + H]⁺ | 1.21 | 19.69 | 0.69 | 26.90 | 0.91 | 27.36 |
| 42 | White solid; mp = 120.5° C.; ¹H NMR (400 MHz, (CD₃)₂CO) δ 7.90 (d, J-6.0 Hz, 2H), 7.79 (d, J-9.2 Hz, 2H), 7.68 (d, J = 8.8 Hz, 1H), 7.48-7.37 (m, 7H), 7.29 (d, J = 9.2 Hz, 1H), 4.59 (s, 2H); LCMS (ESI) m/z 424 [M + H]⁺ | 2.92 | 14.82 | 1.62 | 15.71 | 2.33 | 15.78 |
| 43 | Colorless oil; ¹H NMR (400 MHz, (CD₃)₂CO) δ 7.96 (d, J-8.0 Hz, 2H), 7.68 (d, J = 8.8 Hz, 1H), 7.63-7.57 (m, 3H); 7.55-7.36 (m, 7H, 7.29 (d, J = 9.2 Hz, 1H), 4.58 (s, 2H); LCMS (ESI) m/z 345 [M + H]⁺ | N/D | >50 | >50 | >50 | >50 | >50 |
| 44 | Yellow oil; ¹H NMR (400 MHz, (CD₃)₂CO) δ 7.54 (d, J-8.8 Hz, =1H), 7.43-7.27 (m, 7H), 7.19 (d, J = 8.8 Hz, 1H), 5.16 (s, 2H), 4.28 (s, 2H), 3.23 (s, 3H), 2.28 (s, 3H), 2.11 (s, 3H); LCMS (ESI) m/z 453 [M + H]⁺ | >50 | >50 | >50 | >50 | 29.4 | >50 |
| 45 | Yellow oil; ¹H NMR (400 MHz, (CD₃)₂CO) δ 7.44-7.39 (m, 3H); 7.32-7.25 (m, 5H), 7.17 (d, J = 7.6 Hz, 1H), 5.43 (s, 2H), 4.97 (s, 2H), 2.27 (s, 3H), 2.208 (s, 3H), 2.10 (s, 3H); LCMS (ESI) m/z 481 [M + H]⁺ | 23.8* | 33.46 | 26.17* | 39.68 | 25.78* | >50 |
| 46 | White solid; ¹H NMR (400 MHz, acetone-d₆) δ 7.39-7.30 (m, 4H), 5.54 (s, 2H), 4.28 (s, 2H), 2.31 (s, 3H), 2.09 (s, 3H); LCMS (ESI) m/z 381 [M + H]⁺ | 27.47 | >50 | 24.34 | >50 | 21.78 | >50 |
| 47 | Yellow oil; ¹H NMR (400 MHz, (CD₃)₂CO) δ 9.88 (br, 1H), 7.54 (d, J = 8.8 Hz, 2H), 7.52-7.31 (m, 9H), 7.23-7.18 (m, 1H), 4.06 (s, 2H), 4.04 (s, 2H); LCMS (ESI) m/z 453 [M + H]⁺ | >50 | >50 | >50 | >50 | N/D | >50 |
| 48 | Yellow solid; mp-101.2° C.; ¹H NMR (400 MHz, (CD₃)₂CO) δ 7.88 (s, 1H), 7.24-7.12 (m, 3H), 7.11 (t, J = 7.1 Hz, 1H); 6.61 (s, 1H), 4.33 (s, 2H), 2.60 (s, 3H), 2.42 (s, 3H), 2.28 (s, 3H); LCMS (ESI) m/z 406 [M + H]⁺ | 23.43* | 9.54 | 4.88* | 10.48 | 11.35* | 10.05 |

TABLE 36-continued

| | | | | | | | |
|---|---|---|---|---|---|---|---|
| 49 | Yellow oil; ¹H NMR (400 MHz, (CD₃)₂CO) δ 7.61 (d, J-9.6 Hz. 1H), 7.49-7.37 (m, 7H), 7.28 (d, J-8.8 Hz, 1H), 4.45-4.41 (m, 4H), 3.34 (t, J = 7.0 Hz, 2H), 2.21 (s, 3H), 2.09 (s, 3H); LCMS (ESI) m/z 470 [M + H]⁺ | >50 | >50 | >50 | >50 | >50 | >50 |
| 50 | White solid; ¹H NMR (400 MHz, acetone-d₆) δ 7.98 (d, J-16.0 Hz, 1H), 7.58 (d, J-7.6 Hz, 1H), 7.41-7.37 (m, 2H), 7.28-7.24 (m, 1H), 7.02 (d, J = 16 Hz, 1H), 5.63 (s, 2H), 3.38 (q, J = 6.8 Hz, 1H), 2.40 (s, 3H), 2.12 (s, 3H), 1.27 (d, J = 6.8 Hz, 6H); LCMS (ESI) m/z 401 [M + H]⁺ | 24.49 | >50 | 18.68 | >50 | 11,41 | >50 |

TABLE 37

| | | | | | | | |
|---|---|---|---|---|---|---|---|
| 51 | White solid, mp = 135.4° C.; ¹H NMR (400 MHz, DMSO-d₆) δ 9.27 (t, J = 5.6 Hz, NH), 7.82 (d, J = 1.6 Hz, 2H), 7.80 (d, J = 1.6 Hz, 2H), 7.55 (d, J = 6.0 Hz, 1H), 7.47-7.32 (m, 7H), 7.25 (d, J = 6.0 Hz, 1H), 4.63 (d, J = 5.6 Hz, 2H), 4.4 (s, 2H), LCMS (ESI) m/z 482 [M + H]+. | 6.02 | 28.56 | 4.01 | 28.73 | 5.04 | 28.84 |
| 52 | White solid, mp = 158.2° C.; ¹H NMR (400 MHz, DMSO-d₆) δ 12.11 (s, NH), 7.66 (d, J = 2.0 Hz, 2H), 7.42-7.33 (m, 6H), 7.23-7.13 (m, 5H), 4.09 (s, 2H), LCMS (ESI) m/z 439 [M + H]+. | 16.29 | >50 | >50 | >50 | 8.11 | >50 |
| 53 | Yellow solid; mp = 103.6° C.; ¹H NMR (400 MHz, (CD₃)₂CO) δ 7.60 (d, J = 7.2 Hz, 1H), 7.45-7.40 (e(m, 2H), 7.31-7.26 (m, 1H), 5.53 (s, 2H), 2.44 (s, 3H), 2.27 (s, 3H, 2.13 (s, 3H), LCMS (ESI) m/z 380 (M + H)⁻. | 8.94* | 7.91 | 0.12 | 10.28 | 8.57* | 10.81 |
| 54 | Yellow solid; mp = 103.6° C.; ¹H NMR (400 MHz, (CD₃)₂CO) δ 7.58 (d, J = 7.6 Hz, 1H), 7.43-7.39 (m, 2H), 7.30-7.26 (m, 1H), 4.43 (t, J = 6.8 Hz, 2H), 3.37 (t, J = 6.6 Hz, 2H), 2.47 (s, 3H), 2.19 (s, 3H), 2.06 (s, 3H), LCMS (ESI) m/z 394 [M + H]⁺. | N/D | >50 | N/D | >50 | N/D | >50 |
| 55 | White solid; mp = 123.6° C.; ¹H NMR (400 MHz, (CD₃)₂CO) δ 8.44 (s, 1H), 7.50 (d, J = 8.0 Hz, 1H), 7.25-7.15 (m, 3H), 4.64 (s, 2H), 2.59 (s, 3H), 2.46 (s, 3H), 2.31 (s, 3H), LCMS (ESI) m/z 407 [M + H]⁺. | N/D | >50 | N/D | >50 | N/D | >50 |
| 56 | White solid; mp = 169.7° C.; ¹H NMR (400 MHz, (CD₃)₂CO) δ 7.94 (s, 1H), 7.45 (d, J = 8.0 Hz, 1H), 7.39-7.36 (m, 2H), 7.21 (t, J = 8.4 Hz, 1H), 6.76 (s, 1H), 3.66-3.58 (m, 1H), 7.57 (s, 3H), 2.28 (s, 3H), 1.27 (d, J = 7.2 Hz, 6H), LCMS (ESI) m/z 420 [M + H]⁺. | N/D | >50 | N/D | >50 | N/D | >50 |
| 57 | Yellow solid; mp = 103.3° C.; ¹H NMR (400 MHz, (CD₃)₂CO) δ 7.95 (d, J = 3.2 Hz, 1H), 7.49-7.47 (m, 1H), 7.33-7.29 (m, 2H), 7.25-7.21 (m, 1H), 5.58 (t, J = 3.6 Hz, 1H), 3.33-3.25 (m, 1H), 2.58 (s, 3H), 2.27 (s, 3H), 1.25 (d, J = 6.8 Hz, 6H), LCMS (ESI) m/z 404 (M + H)⁻. | N/D | >50 | N/D | >50 | N/D | >50 |
| 58 | Colorless oil, ¹H NMR (400 MHz, (CD₃)₂CO) δ 7.62 (d, J = 7.6 Hz, 1H), 7.50-7.37 (m, 10H), 7.28 (d, J = 7.2 Hz, 1H), 7.04 (d, J = 7.2 Hz, 2H), 7.35 (s, 2H), 4.52 (s, 2H); LCMS (ESI) m/z 454 [M + H]⁺. | >50 | >50 | >50 | >50 | 44.28 | >50 |
| 59 | Colorless oil, ¹H NMR (400 MHz, (CD₃)₂CO) δ 7.58 (d, J = 6.8 Hz, 2H), 7.50-7.28 (m, 11H), 4.70 (q, J = 14.3 Hz, 2H), 4.32 (s, 2H); LCMS (ESI) m/z 454 (M + H)⁺. | N/D | >50 | N/D | >50 | N/D | >50 |
| 60 | White solid, mp = 134.2° C.; ¹H NMR (400 MHz, (CD₃)₂CO) δ 7.59-7.54 (m, 3H), 7.50-7.37 (m, 5H), 7.35-7.25 (m, 5H), 4.90 (s, 2H), 4.30 (s, 2H), LCMS (ESI) m/z 470 [M H]⁺. | 4.11 | 8.46 | 12.10 | 7.73 | 6.36 | 12.27 |

TABLE 38

| | | | | | | | |
|---|---|---|---|---|---|---|---|
| 61 | White solid; mp = 211.2° C.; ¹H NMR (400 MHz, DMSO-d₆) δ 12.10 (s, NH), 7.45-7.3 (m, 6H), 7.34 (t, J = 3.4 Hz, 2H), 7.28 (d, J = 2.0 Hz, 2H), 7.27 (d, J = 5.2 Hz, 1H), 4.20 (s, 2H), 1.91 (s, 6H); LCMS (ESI) m/z 468 [M + H]−. | 2.30 | 4.02 | 2.30 | 4.32 | 2.61 | 5.70 |
| 62 | White solid; mp = 181.8° C.; ¹H NMR (400 MHz, DMSO-d₆) δ 12.11 (s, NH), 7.66 (d, J = 8.4 Hz, 1H), 7.41-7.32 (m, 6H), 7.21-7.16 (m, 3H), 7.10 (s, 1H), 6.95 (d, J = 6.0 Hz, 1H), 4.08 (s, 2H), 2.33 (s, 3H); LCMS (ESI) m/z 454 [M + H]+. | N/D | >50 | N/D | >50 | N/D | >50 |
| 63 | White solid; mp = 199.0° C.; ¹H NMR (400 MHz, DMSO-d₆) δ 12.72 (s, NH), 7.65 (d, J = 8.8 Hz, 2H), 7.41-7.36 (m, 6H), 7.25-7.20 (m, 3H), 7.15 (d, J = 8.8 Hz, 2H), 4.48 (dd, J₁₂ = 13.0 Hz, J₁₃ = 25.0 Hz, 2H); LCMS (ESI) m/z 456 [M + H]+. | 7.06 | >14.56 | 2.61 | 14.43 | 6.05 | 14.84 |

TABLE 38-continued

| | | | | | | | |
|---|---|---|---|---|---|---|---|
| 64 | White solid; mp = 139.9° C.; ¹H NMR (400 MHz, DMSO-d₆) δ 8.34 (d, J = 8.0 Hz, 2H), 7.78 (t, J = 7.4 Hz, 1H), 7.64-7.57 (m, 4H), 7.36 (d, J = 7.4 Hz, 2H), 4.45 (s, 2H); LCMS (ESI) m/z 344 [M + H]+. | 40.45 | >50 | 5.97 | >50 | >50 | >50 |
| 65 | Colorless oil, ¹H NMR (400 MHz, Acetone-d₆) δ 7.65 (d, J = 4.8 Hz, 2H), 7.46-7.33 (m, 6H), 7.28 (d, J = 2.0 Hz, 2H), 7.23-7.18 (m, 3H), 4.18 (s, 2H), 3.37 (s, 3H); LCMS (ESI) m/z 454 (M + H)+. | N/D | >50 | N/D | >50 | N/D | >50 |
| 66 | White solid; ¹H NMR (400 MHz, acetone-d₆) δ 7.41 (d, J = 7.6 Hz, 1H), 7.32-7.26 (m, 2H), 7.13-7.10 (m, 1H), 5.51 (s, 2H), 4.31 (s, 2H), 3.43 (q, J = 6.8 Hz, 1H), 2.26 (s, 3H), 2.11 (s, 3H), 1.14 (d, J = 6.8 Hz, 6H); LCMS (ESI) m/z 421 [M − H]⁺. | 36.08 | >50 | 2.84 | >50 | >50 | >50 |
| 67 | Colorless oil, ¹H NMR (400 MHz, acetone-d₆) δ 7.28 (d, J = 7.6 Hz, 1H), 7.17 (dd, J = 6.8, 7.6 Hz, 1H), 7.08-7.02 (m, 2H), 5.52 (s, 2H), 3.21-3.11 (m, 5H), 2.30 (s, 3H), 2.11 (s, 3H), 1.20 (d, J = 6.8 Hz, 6H); LCMS (ESI) m/z 403 (M + H)⁺. | N/D | >50 | N/D | >50 | N/D | >50 |
| 68 | White solid; mp = 232.2° C.; ¹H NMR (400 MHz, DMSO-d₆) δ 12.03 (s, NH), 7.42-7.35 (m, 6H), 7.23-7.21 (m, 3H), 7.06 (s, 1H), 6.71 (s, 2H), 4.09 (s, 2H), 2.27 (s, 6H); LCMS (ESI) m/z 388 [M + H]+. | 1.83 | >50 | 2.77 | >50 | 1.60 | >50 |
| 69 | White solid; mp = 166.4° C.; ¹H NMR (400 MHz, DMSO-d₆); δ 8.58 (d, J = 1.2 Hz, 1H), 8.29 (d, J = 7.6 Hz, 1H), 8.06 (d, J = 7.6 Hz, 1H) 7.72-7.70 (m, 3H), 7.58-7.50 (m, 4H), 7.45-7.36 (m, 3H) 4.46 (s, 2H); LCMS (ESI) m/z 420 [M + H]−. | N/D | >50 (CH) | >50 (CR) | >50 | 49.26 (CH) | >50 |
| 70 | White solid; mp = 137.6° C.; ¹H NMR (400 MHz, DMSO-d₆) δ 7.68 (s, 1H), 7.62-7.59 (m, 3H), 7.50-7.38 (m, 7H), 7.25 (d, J = 8.0 Hz, 2H), 6.73 (d, J = 6.0 Hz, 1H), 6.04 (d, J = 5.6 Hz, 1H), 4.26 (s, 2H); LCMS (ESI) m/z 423 [M + H]−. | N/D | >50 | N/D | >50 | 37.45 | >50 |

TABLE 39

| | | | | | | | |
|---|---|---|---|---|---|---|---|
| 71 | White solid; mp = 172.1° C., ¹H NMR (400 MHz, DMSO-d₆); δ 12.06 (s, NH), 7.46-7.32 (m, 9H), 7.25-7.16 (m, 5H), 4.10 (s, 2H); LCMS (ESI) m/z 360 [M + H]+. | 22.77 © | 6.53 | 21.01 © | 5.41 | 14.15 © | 18.41 |
| 72 | White solid; ¹H NMR (400 MHz, (CD₃)₂CO) δ 7.85 (d, J = 8.8 Hz, 2H), 7.69-7.67 (m, 1H), 7.58 (d, J = 11.6 Hz, 2H), 7.50-7.39 (m, 7H), 7.31-7.29 (m, 1H), 4.61 (s, 2H); LCMS (ESI) m/z 467 [M + H]⁺. | N/D | 24.96 | 0.73 | 28.63 | 23.52 | 24.86 |
| 73 | Colorless oil; ¹H NMR (400 MHz, (CD₃)₂CO) δ 7.53 (d, J = 7.6 Hz, 1H), 7.45-7.38 (m, 2H), 7.37-7.33 (m, 7H), 7.30-7.25 (m, 3H), 4.43 (s, 2H), 4.39 (q, J = 7.2 Hz, 1H), 1.67 (d, J = 6.8 Hz, 3H); LCMS (ESI) m/z 373 [M + H]⁺. | >50 © | >50 | 17.21 © | >50 | 41.72 © | >50 |
| 74 | Colorless oil; ¹H NMR (400 MHz, (CD₃)₂CO) δ 7.80 (d, J = 8.0 Hz, 1H, 7.66-7.60 (m, 3H), 7.46-7.41 (m, 7H), 7.30-7.25 (m, 3H), 7.29 (d, J = 7.2 Hz, 1H), 4.57 (s, 2H); LCMS (ESI) m/z 474 [M + H]⁺. | >50 © | >50 | 21.22 © | >50 | 10.99 © | >50 |
| 75 | Yellow oil; ¹H NMR (400 MHz, (CD₃)₂CO) δ 7.24 (d, J = 12.4 Hz, 2H), 7.12 (q, J = 6.9 Hz, 2H), 6.98 (t, J = 7.4 Hz, 1H), 6.87 (d, J = 7.2 Hz, 1H), 6.68 (d, J = 8.8 Hz, 2H), 6.24 (q, J = 4.0 Hz, 2H), 5.62 (br, 1H), 4.31 (d, J = 5.2 Hz, 2H), 4.04 (s, 2H), 2.30 (s, 3H); LCMS (ESI) m/z 389 [M + H]⁻. | >50 © | >50 | 19.66 © | >50 | 15.31 © | >50 |
| 76 | White solid; mp = 236.1° C., ¹H NMR (400 MHz, (CD₃)₂CO); δ 9.0 (s, NH), 8.43 (d, J = 7.6 Hz, 2H), 7.72 (t, J = 7.6 Hz, 1H), 7.59 (t, J = 7.6 Hz, 2H), 7.19 (s, 3H), 2.32 (s, 6H), LCMS (ESI) m/z 294 [M + H]⁺. | >50 | >50 | 14.13 | >50 | 14.13 | >50 |
| 77 | White solid; mp = 179.0° C., ¹H NMR (400 MHz, (CD₃)₂CO); δ 8.20 (s, NH), 7.49 (d, J = 7.6 Hz, 2H), 7.40-7.36 (m, 3H), 7.09 (s, 3H), 5.91 (s, 1H), 5.6 (s, OH), 2.19 (s, 6H); LCMS (ESI) m/z 296 [M + H]⁺. | N/D © | >50 | N/D © | >50 | N/D © | >50 |
| 78 | White solid; mp = 252.8° C., ¹H NMR (400 MHz, DMSO-d6); δ 10.23 (s, NH), 8.51-8.49 (m, 1H), 8.33-8.31 (m, 1H), 7.66 (t, J = 8.8 Hz, 1H), 7.17 (s, 3H), 2.21 (s, 6H); LCMS (ESI) m/z 346 [M − H]⁺. | N/D | >50 | N/D | >50 | N/D | >50 |
| 79 | White solid; mp = 185.8° C., ¹H NMR (400 MHz, (CD3)2CO) δ 7.67-7.65 (m, 1H), 7.49-7.46 (m, 1H), 7.32 (t, J = 8.8 Hz, 1H), 7.10 (s, 3H), 5.95 (s, 1H), 2.20 (s, 6H); LCMS (ESI) m/z 348 [M + H]⁺. | >50 | >50 | >50 | >50 | >50 | >50 |
| 80 | White solid; ¹H NMR (400 MHz, (CD₃)₂CO) δ 7.38-7.29 (m, 5H), 4.23 (s, 3H); LCMS (ESI) m/z 423 [M + H]⁺. | N/D | >50 | N/D | >50 | N/D | >50 |

TABLE 40

| | | | | | | | |
|---|---|---|---|---|---|---|---|
| 81 | White solid; mp = 91.6° C.; ¹H NMR (400 MHz, (CD₃)₂CO) δ 7.96 (d, J = 16.4 Hz, 1H), 7.23 (d, J = 7.6 Hz, 1H), 7.57 (d, J = 8.8 Hz, 2H), 7.39-7.33 (m, 4H), 7.28-7.24 (m, 1H), 7.00 (d, J = 16.4 Hz, 1H), 4.38 (s, 2H), 3.39-3.31 (m, 1H), 1.26 (d, J = 6.8 Hz, 6H); LCMS (ESI) m/z 389 [M + H]⁺. | N/D | >50 | N/D | >50 | N/D | >50 |
| 82 | White solid; mp = 91.6° C.; ¹H NMR (400 MHz, (CD₃)₂CO) δ 7.95 (d, J = 16.0 Hz, 1H), 7.72 (d, J = 8.0 Hz, 1H), 7.56 (d, J = 8.4 Hz, 2H), 7.39-7.34 (m, 4H), 7.27-7.23 (m, 1H), 6.98 (d, J = 16.0 Hz, 1H), 4.31 (s, 2H), 3.39-3.32 (m, 1H), 1.25 (d, J = 6.8 Hz, 6H); LCMS (ESI) m/z 383 [M + H]⁺. | >50 | >50 | N/D | >50 | N/D | >50 |
| 83 | Pale yellow solid; mp = 236.7° C.; ¹H NMR (400 MHz, DMSO-d₆) δ 10.93 (s, NH), 8.03 (d, J = 7.2 Hz, 1H), 7.71 (d, J = 8.0 Hz, 1H), 7.60-7.53 (m, 5H), 7.45 (t, J = 7.4 Hz, 1H), 7.34-7.29 (m, 2H); LCMS (ESI) m/z 423 [M + H]+. | 4.631 7.83 | >50 | 4.251 4.40 | >50 | 4.745 4.44 | >50 |
| 84 | White solid; mp = 175.4° C.; ¹H NMR (400 MHz, DMSO-d₆) δ 10.54 (s, NH), 7.48 (s, 4H), 7.26 (d, J = 6.8 Hz, 1H), 7.19-7.14 (m, 2H), 7.08 (t, J = 7.4 Hz, 1H), 3.15-3.09 (m, 1H), 3.05-2.95 (m, 4H), 1.16 (d, J = 6.4 Hz, 6H); LCMS (ESI) m/z 388 [M + H]+. | >50 | >50 | 34.70 | >50 | 41.68 | >50 |
| 85 | White solid; mp = 234.1° C.; ¹H NMR (400 MHz, DMSO-d₆) δ 9.07 (s, NH), 7.25 (d, J = 8.0 Hz, 1H), 7.16 (t, J = 7.4 Hz, 1H), 7.12-7.02 (m, 5H), 3.12-3.08 (m, 1H), 3.00-2.96 (m, 2H), 2.92-2.88 (m, 2H), 2.14 (s, 6H), 1.16 (d, J = 6.4 Hz, 6H); LCMS (ESI) m/z 336 [M + H]+. | >50 | >50 | >50 | >50 | >50 | >50 |
| 86 | Pale yellow solid; mp = 147.9° C.; ¹H NMR (400 MHz, DMSO-d₆) δ 8.11-8.08 (m, 1H), 7.66 (d, J = 16.4 Hz, 1H), 7.56-7.53 (m, 3H), 7.38-7.28 (m, 4H), 4.32 (s, 2H); LCMS (ESI) m/z 393 [M + H]+. | 41.98 | >50 | 2.7 | >50 | 45.7 | >50 |
| 87 | Pale yellow solid; mp = 218.7° C.; ¹H NMR (400 MHz, DMSO-d₆) δ 10.91 (s, NH), 8.13-8.09 (m, 1H), 7.58-7.49 (m, 6H), 7.33-7.29 (m, 2H); LCMS (ESI) m/z 394 [M + H]+. | 2.521 2.14 | >50 | 2.743 1.71 | >50 | 1.969 1.48 | >50 |
| 88 | White solid; mp = 225.1° C.; ¹H NMR (400 MHz, Acetone-d₆); δ 7.97 (d, J = 8.0 Hz, 1H), 7.86 (d, J = 11.6 Hz, 1H), 7.72-7.62 (m, 3H), 7.50-7.48 (m, 2H), 7.34 (t, J = 7.2 Hz, 1H), 7.14 (d, J = 15.6 Hz, 1H); LCMS (ESI) m/z 439 [M + H]+. | N/D | >50 | >50 | >50 | >50 | >50 |
| 89 | Pale pink solid; mp = 153.5° C.; ¹H NMR (400 MHz, DMSO-d₆) δ 10.55 (s, NH), 7.48 (s, 4H), 7.16-7.12 (m, 4H), 3.02-2.95 (m, 4H), 2.27 (s, 3H); LCMS (ESI) m/z 358 [M + H]+. | N/D | >50 | >50 | >50 | 48.35 | >50 |
| 90 | Pale pink solid; mp = 122.7° C.; ¹H NMR (400 MHz, DMSO-d₆) δ 10.47 (s, NH), 7.49-7.47 (m, 2H), 7.30 (d, J = 11.6 Hz, 1H), 7.16-7.08 (m, 4H), 3.02-2.95 (m, 4H), 2.30 (s, 3H), 2.28 (s, 3H); LCMS (ESI) m/z 372 [M + H]+. | N/D (C) | >50 | >50 (C) | >50 | >50 (C) | >50 |

TABLE 41

| | | | | | | | |
|---|---|---|---|---|---|---|---|
| 91 | Pale pink solid; mp = 151.6° C.; ¹H NMR (400 MHz, DMSO-d₆) δ 10.84 (s, NH), 7.63-7.62 (m, 2H), 7.15 (d, J = 5.2 Hz, 1H), 7.12-7.10 (m, 4H), 3.03-2.99 (m, 4H), 2.28 (s, 3H); LCMS (ESI) m/z 376 [M + H]+. | 19.26 | 6.03 | 9.13 | 15.74 | 8.3 | 6.63 |
| 92 | Colorless oil; ¹H NMR (400 MHz, (CD₃)₂CO) δ 7.54 (d, J = 8.0 Hz, 2H), 7.29 (d, J = 8.8 Hz, 3H), 7.18 (t, J = 7.4 Hz, 1H), 7.10 (d, J = 7.2 Hz, 1H), 7.04 (t, J = 7.2 Hz, 1H), 4.20 (s, 2H), 3.22-3.14 (m, 1H), 3.13-3.05 (m, 4H), 1.20 (d, J = 6.8 Hz, 6H); LCMS (ESI) m/z 386 [M + H]⁺. | 6.59 | >50 | 7.17 | >50 | 6.42 | >50 |
| 93 | Colorless oil; ¹H NMR (400 MHz, (CD₃)₂CO) δ 7.47 (d, J = 9.2 Hz, 2H), 7.33 (d, J = 7.6 Hz, 2H), 7.29 (d, J = 7.6 Hz, 1H), 7.18 (t, J = 7.4 Hz, 1H), 7.10 (d, J = 7.6 Hz, 1H), 7.04 (t, J = 7.2 Hz, 1H), 4.27 (s, 2H), 3.23-3.15 (m, 1H), 3.15-3.06 (m, 4H), 1.20 (d, J = 6.8 Hz, 6H); LCMS (ESI) m/z 391 [M + H]⁺ | 45.13 | >50 | 22.07 | >50 | 31.54 | >50 |
| 94 | Colorless oil; ¹H NMR (400 MHz, (CD₃)₂CO) δ 7.28 (d, J = 7.6 Hz, 1H), 7.17 (d, J = 8.2 Hz, 1H), 7.10 (d, J = 7.6 Hz, 1H), 7.03 (t, J = 7.6 Hz, 1H), 6.93 (s, 3H), 4.09 (s, 2H), 3.24-3.16 (m, 1H), 3.14-3.04 (m, 4H), 2.27 (s, 6H), 1.21 (d, J = 6.4 Hz, 6H); LCMS (ESI) m/z 335 [M + H]⁺. | >50 | >50 | 37.75 | >50 | 43.35 | >50 |
| 95 | Colorless oil; ¹H NMR (400 MHz, (CD₃)₂CO) δ 7.56 (d, J = 8.0 Hz, 1H), 7.47-7.44 (m, 2H), 7.41-7.32 (m, 8H), 7.28 (dd, J = 10.6, 7.4 Hz, 2H), 4.45 (s, 2H), 4.24 (s, 2H); LCMS (ESI) m/z 393 [M + H]⁺. | 37.63 | >50 | 12.46 | >50 | 41.41 | >50 |

TABLE 41-continued

| | | | | | | |
|---|---|---|---|---|---|---|
| 96 | White solid; $^1$H NMR (400 MHz, (CD$_3$)$_2$CO) δ 7.57 (d, J = 6.4 Hz, 1H), 7.50 (t, J = 7.6 Hz, 1H), 7.47-7.39 (m, 4H), 7.28 (d, J = 7.2 Hz, 1H), 7.24-7.21 (m, 2H), 5.66 (s, 2H), 4.98 (s, 2H), 231 (s, 3H), 2.14 (s, 3H); LCMS (ESI) m/z 488 [M + H]$^+$ | 1.03 | >50 | 1.3 | >50 | 1.3 | >50 |
| 97 | Pale pink oil; $^1$H NMR (400 MHz, (CD$_3$)$_2$CO) δ 7.54 (d, J = 6.8 Hz, 1H), 7.48-7.31 (m, 12H), 7.27 (d, J = 7.6 Hz, 1H), 5.63 (s, 1H), 4.46 (s, 2H), 3.40 (s, 3H); LCMS (ESI) m/z 389 [M + H]$^-$ | 2.53 | 6.08 | 4.4 | 6.2 | 5.9 | 6.0 |
| 98 | White solid; $^1$H NMR (400 MHz, (CD$_3$)$_2$CO) δ 8.55 (s, 1H), 8.44-8.09 (m, 3H), 8.02-8.00 (m, 1H), 7.67-7.62 (m, 2H), 7.58 (d, J = 8.4 Hz, 2H), 7.45 (d, J = 8.4 Hz, 2H), 4.41 (s, 2H); LCMS (ESI) m/z 366 [M + H]$^+$ | N/D | >50 | N/D | >50 | N/D | >50 |
| 99 | Yellow oil; $^1$H NMR (400 MHz, (CD$_3$)$_2$CO) δ 7.32 (d, J = 7.2 Hz, 1H), 7.24 (d, J = 8.4 Hz, 2H), 7.19-7.18 (m, 2H), 7.12-7.08 (m, 1H), 7.02 (s, 1H), 6.69 (d, J = 8.4 Hz, 2H), 5.66 (br, 1H), 4.43 (s, 2H), 4.40 (d, J = 5.2 Hz, 2H), 2.39 (s, 3H); LCMS (ESI) m/z 390 [M + H]$^+$ | N/D | >50 | N/D | >50 | N/D | >50 |
| 100 | Yellow oil; $^1$H NMR (400 MHz, (CD$_3$)$_2$CO) δ 8.15 (d, J = 9.2 Hz, 1H), 7.96-7.93 (m, 1H), 7.88 (d, J = 6.8 Hz, 1H), 7.56-7.52 (m, 2H), 7.51-7.46 (m, 4H), 7.24 (d, J = 8.0 Hz, 2H), 4.68 (s, 2H), 4.15 (s, 2H); LCMS (ESI) m/z 380 [M + H]$^-$ | >50 | >50 | >50 | >50 | 49.01 | >50 |

TABLE 42

| | | | | | | |
|---|---|---|---|---|---|---|
| 101 | Yellow oil; $^1$H NMR (400 MHz, (CD$_3$)$_2$CO) δ 7.56 (s, 1H), 7.51-7.48 (m, 1H), 7.34-7.32 (m, 2H), 7.28 (d, J = 7.6 Hz, 1H), 7.18 (t, J = 7.4 Hz, 1H), 7.10 (d, J = 7.2 Hz, 1H), 7.04 (t, J = 7.4 MHz, 1H), 4.24 (s, 2H), 3.22-3.16 (m, 1H), 3.14-3.06 (m, 4H), 1.21 (d, J = 6.8 Hz, 6H); LCMS (ESI) m/z 386 [M + H]$^+$. | 36.54 | >50 | 45.27 | >50 | 45.50 | >50 |
| 102 | Yellow oil; $^1$H NMR (400 MHz, (CD$_3$)$_2$CO) δ 7.41-7.33 (m, 3H), 7.30-7.27 (m, 2H), 7.18 (t, J = 7.4 Hz, 1H), 7.10 (d, J = 7.6 Hz, 1H), 7.04 (d, J = 7.4 Hz, 1H), 4.25 (s, 2H), 3.24-3.16 (m, 1H), 3.15-3.06 (m, 4H), 1.21 (d, J = 6.8 Hz, 6H); LCMS (ESI) m/z 341 [M + H]$^+$. | 2.14 | 47.7 | 1.7 | >50 | 1.5 | >50 |
| 103 | Colorless oil; $^1$H NMR (400 MHz, (CD$_3$)$_2$CO) δ 7.54 (d, J = 8.0 Hz, 2H), 7.29 (d, J = 8.8 Hz, 2H), 7.14-7.03 (m, 4H), 4.20 (s, 2H), 3.12-3.03 (m, 4H), 2.28 (s, 3H); LCMS (ESI) m/z 358 [M + H]$^+$. | 3.15 | >50 | 3.1 | >50 | 3.0 | >50 |
| 104 | Colorless oil; $^1$H NMR (400 MHz, (CD$_3$)$_2$CO) δ 7.56-7.55 (m, 2H), 7.51-7.47 (m, 1H), 7.45 (d, J = 7.2 Hz, 1H), 7.41-7.32 (m, 6H), 7.26 (d, J = 7.6 Hz, 1H), 4.45 (s, 2H), 4.24 (s, 2H); LCMS (ESI) m/z 438 [M + H]$^+$. | 42.84 | >50 | >50 | >50 | >50 | >50 |
| 105 | Yellow oil; $^1$H NMR (400 MHz, (CD$_3$)$_2$CO) δ 7.56 (d, J = 7.2 Hz, 1H), 7.47-7.31 (m, 7H), 7.26 (d, J = 7.6 Hz, 1H), 6.92-6.91 (m, 3H), 4.44 (s, 2H), 4.09 (s, 2H), 2.26 (s, 6H); LCMS (ESI) m/z 387 [M + H]$^+$. | 0.86 | >50 | 1.2 | >50 | 1.0 | >50 |
| 106 | Colorless oil; $^1$H NMR (400 MHz, (CD$_3$)$_2$CO) δ 7.56 (d, J = 7.2 Hz, 1H), 7.49-7.46 (m, 4H), 7.44-7.34 (m, 4H), 7.33-7.32 (m, 3H), 7.27 (d, J = 7.6 Hz, 1H), 4.46 (s, 2H), 4.27 (s, 2H); LCMS (ESI) m/z 443 [M + H]$^+$. | 12.09 | >50 | 11.5 | >50 | 11.8 | >50 |
| 107 | Colorless oil; $^1$H NMR (400 MHz, (CD$_3$)$_2$CO) δ 7.55 (d, J = 7.2 Hz, 1H), 7.47-7.31 (m, 7H), 7.26 (d, J = 7.6 Hz, 1H), 7.23 (s, 4H), 4.44 (s, 2H), 4.15 (s, 2H), 2.91 2.83 (m, 1H), 1.22 (d, J = 6.4 Hz, 6H); LCMS (ESI) m/z 401 [M + H]$^+$. | N/D | >50 | N/D | >50 | 20.61 | >50 |
| 108 | Yellow oil; $^1$H NMR (400 MHz, (CD$_3$)$_2$CO) δ 7.53 (d, J = 6.8 Hz, 1H), 7.37-7.32 (m, 2H), 7.14-7.05 (m, 4H), 4.24 (s, 2H), 3.12-3.03 (m, 4H), 2.28 (s, 3H); LCMS (ESI) m/z 331 [M + H]$^+$. | N/D | >50 | N/D | >50 | >50 | >50 |
| 109 | Yellow oil; $^1$H NMR (400 MHz, (CD$_3$)$_2$CO) δ 7.54 (d, J = 8.0 Hz, 2H), 7.29 (d, J = 8.8 Hz, 2H), 7.13-7.05 (m, 4H), 4.22 (s, 2H), 3.32-3.28 (m, 1H), 3.13 (ddd, J = 46.6, 15.2, 7.4 Hz, 2H), 2.75-2.70 (m, 2H), 1.90-1.83 (m, 2H), 1.74-1.67 (m, 2H); LCMS (ESI) m/z 384 [M + H]$^+$. | 34.72 | >50 | 45.86 | >50 | 32.36 | >50 |
| 110 | Colorless oil; $^1$H NMR (400 MHz, (CD$_3$)$_2$CO) δ 7.51 (d, J = 8.4 Hz, 2H), 7.26 (d, J = 8.0 Hz, 1H), 7.19 (d, J = 8.4 Hz, 2H), 7.14-7.03 (m, 3H), 4.15 (s, 2H), 3.59-3.53 (m, 1H), 3.17-3.06 (m, 2H), 2.23 (s, 3H), 1.28 (d, J = 7.2 Hz, 3H); LCMS (ESI) m/z 372 [M + H]$^+$ | 46.68 | 46.68 | 32.22 | >50 | 41.46 | >50 |

TABLE 43

| 111 | White solid; mp = 117.1° C.; ¹H NMR (400 MHz, (CD₃)₂CO) δ 7.93 (d, J = 16.4 Hz, 1H), 7.73 (d, J = 7.6 Hz, 1H), 7.57 (d, J = 8.8 Hz, 2H), 7.40 (d, J = 8.0 Hz, 2H), 7.37 (d, J = 5.2 Hz, 2H), 7.28-7.23 (m, 1H), 6.98 (d, J = 16.4 Hz, 1H), 4.32 (s, 2H), 2.96-2.90 (m, 1H), 1.89-1.79 (m, 5H), 1.55-1.45 (m, 4H), 1.36-1.20 (m, 1H); LCMS (ESI) m/z 424 [M + H]⁺. | 41.29 | 32.45 | 31.77 | >50 | 34.27 | >50 |
|---|---|---|---|---|---|---|---|
| 112 | White solid; mp = 83.8° C.; ¹H NMR (400 MHz, (CD₃)₂CO) δ 7.97 (d, J = 16.4 Hz, 1H), 7.73 (d, J = 8.0 Hz, 1H), 7.50-7.49 (m, 1H), 7.41-7.34 (m, 5H), 7.28-7.24 (m, 1H), 7.00 (d, J = 16.4 Hz, 1H), 4.36 (s, 2H), 3.41-3.33 (m, 1H), 1.26 (d, J = 6.4 Hz, 6H); LCMS (ESI) m/z 339 [M + H]⁺. | >50 | >50 | >50 | >50 | N/D | >50 |
| 113 | Colorless oil; ¹H NMR (400 MHz, (CD₃)₂CO) δ 7.95 (d, J = 16.4 Hz, 2H), 7.72 (d, J = 8.0 Hz, 2H), 7.40-7.38 (m, 2H), 7.28-7.24 (m, 1H), 7.01-7.00 (m, 1H), 6.96 (s, 1H), 6.94 (s, 1H), 4.26 (s, 2H), 3.40-3.33 (m, 1H), 2.28 (s, 6H), 1.26 (d, J = 6.8 Hz, 6H); LCMS (ESI) m/z 333 [M + H]⁺. | 1.55 | 10 | 1.37 | 25.52 | 1.39 | 40.19 |
| 114 | Yellow oil; ¹H NMR (400 MHz, DMSO-d6) δ 7.36-7.27 (m, 4H), 7.19-7.13 (m, 2H), 7.07 (d, J = 8.4 Hz, 1H), 6.96 (t, J = 7.2 Hz, 1H), 5.37 (s, 2H), 4.30 (s, 2H), 3.17-3.14 (m, 1H), 1.09 (d, J = 6.8 Hz, 6H); LCMS (ESI) m/z 309 [M + H]⁺ | 11.97 | 21.75 | 17.67 | >50 | 17.68 | >50 |
| 115 | Yellow oil; ¹H NMR (400 MHz, DMSO-d6) δ 7.53 (d, J = 8.0 Hz, 2H), 7.26 (d, J = 8.0 Hz, 2H), 7.20 (d, J = 7.6 Hz, 1H), 7.19-7.13 (m, 1H), 7.07 (d, J = 7.6 Hz, 1H), 6.96 (t, J = 7.6 Hz, 2H), 5.37 (s, 2H), 4.30 (s, 2H), 3.18-3.11 (m, 1H), 1.08 (d, J = 6.8 Hz, 6H); LCMS (ESI) m/z 389 [M + H]⁺. | 45.05 | >50 | 44.86 | >50 | 38.17 | >50 |
| 116 | White solid; mp = 228.3° C.; ¹H NMR (400 MHz, DMSO-d₆) δ 10.79 (s, NH), 7.73 (d, J = 7.6 Hz, 1H), 7.63-7.51 (m, 5H), 7.34-7.32 (m, 2H), 7.25-7.21 (m, 1H), 7.04 (d, J = 16.0 Hz, 1H), 2.86-2.84 (m, 1H), 1.82-1.75 (m, 5H), 1.49-1.35 (m, 4H), 1.26-1.23 (m, 1H); LCMS (ESI) m/z 424 [M + H]–. | 34.52 | >50 | 36.23 | >50 | 35.13 | N/D |
| 117 | White solid; mp = 225.6° C.; ¹H NMR (400 MHz, DMSO-d₆) δ 10.83 (s, NH), 7.76 (d, J = 7.6 Hz, 1H), 7.64 (d, J = 16.0 Hz, 1H), 7.59-7.51 (m, 4H), 7.36-7.35 (m, 2H), 7.26-7.23 (m, 1H), 7.07 (d, J = 16.0 Hz, 1H), 3.27-3.25 (m, 1H), 1.21 (d, J = 6.8 Hz, 6H); LCMS (ESI) m/z 384 [M − H]+. | N/D | >50 | 31.37 | >50 | 43.53 | N/D |
| 118 | White solid; mp = 174.4° C.; ¹H NMR (400 MHz, DMSO-d₆) δ 10.44 (s, NH), 7.49-7.36 (m, 9H), 7.35-7.26 (m, 3H), 7.15 (d, J = 7.6 Hz, 1H), 2.95 (t, J = 7.2 Hz, 2H), 2.88 (t, J = 7.2 Hz, 2H); LCMS (ESI) m/z 384 [M − H]+. | >50 | >50 | 43.93 | >50 | >50 | >50 |
| 119 | Colorless oil; ¹H NMR (400 MHz, DMSO-d₆), δ 7.52 (d, J = 6.8 Hz, 2H), 7.50-7.37 (m, 3H), 7.27-7.23 (m, 5H), 7.21 (d, J = 6.8 Hz, 2H), 7.17-7.119 (m, 1H), 4.13 (s, 2H), 2.93-2.91 (m, 4H); LCMS (ESI) m/z 419 [M + H]+. | >50 | >50 | >50 | >50 | >50 | >50 |
| 120 | White solid; mp = 232.4° C.; ¹H NMR (400 MHz, DMSO-d₆) δ 10.82 (s, NH), 7.76 (d, J = 7.2 Hz, 1H), 7.59-7.50 (m, 5H), 7.36 (t, J = 7.2 Hz, 1H), 7.16 (d, J = 16.0 Hz, 1H), 7.8 (d, J = 8.8 Hz, 1H), 6.98 (t, J = 7.6 Hz, 1H), 3.86 (s, 3H); LCMS (ESI) m/z 372 [M + H]+. | 17.40 | >50 | 23.09 | >50 | 18.11 | N/D |

TABLE 44

| 121 | Orange solid; mp = 246.5° C.; ¹H NMR (400 MHz, DMSO-d₆); δ 10.93 (s, NH), 9.08 (d, J = 3.6 Hz, 1H), 8.89 (d, J = 8.8 Hz, 1H), 8.23 (d, J = 7.2 Hz, 1H), 8.15 (d, J = 8.4 Hz, 1H), 8.08 (d, J = 16.0 Hz, 1H), 7.92 (t, J = 8.2 Hz, 1H), 7.80-7.77 (m, 1H), 7.60 (d, J = 9.2 Hz, 2H), 7.54 (d, J = 9.2 Hz, 2H), 7.39 (d, J = 16.0 Hz, 1H); LCMS (ESI) m/z 393 [M + H]+. | N/D | >50 | N/D | >50 | N/D | >50 |
|---|---|---|---|---|---|---|---|
| 122 | White solid; mp = 87.0° C.; ¹H NMR (400 MHz, DMSO-d₆) δ 10.66 (s, NH), 7.81-7.79 (m, 1H), 7.43-7.37 (m, 2H), 7.18-7.10 (m, 4H), 3.04-2.98 (m, 4H), 2.29 (s, 3H); LCMS (ESI) m/z 332 [M + H]+. | >50 | >50 | 37.36 | >50 | 43.93 | N/D |
| 123 | White solid; mp = 164.5° C.; ¹H NMR (400 MHz, DMSO-d₆) δ 10.89 (s, NH), 7.74-7.68 (m, 4H), 7.19-7.11 (m, 4H), 3.07-2.97 (m, 4H), 2.26 (s, 3H); LCMS (ESI) m/z 348 [M + H]+. | 10.96 | 34.99 | 14.24 | >50 | 3.61 | >50 |
| 124 | White solid; mp = 239.3° C.; ¹H NMR (400 MHz, DMSO-d₆) δ 10.73 (s, NH), 8.02-7.99 (m, 1H), 7.58-7.50 (m, 8H), 7.37-7.35 (m, 4H), 7.20 (s, 2H); LCMS (ESI) m/z 418 [M + H]+. | N/D | >50 | N/D | >50 | >50 | >50 |
| 125 | Colorless oil; ¹H NMR (400 MHz, DMSO-d₆), δ 8.00 (d, J = 2.0 Hz, 1H), 7.54 (d, J = 2.0 Hz, 2H), 7.52-7.46 (m, 5H), 7.44-7.31 (m, 4H), 7.26-7.24 (m, 3H), 4.24 (s, 2H); LCMS (ESI) m/z 417 [M + H]+. | N/D | >50 | 36.66 | >50 | >50 | >50 |
| 126 | White solid; mp = 87.4° C.; ¹H NMR (400 MHz, DMSO-d₆) δ 7.99 (d, J = 6.8 Hz, 1H), 7.51 (d, J = 16.4 Hz, 1H), 7.47-7.42 (m, 6H), 7.36 (d, J = 4.4 Hz, 1H), 7.32-7.29 (m, 3H), 7.24-7.19 (m, 3H), 4.22 (s, 2H); LCMS (ESI) m/z 417 [M + H]+. | >50 | >50 | 45.69 | >50 | >50 | >50 |

TABLE 44-continued

| # | Description | | | | | | |
|---|---|---|---|---|---|---|---|
| 127 | White solid; mp = 125.5° C.; ¹H NMR (400 MHz, DMSO-d₆) δ 7.98 (d, J = 7.6 Hz, 1H), 7.65 (d, J = 16.8 Hz, 1H), 7.52 (d, J = 8.4 Hz, 2H), 7.41-7.31 (m, 4H), 7.28-7.23 (m, 2H), 7.20 (t, J = 11.2 Hz, 1H), 7.12 (t, J = 11.2 Hz, 1H), 6.99 (d, J = 7.6 Hz, 2H), 6.90(d, J = 8.0 Hz, 1H), 4.26 (s, 2H); LCMS (ESI) m/z 433 [M + H]+. | 16.00 | >50 | 34.93 | >50 | 24.38 | >50 |
| 128 | White solid; mp = 156.1° C.; ¹H NMR (400 MHz, DMSO-d₆) δ 8.00 (d, J = 6.8 Hz, 1H), 7.72 (d, J = 6.8 Hz, 1H), 7.69 (s, 1H), 7.55 (d, J = 8.4 Hz, 2H), 7.43 (t, J = 7.6 Hz, 2H), 7.36-7.31 (m, 4H), 4.33 (s, 2H); LCMS (ESI) m/z 420 [M + H]+. | N/D | >50 | N/D | >50 | N/D | >50 |
| 129 | White solid; mp = 72.2° C.; ¹H NMR (400 MHz, DMSO-d₆) δ 7.51 (d, J = 8.0 Hz, 2H), 7.18 (d, J = 8.0 Hz, 2H), 7.12-7.04 (m, 4H), 4.16 (m, 2H), 3.12 (s, 2H), 2.17 (s, 3H), 1.22 (t, J = 3.4 Hz, 2H), 0.95 (t, J = 3.4Hz, 2H); LCMS (ESI) m/z 383 [M + H]+. | N/D | >50 | N/D | >50 | 6.13 | >50 |
| 130 | White solid; mp = 79.3° C.; ¹H NMR (400 MHz, (CD₃)₂CO) δ 7.97 (d, J = 16.4 Hz, 1H), 7.73 (d, J = 7.6 Hz, 1H), 7.65 (s 1H), 7.51 (d, J = 7.6 Hz, 1H), 7.44-7.33 (m, 4H), 7.28-7.24 (m, 1H), 7.00 (d, J = 16.4 Hz, 1H), 4.35 (s, 2H), 3.41-3.34 (m, 1H), 1.26 (d, J = 6.8 Hz, 6H), LCMS (ESI) m/z 384 [M − H]⁺. | 36.25* | >50 | 42.36 | >50 | 32.81 | >50 |

TABLE 45

| # | Description | | | | | | |
|---|---|---|---|---|---|---|---|
| 131 | White solid; mp = 86.6° C.; ¹H NMR (400 MHz, (CD₃)₂CO) δ 7.97 (d, J = 16.4 Hz, 1H), 7.73 (d, J = 7.6 Hz, 1H), 7.63 (d, J = 6.8 Hz, 1H), 7.47-7.24 (m, 1H), 7.41-7.37 (m, 2H), 7.32 (t, J = 8.8 Hz, 1H), 7.29-7.24 (m, 1H), 7.00 (δ, J = 16.0 Hz, 1H), 4.36 (s, 2H), 3.41-3.34 (m, 1H), 1.26 (d, J = 6.4 Hz, 6H); LCMS (ESI) m/z 381 [M + H]⁺. | 1.02 / 0.84 | 11.85 / 42.53 | 0.927 / 0.69 | 19.03 / >50 | 0.8354 / 0.62 | 20.13 / >50 |
| 132 | White solid; mp = 148.1° C.; ¹H NMR (400 MHz, (CD₃)₂CO) δ 8.29 (d, J = 8.8 Hz, 1H), 7.97 (d, J = 8.4 Hz, 1H), 7.91 (d, J = 8.0 Hz, 1H), 7.87 (d, J = 16.0 Hz, 1H), 7.70 (d, J = 8.0 Hz, 1H), 7.64-7.57 (m, 2H), 7.52 (q, J = 7.5 Hz, 2H), 7.39-7.36 (m, 2H), 7.26-7.22 (m, 1H), 6.95 (d, J = 16.0 Hz, 1H), 4.79 (s, 2H), 3.31-3.26 (m, 1H), 1.23 (d, J = 7.2 Hz, 6H); LCMS (ESI) m/z 355 [M + H]⁺. | 1.58 | 10.85 | 1.52 | 12.20 | 1.14 | 13.59 |
| 133 | Colorless oil; ¹H NMR (400 MHz, (CD₃)₂CO) δ 7.95 (d, J = 16.0 Hz, 1H), 7.72 (d, J = 7.2 Hz, 1H), 7.41-7.38 (m, 2H), 7.33-7.24 (m, 5H), 6.99 (d, J = 16.4 Hz, 1H), 4.26 (s, 2H), 2.97-2.87 (m, 1H), 1.25 (d, J = 6.8 Hz, 6H), 1.22 (d, J = 7.2 Hz, 6H); LCMS (ESI) m/z 347 [M + H]⁺. | 1.97 | >50 | 2.66 | >50 | 1.40 | >50 |
| 134 | Colorless oil; ¹H NMR (400 MHz, (CD₃)₂CO) δ 7.66 (d, J = 16.8 Hz, 1H), 7.56 (d, J = 8.4 Hz, 2H), 7.40 (d, J = 8.4 Hz 2H), 7.17-7.09 (m, 3H), 6.66 (d, J = 16.8 z, 1H), 4.32 (s, 2H), 2.36 (s, 6H); LCMS (ESI) m/z 370 [M + H]⁺. | N/D | >50 | >50 | >50 | >50 | >50 |
| 135 | Colorless oil; ¹H NMR (400 MHz, (CD₃)₂CO) δ 7.54 (d, J = 8.0 Hz, 2H), 7.31 (d, J = 8.8 Hz, 2H), 6.99-6.98 (m, 3H), 4.22 (s, 2H), 3.10-3.06 (m, 2H), 2.99-2.89 (m, 2H), 2.26 (s, 6H); LCMS (ESI) m/z 372 [M + H]⁺. | 5.63 | >50 | 6.40 | >50 | 4.38 | >50 |
| 136 | Colorless oil; ¹H NMR (400 MHz, (CD₃)₂CO) δ 7.97 (d, J = 16.8 Hz, 1H), 7.73 (d, J = 7.6 Hz, 1H), 7.68-7.65 (m, 6H), 7.28-7.24 (m, 4H), 7.50 (d, J = 7.6 Hz, 2H), 7.46 (t, J = 7.6 Hz, 2H), 7.40-7.34 (m, 3H), 7.28-7.24 (m, 1H), 7.01 (d, J = 16.4 Hz, 1H), 4.37 (s, 2H), 3.39-3.34 (m, 1H), 1.26 (d, J = 6.8 Hz, 6H); LCMS (ESI) m/z 381 [M + H]⁺. | 37.72* | >50 | 28.86* | >50 | 32.55* | >50 |
| 137 | Colorless oil; ¹H NMR (400 MHz, (CD₃)₂CO) δ 7.54 (d, J = 8.4 Hz, 2H), 7.26 (d, J = 8.4 Hz, 2H), 7.11-7.05 (m, 2H), 7.02-6.96 (m, 2H), 4.19 (s, 2H), 3.38-3.33 (m, 1H), 3.07 (q, J = 7.2 Hz, 1H), 3.07 (q, J = 7.2 Hz, 1H), 2.91 (q, J = 7.1 Hz, 1H), 2.24 (s, 3H), LCMS (ESI) m/z 372 [M + H]⁺. | 1.83 | >50 | 2.32 | >50 | 2.87 | >50 |
| 138 | Pale yellow oil; ¹H NMR (400 MHz, (CD₃)₂CO) δ 7.57-7.53 (m, 3H), 7.40 (d, J = 8.0 Hz, 2H), 7.32-7.24 (m, 4H), 4.32 (s, 2H), 2.28 (s, 3H), 2.16 (s, 3H); LCMS (ESI) m/z 370 [M + H]⁺. | 0.1825 / 0.07 | >50 | 0.1606 / 0.09 | >50 | 0.2164 / 0.08 | >50 |
| 139 | Colorless oil; ¹H NMR (400 MHz, (CD₃)₂CO) δ 7.97 (d, J = 16.8 Hz, 1H), 7.73 (d, J = 7.6 Hz, 1H), 7.68-7.65 (m, 6H), 7.28-7.24 (m, 4H), 7.50 (d, J = 7.6 Hz, 2H), 7.46 (t, J = 7.6 Hz, 2H), 7.40-7.34 (m, 3H), 7.28-7.24 (m, 1H), 7.01 (d, J = 16.4 Hz, 1H), 4.37 (s, 2H), 3.39-3.31 (m, 1H), 1.26 (d, J = 6.8 Hz, 6H); LCMS (ESI) m/z 381 [M + H]⁺. | 35.87 | >50 | 32.17 | >50 | 45.76 | >50 |
| 140 | Colorless oil; ¹H NMR (400 MHz, (CD₃)₂CO) δ 7.54 (d, J = 8.4 Hz, 2H), 7.26 (d, J = 8.4 Hz, 2H), 7.02-6.96 (m, 2H), 4.19 (s, 2H), 3.38-3.33 (m, 1H), 3.07 (q, J = 7.2 1H), 3.07 (q, J = 7.2 Hz, 1H), 2.91 (q, J = 7.1 Hz, 1H), 2.24 (s, 3H), LCMS (ESI) m/z 372 [M + H]⁻. | 14.11 | >50 | 18.19 | >50 | 19.88 | >50 |

TABLE 46

| # | Description | | | | | | |
|---|---|---|---|---|---|---|---|
| 141 | Pale yellow oil; ¹H NMR (400 MHz, (CD₃)₂CO) δ 7.57-7.53 (m, 3H), 7.40 (d, J = 8.0 Hz, 2H), 7.32-7.24 (m, 4H), 4.32 (s, 2H), 2.28 (s, 3H), 2.16 (s, 3H); LCMS (ESI) m/z 370 [M + H]⁺. | 3.65 | 11.41 | 2.62 | 20.52 | 3.68 | 14.29 |
| 142 | Colorless oil; ¹H NMR (400 MHz, (CD₃)₂CO) δ 7.97 (d, J = 16.8 Hz, 1H), 7.73 (d, J = 7.6 Hz, 1H), 7.68-7.65 (m, 6H), 7.28-7.24 (m, 4H), 7.50 (d, J = 7.6 Hz, 2H), 7.46 (t, J = 7.6 Hz, 2H), 7.40-7.34 (m, 3H), 7.28-7.24 (m, 1H), 7.01 (d, J = 16.4 Hz, 1H), 4.37 (s, 2H), 3.39-3.34 (m, 1H), 1.26 (d, J = 6.8 Hz, 6H); LCMS (ESI) m/z 381 [M + H]⁺. | N/D | >50 | N/D | >50 | N/D | >50 |
| 143 | Colorless oil; ¹H NMR (400 MHz, (CD₃)₂CO) δ 7.54 (d, J = 8.4 Hz, 2H), 7.26 (d, J = 8.4 Hz, 2H), 7.11-7.05 (m, 2H), 7.02-6.96 (m, 2H), 4.19 (s, 2H), 3.38-3.33 (m, 1H), 3.07 (q, J = 7.2 Hz, 1H), 3.07 (q, J = 7.2 Hz, 1H), 2.91 (q, J = 7.1 Hz, 1H), 2.24 (s, 3H); LCMS (ESI) m/z 372 [M + H]⁺. | N/D | >50 | N/D | >50 | N/D | >50 |
| 144 | Pale yellow oil; ¹H NMR (400 MHz, (CD₃)₂CO) δ 7.57-7.53 (m, 3H), 7.40 (d, J = 8.0 Hz, 2H), 7.32-7.24 (m, 4H), 4.32 (s, 2H), 2.28 (s, 3H), 2.16 (s, 3H); LCMS (ESI) m/z 370 [M + H]⁺. | >50 | >50 | 48.67 | >50 | 49.30 | >50 |
| 145 | White solid; mp = 111.2° C.; ¹H NMR (400 MHz, (CD₃)₂CO) δ 7.96 (d, J = 16.0 Hz, 1H), 7.73 (d, J = 8.0 Hz, 1H), 7.65 (s, 1H), 7.40-7.38 (m, 2H), 7.33-7.32 (m, 2H), 7.28-7.24 (m, 1H), 7.00 (d, J = 16.4 Hz, 1H), 4.30 (s, 2H), 3.41-3.34 (m, 1H), 2.37 (s, 3H), 1.26 (d, J = 6.8 Hz, 6H); LCMS (ESI) m/z 398 [M − H]⁺. | >50 | >50 | N/D | >50 | 49.10 | >50 |
| 146 | Colorless oil; ¹H NMR (400 MHz, (CD₃)₂CO) δ 7.94 (d, J = 16.4 Hz, 1H), 7.72 (d, J = 8.0 Hz, 1H), 7.40-7.38 (m, 2H), 7.28-7.24 (m, 1H), 7.16 (s, 1H), 7.13-7.08 (m, 2H), 6.98 (d, J = 16.4 Hz, 1H), 4.21 (s, 2H), 3.41-3.33 (m, 1H), 2.24 (s, 3H), 2.23 (s, 3H), 1.26 (d, J = 6.4 Hz, 6H); LCMS (ESI) m/z 333 [M − H]⁺. | 3.07 | 24.10 | 5.27 | >50 | 3.74 | >50 |
| 147 | Colorless oil; ¹H NMR (400 MHz, (CD₃)₂CO) δ 7.94 (d, J = 16.4 Hz, 1H), 7.71 (d, J = 8.4 Hz, 1H), 7.40-7.35 (m, 6H), 7.33-7.23 (m, 2H), 6.97 (d, J = 16.4 Hz, 1H), 4.51 (q, J = 7.3 Hz, 1H), 3.38-3.31 (m, 1H), 1.75 (d, J = 6.8 Hz, 3H), 1.25 (d, J = 6.8 Hz, 6H); LCMS (ESI) m/z 319 [M + H]⁺. | 4.40 | >50 | 6.00 | >50 | 6.00 | >50 |
| 148 | Colorless oil; ¹H NMR (400 MHz, (CD₃)₂CO) δ 7.93 (d, J = 16.4 Hz, 1H), 7.71 (d, J = 8.0 Hz, 1H), 7.39-7.35 (m, 2H), 7.30-7.23 (m, 3H), 7.18 (d, J = 7.6 Hz, 2H), 6.98 (d, J = 16.4 Hz, 1H), 4.47 (q, J = 7.1 Hz, 1H), 3.38-3.31 (m, 1H), 2.47 (d, J = 6.8 Hz, 2H), 1.89-1.82 (m, 1H), 1.74 (d, J = 7.2 Hz, 3H), 1.25 (d, J = 6.8 Hz, 6H), 0.88 (d, J = 6.8 Hz, 6H); LCMS (ESI) m/z 375 [M + H]⁺. | 45.06 | >50 | 39.83 | >50 | 38.85 | >50 |
| 149 | White solid; mp = 164.5° C.; ¹H NMR (400 MHz, (CD₃)₂CO) δ 7.98 (s, 1H), 7.73 (d, J = 6.0 Hz, 1H), 7.57-7.55 (m, 2H), 7.52 (s, 1H), 7.37 (d, J = 8.4 Hz, 2H), 7.28 (d, J = 16.4 Hz, 1H), 4.32 (s, 2H); LCMS (ESI) m/z 411 [M − H]⁺. | N/D | >50 | N/D | >50 | N/D | >50 |
| 150 | White solid; mp = 126.9° C.; ¹H NMR (400 MHz, (CD₃)₂CO) δ 7.88 (d, J = 16.4 Hz, 1H), 7.56 (d, J = 6.4 Hz, 3H), 7.39 (d, J = 8.4 Hz, 2H), 7.21 (d, J = 7.6 Hz, 1H), 7.15 (t, J = 8.4 Hz, 1H), 6.94 (d, J = 16.4 Hz, 1H), 4.31 (s, 2H), 2.33 (s, 3H), 2.31 (s, 3H); LCMS (ESI) m/z 370 [M + H]⁺. | N/D | >50 | N/D | >50 | >50 | >50 |

TABLE 47

| # | Description | | | | | | |
|---|---|---|---|---|---|---|---|
| 151 | White solid; mp = 61.8° C.; ¹H NMR (400 MHz, (CD₃)₂CO) δ 7.62 (s, 1H), 7.58-7.52 (m, 4H), 7.40-7.29 (m, 4H), 7.16 (d, J = 16.4 Hz, 1H), 4.31 (s, 2H), 3.00-2.93 (m, 1H), 1.27 (d, J = 7.2 Hz, 6H); LCMS (ESI) m/z 384 [M + H]⁺. | 6.39 | >50 | 21.29 | >50 | 6.38 | >50 |
| 152 | Ivory solid; mp = 118.9° C.; ¹H NMR (400 MHz, (CD₃)₂CO) δ 8.26 (d, J = 7.6 Hz, 1H), 7.96 (d, J = 16.4 Hz, 1H), 7.90 (d, J = 7.6 Hz, 1H), 7.65 (t, J = 8.0 Hz, 1H), 7.57 (t, J = 6.8 Hz, 2H), 7.40 (d, J = 8.4 Hz, 2H), 7.31 (d, J = 16.4 Hz, 1H), 4.36 (s, 2H); LCMS (ESI) m/z 444 [M + H]⁻. | >50 | >50 | N/D | >50 | >50 | >50 |
| 153 | White solid; mp = 123.7° C.; ¹H NMR (400 MHz, (CD₃)₂CO) δ 7.96 (d, J = 8.8 Hz, 1H), 7.55-7.47 (m, 6H), 7.43-7.37 (m, 4H), 7.31 (d, J = 6.4 Hz, 2H), 7.09 (d, J = 16.4 Hz, 1H), 4.24 (s, 2H); LCMS (ESI) m/z 452 [M + H]⁻. | N/D | >50 | N/D | >50 | N/D | >50 |
| 154 | White solid; mp = 139.8° C.; ¹H NMR (400 MHz, (CD₃)₂CO) δ 7.64 (d, J = 8.0 Hz, 2H), 7.56 (d, J = 8.4 Hz, 2H), 7.52 (d, J = 16.4 Hz, 1H), 7.38 (d, J = 8.8 Hz, 2H), 7.33 (d, J = 8.0 Hz, 2H), 7.09 (d, J = 16.4 Hz, 1H), 4.30 (s, 2H), 2.97-2.93 (m, 1H), 1.26 (d, J = 10.4 Hz, 6H); LCMS (ESI) m/z 384 [M − H]⁺. | >50 | >50 | N/D | >50 | >50 | >50 |

TABLE 47-continued

| | | | | | | | |
|---|---|---|---|---|---|---|---|
| 155 | Colorless oil; ¹H NMR (400 MHz, (CD₃)₂CO) δ 7.92 (d, J = 8.0 Hz, 1H), 7.79 (d, J = 16.8 Hz, 1H), 7.54 (d, J = 6.0 Hz, 2H), 7.41 (t, J = 7.8 Hz, 1H), 7.35 (d, J = 8.8 Hz, 2H), 7.26-7.17 (m, 4H), 7.13-7.07 (m, 2H), 6.90 (d, J = 8.4 Hz, 1H), 4.29 (s, 2H); LCMS (ESI) m/z 452 [M + H]⁻. | N/D | >50 | N/D | >50 | N/D | >50 |
| 156 | White solid; mp = 145.7° C.; ¹H NMR (400 MHz, DMSO-d₆) δ 7.79-7.73 (m, 3H), 7.56 (d, J = 8.4 Hz, 2H), 7.47 (t, J = 4.4 Hz, 1H), 7.38-7.34 (m, 3H), 4.39 (s, 2H); LCMS (ESI) m/z 355 [M + H]−. | N/D | >50 | N/D | >50 | N/D | >50 |
| 157 | White solid; mp = 149.7° C.; ¹H NMR (400 MHz, DMSO-d₆) δ 7.86 (s, 1H), 7.80 (d, J = 9.2 Hz, 1H), 7.72 (s, 1H), 7.57-7.49 (m, 3H), 7.35 (d, J = 8.4 Hz, 2H), 4.39 (s, 2H); LCMS (ESI) m/z 389 [M + H]+. | N/D | >50 | N/D | >50 | N/D | >50 |
| 158 | White solid; mp = 125.9° C.; ¹H NMR (400 MHz, DMSO-d₆) δ 8.12-8.08 (m, 1H), 7.67 (d, J = 16.4 Hz, 1H), 7.54 (d, J = 6.0 Hz, 1H), 7.38-7.27 (m, 7H), 4.32 (s, 2H); LCMS (ESI) m/z 315 [M + H]+. | >50 | >50 | >50 | >50 | >50 | >50 |
| 159 | Pale yellow oil; mp = 142.2° C.; ¹H NMR (400 MHz, DMSO-d₆) δ 8.13-8.09 (m, 1H), 7.69 (d, J = 16.4 Hz, 1H), 7.63 (d, J = 6.8 Hz, 1H), 7.56 (d, J = 6.0 Hz, 1H), 7.41-7.31 (m, 4H), 4.35 (s, 2H); LCMS (ESI) m/z 367 [M − H]+. | N/D | >50 | >50 | >50 | 39.71 | >50 |
| 160 | Pale yellow oil; mp = 195.7° C.; ¹H NMR (400 MHz, DMSO-d₆) δ 11.16 (s, NH), 8.14-8.10 (m, 1H), 7.69-7.63 (m, 2H), 7.56-7.50 (m, 2H), 7.35-7.28 (m, 3H); LCMS (ESI) m/z 412 [M + H]+. | N/D | >50 | >50 | >50 | >50 | >50 |

TABLE 48

| | | | | | | | |
|---|---|---|---|---|---|---|---|
| 161 | Pale yellow solid; mp = 172.5° C.; ¹H NMR (400 MHz, DMSO-d₆) δ 8.09-8.06 (m, 1H), 7.75-7.70 (m, 2H), 7.54-7.48 (m, 2H), 7.41 (d, J = 6.0 Hz, 1H), 7.31-7.27 (m, 2H), 3.54 (s, 3H); LCMS (ESI) m/z 426 [M + H]+. | >50 36.24 | >50 | 48.26 21.34 | >50 | 43.10 25.34 | >50 41.49 |
| 162 | Yellow solid; mp = 186.2° C.; ¹H NMR (400 MHz, (CD₃)₂CO) δ 7.79 (d, J = 16.8 Hz, 1H), 7.56 (d, J = 8.8 Hz, 2H), 7.49 (s, 1H), 7.38 (d, J = 8.8 Hz, 2H), 7.10 (d, J = 16.4 Hz, 1H), 7.02 (s, 1H), 6.14 (s, 2H), 4.32 (s, 2H); LCMS (ESI) m/z 420 [M H]⁺. | >50 | >50 | 30.52 15.87 | >50 | >50 | >50 |
| 163 | Ivory solid; mp = 106.3° C.; ¹H NMR (400 MHz, (CD₃)₂CO) δ 7.78 (d, J = 16.4 Hz, 1H), 7.71 (d, J = 8.0 Hz, 1H), 7.56 (d, J = 6.4 Hz, 2H), 7.41-7.37 (m, 3H), 7.17 (d, J = 16.8 Hz, 1H), 7.10 (d, J = 8.4 Hz, 1H), 7.01 (t, J = 7.0 Hz, 1H), 4.31 (s, 2H), 3.95 (s, 3H); LCMS (ESI) m/z 372 [M + H]⁺. | >50 | >50 | 32.33 | >50 | N/D | >50 |
| 164 | Colorless oil; ¹H NMR (400 MHz, (CD₃)₂CO) δ 7.97 (d, J = 16.4 Hz, 1H), 7.73 (d, J = 7.6 Hz, 1H), 7.67 (t, J = 7.8 Hz, 1H), 7.41-7.37 (m, 3H), 7.28-7.23 (m, 2H), 7.00 (d, J = 16.0 Hz, 1H), 4.37 (s, 2H), 3.40-3.33 (m, 1H), 1.26 (d, J = 6.4 Hz, 6H); LCMS (ESI) m/z 402 [M + H]⁺. | 8.35 | >50 | 5.16 | >50 | 4.32 | >50 |
| 165 | White solid; mp = 110.6° C.; ¹H NMR (400 MHz, (CD₃)₂CO) δ 7.72 (d, J = 7.6 Hz, 2H), 7.57-7.53 (m, 3H), 7.46-7.37 (m, 5H), 7.15 (d, J = 16.4 Hz, 1H), 4.31 (s, 2H; LCMS (ESI) m/z 342 [M + H]⁺. | 2.84 | 12.63 | 1.95 | 13.49 | 3.76 | 10.13 |
| 166 | White solid; mp = 136.3° C.; ¹H NMR (400 MHz, (CD₃)₂CO) δ 7.99 (d, J = 6.0 Hz, 1H), 16.4 (d, J = 16.4 Hz, 1H), 7.58-7.50 (m, 3H), 7.46-7.38 (m, 4H), 7.22 (d, J = 16.4 Hz, 1H), 4.31 (s, 2H); LCMS (ESI) m/z 376 [M + H]⁻. | N/D | >50 | N/D | >50 | N/D | >50 |
| 167 | White solid; mp = 105.1° C.; ¹H NMR (400 MHz, (CD₃)₂CO) δ 7.79 (s, 1H), 7.69 (d, J = 6.8 Hz, 1H), 7.57-7.55 (m, 3H), 7.52-7.40 (m, 2H), 7.38 (d, J = 8.4 Hz, 2H), 7.25 (d, J = 16.4 Hz, 1H), 4.32 (s, 2H); LCMS (ESI) m/z 376 [M + H]⁺. | N/D | >50 | N/D | >50 | N/D | >50 |
| 168 | White solid; mp = 139.3° C.; ¹H NMR (400 MHz, (CD₃)₂CO) δ 7.62-7.53 (m, 5H), 7.43-7.39 (m, 3H), 7.18 (d, J = 16.8 Hz, 1H), 4.36 (s, 2H); LCMS (ESI) m/z 411 [M + H]⁺. | N/D | >50 | N/D | >50 | N/D | >50 |
| 169 | White solid; mp = 71.9° C.; ¹H NMR (400 MHz, (CD₃)₂CO) δ 7.96 (d, J = 16.0 Hz, 1H), 7.73 (d, J = 8.0 Hz, 1H), 7.49-7.36 (m, 5H), 7.29-7.24 (m, 1H), 7.00 (d, J = 16.0 Hz, 1H), 4.35 (s, 2H), 3.40-3.33 (m, 1H), 1.26 (d, J = 6.8 Hz, 1H); LCMS (ESI) m/z 402 [M + H]⁺. | 3.08 | 20.30 | 2.13 | >50 | 2.22 | 37.24 |
| 170 | White solid; mp = 108.5° C.; ¹H NMR (400 MHz, (CD₃)₂CO) δ 7.80 (d, J = 16.4 Hz, 1H), 7.77-7.75 (m, 1H), 7.56 (d, J = 8.4 Hz, 2H), 7.39 (d, J = 8.4 Hz, 2H), 7.30-7.25 (m, 3H), 7.03 (d, J = 16.4 Hz, 1H), 4.32 (s, 2H), 2.44 (s, 3H); LCMS (ESI) m/z 356 [M + H]⁻. | 2.05 | 8.53 | 2.00 | 6.63 | 2.04 | 9.08 |

TABLE 49

| | | | | | | | |
|---|---|---|---|---|---|---|---|
| 171 | White solid; mp = 129.0° C.; ¹H NMR (400 MHz, (CD₃)₂CO) δ 7.76 (d, J = 8.4 Hz, 2H), 7.58-7.52 (m, 3H), 7.48 (d, J = 8.8 Hz, 2H), 7.37 (d, J = 8.4 Hz, 2H), 7.19 (d, J = 16.4 Hz, 1H), 4.31 (s, 2H); LCMS (ESI) m/z 376 [M + H]⁺. | 4.30 | >50 | 3.74 | 49.513 | 3.63 | 36.20 |
| 172 | White solid; mp = 117.1° C.; ¹H NMR (400 MHz, (CD₃)₂CO) δ 7.95 (d, J = 16.4 Hz, 1H), 7.72 (d, J = 7.6 Hz, 1H), 7.56 (d, J = 8.4 Hz, 1H), 7.40-7.37 (m, 3H), 7.28-7.24 (m, 1H), 7.18 (d, J = 8.0 Hz, 1H), 6.99 (d, J = 16.8 Hz, 1H), 4.27 (s, 2H), 3.40-3.33 (m, 1H), 2.38 (s, 3H), 1.26 (d, J = 7.2 Hz, 6H); LCMS (ESI) m/z 398 [M + H]⁺. | N/D | >50 | N/D | >50 | N/D | >50 |
| 173 | Colorless oil; ¹H NMR (400 MHz, (CD₃)₂CO) δ 7.96 (d, J = 16.0 Hz, 1H), 7.73 (d, J = 7.6 Hz, 1H), 7.40-7.36 (m, 2H), 7.28-7.24 (m, 2H), 7.19-7.15 (m, 1H), 7.05 (t, J = 7.6 Hz, 1H), 6.99 (d, J = 15.6 Hz, 1H), 4.30 (s, 2H), 3.40-3.33 (m, 1H), 2.31 (s, 3H), 1.24 (d, J = 8.0 Hz, 6H); LCMS (ESI) m/z 337 [M + H]⁺. | 1.91 | 13.52 | 1.77 | 12.64 | 1.71 | 15.85 |
| 174 | White solid; mp = 86.7° C.; ¹H NMR (400 MHz, DMSO-d₆) δ 7.83-7.78 (m, 3H), 7.77 (d, J = 2.0 Hz, 2H), 7.53-7.43 (m, 3H), 7.42-7.27 (m, 3H), 4.09 (s, 2H); LCMS (ESI) m/z 341 [M − H]⁺. | 1.45 | 6.53 | 3.78 | 5.46 | 1.54 | 6.30 |
| 175 | White solid; mp = 81.5° C.; ¹H NMR (400 MHz, DMSO-d₆) δ 8.10 (d, J = 16.4 Hz, 1H), 7.76 (d, J = 7.2 Hz, 1H), 7.52 (d, J = 6.8 Hz, 2H), 7.40-7.37 (m, 2H), 7.29-7.25 (m, 3H), 7.16 (d, J = 16.4 Hz, 1H), 4.10 (s, 2H), 3.32 (m, 1H), 1.19 (d, J = 6.8 Hz, 6H); LCMS (ESI) m/z 383 [M + H] +. | N/D | >50 | N/D | >50 | N/D | >50 |
| 176 | White solid; mp = 119.9° C.; ¹H NMR (400 MHz, DMSO-d₆) δ 8.12-8.08 (m, 1H), 7.67 (d, J = 16.0 Hz, 1H), 7.55 (d, J = 6.4 Hz, 2H), 7.34-7.31 (m, 2H), 7.11 (d, J = 6.0 Hz, 1H), 4.28 (s, 2H), 2.31 (s, 3H); LCMS (ESI) m/z 407 [M + H]+. | N/D | 6.53 | N/D | >50 | N/D | >50 |
| 177 | Pale yellow solid; mp = 136.9° C.; ¹H NMR (400 MHz, DMSO-d₆) δ 8.12-8.08 (m, 1H), 7.67 (d, J = 16.0 Hz, 1H), 7.55 (d, J = 4.8 Hz, 1H), 7.39-7.31 (m, 2H), 7.21-7.10 (m, 3H), 4.30 (s, 2H), 2.26 (s, 3H); LCMS (ESI) m/z 346 [M − H]+. | 1.074 1.03 | >50 | 0.8348 0.78 | >50 | 0.7526 0.81 | >50 |
| 178 | Pale yellow solid; mp = 121.7° C.; ¹H NMR (400 MHz, DMSO-d₆) δ 8.12-8.09 (m, 1H), 7.69 (d, J = 16.0 Hz, 1H), 7.61 (s, 1H), 7.55 (d, J = 5.6 Hz, 1H), 7.49 (d, J = 7.2 Hz, 1H), 7.39-7.29 (m, 4H), 4.35 (s, 2H); LCMS (ESI) m/z 393 [M − H]+. | 0.95 | >50 | 0.99 | >50 | 0.75 | >50 |
| 179 | White solid; mp = 104.0° C.; ¹H NMR (400 MHz, DMSO-d₆) δ 8.13-8.09 (m, 1H), 7.68 (d, J = 16.0 Hz, 1H), 7.55 (d, J = 6.4 Hz, 1H), 7.46 (s, 1H), 7.39-7.31 (m, 5H), 4.36 (s, 2H); LCMS (ESI) m/z 349 [M + H]⁺. | 0.5142 0.09 0.51 | >50 | 0.6315 0.73 0.42 | >50 | 0.3507 0.73 0.37 | >50 |
| 180 | White solid; mp = 163.0° C.; ¹H NMR (400 MHz, DMSO-d₆) δ 8.45 (s, 1H), 8.13-8.09 (m, 1H), 7.87 (d, J = 6.4 Hz, 1H), 7.69 (d, J = 16.0 Hz, 1H), 7.57-7.54 (m, 2H), 7.38 (d, J = 16.0 Hz, 1H), 7.31 (t, J = 4.2 Hz, 1H), 4.40 (s, 2H); LCMS (ESI) m/z 350 [M + H]+. | 0.98 | >50 | 1.05 | >50 | 0.51 | >50 |

TABLE 50

| | | | | | | | |
|---|---|---|---|---|---|---|---|
| 181 | Pale yellow solid; mp = 139.0° C.; ¹H NMR (400 MHz, DMSO-d₆) δ 8.12-8.08 (m, 1H), 7.63 (d, J = 16.0 Hz, 1H), 7.60 (s, 1H), 7.55 (d, J = 6.4 Hz, 1H), 7.39-7.24 (m, 4H), 4.31 (s, 2H), 2.31 (s, 3H); LCMS (ESI) m/z 407 [M + H]+. | 8.29 | >50 | 10.89 | >50 | 5.56 | >50 |
| 182 | Pale yellow solid; mp = 117.3° C.; ¹H NMR (400 MHz, DMSO-d₆) δ 8.1--8.08 (m, 1H), 7.60 (d, J = 16.0 Hz, 1H), 7.54 (d, J = 6.0 Hz, 1H), 7.35 (d, J = 16.0 Hz, 1H), 7.31 (t, J = 7.2 Hz, 1H), 7.25-7.20 (m, 4H), 4.26 (s, 2H), 2.86-2.83 (m, 1H), 1.16 (d, J = 6.4 Hz, 6H); LCMS (ESI) m/z 356 [M + H]+. | 0.5493 0.61 | >50 | 0.6166 0.52 | >50 | 0.3727 0.43 | >50 |
| 183 | White solid; mp = 78.4° C.; ¹H NMR (400 MHz, DMSO-d₆) δ 7.73 (d, J = 6.8 Hz, 2H), 7.63-7.57 (m, 3H), 7.41-7.35 (m, 5H), 7.27 (d, J = 16.0 Hz, 1H), 4.39 (s, 2H); LCMS (ESI) m/z 341 [M + H]+. | 1.865 1.31 | >50 | 1.335 1.20 | >50 | 0.9037 0.83 | >50 |
| 184 | Pale yellow solid; mp = 166.2° C.; ¹H NMR (400 MHz, DMSO-d₆) δ 8.12-8.09 (m, 1H), 7.71-7.66 (m, 2H), 7.55 (d, J = 8.4 Hz, 1H), 7.44-7.35 (m, 2H), 7.31 (t, J = 7.2 Hz, 1H), 7.17 (d, J = 8.0 Hz, 1H) 4.36 (s, 2H); LCMS (ESI) m/z 411 [M + H]+. | >50 | >50 | >50 | >50 | >50 | >50 |

TABLE 50-continued

| | | | | | | | |
|---|---|---|---|---|---|---|---|
| 185 | Pale yellow solid; mp = 152.7° C.; $^1$H NMR (400 MHz, DMSO-d$_6$) δ 8.14 (d, J = 8.0 Hz, 1H), 8.09-7.96 (m, 1H), 7.91 (d, J = 1.2 Hz, 1H), 7.89 (d, J = 1.2 Hz, 1H), 7.62 (d, J = 16.4 Hz, 1H), 7.58-7.35 (m, 5H), 7.33 (d, J = 16.4 Hz, 1H), 7.28 (d, J = 6.4 Hz, 1H) 4.79 (s, 2H), LCMS (ESI) m/z 364 [M + H]+. | >50 | >50 | >50 | >50 | >50 | >50 |
| 186 | Yellow oil, $^1$H NMR (400 MHz, (CD$_3$)$_2$CO) δ 7.83 (dd, J = 8.4, 6.0 Hz, 1H), 7.75 (d, J = 16.8 Hz, 1H), 7.64 (s, 1H), 7.50 (d, J = 7.6 Hz, 1H), 7.43 (d, J = 8.0 Hz, 1H), 7.34 (t, J = 8.0 Hz, 1H), 7.08-7.01 (m, 2H), 7.01 (d, J = 16.4 Hz, 1H), 4.35 (s, 2H), 2.47 (s, 3H); LCMS (ESI) m/z 374 [M + H]$^+$. | 0.7784 0.37 | >50 | 1.149 0.31 | >50 | 1.383 0.27 | >50 |
| 187 | White solid; mp = 117.3° C.; 1H NMR (400 MHz, (CD$_3$)$_2$CO) δ 7.87 (t, J = 7.6 Hz, 1H), 7.65 (d, J = 16.8 Hz, 1H), 7.49-7.21 (m, 8H), 4.37 (s, 2H), LCMS (ESI) m/z 315 [M + H]$^+$. | 1.70 | >50 | 1.89 | >50 | 1.51 | >50 |
| 188 | White solid; mp = 95.3° C.; $^1$H NMR (400 MHz, (CD$_3$)$_2$CO) δ 7.80 (dd, J = 8.6, 5.4 Hz, 2H), 7.62 (s, 1H), 7.55 (d, J = 16.4 Hz, 1H), 7.50 (d, J = 8.0 Hz, 1H), 7.41 (d, J = 8.0 Hz, 1H), 7.34 (t, J = 7.8 Hz, 1H), 7.21 (t, J = 7.8 Hz, 2H), 7.11 (d, J = 16.4 Hz, 1H), 4.34 (s, 2H), LCMS (ESI) m/z 360 [M + H]$^+$. | 12.24 | >50 | 9.58 | >50 | 11.56 | >50 |
| 189 | Yellow solid; mp = 87.7° C.; $^1$H NMR (400 MHz, (CD$_3$)$_2$CO) δ 7.96 (q, J = 8.1 Hz, 1H), 7.64 (s, 1H), 7.59 (d, J = 16.8 Hz, 1H), 7.51 (d, J = 7.6 Hz, 1H), 7.43 (d, J = 7.6 Hz, 1H), 7.35 (t, J = 8.0 Hz, 1H), 7.20 (d, J = 16.8 Hz, 1H), 7.17-7.10 (m, 2H), 4.36 (s, 2H), LCMS (ESI) m/z 378 [M + H]$^+$. | 4.883 1.51 | >50 | 4.012 1.32 | >50 | 3.138 1.15 | >50 |
| 190 | White solid; mp = 107.2° C.; $^1$H NMR (400 MHz, (CD$_3$)$_2$CO) δ 7.92 (t, J = 8.2 Hz, 1H), 7.64 (s, 1H), 7.59 (d, J = 16.8 Hz, 1H), 7.51 (d, J = 7.6 Hz, 1H), 7.43 (d, J = 7.2 Hz, 1H), 7.40-7.32 (m, 3H), 7.26 (d, J = 16.4 Hz, 1H), 4.36 (s, 2H), LCMS (ESI) m/z 394 [M + H]$^+$. | 1.85 0.84 | 20.9 >50 | 2.417 0.85 | 40.05 >50 | 1.515 0.69 | 17.88 >50 |

TABLE 51

| | | | | | | | |
|---|---|---|---|---|---|---|---|
| 191 | White solid, mp = 112.8° C., $^1$H NMR (400 MHz, (CD$_3$)$_2$CO) δ 7.82-7.76 (m, 1H), 7.62-7.49 (m, 4H), 7.44-7.332 (m, 3H), 7.20 (d, J = 16.8 Hz, 1H), 4.35 (s, 2H); LCMS (ESI) m/z 378 [M + H]$^+$. | 13.25 | >50 | 8.24 | >50 | 4.99 | >50 |
| 192 | Yellow solid, mp = 142.4° C., $^1$H NMR (400 MHz, (CD$_3$)$_2$CO) δ 8.01 (d, J = 8.8 Hz, 1H), 7.81 (d, J = 16.4 Hz, 1H), 7.65 (s, 1H), 7.61 (s, 1H), 7.52-7.42 (m, 3H), 7.35 (t, J = 8.0 Hz, 1H), 7.26 (d, J = 16.4 Hz, 1H), 4.38 (s, 2H), LCMS (ESI) m/z 411 [M + H]$^+$. | 5.49 | >50 | 4.66 | >50 | 2.60 | >50 |
| 193 | Ivory solid; mp = 97.1° C., $^1$H NMR (400 MHz, (CD$_3$)$_2$CO) δ 7.84-7.80 (m, 2H), 7.66 (s, 1H), 7.57 (dd, J = 8.2, 5.2 Hz, 1H), 7.51 (d, J = 8.0 Hz, 1H), 7.44 (d, J = 7.6 Hz, 1H), 7.35 (t, J = 7.8 Hz, 1H), 7.31 (s, 1H), 7.25 (t, J = 8.6 Hz, 1H), 4.38 (s, 2H); LCMS (ESI) m/z 394 [M + H]$^+$. | >50 | >50 | >50 | >50 | >50 | >50 |
| 194 | Ivory solid, mp = 140.2° C., $^1$H NMR (400 MHz, (CD$_3$)$_2$CO) δ 7.86 (d, J = 16.4 Hz, 1H), 7.84 (d, J = 8.0 Hz, 1H), 7.66 (s, 1H), 7.52-7.33 (m, 6H), 7.29 (d, J = 16.4 Hz, 1H), 4.38 (s, 2H); LCMS (ESI) m/z 394 [M + H]$^+$. | 1.53 | 49.85 | 1.31 | >50 | 1.43 | >50 |
| 195 | Yellow solid, $^1$H NMR (400 MHz, (CD$_3$)$_2$CO) δ 7.85 (d, J = 8.0 Hz, 1H), 7.83 (d, J = 16.4 Hz, 1H), 7.63 (s, 1H), 7.48 (d, J = 8.0 Hz, 1H), 7.42 (d, J = 8.0 Hz, 1H), 7.35-7.31 (m, 2H), 7.23 (d, J = 8.0 Hz, 1H), 7.15 (d, J = 16.4 Hz, 1H), 4.35 (s, 2H), 2.36 (s, 3H), LCMS (ESI) m/z 390 [M + H]$^+$. | 5.74 | >50 | 6.14 | >50 | 5.79 | >50 |
| 196 | Yellow solid, $^1$H NMR (400 MHz, (CD$_3$)$_2$CO) δ 7.95 (d, J = 16.4 Hz, 1H), 7.72 (d, J = 7.6 Hz, 1H), 7.42-7.24 (m, 6H), 6.99 (d, J = 16.4 Hz, 1H), 4.31 (s, 2H), 3.38-3.34 (m, 1H), 1.25 (d, J = 6.4 Hz, 6H), LCMS (ESI) m/z 305 [M + H]$^+$. | 13.1 >50 | >50 | 3.675 8.76 | >50 | 5.443 0.83 | >50 |
| 197 | Yellow solid, mp = 116° C., $^1$H NMR (400 MHz, (CD$_3$)$_2$CO) δ 8.39 (d, J = 16.4 Hz, 1H), 8.27 (d, J = 8.0 Hz, 1H), 8.02-7.98 (m, 3H), 7.67-7.57 (m, 5H), 7.43 (d, J = 8.4 Hz, 2H), 7.22 (d, J = 16.4 Hz, 1H), 4.36 (s, 2H), LCMS (ESI) m/z 392 [M + H]$^+$. | 44.08 | >50 | 26.94 | >50 | 46.11 | >50 |

TABLE 51-continued

| | | | | | | |
|---|---|---|---|---|---|---|
| 198 | White solid, mp = 116.0° C., ¹H NMR (400 MHz, (CD₃)₂CO) δ 7.99 (d, J = 8.0 Hz, 1H), 7.83 (d, J = 16.4 Hz, 1H), 7.65-7.58 (m, 3H), 7.51 (d, J = 8.0 Hz, 1H), 7.44 (d, J = 8.0 Hz, 1H), 7.35 (t, J = 7.8 Hz, 1H), 7.19 (d, J = 16.40 Hz, 1H), 4.37 (s, 2H), 2.55 (s, 3H). LCMS (ESI) m/z 424 [M + H]⁺. | 47.85 | >50 | 35.69 | >50 | >50 | >50 |
| 199 | Yellow solid, mp = 106.9° C., ¹H NMR (400 MHz, (CD₃)₂CO) δ 8.35 (s, 1H), 7.89 (d, J = 16.4 Hz, 1H), 7.77-7.67 (m, 2H), 7.66 (s, 1H), 7.52-7.43 (m, 3H), 7.35 (t, J = 7.8 Hz, 1H), 4.39 (s, 1H), LCMS (ESI) m/z 444 [M + H]⁺. | 9.89 | >50 | 8.55 | >50 | 6.30 | >50 |
| 200 | White solid, mp = 74.2° C., ¹H NMR (400 MHz, (CD₃)₂CO) δ 7.77 (d, J = 16.4 Hz, 1H), 7.68-7.64 (m, 2H), 7.50 (d, J = 7.2 Hz, 1H), 7.43 (d, J = 8.4 Hz, 1H), 7.34 (t, J = 8.0 Hz, 1H), 7.10-7.08 (m, 2H), 6.98 (d, J = 16.4 Hz, 1H), 4.34 (s, 2H), 2.41 (s, 3H), 2.31 (s, 3H), LCMS (ESI) m/z 370 [M + H]⁺. | 10.24 | >50 | 11.70 | >50 | 11.91 | >50 |

TABLE 52

| | | | | | | | |
|---|---|---|---|---|---|---|---|
| 201 | White solid, mp = 152.7° C.; ¹H NMR (400 MHz, acetone-d₆) δ 8.40 (brs, 1H), 8.07-8.03 (m, 1H), 7.80 (d, J = 16.8 Hz, 1H), 7.38 (dd, J = 8.8, 2.8 Hz, 1H), 7.27-7.23 (m, 1H), 7.22-7.16 (m, 1H), 7.19 (d, J = 16.8 Hz, 1H), 6.85-6.83 (m, 2H), 6.78-6.75 (m, 1H), 4.24 (s, 2H); LCMS (ESI) m/z 331 [M + H]⁺. | 3.70 | >50 | 3.25 | >50 | 3.05 | >50 |
| 202 | White solid, mp = 131.7° C., ¹H NMR (400 MHz, acetone-d₆) δ 8.07-8.03 (m, 1H), 7.80 (d, J = 16.8 Hz, 1H), 7.38 (dd, J = 8.8, 2.4 Hz, 1H), 7.30-7.23 (m, 2H), 7.19 (d, J = 16.8 Hz, 1H), 6.98-6.94 (m, 2H), 6.88-6.86 (m, 2H), 4.29 (s, 2H), 3.80 (s, 3H); LCMS (ESI) m/z 345 [M + H]⁺. | >50 | >50 | N/D | >50 | >50 | >50 |
| 203 | Pale yellow solid, ¹H NMR (400 MHz, acetone-d₆) δ 8.06-8.02 (m, 1H), 7.81 (d, J = 16.4 Hz, 1H), 7.61-7.56 (m, 2H), 7.39 (dd, J = 8.8 2.4 Hz, 1H), 7.26-7.17 (m, 4H), 5.86 (s, 2H), 2.72 (s, 3H), LCMS (ESI) m/z 369 [M + H]⁺. | N/D | >50 | N/D | >50 | 15.38 | >50 |
| 204 | White solid, ¹H NMR (400 MHz, (CD₃)₂CO) δ 8.45 (d, J = 4.0 Hz, 1H), 8.11 (d, J = 8.4 Hz, 1H), 7.76 (d, J = 16.4 Hz, 1H), 7.64 (s, 1H), 7.50 (d, J = 7.6 Hz, 1H), 7.43 (d, J = 7.6 Hz, 1H), 7.34 (t, J = 8.0 Hz, 1H), 7.29-7.26 (m, 1H), 7.11 (d, J = 16.4 Hz, 1H), 4.36 (s, 2H), 2.63 (s, 3H), LCMS (ESI) m/z 356 [M − H]⁺. | 2.499 1.32 | >50 | 16.31 0.49 | >50 | 1.588 0.31 | >50 |
| 205 | White solid, ¹H NMR (400 MHz, (CD₃)₂CO) δ 8.65 (d, J = 6.0 Hz, 1H), 8.12 (s, 1H), 8.09-8.05 (m, 1H), 7.83 (d, J = 16.0 Hz, 1H), 7.40 (d, J = 7.6 Hz, 1H), 7.28 (d, J = 8.0 Hz, 1H), 7.21 (d, J = 16.4 Hz, 1H), 1.53 (s, 2H); LCMS (ESI) m/z 394 [M − H]⁺. | 34.85 | >50 | 42.95 | >50 | 21.59 | >50 |
| 206 | White solid, ¹H NMR (400 MHz, (CD₃)₂CO) δ 8.49 (d, J = 5.2 Hz, 1H), 8.07 (dd, J = 8.4, 5.6 Hz, 1H), 7.81 (d, J = 16.4 Hz, 1H), 7.63 (s, 1H), 7.43-7.38 (m, 2H), 7.27 (t, J = 8.0 Hz, 1H), 7.20 (d, J = 16.4 Hz, 1H), 4.54 (s, 2H), LCMS (ESI) m/z 356 [M − H]⁺. | 2.263 1.90 | >50 | 5.155 1.55 | >50 | 1.282 1.56 | >50 |
| 207 | White solid, mp = 123.0° C., ¹H NMR (400 MHz, (CD₃)₂CO) δ 8.06 (dd, J = 8.6, 5.8 Hz, 1H), 7.82 (d, J = 16.4 Hz, 1H), 7.77 (d, J = 6.8 Hz, 1H), 7.50-7.48 (m, 1H), 7.40 (d, J = 8.8 Hz, 1H), 7.32-7.24 (m, 2H), 7.21 (d, J = 16.4 Hz, 1H), 4.38 (s, 2H), LCMS (ESI) m/z 412 [M − H]⁺. | 7.25 11.90 3.68 | >50 | 23.84 8.94 1.76 | >50 | 7.56 9.54 1.46 | >50 |
| 208 | White solid, mp = 179.9° C., ¹H NMR (400 MHz, (CD₃)₂CO) δ 8.07 (dd, J = 8.9, 6.0 Hz, 1H), 7.82 (d, J = 16.4 Hz, 1H), 7.69-7.68 (m, 1H), 7.59 (d, J = 8.4 Hz, 1H), 7.44-7.39 (m, 2H), 7.59 (t, J = 8.4 Hz, 1H), 7.21 (d, J = 16.8 Hz, 1H), 4.40 (s, 2H), LCMS (ESI) m/z 384 [M − H]⁺. | 1.191 0.98 | >50 | 5.194 0.76 | >50 | 0.7202 0.74 | >50 |
| 209 | Yellow solid, mp = 168.3° C., ¹H NMR (400 MHz, (CD₃)₂CO) δ 9.14 (br, 1H), 7.79 (d, J = 16.4 Hz, 1H), 7.65 (d, J = 8.0 Hz, 1H), 7.56 (d, J = 8.4 Hz, 2H), 7.38 (d, J = 8.4 Hz, 2H), 7.26-7.20 (m, 2H), 6.98 (d, J = 8.4 Hz, 1H), 6.92 (t, J = 7.6 Hz, 1H), 4.31 (s, 2H), LCMS (ESI) m/z 358 [M + H]⁺. | >50 | >50 | 46.82 | >50 | 28.58 | >50 |
| 210 | Yellow oil, ¹H NMR (400 MHz, (CD₃)₂CO) δ 7.79 (d, J = 16.4 Hz, 1H), 7.72 (d, J = 7.2 Hz, 1H), 7.64 (s, 1H), 7.50 (d, J = 8.0 Hz, 1H), 7.43-7.33 (m, 3H), 7.18 (d, J = 16.8 Hz, 1H), 7.10 (d, J = 8.4 Hz, 1H), 7.01 (d, J = 7.4 Hz, 1H), 4.35 (s, 2H), 3.95 (s, 3H), LCMS (ESI) m/z 372 [M + H]⁺. | 36.20 | 48.09 | 47.30 | 48.08 | 23.49 | 46.75 |

TABLE 53

| | | | | | | |
|---|---|---|---|---|---|---|
| 211 | White solid, mp = 100.5° C., ¹H NMR (400 MHz, (CD₃)₂CO) 8.06 (dd, J = 8.8, 6.0 Hz, 1H), 7.80 (d, J = 16.4 Hz, 1H), 7.39 (d, J = 8.0 Hz, 1H), 7.28-7.17 (m, 5H), 7.12 (d, J = 7.2 Hz, 1H), 4.27 (s, 2H), 2.32 (s, 3H), LCMS (ESI) m/z 329 [M + H]⁺. | 3.323 3.08 | >50 | 12.72 2.95 | >50 | 3.017 2.93 | >50 |
| 212 | Ivory solid, mp = 195.4° C., ¹H NMR (400 MHz, (CD₃)₂CO) δ 8.06 (dd, J = 8.8, 6.0 Hz, 1H), 7.80 (d, J = 16.4 Hz, 1H), 7.39 (d, J = 8.0 Hz, 1H), 7.28-7.17 (m, 5H), 7.12 (d, J = 7.2 Hz, 1H), 4.27 (s, 2H), 2.32 (s, 3H), LCMS (ESI) m/z 329 [M − H]⁺. | 1.09 | >50 | 2.33 | >50 | 1.99 | >50 |
| 213 | Yellow solid, mp = 148.1° C., ¹H NMR (400 MHz, (CD₃)₂CO) δ 8.04 (dd, J = 8.6, 6.2 Hz, 1H), 7.78 (d, J = 16.4 Hz, 1H), 7.69 (d, J = 8.0 Hz, 1H), 7.40-7.37 (m, 5H), 7.32 (s, 1H), 7.25 (t, J = 10.2 Hz, 1H), 7.20-7.15 (m, 2H), 7.09 (t, J = 7.6 Hz, 1H), 4.42 (s, 2H), 3.82 (s, 3H), LCMS (ESI) m/z 368 [M + H]⁺. | >50 | >50 | >50 | >50 | 7.26 | >50 |
| 214 | White solid, ¹H NMR (400 MHz, acetone-d₆) δ 8.06-8.02 (m, 1H), 7.83-7.82 (m, 1H), 7.78 (d, J = 16.8 Hz, 1H), 7.56-7.54 (m, 1H), 7.43-7.36 (m, 2H), 7.26-7.14 (m, 2H), 7.18 (d, J = 16.8 Hz, 1H), 4.66 (s, 2H), 4.04 (m, 3H); LCMS (ESI) m/z 369 [M + H]⁺. | 34.15 >50 | >50 >50 | >50 >50 | >50 >50 | 7.747 8.73 | >50 >50 |
| 215 | White solid, mp = 129.5° C., ¹H NMR (400 MHz, (CD₃)₂CO) δ 8.05 (dd, J = 6.8, 7.6 Hz, 1H), 7.80 (d, J = 16.4 Hz, 1H), 7.65 (s, 1H), 7.57 (d, J = 8.0 Hz, 1H), 7.51 (d, J = 6.0 Hz, 1H), 7.44 (d, J = 7.2 Hz, 1H), 7.37-7.28 (m, 2H), 7.17 (d, J = 16.0 Hz, 1H), 4.37 (s, 2H), LCMS (ESI) m/z 439 [M − H]⁺. | 1.08 | >50 | 1.71 | >50 | 0.81 | >50 |
| 216 | Yellow oil, ¹H NMR (400 MHz, (CD₃)₂CO) δ 8.49-8.46 (m, 2H), 7.74 (d, J = 16.4 Hz, 1H), 7.67 (d, J = 5.2 Hz, 1H), 7.64 (s, 1H), 7.51 (d, J = 7.2 Hz, 1H), 7.43 (d, J = 8.0 Hz, 1H), 7.35 (t, J = 8.0 Hz, 1H), 7.29 (d, J = 16.4 Hz, 1H), 4.37 (s, 2H), 2.44 (s, 3H); LCMS (ESI) m/z 357 [M + H]⁺. | 0.9592 0.51 | >50 | 1.107 0.47 | >50 | 0.948 0.38 | >50 |
| 217 | White solid, mp = 134.2° C., ¹H NMR (400 MHz, (CD₃)₂CO) δ 8.06 (dd, J = 8.8, 6.0 Hz, 1H), 7.80 (d, J = 16.4 Hz, 1H), 7.39 (d, J = 9.2 Hz, 1H), 7.26 (t, J = 8.0 Hz, 1H), 7.21-7.14 (m, 2H), 6.79 (s, 1H), 6.66 (t, J = 8.0 Hz, 2H), 4.23 (s, 2H), 2.94 (s, 6H), LCMS (ESI) m/z 358 [M − H]⁺. | N/D | >50 | >50 | >50 | N/D | >50 |
| 218 | Yellow solid, mp = 179.9° C., ¹H NMR (400 MHz, (CD₃)₂CO) δ 9.12 (br, 1H), 7.80 (d, J = 16.8 Hz, 1H), 7.66-7.64 (m, 2H), 7.50 (d, J = 8.0 Hz, 1H), 7.42 (d, J '2 8.0 Hz, 1H), 7.34 (t, J = 7.8 Hz, 1H), 7.25-7.20 (m, 2H), 6.98 (d, J = 8.0 Hz, 1H), 6.92 (t, J = 7.4 Hz, 1H), 4.34 (s, 2H); LCMS (ESI) m/z 358 [M + H]⁺. | 24.71 6.02 | >50 | 8.668 4.51 | >50 | 4.277 1.21 | >50 |
| 219 | Yellow solid, mp = 145.2° C., ¹H NMR (400 MHz, (CD₃)₂CO) δ 8.08 (dd, J = 8.8, 6.4 Hz, 1H), 7.88 (t, J = 7.8 Hz, 1H), 7.83 (d, J = 16.4 Hz, 1H), 7.52 (d, J = 7.2 Hz, 1H), 7.41 (t, J = 8.4 Hz, 1H), 7.29-7.26 (m, 1H), 7.22 (d, J = 16.0 Hz, 1H), 4.51 (s, 2H); LCMS (ESI) m/z 351 [M + H]⁺. | 26.1 >50 | >50 | 10.52 45.39 | >50 | 4.01 0.91 | >50 |
| 220 | Yellow oil, ¹H NMR (400 MHz, (CD₃)₂CO) δ 7.68 (d, J = 16.0 Hz, 1H), 7.78 (d, J = 8.0 Hz, 1H), 7.66 (s, 1H), 7.51 (d, J = 7.6 Hz, 1H), 7.44 (d, J = 7.6 Hz, 1H), 7.35 (t, J = 7.8 Hz, 2H), 7.30-7.26 (m, 2H), 7.05 (d, J = 16.4 Hz, 1H), 4.35 (s, 2H), 7.51 (q, J = 7.6 Hz, 2H), 1.21 (t, J = 7.4 Hz, 3H); LCMS (ESI) m/z 370 [M + H]⁺. | >50 N/D | >50 | 15 >50 | >50 | 30.76 >50 | >50 |

TABLE 54

| | | | | | | |
|---|---|---|---|---|---|---|
| 221 | Yellow solid, mp = 139.3° C., ¹H NMR (400 MHz, (CD₃)₂CO) δ 8.05 (dd, J = 8.8, 6.0 Hz, 1H), 7.79 (d, J = 16.4 Hz, 1H), 7.39 (d, J = 8.8 Hz, 1H), 7.26 (t, J = 8.4 Hz, 1H), 7.18 (d, J = 16.4 Hz, 1H), 7.14-7.04 (m, 3H), 4.33 (s, 2H), 2.30 (s, 3H), 2.29 (s, 3H), LCMS (ESI) m/z 343 [M + H]⁺. | 1.70 | >50 | 0.22 | >50 | 1.24 | >50 |
| 222 | White solid, mp = 155.2° C., ¹H NMR (400 MHz, (CD₃)₂CO) δ 8.08 (t, J = 7.6 Hz, 1H), 7.82 (d, J = 16.0 Hz, 1H), 7.68 (d, J = 8.0 Hz, 1H), 7.52 (d, J = 7.6 Hz, 1H), 7.44-7.39 (m, 2H), 7.31-7.22 (m, 2H), 7.21 (d, J = 16.4 Hz, 1H), 4.48 (s, 2H); LCMS (ESI) m/z 394 [M + H]⁺. | 0.8903 0.37 | >50 | 0.436 0.31 | >50 | 0.6745 0.33 | >50 |

TABLE 54-continued

| | | | | | | |
|---|---|---|---|---|---|---|
| 223 | Yellow solid, mp = 108.7° C., ¹H NMR (400 MHz, (CD₃)₂CO) δ 8.07 (t, J = 7.6 Hz, 1H), 7.78 (d, J = 19.2 Hz, 1H), 7.55 (s, 1H), 7.41-7.22 (m, 5H), 7.19 (d, J = 16.4 Hz, 1H), 3.29 (t, J = 6.8 Hz, 2H), 3.20 (t, J = 6.8 Hz, 21H); LCMS (ESI) m/z 408 [M + H]⁺. | N/D | >50 | N/D | >50 | >50 | >50 |
| 224 | Yellow oil, ¹H NMR (400 MHz, (CD₃)₂CO) δ 7.86 (d, J = 16.8 Hz, 1H), 7.72 (d, J = 7.6 Hz, 1H), 7.66 (s, 1H), 7.51 (d, J = 8.0 Hz, 1H), 7.44 (d, J = 8.0 Hz, 1H), 7.38-7.32 (m, 2H), 7.16 (d, J = 8.4 Hz, 1H), 7.09-7.05 (m, 2H), 4.35 (s, 2H), 2.74 (s, 6H); LCMS (ESI) m/z 385 [M + H]⁺. | N/D | >50 | N/D | >50 | >50 | >50 |
| 225 | White solid, mp = 162.5° C., ¹H NMR (400 MHz, (CD₃)₂CO) δ 8.43-8.39 (m, 2H), 7.79 (d, J = 16.4 Hz, 1H), 7.66 (s, 1H), 7.53-7.51 (m, 2H), 7.43 (t, J = 9.2 Hz, 1H), 7.35 (t, J = 7.8 Hz, 1H), 7.32 (d, J = 16.4 Hz, 1H), 4.39 (s, 2H); LCMS (ESI) m/z 377 [M + H]⁺. | 2.305<br>1.49 | >50 | 1.886<br>1.08 | >50 | 2.786<br>1.21 | 29.8<br>>50 |
| 226 | Yellow solid, mp = 132.5° C., ¹H NMR (400 MHz, (CD₃)₂CO) δ 8.07 (dd, J = 8.6, 6.2 Hz, 1H), 7.82 (d, J = 16.4 Hz, 1H), 7.45-7.38 (m, 2H), 7.27-7.18 (m, 4H), 7.09 (t, J = 7.4 Hz, 1H), 4.38 (s, 2H), LCMS (ESI) m/z 333 [M + H]⁺. | >50 | >50 | >50 | >50 | 28.37 | >50 |
| 227 | Pale yellow solid, ¹H NMR (400 MHz, CDCl₃) δ 7.83 (d, J = 16.0 Hz, 1H), 7.67-7.63 (m, 1H), 7.46 (s, 2H), 7.19 (dd, J = 8.0, 2.4 Hz, 1H), 7.08-7.01 (m, 1H), 6.95 (d, J = 16.4 Hz, 1H), 4.20 (s, 2H), LCMS (ESI) m/z 473 [M + H]⁺. | N/D | >50 | N/D | >50 | N/D | >50 |
| 228 | Pale yellow solid, ¹H NMR (400 MHz, CDCl₃) δ 7.86-7.78 (m, 5H), 7.65-7.61 (m, 1H), 7.52-7.46 (m, 3H), 7.17 (dd, J = 8.4, 2.4 Hz, 1H), 7.06-6.99 (m, 1H), 6.88 (d, J = 24.0 Hz, 1H), 4.42 (s, 2H), LCMS (ESI) m/z 365 [M − H]⁺. | N/D | >50 | N/D | >50 | N/D | >50 |
| 229 | White solid, ¹H NMR (400 MHz, (CD₃)₂CO) δ 8.06 (dd, J = 8.8, 6.4 Hz, 1H), 7.81 (d, J = 16.4 Hz, 1H), 7.64 (s, 1H), 7.40-7.38 (m, 2H), 7.26 (t, J = 8.4 Hz, 1H), 7.19 (d, J = 16.4 Hz, 1H), 7.09 (d, J = 8.4 Hz, 1H), 4.29 (s, 2H), 3.89 (s, 3H), LCMS (ESI) m/z 423 [M + H]⁺. | 13.58<br>>50 | >50 | 1.913<br>7.16 | >50 | 1.584<br>0.73 | >50 |
| 230 | Yellow solid, ¹H NMR (400 MHz, (CD₃)₂CO) δ 8.06 (dd, J = 8.4, 5.6 Hz, 1H), 7.81 (d, J = 16.8 Hz, 1H), 7.58 (s, 1H), 7.39 (dd, J = 8.4, 2.4 Hz, 1H), 7.28-7.23 (m, 2H), 7.19 (d, J = 16.8 Hz, 1H), 7.00 (d, J = 8.4 Hz, 1H), 4.25 (s, 2H) LCMS (ESI) m/z 409 [M + H]⁺. | N/D | >50 | N/D | >50 | >50 | >50 |

TABLE 55

| | | | | | | |
|---|---|---|---|---|---|---|
| 231 | Yellow solid, ¹H NMR (400 MHz, (CD₃)₂CO) δ 7.75-7.71 (m, 2H), 7.64 (s, 1H), 7.49 (d, J = 8.0 Hz, 1H), 7.43-7.31 (m, 2H), 7.02 (d, J = 16.8 Hz, 1H), 6.89-6.79 (m, 2H), 4.34 (s, 2H), 2.78 (s, 6H); LCMS (ESI) m/z 402 [M + H]⁺. | 8.43 | >50 | 6.58 | >50 | 6.29 | >50 |
| 232 | Yellow solid, ¹H NMR (400 MHz, (CD₃)₂CO) δ 7.75 (d, J = 16.4 Hz, 1H), 7.64 (s, 1H), 7.59 (t, J = 8.0 Hz, 1H), 7.50 (d, J = 7.6 Hz, 1H), 7.42 (d, J = 8.0 Hz, 1H), 7.33 (t, J = 8.0 Hz, 1H), 6.81 (d, J = 16.4 Hz, 1H), 6.67-6.59 (m, 2H), 4.32 (s, 2H), 3.31-3.29 (m, 4H), 1.98-1.94 (m, 4H); LCMS (ESI) m/z 428 [M + H]⁺. | 2.48 | 30.86 | 2.40 | >50 | 1.30 | 12 |
| 233 | Yellow oil, ¹H NMR (400 MHz, (CD₃)₂CO) δ 7.64 (s, 1H), 7.51-7.42 (m, 3H), 7.34 (t, J = 8.0 Hz, 1H), 7.22 (d, J = 16.8 Hz, 1H), 7.13-7.08 (m, 2H), 4.36 (s, 2H), LCMS (ESI) m/z 395 [M + H]⁺. | 8.949<br>40.3<br>20.41 | >50<br><br>>50 | 10.23<br>34.41<br>14.51 | >50<br><br>>50 | 3.934<br>7.13<br>7.06 | 27.64<br><br>>50 |
| 234 | Pale yellow solid, ¹H NMR (400 MHz, CDCl₃) δ 7.82 (d, J = 16.4 Hz, 1H), 7.61-7.67 (m, 4H), 7.49 (t, J = 8.0 Hz, 1H), 7.21-7.19 (m, 1H), 7.08-7.04 (m, 1H), 6.95 (d, J = 16.4 Hz, 1H), 4.30 (s, 2H), LCMS (ESI) m/z 340 [M + H]⁺. | 0.53 | >50 | 0.75 | >50 | 0.46 | 16.94 |
| 235 | Pale yellow solid, ¹H NMR (400 MHz, CDCl₃) δ 7.88 (d, J = 16.4 Hz, 1H), 7.68 (dd, J = 8.8, 2.8 Hz, 1H), 7.41 (t, J = 8.0 Hz, 1H), 7.29 (d, J = 8.0 Hz, 1H), 7.24 (brs, 1H), 7.19 (dd, J = 8.4, 2.8 Hz, 2H), 7.19 (dd, J = 8.8, 2.8 Hz, 1H), 7.02 (d, J = 16.8 Hz, 1H), 4.28 (s, 2H), LCMS (ESI) m/z 399 [M + H]⁺. | >50 | >50 | >50 | >50 | >50 | >50 |
| 236 | White solid, mp = 171.9° C., ¹H NMR (400 MHz, (CD₃)₂CO) δ 8.95 (s, 1H), 8.38 (d, J = 8.4 Hz, 1H), 8.04 (dd, J = 8.6, 6.2 Hz, 1H), 7.95 (d, J = 8.0 Hz, 1H), 7.81 (d, J = 6.8 Hz, 1H), 7.75 (d, J = 16.4 Hz, 1H), 7.62 (t, J = 7.6 Hz, 1H), 7.57 (dd, J = 8.4, 4.0 Hz, 1H), 7.38 (d, J = 8.8 Hz, 1H), 7.25 (t, J = 8.6 Hz, 1H), 7.17 (d, J = 16.4 Hz, 1H), 4.96 (s, 2H); LCMS (ESI) m/z 366 [M + H]⁺. | 3.614<br>N/D<br>34.74 | >50 | 5.962<br>N/D<br>13.90 | >50 | 3.392<br>17.02<br>2.55 | >50 |

TABLE 55-continued

| | | | | | | | |
|---|---|---|---|---|---|---|---|
| 237 | Yellow solid, mp = 171.4° C., ¹H NMR (400 MHz, (CD₃)₂CO) δ 8.43-8.40 (m, 2H), 8.06 (dd, J = 9.2, 6.0 Hz, 1H), 8.01 (d, J = 8.4 Hz, 1H), 7.84-7.76 (m, 4H), 7.38 (d, J = 8.8 Hz, 1H), 7.27-7.23 (m, 1H), 7.21 (d, J = 16.8 Hz, 1H), 5.06 (s, 2H); LCMS (ESI) m/z 366 [M + H]⁻. | 1.36 | >50 | 0.91 | >50 | 0.71 | >50 |
| 238 | Yellow solid, mp = 171.3° C., ¹H NMR (400 MHz, (CD₃)₂CO) δ 9.29 (s, 1H), 8.62 (s, 1H), 8.26 (d, J = 8.0 Hz, 1H), 8.17 (d, J = 8.0 Hz, 1H), 8.03 (dd, J = 7.6, 6.8 Hz, 1H), 7.87 (t, J = 7.6 Hz, 1H), 7.78-7.71 (m, 2H), 7.38 (d, J = 11.2 Hz, 1H), 7.24 (t, J = 8.6 Hz, 1H), 7.16 (d, J = 16.4 Hz, 1H), 4.81 (s, 2H); LCMS (ESI) m/z 366 [M + H]⁺. | 0.70 | >50 | 0.76 | >50 | 0.49 | >50 |
| 239 | White solid, mp = 127.5° C., ¹H NMR (400 MHz, (CD₃)₂CO) δ 8.58 (s, 1H), 7.80-7.76 (m, 1H), 7.70 (d, J = 10.0 Hz, 1H), 7.64-7.58 (m, 2H), 7.52-7.42 (m, 3H), 7.35 (t, J = 2.8 Hz, 1H), 4.36 (s, 2H); LCMS (ESI) m/z 361 [M + H]⁺. | 1.31 | >50 | 1.53 | >50 | 1.08 | >50 |
| 240 | Yellow solid, ¹H NMR (400 MHz, (CD₃)₂CO) δ 8.77 (s, 1H), 8.56 (d, J = 4.8 Hz, 1H), 8.08 (dd, J = 8.6, 6.2 Hz, 1H), 7.84 (d, J = 16.8 Hz, 1H), 7.54 (d, J = 4.4 Hz, 1H), 7.41 (d, J = 8.8 Hz, 1H), 7.29-7.25 (m, 1H), 7.22 (d, J = 16.4 Hz, 1H), 4.53 (s, 2H), LCMS (ESI) m/z 395 [M + H]⁺. | 6.493 1.74 | >50 | 17.39 1.12 | >50 | 0.9996 0.53 | >50 |

TABLE 56

| | | | | | | | |
|---|---|---|---|---|---|---|---|
| 241 | Yellow solid, ¹H NMR (400 MHz, (CD₃)₂CO) δ 8.77 (s, 1H), 8.56 (d, J = 4.8 Hz, 1H), 8.08 (dd, J = 8.6, 6.2 Hz, 1H), 7.84 (d, J = 16.8 Hz, 1H), 7.54 (d, J = 4.4 Hz, 1H), 7.41 (d, J = 8.8 Hz, 1H), 7.29-7.25 (m, 1H), 7.22 (d, J = 16.4 Hz, 1H), 4.53 (s, 2H), LCMS (ESI) m/z 395 [M + H]⁺. | 4.124 15.93 5.82 | >50 | 5.946 10.48 4.36 | >50 | 5.242 4.32 3.84 | >50 |
| 242 | White solid, mp = 131.1° C., ¹H NMR (400 MHz, (CD₃)₂CO) δ 8.36 (d, J = 16.4 Hz, 1H), 7.98 (d, J = 8.0 Hz, 1H), 7.94 (d, J = 7.6 Hz, 1H), 7.69-7.65 (m, 2H), 7.56-7.50 (m, 2H), 7.44 (d, J = 7.6 Hz, 1H), 7.35 (t, J = 7.6 Hz, 1H), 7.07 (d, J = 16.4 Hz, 1H), 4.38 (s, 2H), 3.91 (s, 3H), LCMS (ESI) m/z 400 [M + H]⁺. | N/D | >50 | N/D | >50 | N/D | >50 |
| 243 | White solid, mp = 167.7° C., ¹H NMR (400 MHz, (CD₃)₂CO) δ 8.56 (d, J = 16.8 Hz, 1H), 8.03 (d, J = 7.6 Hz, 1H), 7.90 (d, J = 8.0 Hz, 1H), 7.63 (s, 1H), 7.59 (t, J = 7.6 Hz, 1H), 7.51-7.47 (m, 2H), 7.42 (d, J = 7.2 Hz, 1H), 7.33 (t, J = 7.6 Hz, 1H), 7.02 (d, J = 16.0 Hz, 1H), 4.34 (s, 2H); LCMS (ESI) m/z 386 [M + H]⁺. | N/D | >50 | N/D | >50 | N/D | >50 |
| 244 | White solid, mp = 165.8° C., ¹H NMR (400 MHz, (CD₃)₂CO) δ 9.60 (br, 1H), 8.15-8.10 (m, 1H), 7.66 (s, 1H), 7.52 (d, J = 8.8 Hz, 1H), 7.45 (d, J = 6.0 Hz, 2H), 7.36 (t, J = 7.8 Hz, 1H), 7.26 (t, J = 8.6 Hz, 1H), 4.46 (s, 2H); LCMS (ESI) m/z 411 [M + H]⁺. | N/D | >50 | N/D | >50 | N/D | >50 |
| 245 | Yellow solid, mp = 112° C., ¹H NMR (400 MHz, (CD₃)₂CO) δ 7.66 (s, 1H), 7.62 (d, J = 16.8 Hz, 1H), 7.51 (d, J = 8.0 Hz, 1H), 7.44 (d, = 7.6 Hz, 1H), 7.37-7.33 (m, 2H), 7.25 (t, J = 10.2 Hz, 1H), 7.23 (d, J = 16.8 Hz, 1H), 4.38 (s, 2H), LCMS (ESI) m/z 412 [M − H]⁺. | N/D | >50 | N/D | >50 | N/D | >50 |
| 246 | Pale yellow solid; ¹H NMR (400 MHz, DMSO-d₆) δ 8.35-8.31 (m, 1H), 7.69-7.67 (m, 1H), 7.53-7.44 (m, 3H), 7.32-7.29 (m, 2H), 3.95 (s, 2H), LCMS (ESI) m/z 446 [M + H]⁺. | 0.26 | >50 | 0.25 | >50 | 0.19 | >50 |
| 247 | pale yellow solid, ¹H NMR (400 MHz, (CD₃)₂CO) δ 8.06 (dd, J = 6.4, 2.4 Hz, 1H), 7.82 (t, J = 6.8 Hz, 2H), 7.74 (d, J = 7.6 Hz, 1H), 7.69-7.62 (m, 2H), 7.39 (dd, J = 8.8, 2.8 Hz, 1H), 7.28-7.26 (m, 1H), 7.21 (d, J = 16.4 Hz, 1H), 4.49 (s, 2H); LCMS (ESI) m/z 393 [M + H]⁺. | 48.41 | >50 | 26.34 | >50 | 24.61 | >50 |
| 248 | pale yellow solid, ¹H NMR (400 MHz, (CD₃)₂CO) δ 7.62 (d, J = 16.0 Hz, 2H), 7.44 (d, J = 6H, 2H), 7.39 (d, J = 7.6 Hz, 1H), 7.28 (t, J = 8.0 Hz, 1H), 6.68 (d, J = 15.6 Hz, 1H), 6.58 (s, 1H), 4.84 (q, J = 6.4 Hz, 1H), 3.66 (s, 2H), 1.45 (d, J = 3.2 Hz, 6H), LCMS (ESI) m/z 393 [M + H]⁺. | 0.5686 0.62 | >50 | 0.5605 0.29 | >50 | 0.3779 0.25 | >50 |
| 249 | Pale yellow solid, ¹H NMR (400 MHz, DMSO-d₆) δ 12.99 (s, 1H), 8.10 (t, J = 7.2 Hz, 1H), 7.77 (d, J = 8.0 Hz, 1H), 7.66 (d, J = 16.4 Hz, 1H), 7.53 (t, J = 8.0 Hz, 2H), 7.40-7.28 (m, 3H), 7.13 (t, J = 7.2 Hz, 1H), 4.69 (s, 2H), LCMS (ESI) m/z 355 [M + H]⁺. | N/D | >50 | N/D | >50 | N/D | >50 |

TABLE 56-continued

| | | | | | | |
|---|---|---|---|---|---|---|
| 250 White solid, $^1$H NMR (400 MHz, (CD$_3$)$_2$CO) δ 8.07 (dd, J = 6.4, 2.4 Hz, 1H), 7.81 (d, J = 16.4 Hz, 1H), 7.39 (dd, J = 8.4, 2.4 Hz, 1H), 7.26 (t, J = 8.4 Hz, 1H), 7.20 (d, J = 16.4 Hz, 1H), 2.81 (d, J = 6.8 Hz, 2H), 2.69 (d, J = 6.8 Hz, 1H), 1.90-1.70 (m, 10H), LCMS (ESI) m/z 321 [M + H]$^+$. | N/D | >50 | N/D | >50 | N/D | >50 |

TABLE 57

| | | | | | | |
|---|---|---|---|---|---|---|
| 251 Yellow solid; $^1$H NMR (400 MHz, (CD$_3$)$_2$CO) δ 8.05-8.03 (m, 1H), 8.01-7.97 (m, 2H), 7.79 (d, J = 16.4 Hz, 1H), 7.70 (s, 1H), 7.47-7.37 m, 3H), 7.25 (m, 1H), 7.18 (d, J = 16.8 Hz, 1H), 4.62 (s, 2H); LCMS (ESI) m/z 371 [M + H]$^-$. | N/D | >50 | N/D | >50 | N/D | >50 |
| 252 Bown oil; $^1$H NMR (400 MHz, (CD$_3$)$_2$CO) δ 7.78-7.74 (m, 1H), 7.71 (d, J ' 16.4 Hz, 1H), 7.66 (s, 1H), 7.51 (d, J = 7.6 Hz, 1H), 7.44 (d, J = 8.4 Hz, 1H), 7.34 (t, J = 8.4 Hz, 1H), 7.02 (d, J = 16.8 Hz, 1H), 6.86-6.80 (m, 2H), 4.34 (s, 2H), 2.91-2.88 (m, 4H), 1.73-1.67 (m, 4H), 1.63-1.60 (m, 2H); LCMS (ESI) m/z 442 [M + H]$^+$. | 5.464 >50 4.20 | >50 | 0.8783 >50 0.86 | >50 | 0.904 8.81 0.34 | >50 |
| 253 White solid; mp = 254.2° C., $^1$H NMR (400 MHz, (CD$_3$)$_2$CO) δ 8.25 (s, 1H), 8.14 (dd, J = 8.0, 6.8 Hz, 1H), 8.06 (d, J = 16.8 Hz, 1H), 7.91-7.90 (m, 1H), 7.46-7.28 (m, 5H), LCMS (ESI) m/z 423 [M + H]$^+$. | 6.835 16.57 | 38.46 | 3.723 13.54 | >50 | 5.315 5.61 | >50 |
| 254 Pale yellow solid, $^1$H NMR (400 MHz, DMSO-d$_6$) δ 8.17 (s, 1H), 7.61 (s, 1H), 7.49 (d, J = 7.6 Hz, 1H), 7.38-7.31 (m, 2H), 7.26 (s, 1H), 7.13 (d, J = 16.4 Hz, 1H), 7.53-7.47 (m, 1H), 4.30 (s, 2H), 1.35 (d, J = 6.4 Hz, 6H), LCMS (ESI) m/z 407 [M + H]$^+$. | 12.65 | >50 | 11.86 | >50 | 12.38 | >50 |
| 255 Ivory solid; mp = 117.0° C., $^1$H NMR (400 MHz, (CD$_3$)$_2$CO) δ 8.06 (dd, J = 9.2, 6.4 Hz, 1H), 7.82 (d, J = 16.4 Hz, 1H), 7.40 (d, J = 9.2 Hz, 1H), 7.26 (t, J = 8.4 Hz, 1H), 7.20 (d, J = 16.4 Hz, 1H), 7.07 (s, 1H), 7.00 (d, J = 9.6 Hz, 1H), 6.91 (d, J = 10.0 Hz, 1H), 4.32 (s, 2H), 2.35 (s, 3H); LCMS (ESI) m/z 347 [M + H]$^+$. | 6.255 1.55 | >50 | 2.756 0.85 | >50 | 0.853 0.30 | >50 |
| 256 White solid; mp = 103.6° C., $^1$H NMR (400 MHz, (CD$_3$)$_2$CO) δ 8.06 (d, J = 8.0 Hz, 1H), 7.73 (d, J = 16.4 Hz, 1H), 7.65 (s, 1H), 7.58 (t, J = 7.8 Hz, 1H), 7.52-7.43 (m, 4H), 7.35 (t, J = 8.0 Hz, 1H), 7.29 (d, J = 16.0 Hz, 1H), 4.37 (s, 2H), LCMS (ESI) m/z 426 [M + H]$^+$. | N/D 5.72 | >50 | >50 1.44 | >50 | 4.253 1.42 | >50 |
| 257 Bown oil; $^1$H NMR (400 MHz, (CD$_3$)$_2$CO) δ 8.60 (s, 1H), 7.93 (d, J = 8.4 Hz, 1H), 7.88 (d, J = 16.0 Hz, 1H), 7.66 (s, 1H), 7.60 (d, J = 15.6 Hz, 1H), 7.51 (d, J = 7.6 Hz, 1H), 7.44 (d, J = 8.0 Hz, 1H), 7.35 (t, J = 7.8 Hz, 1H), 4.39 (s, 2H); LCMS (ESI) m/z 395 [M + H]$^+$. | 0.93 | >50 | 0.79 | >50 | 0.46 | >50 |
| 258 White solid; mp = 156.6° C., $^1$H NMR (400 MHz, (CD$_3$)$_2$CO) δ 8.07 (dd, J = 8.8, 6.0 Hz, 1H), 7.83 (d, J = 16.8 Hz, 1H), 7.72 (d, J = 6.0 Hz, 1H), 7.59-7.54 (m, 1H), 7.41 (d, J = 8.4 Hz, 1H), 7.27 (t, J = 8.4 Hz, 1H), 7.27 (d, J = 16.8 Hz, 1H), 7.20 (t, J = 9.2 Hz, 1H), 4.40 (s, 2H), LCMS (ESI) m/z 412 [M + H]$^+$. | >50 3.54 | >50 | >50 0.26 | >50 | 0.2679 0.12 | >50 |
| 259 Pale yellow solid; $^1$H NMR (400 MHz, (CD$_3$)$_2$CO) δ 7.63 (s, 1H), 7.54-7.49 (m, 2H), 7.41 (d, J = 7.2 Hz, 1H), 7.37-7.36 (m, 1H), 7.35 (s, 1H), 7.31-7.29 (m, 1H), 7.10 (s, 1H), 4.81 (q, J = 6.8 Hz, 1H), 4.21 (s, 2H), 1.48 (d, J = 6.4 Hz, 6H); LCMS (ESI) m/z 373 [M + H]$^+$. | N/D | >50 | N/D | >50 | N/D | >50 |
| 260 Yellow solid; $^1$H NMR (400 MHz, (CD$_3$)$_2$CO) δ 7.65-7.66 (m, 1H), 7.53-7.50 (m, 2H), 7.47 (s, 1H), 7.44-7.42 (m, 2H), 7.35 (t, J = 7.6 Hz, 1H), 7.16 (d, J = 16.8 Hz, 1H), 4.39 (s, 2H); LCMS (ESI) m/z 426 [M + H]$^+$. | 0.57 | >50 | 0.56 | >50 | 0.24 | >50 |

TABLE 58

| | | | | | | | |
|---|---|---|---|---|---|---|---|
| 261 | Pale yellow solid; ¹H NMR (400 MHz, (CD₃)₂CO) δ 8.07-8.03 (m, 1H), 7.83-7.77 (m, 2H), 7.62 (d, J = 12.0 Hz, 1H), 7.41-7.27 (m, 2H), 7.27-7.19 (m, 2H), 7.18-7.12 (m, 1H), 4.96 (q, J = 6.8 Hz, 1H), 7.51 (d, J = 5.2 Hz, 6H); LCMS (ESI) m/z 397 [M + H]⁺. | N/D | >50 | N/D | >50 | N/D | >50 |
| 262 | White solid; mp = 132.0° C., ¹H NMR (400 MHz, (CD₃)₂CO) δ 7.96 (q, J = 8.1 Hz, 1H), 7.63 (s, 1H), 7.58 (d, J = 16.4 Hz, 1H), 7.35-7.30 (m, 2H), 7.20 (d, J = 16.4 Hz, 1H), 7.18-7.10 (m, 2H), 4.31 (s, 2H), 2.36 (s, 3H); LCMS (ESI) m/z 392 [M + H]⁺. | 1.00 | >50 | 0.72 | >50 | 0.39 | >50 |
| 263 | Ivory solid; mp = 115.0° C., ¹H NMR (400 MHz, (CD₃)₂CO) δ 7.96 (q, J = 8.3 Hz, 1H), 7.76 (d, J = 6.4 Hz, 1H), 7.59 (d, J = 16.4 Hz, 1H), 7.50-7.46 (m, 1H), 7.30 (t, J = 8.6 Hz, 1H), 7.20 (d, J = 16.8 Hz, 1H), 7.17-7.10 (m, 2H), 4.37 (s, 2H); LCMS (ESI) m/z 396 [M + H]⁻. | 1.34 | >50 | 0.73 | >50 | 0.76 | >50 |
| 264 | Ivory solid; mp = 137.3° C., ¹H NMR (400 MHz, (CD₃)₂CO) δ 8.06 (dd, J = 9.2, 5.6 Hz, 1H), 7.78 (d, J = 16.0 Hz, 1H), 7.65-7.49 (m, 4H), 7.44 (d, J = 7.2 Hz, 1H), 7.35 (t, J = 7.8 Hz, 1H), 7.24 (d, J = 16.0 Hz, 1H), 4.38 (s, 2H); LCMS (ESI) m/z 428 [M + H]⁺. | N/D | >50 | N/D | >50 | N/D | >50 |
| 265 | White solid; mp = 152.6° C., ¹H NMR (400 MHz, (CD₃)₂CO) δ 8.49 (dd, J = 8.6, 6.2 Hz, 1H), 8.24 (d, J = 16.4 Hz, 1H), 8.09 (s, 1H), 8.01 (d, J = 8.8 Hz, 1H), 7.77-7.72 (m, 3H), 7.60 (d, J = 16.0 Hz, 1H), 4.76 (s, 2H), 2.81 (s, 3H); LCMS (ESI) m/z 453 [M + H]⁺. | 4.001 / 1.80 | >50 | 0.38 / 0.25 | >50 | 0.3758 / 0.12 | >50 |
| 266 | Ivory solid; mp = 124.9° C., ¹H NMR (400 MHz, (CD₃)₂CO) δ 8.05 (dd, J = 9.0, 5.8 Hz, 1H), 7.82 (s, 1H), 7.79-7.76 (m, 1H), 7.57 (d, J = 8.0 Hz, 1H), 7.51-7.47 (m, 1H), 7.33-7.27 (m, 2H), 7.17 (d, J = 16.8 Hz, 1H), 4.38 (s, 2H); LCMS (ESI) m/z 457 [M − H]⁺. | 2.541 / 0.43 | >50 | 0.5128 / 0.22 | >50 | 0.3832 / 0.20 | >50 |
| 267 | Yellow solid; mp = 110.2° C., ¹H NMR (400 MHz, (CD₃)₂CO) δ 8.06 (dd, J = 9.0, 6.2 Hz, 1H), 7.80 (d, J = 16.4 Hz, 1H), 7.40 (d, J = 8.8 Hz, 1H), 7.28-7.21 (m, 3H), 7.17-7.14 (m, 2H), 7.02 (d, J = 7.2 Hz, 1H), 4.27 (s, 2H), 1.95-1.91 (m, 1H), 0.98-0.94 (m, 2H), 0.71-0.66 (m, 2H); LCMS (ESI) m/z 355 [M + H]⁺. | 1.48 | >50 | 0.87 | >50 | 0.79 | >50 |
| 268 | Paly yellow sticky oil; ¹H NMR (400 MHz, acetone-d₆) δ 7.81 (d, J = 16.8 Hz, 1H), 7.76-7.72 (m, 1H), 7.64-7.63 (m, 1H), 7.51-7.48 (m, 1H), 7.43-7.41 (m, 1H), 7.34 (dd, J = 8.0, 7.6 Hz, 1H), 7.01 (d, J = 16.8 Hz, 1H), 6.96-6.93 (m, 1H), 6.85-6.80 (m, 1H), 4.34 (s, 2H), 3.55-3.52 (m, 2H), 3.25 (s, 3H), 3.15 (t, J = 5.6 Hz, 2H), 2.83 (s, 3H); LCMS (ESI) m/z 446, 448 [M + H]+. | 11.74 / 6.31 | >50 / 43.24 | 5.811 / 4.01 | >50 / >50 | 4.295 / 0.81 | >50 / 43.24 |
| 269 | Yellow solid; ¹H NMR (400 MHz, (CD₃)₂CO) δ 7.93 (dd, J = 8.8, 5.6 Hz, 1H), 7.79-7.68 (m, 3H), 7.60 (s, 1H), 7.48 (d, J = 8.0 Hz, 1H), 7.39 (d, J = 7.6 Hz, 1H), 7.32 (t, J = 8.0 Hz, 1H), 7.26-7.17 (m, 2H), 7.05 (d, J = 16.4 Hz, 1H), 6.73 (s, 1H), 4.31 (s, 2H); LCMS (ESI) m/z 425 [M − H]⁺. | 5.88 | >50 | 5.79 | >50 | 5.54 | >50 |
| 270 | White solid; ¹H NMR (400 MHz, (CD₃)₂CO) δ 7.94 (dd, J = 8.4, 5.6 Hz, 1H), 7.64-7.56 (m, 3H), 7.52 (s, 1H), 7.47 (d, J = 7.6 Hz, 1H), 7.36 (d, J = 8.0 Hz, 1H), 7.31 (t, J = 8.0 Hz, 1H), 7.24-7.17 (m, 3H), 7.03 (d, J = 16.4 Hz, 1H), 4.27 (s, 2H); LCMS (ESI) m/z 44 [M + H]⁺. | 3.26 | >50 | 2.99 | >50 | 3.07 | >50 |

TABLE 59

| | | | | | | | |
|---|---|---|---|---|---|---|---|
| 271 | Yellow solid; ¹H NMR (400 MHz, (CD₃)₂CO) δ 7.79 (d, J = 8.0 Hz, 1H), 7.75 (d, J = 16.4 Hz, 1H), 7.65 (s, 1H), 7.51 (d, J = 8.0 Hz, 1H), 7.45 (d, J = 7.6 Hz, 1H), 7.35 (t, J = 8.0 Hz, 1H), 7.05 (d, J = 16.4 Hz, 1H), 6.92-6.88 (m, 2H), 4.34 (s, 2H), 3.81-3.78 (m, 4H), 2.96-2.94 (m, 4H); LCMS (ESI) m/z 444 [M + H]⁻. | >50 | >50 | 35.13 | >50 | 13.32 | >50 |
| 272 | Yellow solid; ¹H NMR (400 MHz, (CD₃)₂CO) δ 8.04 (dd, J = 8.8, 5.6 Hz, 1H), 7.97 (s, 1H), 7.80 (d, J = 16.4 Hz, 1H), 7.74 (d, J = 7.6 Hz, 1H), 7.53 (d, J = 8.0 Hz, 1H), 7.40-7.22 (m, 4H), 7.19 (d, J = 16.4 Hz, 1H), 4.47 (s, 2H); LCMS (ESI) m/z 355 [M + H]⁺. | N/D | >50 | N/D | >50 | N/D | >50 |
| 273 | Pale yellow solid; ¹H NMR (400 MHz, (CD₃)₂CO) δ 7.89 (dd, J = 16.0, 2.4 Hz, 1H), 7.82-7.78 (m, 1H), 7.65 (s, 1H), 7.44-7.36 (m, 2H), 7.35-7.32 (m, 1H), 7.16-7.12 (m, 1H), | 1.20 | >50 | 0.79 | >50 | 0.95 | >50 |

TABLE 59-continued

| | | | | | | | |
|---|---|---|---|---|---|---|---|
| | 7.06-6.96 (m, 2H), 4.34 (d, J = 2.8 Hz, 1H), 3.40-3.36 (m, 1H), 1.26 (d, J = 7.2, 2.8 Hz, 1H); LCMS (ESI) m/z 401 [M + H]⁺. | | | | | | |
| 274 | White solid; ¹H NMR (400 MHz, (CD₃)₂CO) δ 7.99 (dd, J = 7.6, 2.0 Hz, 1H), 7.59-7.48 (m, 4H), 7.42-7.37 (m, 2H), 7.34 (d, J = 6.8 Hz, 1H), 7.32-7.23 (m, 1H), 7.04 (d, J = 16.4 Hz, 1H), 6.91 (t, J = 2.0 Hz, 2H), 6.33 (t, J = 2.4 Hz, 2H) 4.29 (s, 2H); LCMS (ESI) m/z 406 [M + H]⁺. | N/D | >50 | N/D | >50 | N/D | >50 |
| 275 | White oil; ¹H NMR (400 MHz, (CD₃)₂CO) δ 7.55 (s, 1H), 7.52-7.19 (m, 1H), 7.38-7.31 (m, 3H), 7.22 (dd, J = 8.8, 2.4 Hz, 1H), 7.01 (td, J = 8.4, 2.4 Hz, 1H), 4.24 (s, 2H), 3.19-3.14 (m, 4H), LCMS (ESI) m/z 395 [M + H]⁻. | 24.88 | >50 | 17.59 | >50 | 15.94 | >50 |
| 276 | Yellow solid; ¹H NMR (400 MHz, (CD₃)₂CO) δ 8.40 (d, J = 16.0 Hz, 1H), 8.27 (d, J = 8.4 Hz, 1H), 8.02-7.94 (m, 3H), 7.71-7.54 (m, 4H), 7.53-7.44 (m, 2H), 7.34 (t, J = 8.0 Hz, 1H), 7.23 (d, J = 114.0 Hz, 1H), 4.39 (s, 2H); LCMS (ESI) m/z 391 [M + H]⁻. | 1.69 | >50 | 1.50 | >50 | 1.42 | >50 |
| 277 | Yellow solid; ¹H NMR (400 MHz, (CD₃)₂CO) δ 8.36-8.31 (m, 2H), 8.18-8.15 (m, 1H), 8.03 (dd, J = 5.2, 2.4 Hz, 1H), 7.78-7.62 (m, 3H), 7.53-7.43 (m, 2H), 7.36-7.31 (m, 2H), 7.20 (d, J = 16.0 Hz, 1H), 4.03 (s, 2H); LCMS (ESI) m/z 109 [M + H]⁺. | 2.15 | >50 | 1.73 | >50 | 2.13 | >50 |
| 278 | Pale yellow solid; ¹H NMR (400 MHz, DMSO-d₆) δ 12.99 (s, 1H), 8.10 (t, J = 7.2 Hz, 1H), 7.77 (d, J = 8.0 Hz, 1H), 7.66 (d, J = 16.4 Hz, 1H), 7.53 (t, J = 8.0 Hz, 2H), 7.40-7.28 (m, 3H), 7.13 (t, J = 7.2 Hz, 1H), 4.69 (s, 2H); LCMS (ESI) m/z 355 [M + H]⁻. | >50 | >50 | >50 | >50 | 26.31 | >50 |
| 279 | Pale yellow solid; ¹H NMR (400 MHz, (CD₃)₂CO) δ 8.02 (dd, J = 8.8 6.0 Hz, 1H), 7.78 (d, J = 16.4 Hz, 1H), 7.53 (d, J = 8.0 Hz, 1H), 7.46 (d, J = 7.6 Hz, 1H), 7.38 (dd, J = 8.8, 2.4 Hz, 1H), 7.22 (td, J = 8.4, 2.4 Hz, 1H), 7.18-7.11 (m, 2H), 7.03-7.01 (m, 1H), 6.31 (s, 1H), 5.73 (s, 2H), 2.59 (s, 3H); LCMS (ESI) m/z 368 [M + H]⁺. | N/D | >50 | N/D | >50 | N/D | >50 |
| 280 | White solid; mp = 97.4° C., ¹H NMR (400 MHz, (CD₃)₂CO) δ 7.69 (t, J = 6.4 Hz, 1H), 7.66-7.60 (m, 2H), 7.50 (d, J = 7.6 Hz, 1H), 7.43 (d, J = 8.8 Hz, 1H), 7.40-7.26 (m, 5H), 4.37 (s, 2H); LCMS (ESI) m/z 378 [M + H]⁺. | 2.03 | 14.57 | 1.11 | >50 | 0.37 | 26.71 |

TABLE 60

| | | | | | | | |
|---|---|---|---|---|---|---|---|
| 281 | White solid; mp = 107.2° C., ¹H NMR (400 MHz, (CD₃)₂CO) δ 8.11 (d, J = 8.0 Hz, 1H), 7.87-7.78 (m, 2H), 7.76 (d, J = 7.6 Hz, 1H), 7.66-7.62 (m, 2H), 7.51 (d, J = 7.6 Hz, 1H), 7.44 (d, J = 7.6 Hz, 1H), 7.35 (t, J = 7.8 Hz, 1H), 7.25 (d, J = 16.8 Hz, 1H), 4.38 (s, 2H); LCMS (ESI) m/z 410 [M + H]⁺. | 1.12 | >50 | 0.67 | >50 | 0.63 | >50 |
| 282 | White solid; mp = 169.3° C., ¹H NMR (400 MHz, (CD₃)₂CO) δ 8.07 (dd, J = 9.6, 6.2 Hz, 1H), 7.82 (d, J = 16.4 Hz, 1H), 7.54 (s, 1H), 7.41-7.38 (m, 2H), 7.28-7.17 (m, 3H), 4.35 (s, 2H), 2.38 (s, 3H); LCMS (ESI) m/z 408 [M + H]⁺. | N/D | >50 | N/D | >50 | N/D | >50 |
| 283 | Beige solid; mp = 149.5° C., ¹H NMR (400 MHz, (CD₃)₂CO) δ 8.41 (d, J = 6.0 Hz, 1H), 8.06 (dd, J = 10.8, 8.0 Hz, 1H), 7.84-7.80 (m, 2H), 7.57 (d, J = 5.6 Hz, 1H), 7.39 (d, J = 11.6 Hz, 1H), 7.28-7.20 (m, 2H), 4.54 (s, 2H); LCMS (ESI) m/z 395 [M + H]⁺. | 1.23 | >50 | 0.67 | >50 | 0.77 | >50 |
| 284 | Yellow oil; ¹H NMR (400 MHz, (CD₃)₂CO) δ 8.52 (s, 1H), 7.74 (t, J = 8.0 Hz, 1H), 7.68-7.64 (m, 2H), 7.56-7.44 (m, 3H), 7.34 (t, J = 7.6 Hz, 1H), 4.38 (s, 2H), LCMS (ESI) m/z 379 [M + H]⁺. | 1.40 | >50 | 0.86 | >50 | 0.80 | >50 |
| 285 | Colorless oil; ¹H NMR (400 MHz, (CD₃)₂CO) δ 7.55 (s, 1H), 7.36-7.30 (m, 2H), 7.24-7.20 (m, 2H), 7.01 (t, J = 8.4 Hz, 1H), 4.18 (s, 2H), 3.23-3.11 (m, 4H), 2.43 (s, 3H); LCMS (ESI) m/z 410 [M + H]⁺. | 18.82 | 30.31 | 15.49 | 39.03 | 7.05 | 30.31 |
| 286 | Yellow solid; ¹H NMR (400 MHz, (CD₃)₂CO) δ 8.05 (dd, J = 8.8, 6.0 Hz, 1H), 7.81 (d, J = 16.4 Hz, 1H), 7.49-7.47 (m, 1H), 7.42 (s, 1H), 7.38 (dd, J = 8.8, 2.4 Hz, 1H), 7.27-7.15 (m, 3H), 4.35 (s, 2H); LCMS (ESI) m/z 321 [M + H]⁺. | >50 | >50 | >50 | >50 | >50 | >50 |

TABLE 60-continued

| | | | | | | | |
|---|---|---|---|---|---|---|---|
| 287 | Yellow solid; $^1$H NMR (400 MHz, (CD$_3$)$_2$CO) δ 8.13 (s, 1H), 7.96-7.91 (m, 4H), 7.71 (d, J = 16.4 Hz, 1H), 7.65 (s, 1H), 7.56-7.49 (m, 3H), 7.43 (d, J = 7.6 Hz, 1H), 7.34 (t, J = 8.0 Hz, 1H), 7.27 (d, J = 16.4 Hz, 1H), 4.36 (s, 2H); LCMS (ESI) m/z 391 [M + H]$^+$. | 4.02 | >50 | 2.86 | >50 | 3.11 | >50 |
| 288 | White solid; $^1$H NMR (400 MHz, (CD$_3$)$_2$CO) δ 7.88 (d, J = 16.0 Hz, 1H), 7.64 (s, 1H), 7.56 (d, J = 7.2 Hz, 1H), 7.49 (d, J = 8.4 Hz, 1H), 7.43 (d, J = 8.0 Hz, 1H), 7.34 (t, J = 8.0 Hz, 1H), 7.20 (d, J = 7.2 Hz, 1H), 7.14 (t, J = 8.0 Hz, 1H), 6.95 (d, J = 16.4 Hz, 1H), 4.36 (s, 2H), 2.32 (s, 3H), 2.30 (s, 3H); LCMS (ESI) m/z 369 [M + H]$^+$. | 0.51 | 49.76 | 0.26 | >50 | 0.16 | 38.35 |
| 289 | Yellow solid; $^1$H NMR (400 MHz, (CD$_3$)$_2$CO) δ 8.97 (m, 1H), 8.71 (d, J = 8.8 Hz, 1H), 8.37 (d, J = 16.0 Hz, 1H), 8.13-8.10 (m, 2H), 7.83 (d, J = 8.0 Hz, 1H), 7.67 (m, 1H), 7.63-7.59 (m, 2H), 7.51-7.45 (m, 2H), 7.36 (t, J = 8.0 Hz, 1H), 7.28 (d, J = 16.0 Hz, 1H), 4.39 (s, 2H); LCMS (ESI) m/z 392 [M + H]$^+$. | 44.93 | >50 | 22.93 | >50 | 13.71 | >50 |
| 290 | White solid; mp = 118.2° C.; $^1$H NMR (400 MHz, (CD$_3$)$_2$CO) δ 7.66 (s, 1H), 7.60 (d, J = 16.8 Hz, 1H), 7.53-7.49 (m, 2H), 7.44 (d, J = 8.4 Hz, 1H), 7.36 (d, J = 7.6 Hz, 1H), 7.33-7.26 (m, 1H), 7.19 (d, J = 16.8 Hz, 1H), 4.38 (s, 2H), 2.38 (s, 3H); LCMS (ESI) m/z 457 [M + H]$^+$. | 0.25 | 0.50 | 0.16 | >50 | 0.10 | >50 |

TABLE 61

| | | | | | | | |
|---|---|---|---|---|---|---|---|
| 291 | White solid; mp = 118.1° C.; $^1$H NMR (400 MHz, (CD$_3$)$_2$CO) δ 8.07 (dd, J = 9.0, 5.8 Hz, 1H), 7.83 (d, J = 16.0 Hz, 1H), 7.54-7.45 (m, 2H), 7.40 (d, J = 8.4 Hz, 1H), 7.92-7.23 (m, 2H), 7.21 (d, J = 16.8 Hz, 1H), 4.44 (s, 2H); LCMS (ESI) m/z 368 [M − H]$^+$. | 0.74 | 0.50 | 0.42 | >50 | 0.39 | >50 |
| 292 | White solid; mp = 143.0° C.; $^1$H NMR (400 MHz, (CD$_3$)$_2$CO) δ 8.07 (dd, J = 8.8, 6.0 Hz, 1H), 7.83 (d, J = 16.4 Hz, 1H), 7.52 (s, 1H), 7.52-7.35 (m, 2H), 7.30-7.24 (m, 2H), 7.21 (d, J = 16.4 Hz, 1H), 4.42 (s, 2H), LCMS (ESI) m/z 412 [M + H]$^+$. | N/D | >50 | N/D | >50 | N/D | >50 |
| 293 | Ivory solid; mp = 135.8° C.; $^1$H NMR (400 MHz, (CD$_3$)$_2$CO) δ 8.07 (dd, J = 8.8, 6.0 Hz, 1H), 7.83 (d, J = 16.8 Hz, 1H), 7.65 (t, J = 7.2 Hz, 1H), 7.51 (t, J = 7.2 Hz, 1H), 7.40 (d, J = 8.4 Hz, 1H), 7.27 (t, J = 8.6 Hz, 1H), 7.21 (d, J = 16.8 Hz, 1H), 7.19 (t, J = 7.8 Hz, 1H), 4.44 (s, 2H), LCMS (ESI) m/z 412 [M + H]$^+$. | 0.70 | >50 | 0.41 | >50 | 0.38 | >50 |
| 294 | White solid; mp = 158.3° C.; $^1$H NMR (400 MHz, (CD$_3$)$_2$CO) δ 8.06 (dd, J = 8.0, 6.2 Hz, 1H), 7.80 (d, J = 16.48 Hz, 1H), 7.57 (d, J = 8.0 Hz, 1H), 7.40 (d, J = 8.4 Hz, 1H), 7.36 (d, J = 6.8 Hz, 1H), 7.26 (t, J = 8.6 Hz, 1H), 7.20 (d, J = 16.4 Hz, 1H), 7.15 (t, J = 7.8 Hz, 1H), 4.43 (s, 2H), 2.50 (s, 3H); LCMS (ESI) m/z 408 [M + H]$^+$. | 0.93 | >50 | 0.36 | >50 | N/D 0.1360 | >50 |
| 295 | White solid; mp = 191.2° C.; $^1$H NMR (400 MHz, (CD$_3$)$_2$CO) δ 8.24 (d, J = 8.8 Hz, 1H), 8.05 (dd, J = 8.8, 6.0 Hz, 1H), 7.88 (d, J = 8.4 Hz, 1H), 7.79-7.73 (m, 2H), 7.53 (t, J = 7.8 Hz, 1H), 7.45 (d, J = 8.4 Hz, 1H), 7.38 (d, J = 8.8 Hz, 1H), 7.25 (t, J = 8.6 Hz, 1H), 7.18 (d, J = 16.4 Hz, 1H), 4.93 (s, 2H), 2.69 (s, 3H); LCMS (ESI) m/z 380 [M + H]$^+$. | N/D | >50 | N/D | >50 | N/D | >50 |
| 296 | White solid; mp = 168.6° C.; $^1$H NMR (400 MHz, (CD$_3$)$_2$CO) δ 8.45 (d, J = 8.4 Hz, 1H), 8.06 (dd, J = 8.8, 6.0 Hz, 1H), 8.02 (d, J = 8.4 Hz, 1H), 7.89 (d, J = 8.8, 6.0 Hz, 1H), 8.02 (d, J = 8.4 Hz, 1H), 7.89 (d, J = 6.0 Hz, 1H), 7.79 (d, J = 16.8 Hz, 1H0, 7.69-7.65 (m, 1H), 7.59 (d, J = 8.4 Hz, 1H), 7.39 (d, J =+ 8.8 Hz, 1H), 7.26 (t, J = 8.8 Hz, 1H), 7.19 (d, J = 16.4 Hz, 1H), 4.89 (s, 2H), LCMS (ESI) m/z 401 [M + H]$^−$. | N/D | >50 | 25.00 | >50 | 5.12 | >50 |
| 297 | White solid; mp = 165.8° C.; $^1$H NMR (400 MHz, (CD$_3$)$_2$CO) δ 8.21 (d, J = 8.4 Hz, 1H), 8.03 (dd, J = 8.8, 6.0 Hz, 1H), 7.85 (d, J = 8.4 Hz, 1H), 7.76-7.71 (m, 2H), 7.46-7.42 (m, 1H), 7.38 (d, J = 8.4 Hz, 1H), 7.24 (t, J = 8.8 Hz, 1H), 7.16 (d, J = 16.4 Hz, 1H), 6.99 (d, J = 9.2 Hz, 1H), 4.80 (s, 2H), 3.99 (s, 3H); LCMS (ESI) m/z 397 [M + H]$^+$. | N/D | >50 | 10.51 | >50 | 23.93 | >50 |

TABLE 61-continued

| # | Description | | | | | |
|---|---|---|---|---|---|---|
| 298 | White solid; mp = 179.9° C.; ¹H NMR (400 MHz, (CD₃)₂CO) δ 8.03 (dd, J = 9.0, 6.2 Hz, 1H), 7.87 (d, J = 8.8 Hz, 1H), 7.83 (d, J = 8.0 Hz, 1H), 7.74 (d, J = 16.4 Hz, 1H), 7.62 (s, 1H), 7.55 (d, J = 6.8 Hz, 1H), 7.38-7.33 (m, 2H), 7.25-7.17 (m, 2H), 7.16 (d, J = 16.4 Hz, 1H), 4.76 (s, 2H), 3.96 (s, 3H); LCMS (ESI) m/z 395 [M + H]⁺. | N/D | >50 | 18.85 | >50 | 30.24 | >50 |
| 299 | White solid; mp = 108.1° C.; ¹H NMR (400 MHz, (CD₃)₂CO) δ 8.06 (dd, J = 9.2, 6.4 Hz, 1H), 7.81 (d, J = 16.4 Hz, 1H), 7.65 (s, 1H), 7.61-7.55 (m, 1H), 7.54-7.53 (m, 2H), 7.40 (d, J = 8.8 Hz, 1H), 7.26 (t, J = 8.6 Hz, 1H), 7.20 (d, J = 16.4 Hz, 1H), 6.92 (t, J = 55.8 Hz, 1H), 4.33 (s, 2H); LCMS (ESI) m/z 365 [M + H]⁺. | 0.95 | >50 | 0.56 | >50 | 0.45 | >50 |
| 300 | White solid; mp = 161.4° C.; ¹H NMR (400 MHz, (CD₃)₂CO) δ 8.06 (dd, J = 9.0, 6.2 Hz, 1H), 7.81 (d, J = 16.4 Hz, 1H), 7.45 (s, 1H), 7.40 (d, J = 8.8 Hz, 1H), 7.33 (d, J = 7.6 Hz, 1H), 7.28-7.23 (m, 2H), 7.20 (d, J = 16.4 Hz, 1H), 4.32 (s, 2H), 2.35 (s, 3H); LCMS (ESI) m/z 364 [M + H]⁺. | 7.75 | >50 | 0.33 | >50 | 0.24 | >50 |

TABLE 62

| # | Description | | | | | |
|---|---|---|---|---|---|---|
| 301 | Yellow solid; ¹H NMR (400 MHz, (CD₃)₂CO) δ 9.02 (dd, J = 4.0, 2.0 Hz, 1H), 8.81 (d, J = 16.0 Hz, 1H), 8.40 (dd, J = 8.4, 1.6 Hz, 1H), 8.30 (dd, J = 7.2, 1.2 Hz, 1H), 8.04 (dd, J = 8.4, 1.2 Hz, 1H), 7.71-7.67 (m, 1H), 7.63-7.56 (m, 2H), 7.51 (d, J = 8.0 Hz, 1H), 7.46 (d, J = 8.0 Hz, 1H), 7.36 (t, J = 8.0 Hz, 1H), 4.41 (s, 2H); LCMS (ESI) m/z 392 [M + H]⁺. | 2.05 | 43.85 | 1.00 | >50 | 1.32 | 18.84 |
| 302 | Yellow oil; ¹H NMR (400 MHz, (CD₃)₂CO) δ 7.72-7.62 (m, 3H), 7.49 (d, J = 7.6 Hz, 1H), 7.42-7.34 (m, 3H), 6.93 (d, J = 11.2 Hz, 1H), 6.78 (m, 1H), 4.33 (s, 2H0, 4.29-4.26 (m, 2H), 3.64-3.62 (m, 4H), 2.86-2.83 (m, 2H), 2.56-2.54 (m, 4H); LCMS (ESI) m/z 488 [M + H]⁺. | 5.64 | 31.29 | 4.38 | 43.59 | 3.10 | 30.09 |
| 303 | Yellow solid; ¹H NMR (400 MHz, (CD₃)₂CO) δ 9.35 (s, 1H), 8.61 (d, J = 6.0 Hz, 1H), 8.33 (d, J = 16.4 Hz, 1H), 8.29 (d, J = 7.6 Hz, 1H), 8.20 (d, J = 8.0 Hz, 1H), 8.11 (d, J = 6.0 Hz, 1H), 7.77 (t, J = 8.0 Hz, 1H), 7.67 (s, 1H), 7.52 (d, J = 7.6 Hz, 1H), 7.46 (d, J = 7.6 Hz, 1H), 7.36 (t, J = 8.0 Hz, 1H), 7.32 (d, J = 16.4 Hz, 1H), 4.39 (s, 2H); LCMS (ESI) m/z 392 [M + H]⁺. | N/D | >50 | 32.84 | >50 | 16.85 | >50 |
| 304 | Brown oil; ¹H NMR (400 MHz, (CD₃)₂CO) δ 7.98 (dd, J = 8.4, 1.2 Hz, 1H), 7.72 (d, J = 16.4 Hz, 1H), 7.73 (s, 1H), 7.63 (s, 1H), 7.50-7.46 (m, 2H), 7.42 (dd, J = 6.8, 1.2 Hz, 1H), 7.36-7.23 (m, 3H), 6.91 (d, J = 16.4 Hz, 1H), 4.31 (s, 2H), 3.88 (s, 3H); LCMS (ESI) m/z 394 [M + H]⁺. | N/D | 6.54 | N/D | 13.24 | N/D | 8.33 |
| 305 | Yellow solid; mp = 80.7° C.; ¹H NMR (400 MHz, (CD₃)₂CO) δ 7.76 (dd, J = 8.8, 6.8 Hz, 1H), 7.72 (d, J = 17.2 Hz, 1H), 7.63 (s, 1H), 7.31-7.23 (m, 2H), 7.19-7.06 (m, 5H), 7.01 (d, J = 16.4 Hz, 1H), 6.96 (d, J = 11.2 Hz, 1H), 6.84 (t, J = 8.2 Hz, 1H), 4.14 (s, 2H), 3.23-3.16 (m, 2H), 2.92-2.85 (m, 2H), 2.84 (s, 3H), 2.30 (s, 3H), LCMS (ESI) m/z 507 [M + H]⁻. | 4.46 | >50 | 2.91 | >50 | 4.06 | >50 |
| 306 | Yellow solid; ¹H NMR (400 MHz, (CD₃)₂CO) δ 8.76 (d, J = 7.2 Hz, 1H), 8.23 (s, 1H), 7.87 (d, J = 16.8 Hz, 1H), 7.66-7.63 (m, 2H), 7.50 (d, J = 8.0 Hz, 1H), 7.43-7.33 (m, 3H), 7.12 (d, J = 16.4 Hz, 1H), 7.10 (t, J = 7.2 Hz, 1H), 4.34 (s, 2H); LCMS (ESI) m/z 381 [M + H]⁺. | N/D | >50 | N/D | >50 | N/D | >50 |
| 307 | Brown oil; ¹H NMR (400 MHz, (CD₃)₂CO) δ 7.90 (d, J = 16.4 Hz, 1H), 7.65 (s, 1H), 7.51-7.33 (m, 6H), 7.26-7.18 (m, 2H), 6.81 (s, 1H), 4.35 (s, 2H), 3.87 (s, 3H); LCMS (ESI) m/z 394 [M + H]⁺. | 3.35 | >50 | 1.65 | >50 | 2.43 | >50 |

As shown in Tables 32 to 62, it was found that the novel compounds of Chemical formula 1 or Chemical formula 2 according to the present invention had an excellent antiviral activity against an A type influenza virus and a B type influenza virus, and it was confirmed that the compounds had low cytotoxicity.

Thus, the novel compounds of Chemical formula 1 or Chemical formula 2 of the present invention can be usefully used for prevention or treatment of diseases caused by influenza virus infection.

What is claimed is:

1. A compound, or a pharmaceutically acceptable salt thereof, wherein the compound is one selected from the group consisting of:
   (E)-2-((4-bromo-3,5-dimethyl-1H-pyrazol-1-yl)methyl)-5-(2-isopropylstyryl)-1,3,4-oxadiazole;
   (E)-2-(4-bromobenzyl)-5-(2-chloro-4-fluorostyryl)-1,3,4-oxadiazole;
   2-(4-bromobenzyl)-5-(2-isopropylphenethyl)-1,3,4-oxadiazole;

2-(2-isopropylphenethyl)-5-(4-(trifluoromethoxy)benzyl)-1,3,4-oxadiazole;
2-(3,5-dimethylbenzyl)-5-(2-isopropylphenethyl)-1,3,4-oxadiazole;
2-(3-bromobenzyl)-5-(2-isopropylphenethyl)-1,3,4-oxadiazole;
2-(3-chlorobenzyl)-5-(2-isopropylphenethyl)-1,3,4-oxadiazole;
2-(4-bromobenzyl)-5-(2-methylphenethyl)-1,3,4-oxadiazole;
2-(3,5-dimethylbenzyl)-5-(2-isopropylstyryl)-1,3,4-oxadiazole;
(E)-2-(4-bromobenzyl)-5-(2-phenoxystyryl)-1,3,4-oxadiazole;
2-(3-bromobenzyl)-5-(2-isopropylstyryl)-1,3,4-oxadiazole;
2-(3-chloro-4-fluorobenzyl)-5-(2-isopropylstyryl)-1,3,4-oxadiazole;
2-(4-isopropylbenzyl)-5-(2-isopropylstyryl)-1,3,4-oxadiazole;
2-(4-bromobenzyl)-5-(2,6-dimethylphenethyl)-1,3,4-oxadiazole;
2-([1,1'-biphenyl]-4-ylmethyl)-5-(2-isopropylstyryl)-1,3,4-oxadiazole;
2-(4-bromobenzyl)-5-(1-(o-tolyl)propan-2-yl)-1,3,4-oxadiazole;
2-(4-bromobenzyl)-5-(1-(o-tolyl)prop-1-en-2-yl)-1,3,4-oxadiazole;
2-(3,4-dimethylbenzyl)-5-(2-isopropylstyryl)-1, 3,4-oxadiazole;
2-(2-isopropylstyryl)-5-(1-phenylethyl)-1,3,4-oxadiazole;
2-(1-(4-isobutylphenyl)ethyl)-5-(2-isopropylstyryl)-1,3, 4-oxadiazole;
2-(4-bromobenzyl)-5-(3-isopropylstyryl)-1,3,4-oxadiazole;
(E)-2-(3-chloro-4-fluorobenzyl)-5-(2-chloro-4-fluorostyryl)-1,3,4-oxadiazole;
(E)-N-(4-bromo-3-fluorophenyl)-5-(2-chloro-4-fluorostyryl)-N-methyl-1,3,4-oxadiazol-2-amine;
2-(4-bromobenzyl)-5-(2-(6-chlorobenzo[d][1,3]dioxol-5-yl)vinyl)-1,3,4-oxadiazole;
2-(4-bromo-3-fluorobenzyl)-5-(2-isopropylstyryl)-1,3,4-oxadiazole;
2-(4-bromobenzyl)-5-styryl-1,3,4-oxadiazole;
2-(4-bromo-2-fluorobenzyl)-5-(2-isopropylstyryl)-1,3,4-oxadiazole;
2-(4-bromobenzyl)-5-(2-methylstyryl)-1,3,4-oxadiazole;
2-(4-bromobenzyl)-5-(4-chlorostyryl)-1,3,4-oxadiazole;
2-(2-fluoro-5-methylbenzyl)-5-(2-isopropylstyryl)-1, 3,4-oxadiazole;
(E)-2-(2-chloro-4-fluorostyryl)-5-(2-fluoro-5-methylbenzyl)-1, 3,4-oxadiazole;
(E)-2-(3-bromobenzyl)-5-(2-chloro-4-fluorostyryl)-1, 3,4-oxadiazole;
(E)-2-(2-chloro-4-fluorostyryl)-5-(3-chlorobenzyl)-1,3,4-oxadiazole;
(E)-2-(2-chloro-4-fluorostyryl)-54(6-chloropyridin-3-yl)methyl)-1,3,4-oxadiazole;
(E)-2-(3-bromo-4-methylbenzyl)-5-(2-chloro-4-fluorostyryl)-1, 3,4-oxadiazole;
(E)-2-(2-chloro-4-fluorostyryl)-5-(3-isopropylbenzyl)-1, 3,4-oxadiazole;
2-(3-bromobenzyl)-5-(4-fluoro-2-methylstyryl)-1, 3,4-oxadiazole;
2-(3-chlorobenzyl)-5-(2-fluorostyryl)-1,3,4-oxadiazole;
2-(3-bromobenzyl)-5-(4-fluorostyryl)-1,3,4-oxadiazole;
2-(3-bromobenzyl)-5-(2,4-difluorostyryl)-1,3,4-oxadiazole;
2-(3-bromobenzyl)-5-(4-chloro-2-fluorostyryl)-1,3,4-oxadiazole;
2-(3-bromobenzyl)-5-(3,4-difluorostyryl)-1,3,4-oxadiazole;
2-(3-bromobenzyl)-5-(2,4-dichlorostyryl)-1,3,4-oxadiazole;
2-(3-bromobenzyl)-5-(2-chloro-3-fluorostyryl)-1,3,4-oxadiazole;
2-(3-bromobenzyl)-5-(2-chloro-4-methylstyryl)-1,3,4-oxadiazole;
2-benzyl-5-(2-isopropylstyryl)-1,3,4-oxadiazole;
2-(4-bromobenzyl)-5-(2-(naphthalen-1-yl)vinyl)-1,3,4-oxadiazole;
2-(3-bromobenzyl)-5-(2-methyl-4-(trifluoromethyl)styryl)-1,3,4-oxadiazole;
2-(3-bromobenzyl)-5-(2-chloro-5-(trifluoromethyl)styryl)-1,3,4-oxadiazole;
2-(3-bromobenzyl)-5-(2,4-dimethylstyryl)-1,3,4-oxadiazole;
(E)-3-((5-(2-chloro-4-fluorostyryl)-1,3,4-oxadiazol-2-yl)methyl)phenol;
(E)-2-(2-chloro-4-fluorostyryl)-5-((2-methyl-1H-benzo[d]imidazol-1-yl)methyl)-1,3,4-oxadiazole;
(E)-2-(3-bromobenzyl)-5-(2-(2-methylpyridin-3-yl)vinyl)-1,3,4-oxadiazole;
(E)-2-((5-bromopyridin-3-yl)methyl)-5-(2-chloro-4-fluorostyryl)-1,3,4-oxadiazole;
(E)-2-(2-chloro-4-fluorostyryl)-5-((4-chloropyridin-2-yl)methyl)-1,3,4-oxadiazole;
2-(3-bromo-4-fluorobenzyl)-5-(2-chloro-4-fluorostyryl)-1,3,4-oxadiazole;
2-(2-chloro-4-fluorostyryl)-5-(3,4-dichlorobenzyl)-1,3,4-oxadiazole;
2-(2-(5-(4-bromobenzyl)-1,3,4-oxadiazol-2-yl)vinyl)phenol;
2-(2-chloro-4-fluorostyryl)-5-(3-methylbenzyl)-1,3,4-oxadiazole;
2-((1H-benzo[d][1,2,3]triazol-1-yl)methyl)-5-(2-chloro-4-fluorostyryl)-1,3,4-oxadiazol;
2-(2-chloro-4-fluorostyryl)-5-((1-methyl-1H-indol-3-yl)methyl)-1,3,4-oxadiazole;
(E)-2-(2-chloro-4-fluorostyryl)-5-((1-methyl-1H-indazol-3-yl)methyl)-1,3,4-oxadiazole;
2-(2-bromo-4-fluorostyryl)-5-(3-bromobenzyl)-1,3,4-oxadiazole;
2-(3-bromobenzyl)-5-(2-(3-methylpyridin-4-yl)vinyl)-1, 3,4-oxadiazole;
2-(2-(5-(3-bromobenzyl)-1,3,4-oxadiazol-2-yl)vinyl)phenol;
2-(2-chloro-4-fluorostyryl)-5-((6-chloropyridin-2-yl)methyl)-1,3,4-oxadiazole;
2-(3-bromobenzyl)-5-(2-ethylstyryl)-1,3,4-oxadiazole;
2-(2-chloro-4-fluorostyryl)-5-(2,3-dimethylbenzyl)-1,3, 4-oxadiazole;
2-(2-bromobenzyl)-5-(2-chloro-4-fluorostyryl)-1,3,4-oxadiazole;
2-(3-bromobenzyl)-5-(2-(2-chloropyridin-3-yl)vinyl)-1, 3,4-oxadiazole;
2-(2-chloro-4-fluorostyryl)-5-(3-fluorobenzyl)-1,3,4-oxadiazole;
(E)-2-(2-(5-(3-bromobenzyl)-1,3,4-oxadiazol-2-yl)vinyl)-5-fluoro-N,N-dimethylaniline;
(E)-2-(3-bromobenzyl)-5-(4-fluoro-2-(pyrrolidin-1-yl)styryl)-1,3,4-oxadiazole;

(E)-2-(3-bromobenzyl)-5-(2,4,6-trifluorostyryl)-1,3,4-oxadiazole;
(E)-3-((5-(2-chloro-4-fluorostyryl)-1,3,4-oxadiazol-2-yl)methyl)benzonitrile;
2-(2-chloro-4-fluorostyryl)-5-(quinolin-8-ylmethyl)-1,3,4-oxadiazole;
2-(2-chloro-4-fluorostyryl)-5-(isoquinolin-1-ylmethyl)-1,3,4-oxadiazole;
2-(2-chloro-4-fluorostyryl)-5-(isoquinolin-4-ylmethyl)-1,3,4-oxadiazole;
2-(3-bromobenzyl)-5-(2-(5-fluoropyridin-2-yl)vinyl)-1,3,4-oxadiazole;
2((6-bromopyridin-3-yl)methyl)-5-(2-chloro-4-fluorostyryl)-1,3,4-oxadiazole;
2((6-bromopyridin-3-yl)methyl)-5-(2-chloro-4-fluorostyryl)-1,3,4-oxadiazole;
(E)-2-(2-chloro-4-fluorostyryl)-5-(3-(trifluoromethyl)benzyl)-1,3,4-oxadiazole;
(E)-2-(3-bromobenzyl)-5-(2-(1-isopropyl-1H-pyrazol-5-yl)vinyl)-1,3,4-oxadiazole;
(E)-2-(3-bromobenzyl)-5-(4-fluoro-2-(piperidin-1-yl)styryl)-1,3,4-oxadiazole;
N-(3-bromophenyl)-5-(2-chloro-4-fluorostyryl)-1,3,4-oxadiazole-2-carboxamide;
(E)-2-(3-bromobenzyl)-5-(2-(4-chloro-1-isopropyl-1H-pyrazol-3-ylvinyl)-1,3,4-oxadiazole;
2-(2-chloro-4-fluorostyryl)-5-(3-fluoro-5-methylbenzyl)-1,3,4-oxadiazole;
2-(3-bromobenzyl)-5-(2-(trifluoromethoxy)styryl)-1,3,4-oxadiazole;
2-(3-bromobenzyl)-5-(2-(3-chloro-5-fluoropyridin-2-yl)vinyl)-1,3,4-oxadiazole;
2-(5-bromo-2-fluorobenzyl)-5-(2-chloro-4-fluorostyryl)-1,3,4-oxadiazole;
(E)-2-(3-bromobenzyl)-5-(2,6-dichloro-4-fluorostyryl)-1,3,4-oxadiazole;
2-(3-bromo-4-methylbenzyl)-5-(2,4-difluorostyryl)-1,3,4-oxadiazole;
2-(3-bromo-4-fluorobenzyl)-5-(2,4-difluorostyryl)-1,3,4-oxadiazole;
2-(3-bromobenzyl)-5-(4-fluoro-2-(trifluoromethyl)styryl)-1,3,4-oxadiazole;
2-(2-bromo-4-fluorostyryl)-5-(3-bromo-4-methylbenzyl)-1,3,4-oxadiazole;
2-(3-bromo-4-fluorobenzyl)-5-(2-bromo-4-fluorostyryl)-1,3,4-oxadiazole;
2-(2-chloro-4-fluorostyryl)-5-(3-cyclopropylbenzyl)-1,3,4-oxadiazole;
(E)-2-(2-(5-(3-Bromobenzyl)-1,3,4-oxadiazol-2-yl)vinyl)-5-fluoro-N-(2-methoxyethyl)-N-methylaniline;
(E)-2-(3-bromobenzyl)-5-(4-fluoro-2-(furan-3-yl)styryl)-1,3,4-oxadiazole;
(E)-2-(3-bromobenzyl)-5-(4-fluoro-2-(thiophen-3-yl)styryl)-1,3,4-oxadiazole;
(E)-4-(2-(2-(5-(3-bromobenzyl)-1,3,4-oxadiazol-2-yl)vinyl)-5-fluorophenyl)morpholine;
(E)-2-(3-bromobenzyl)-5-(4-fluoro-2-isopropylstyryl)-1,3,4-oxadiazole;
2-(3-bromobenzyl)-5-(2-chloro-4-fluorophenethyl)-1,3,4-oxadiazole;
(E)-2-(3-bromobenzyl)-5-(2-(naphthalen-1-yl)vinyl)-1,3,4-oxadiazole;
(E)-2-(3-bromobenzyl)-5-(2-(4-fluoronaphthalen-1-yl)vinyl)-1,3,4-oxadiazole;
(E)-2-((1H-indazol-3-yl)methyl)-5-(2-chloro-4-fluorostyryl)-1,3,4-oxadiazole;
2-(3-bromobenzyl)-5-(2,3-difluorostyryl)-1,3,4-oxadiazole;
2-(3-bromobenzyl)-5-(2-(trifluoromethyl)styryl)-1,3,4-oxadiazole;
2-((4-bromopyridin-2-yl)methyl)-5-(2-chloro-4-fluorostyryl)-1,3,4-oxadiazole;
2-(3-bromobenzyl)-5-(2-(3,5-difluoropyridin-2-yl)vinyl)-1,3,4-oxadiazole;
2-(3-bromo-4-methylbenzyl)-5-(2-chloro-4-fluorophenethyl)-1,3,4-oxadiazole;
(E)-2-(3-bromobenzyl)-5-(2-(naphthalen-2-yl)vinyl)-1,3,4-oxadiazole;
(E)-2-(3-bromobenzyl)-5-(2,3-dimethylstyryl)-1,3,4-oxadiazole;
(E)-2-(3-bromobenzyl)-5-(2-(quinolin-5-yl)vinyl)-1,3,4-oxadiazole;
2-(2-bromo-4,6-difluorostyryl)-5-(3-bromobenzyl)-1,3,4-oxadiazole;
2-(3-chloro-2-fluorobenzyl)-5-(2-chloro-4-fluorostyryl)-1,3,4-oxadiazole;
2-(3-bromo-2-fluorobenzyl)-5-(2-chloro-4-fluorostyryl)-1,3,4-oxadiazole;
2-(3-bromo-2-methylbenzyl)-5-(2-chloro-4-fluorostyryl)-1,3,4-oxadiazole;
2-(2-chloro-4-fluorostyryl)-5-((3-chloroisoquinolin-1-yl)methyl)-1,3,4-oxadiazole;
2-(2-chloro-4-fluorostyryl)-5-((3-methoxyisoquinolin-1-yl)methyl)-1,3,4-oxadiazole;
2-(2-chloro-4-fluorostyryl)-5-((7-methoxynaphthalen-1-yl)methyl)-1,3,4-oxadiazole;
2-(2-chloro-4-fluorostyryl)-5-(3-(difluoromethyl)benzyl)-1,3,4-oxadiazole;
2-(2-chloro-4-fluorostyryl)-5-(3-chloro-4-methylbenzyl)-1,3,4-oxadiazole;
(E)-2-(3-bromobenzyl)-5-(2-(quinolin-8-yl)vinyl)-1,3,4-oxadiazole;
(E)-4-(2-(2-(2-(5-(3-bromobenzyl)-1,3,4-oxadiazol-2-yl)vinyl)-5-fluorophenoxy)ethyl)morpholine;
(E)-2-(3-bromobenzyl)-5-(2-(isoquinolin-5-yl)vinyl)-1,3,4-oxadiazole;
2-(2-(5-(3-bromo-4-methylbenzyl)-1,3,4-oxadiazol-2-yl)vinyl)-5-fluoro-N-methyl-N-phenethylaniline; and
(E)-2-(3-bromobenzyl)-5-(2-(1-methyl-1H-indol-4-yl)vinyl)-1,3,4-oxadiazole.

2. An antiviral pharmaceutical composition comprising the compound according to claim 1, or a pharmaceutically acceptable salt thereof as an active ingredient.

3. The pharmaceutical composition according to claim 2, wherein the virus is an influenza virus.

4. The pharmaceutical composition according to claim 3, wherein the influenza virus is an A type influenza virus or a B type influenza virus.

5. The pharmaceutical composition according to claim 4, wherein the influenza virus is A/California/07/2009 (H1N1), A/Perth/16/2009 (H3N2) or B/Florida/04/2006.

* * * * *